US009624270B2

United States Patent
Smith et al.

(10) Patent No.: US 9,624,270 B2
(45) Date of Patent: Apr. 18, 2017

(54) ENGINEERING THE PRODUCTION OF A CONFORMATIONAL VARIANT OF OCCIDIOFUNGIN THAT HAS ENHANCED INHIBITORY ACTIVITY AGAINST FUNGAL SPECIES

(71) Applicants: THE TEXAS A&M UNIVERSITY SYSTEM, College Station, TX (US); MISSISSIPPI STATE UNIVERSITY, Starkville, MS (US)

(72) Inventors: James Leif Smith, College Station, TX (US); Akshaya Ravichandran, College Station, TX (US); Shien Lu, College Station, TX (US); Ganyu Gu, Painter, VA (US)

(73) Assignees: MISSISSIPPI STATE UNIVERSITY, Starkville, MS (US); THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 14/090,679

(22) Filed: Nov. 26, 2013

(65) Prior Publication Data

US 2014/0147416 A1 May 29, 2014

Related U.S. Application Data

(60) Provisional application No. 61/731,105, filed on Nov. 29, 2012.

(51) Int. Cl.
| | | |
|---|---|---|
| C07K 7/54 | (2006.01) | |
| A61K 38/12 | (2006.01) | |
| A01N 43/713 | (2006.01) | |
| A01N 63/00 | (2006.01) | |
| A01N 63/02 | (2006.01) | |
| C12N 9/16 | (2006.01) | |
| C07K 7/56 | (2006.01) | |

(52) U.S. Cl.
CPC .............. *C07K 7/54* (2013.01); *A01N 43/713* (2013.01); *A01N 63/00* (2013.01); *A01N 63/02* (2013.01); *A61K 38/12* (2013.01); *C07K 7/56* (2013.01); *C12N 9/16* (2013.01); *C12Y 301/02* (2013.01)

(58) Field of Classification Search
CPC ........ C07K 7/54; A01N 43/713; A01N 63/00; A61K 38/12
See application file for complete search history.

(56) References Cited

U.S. PATENT DOCUMENTS

| 7,560,252 B2 * | 7/2009 | Salas et al. ............... 435/76 |
| 2011/0136729 A1 | 6/2011 | Lu et al. |

OTHER PUBLICATIONS

Thomson, E.L., and Dennis J.J. "A Burkholderia cepacia complex non-ribosomal peptide-synthesized toxin is hemolytic and required for full virulence", Virulence, May 2012, vol. 3, pp. 286-298.*
Baysal, C. et al. "Free Energy Based Populations of Interconverting Microstates of a Cyclic Peptide Lead to the Experimental NMR Data," *Biopolymers*, Feb. 1999, pp. 329-344, vol. 50.
Boddy, C. N. "Sweetening Cyclic Peptide Libraries," *Chemistry & Biology*, Dec. 2004, pp. 1599-1606, vol. 11, No. 15.
Boguslavsky, V. et al. "Effect of peptide conformation on membrane permeability," *J. Peptide Res.*, 2003, pp. 287-297, vol. 61.
Delagio, F. et al. "NMRPipe: A multidimensional spectral processing system based on UNIX pipes," *Journal of Biomolecular NMR*, 1995, pp. 277-293, vol. 6.
Ellis, D. et al. "Occidiofungin's Chemical Stability and In Vitro Potency against *Candida* Species," *Antimicrobial Agents and Chemotherapy*, Nov. 2011, pp. 765-769, vol. 56, No. 2.
Fernandez-Lopez, S. et al. "Antibacterial agents based on the cyclic D,L-α-peptide architecture," *Nature*, Jul. 26, 2001, pp. 452-455, vol. 412.
Fischbach, M. A. et al. "Assembly-Line Enzymology for Polyketide and Nonribsomal Peptide Antibiotics: Logic, Machinery, and Mechanisms," *Chem. Rev.*, Jul. 7, 2006, pp. 3468-3496, vol. 106, No. 8.
Fridkin, G. et al. "Azo cyclization: peptide cyclization via azo bridge formation," *The Journal of Peptide Research*, 2002, pp. 104-111, vol. 60.
Gu, G. et al. "Biosynthesis of an antifungal oligopeptide in Burkholderia contaminans strain MS14," *Biochemical and Biophysical Research Communications*, 2009, pp. 328-332, vol. 380.
Gu, G. et al. "AmbR1 is a key transcriptional regulator for production of antifungal activity of *Burkholderia contaminans* strain MS14," *FEMS Microbiol Lett*, 2009, pp. 54-60, vol. 297.
Gu, G. et al. "Genetic and Biochemical Map for the Biosynthesis of Occidiofungin, an Anitfungal Produced by *Burkholderia contaminans* Strain MS14," *Applied and Environmental Microbiology*, Sep. 2011, pp. 6189-6198, vol. 77, No. 17.
Heikkinen, S. et al. "Quantitative 2D HSQC (Q-HSQC) via Suppression of J-Dependence of Polarization Transfer in NMR Spectroscopy: Application to Wood Lignin," *J. Am. Chem. Soc.*, 2003, pp. 4362-4367, vol. 125, No. 14.
Jelokhani-Niaraki, M. et al. "Conformation and other biophysical properties of cyclic antimicrobial peptides in aqueous solutions," *J. Peptide Res.*, 2001, pp. 293-306, vol. 58.
Jelokhani-Niaraki, M. et al. "Interaction of Gramicidin S and its Aromatic Amino-Acid Analog with Phospholipid Membranes," *Biophysical Journal*, Oct. 2008, pp. 3306-3321, vol. 95, No. 7.
Johnson, B. A. et al. "NMR View: A computer program for the visualization and analysis of NMR data," *Journal of Biomolecular NMR*, 1994, pp. 603-614, vol. 4.
Koglin, A. et al. "Conformational Switches Modulate Protein Interactions in Peptide Antibiotic Synthetases," *Science*, Apr. 14, 2006, pp. 273-276, vol. 312, No. 5571.

(Continued)

*Primary Examiner* — Paul Holland
(74) *Attorney, Agent, or Firm* — Butler Snow LLP

(57) ABSTRACT

Occidiofungin is a cyclic nonribosomally synthesized antifungal peptide with submicromolar activity. This invention is directed to compositions enriched for particular occidiofungin diastereomers/conformers, methods of making compositions enriched for particular diastereomers/conformers and microorganisms suitable for producing enriched compositions of particular diastereomers/conformers. Methods of treating fungal infections or plants infected by fungi are also provided.

Figure 1:
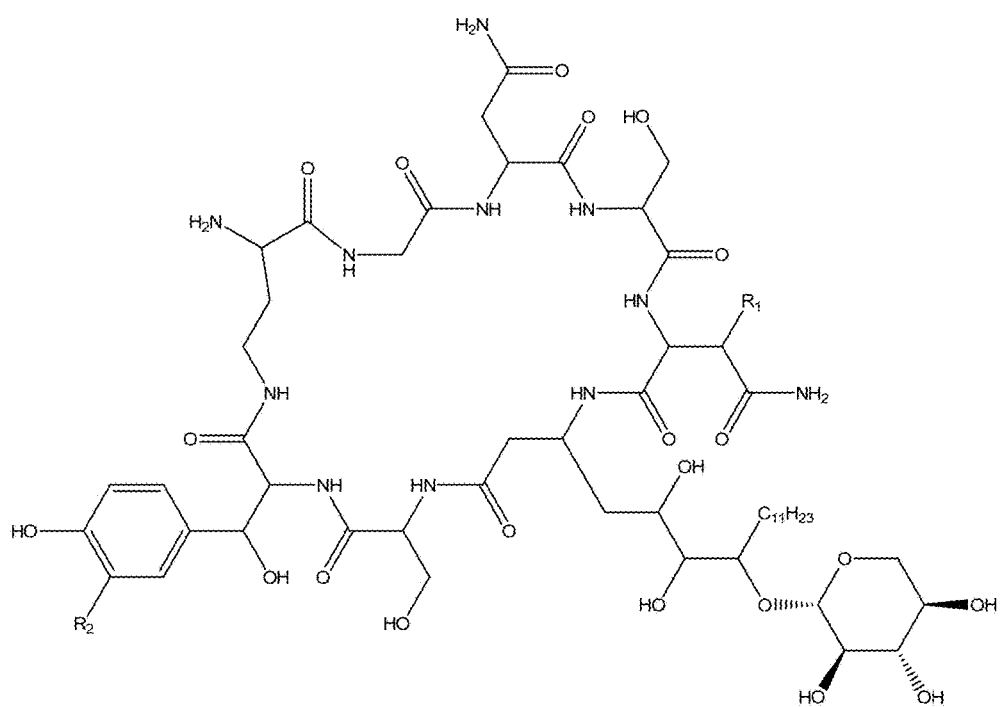

1 Claim, 14 Drawing Sheets
(4 of 14 Drawing Sheet(s) Filed in Color)

(56) References Cited

OTHER PUBLICATIONS

Koglin, A. et al. "Structural basis for the selectivity of the external thioesterase of the surfactin synthetase," *Nature*, Aug. 14, 2008, pp. 907-912, vol. 454.

Kohli, R. M. et al. "The thioesterase domain from a nonribosomal peptide synthetase as a cyclization catalyst for integrin binding peptides," *PNAS*, Feb. 5, 2002, pp. 1247-1252, vol. 99, No. 3.

Kohli, R. M. et al. "Biomimetic synthesis and optimization of cyclic peptide antibiotics," *Nature*, Aug. 8, 2002, pp. 658-661, vol. 418.

Lautru, S. et al. "Substrate recognition by nonribosomal peptide synthetase multi-enzymes," *Microbiology*, 2004, pp. 1629-1636, vol. 150.

Un, Z. et al. "Burkholdines from *Burkholderia ambifaria*: Antifungal Agents and Possible Virulence Factors," *Journal of Natural Products*, Sep. 18, 2012, pp. 1518-1523, vol. 75, No. 9.

Liao, G. et al. "Regulation Mechanisms Underlying the Biosynthesis of Daptomycin and Related Lipopeptides," *Journal of Cellular Biochemistry*, 2012, pp. 735-741, vol. 113.

Lu, S. et al "Occidiofungin, a Unique Antifungal Glycopeptide Produced by a Strain of *Burkholderia contaminans*," *Biochemistry*, 2009, pp. 8312-8321, vol. 48, No. 35.

Lu, S. et al. "Characterization of the salA, syrF, and syrG Regulatory Genes Located at the Right Border of the Syringomycin Gene Cluster of *Pseudomonas syringae* pv. *syringae*," MPMI, 2002, pp. 43-53, vol. 15, No. 1.

NCBI, GenBank accession No. ADT64850.1, "putatitve thioesterase [Burkholderia contaminans]," Dec. 13, 2010.

NCBI, GenBank accession No. ACL81527.1, "putative nonribosomal peptide synthetase [Burkholderia contaminans]," Dec. 13, 2010.

Prentki, P. et al. "The Plasmid cloning vector pBR325 contains a 482 base-pair-long inverted duplication," *Gene*, 1981, pp. 289-299, vol. 14.

Rai, R. K. et al. "Quantification of Metabolites from Two-Dimensional Nuclear Magnetic Resonance Spectroscopy: Application to Human Urine Samples," *Analytical Chemistry*, Dec. 15, 2009, pp. 10232-10238, vol. 81, No. 24.

Rayan, A. et al. "Exploring the conformational space of cyclic peptides by a stochastic search method," *Journal of Molecular Graphics and Modeling*, 2004, pp. 319-333, vol. 22.

Ravichandran, A. et al. "The Presence of Two Cyclase Thioesterases Expands the Conformational Freedom of the Cyclic Peptide Occidiofungin," *Journal of Natural Products*, Feb. 8, 2013, pp. 150-156, vol. 76. No. 2.

Samel, S. A. et al. "The Thioesterase Domain of the Fengycin Biosynthesis Cluster: A Structural Base for the Macrocyclization of a Non-ribosomal Lipopeptide," *J. Mol. Biol.*, 2006, pp. 876-889, vol. 359.

Schwarzer, D. et al. "Exploring the impact of different thioesterase domains for the design of hybrid peptide synthetases," *Chemistry & Biology*, 2001, pp. 997-1010, vol. 8, No. 10.

Sieber, S. A. et al. "Learning from Nature's Drug Factories: Nonribosomal Synthesis of Macrocyclic Peptides," *Journal of Bacteriology*, Dec. 2003, pp. 7036-7043, vol. 185, No. 24.

Tan, W. et al. "Nonclinical Toxicological Evaluation of Occidiofungin, a Unique Glycolipopeptide Antifungal," *International Journal of Toxicology*, Jun. 11, 2012, pp. 326-336, vol. 31, No. 4.

Thomson, E. L. S. et al. "A *Burhholderia cepacia* complex non-ribosomal peptide-synthesized toxin is hemolytic and required for full virulence," *Virulence*, May/Jun. 2012, pp. 286-298, vol. 3, No. 3.

Tseng, C. C. et al. "Characterization of the Surfactin Synthetase C-Terminal Thioesterase Domain as a Cyclic Depsipeptide Synthase," *Biochemistry*, 2002, pp. 13350-13359, vol. 41, No. 45.

Walsh, C. T. "Polyketide and Nonribosomal Peptide Antibiotics: Modularity and Versatility," *Science*, Mar. 19, 2004, pp. 1805-1810, vol. 303, No. 5665.

White, C. J. et al. "Contemporary strategies for peptide macrocyclization," *Nature Chemistry*, Jul. 23, 2011, pp. 509-524, vol. 3.

Yeh, E. et al. "Type II Thioesterase Restores Activity of a NRPS Module Stalled with an Aminoacyl-S-enzyme that Cannot Be Elongated," *ChemBioChem*, 2004, pp. 1290-1293, vol. 5.

Bonmatin, J.-M. et al. "Diversity Among Microbial Cyclic Lipopeptides: Iturins and Surfactins. Activity-Structure Relationships to Design New Bioactive Agents" *Combinatorial Chemistry & High Throughput Screening*, 2003, pp. 541-556, vol. 6, No. 6.

Alexeyev, M. F. et al. "Three Kanamycin Resistance Gene Cassettes with Different Polylinkers" *Biotechniques*, 1995, pp. 52 and 54, vol. 18, No. 1.

Vilhena, C. et al. "Daptomycin: A Review of Properties, Clinical Use, Drug Delivery and Resistance" *Mini-Reviews in Medicinal Chemistry*, 2012, pp. 202-209, vol. 12.

\* cited by examiner

Occidiofungin: R1 (-H or -OH); R2 (-H or -Cl)

Occidiofungin: (R1,-H or -OH); (R2,-H or -Cl)

Occidiofungin: (R1,-H or -OH); (R2,-H or -Cl)

Occidiofungin: (R1,-H or -OH); (R2,-H or -Cl)

ENGINEERING THE PRODUCTION OF A CONFORMATIONAL VARIANT OF OCCIDIOFUNGIN THAT HAS ENHANCED INHIBITORY ACTIVITY AGAINST FUNGAL SPECIES

CROSS-REFERENCE TO RELATED APPLICATION

This application claims the benefit of U.S. Provisional Application Ser. No. 61/731,105, filed Nov. 29, 2012, the disclosure of which is hereby incorporated by reference in its entirety, including all figures, tables and amino acid or nucleic acid sequences.

The Sequence Listing for this application is labeled "Seq-List.txt" which was created on Nov. 26, 2013 and is 264 KB. The entire contents of the sequence listing is incorporated herein by reference in its entirety.

This invention was made with government support under 0204332 awarded by the National Institute of Food and Agriculture, USDA. The government has certain rights in the invention.

BACKGROUND OF THE INVENTION

Nonribosomal peptide synthetases (NRPSs) produce a wide array of small and structurally complex peptides that have therapeutic potential. The system enables the incorporation of nonproteinogenic amino acids into the polypeptide. Polyketide synthetases (PKSs) are a family of enzymes or enzyme complexes that produce polyketides. Integration of PKSs into the NRPSs system further increases the variety of polypeptides that can be produced by these systems. Recent studies are aimed at exploiting NRPSs for producing peptide libraries that can be screened for therapeutic applications.[1-9]

Unlike linear peptides, cyclic peptides are restrained to fewer conformations that facilitate their interaction with their molecular target.[10-18] These structural constraints provide resistance to proteases, extreme pH, and temperature.[10, 19] These attributes make them one of the most promising scaffolds for pharmacophores. Synthetic design of cyclic peptides is hindered by regioselectivity.

Classical total synthesis of peptides by solid phase or solution phase peptide synthesis followed by subsequent cyclization reactions requires the addition and removal of protecting groups at the right stages to drive the cyclization among the correct residues.[8] Even with these considerations, proper cyclization is hindered by intermolecular interactions and entropically disfavoured pre-cyclization conformations resulting in a vast mixture of compounds or low yields. Microorganisms ensure the formation of a functional cyclic peptide conformation by enzymatically catalyzing the cyclization and release of the peptide with regioselectivity using a cyclase thioesterase.[1, 7] The cyclase thioesterase is often located at the C-terminal end of the last NRPS involved in the synthesis of the peptide and is referred to as the TE (Thioesterase) domain.

The TE domain can hydrolyze the bound peptide as a linear peptide or it can catalyze an intramolecular reaction resulting in the formation of a cyclic peptide. At present, very little is known about the cyclization mechanism of peptides. The crystal structure of the surfactin peptide cyclase provided the first basic understanding of its mechanism of action.[20, 21] The peptidyl chain bound to 4-phosphopantetheine cofactor (ppan) that is attached to the thiolation (T)-domain is transferred to a serine in the adjacent TE domain. Ser80 is part of a catalytic triad of residues (His 207 and Asp107) in the surfactin cyclase. His207 and Asp107 activate the Ser80, facilitating the transfer of the peptidyl chain to the TE domain. Once the peptide is transferred to the TE domain, the cyclase binding pocket enables proper orientation and cyclization of the peptide substrate. The enzyme was found to share structural homology to α,β-hydrolase family. The lack of water in the binding cleft of the cyclase, which prevents hydrolysis, is the significant alteration from the hydrolase family that gives the cyclase thioesterase its ability to form cyclic peptides.

Occidiofungin is a broad spectrum nonribosomally synthesized cyclic antifungal peptide that has submicro/nanomolar activity and low toxicity.[19, 22-26] An interesting feature in occidiofungin's biosynthetic pathway is the presence of two putative thioesterases. One is present as an independently expressed thioesterase, OcfN, and the other is a C-terminal TE domain of OcfD. There remains a need for the production of anti-fungal agents that have increased cidal activity against various fungi.

BRIEF SUMMARY OF THE INVENTION

This invention relates to antifungal compounds and their therapeutic use in the prevention or treatment of fungal infections and diseases. Particularly, various aspects of the invention provide compositions enriched for occidiofungin diastereomers/conformers that have higher activity against fungal infections or diseases (in mammals or plants).

Other aspects of the invention provide for compositions enriched for particular diastereomers/conformers produced by genetic modification of occidiofungin producing microorganisms such that the production of a particular occidiofungin diastereomer/conformer is favored. Thus, the invention relates to methods of making such occidiofungin diastereomers/conformers, compositions enriched for such diastereomers/conformers and methods of using compositions comprising occidiofungin diastereomers/conformers disclosed herein as fungicides for animals and plants. The invention further relates to the microorganisms that produce compositions enriched for occidiofungin enriched for occidiofungin diastereomers/conformers corresponding to diastereomers/conformers having the TOCSY fingerprint identified in FIG. 5C (the green NH correlations). Methods of increasing the production of occidiofungin diastereomers/conformers corresponding to diastereomers/conformers having the TOCSY fingerprint identified in FIG. 5C (the green NH correlations) in microorganisms and productions systems are also provided.

Figure 5:
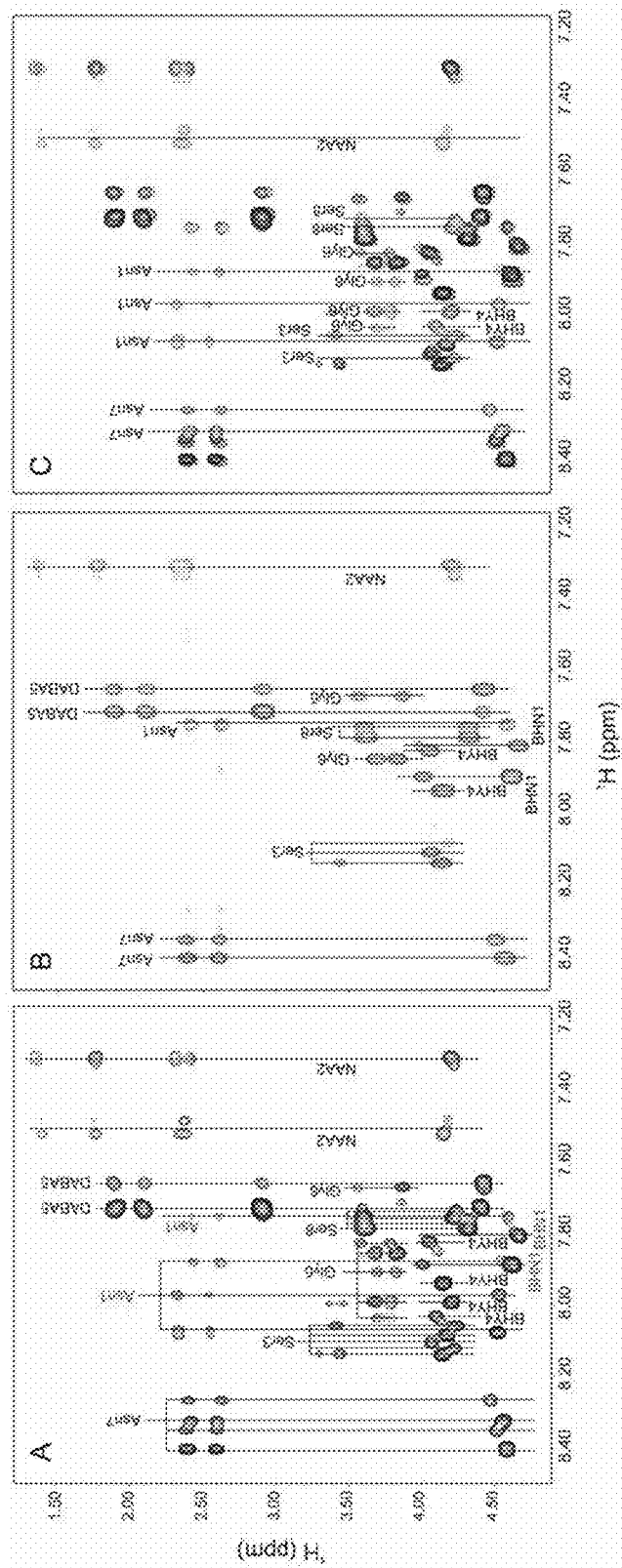

As discussed above, one aspect of the invention provides compositions enriched for occidiofungin diastereomers/conformers, in particular the occidiofungin diastereomers/conformers corresponding to the diastereomers/conformers having the TOCSY fingerprint identified in FIG. 5C (the green NH correlations). Thus, the invention provides compositions enriched for such antifungal diastereomers/conformers for treating fungal infection. In certain embodiments of this aspect of the invention, pharmaceutical and agricultural compositions that contain a composition enriched for diastereomers/conformers having the TOCSY fingerprint identified in FIG. 5C (the green NH correlations) are provided. Compositions enriched for a particular occidiofungin diastereomer/conformer can also be produced by the genetically modified microorganisms discussed below (e.g., micororganisms in which the function of ocfD and/or ocfN has been altered in order to favor the production of a particular diastereomer/conformer).

Figure 10:
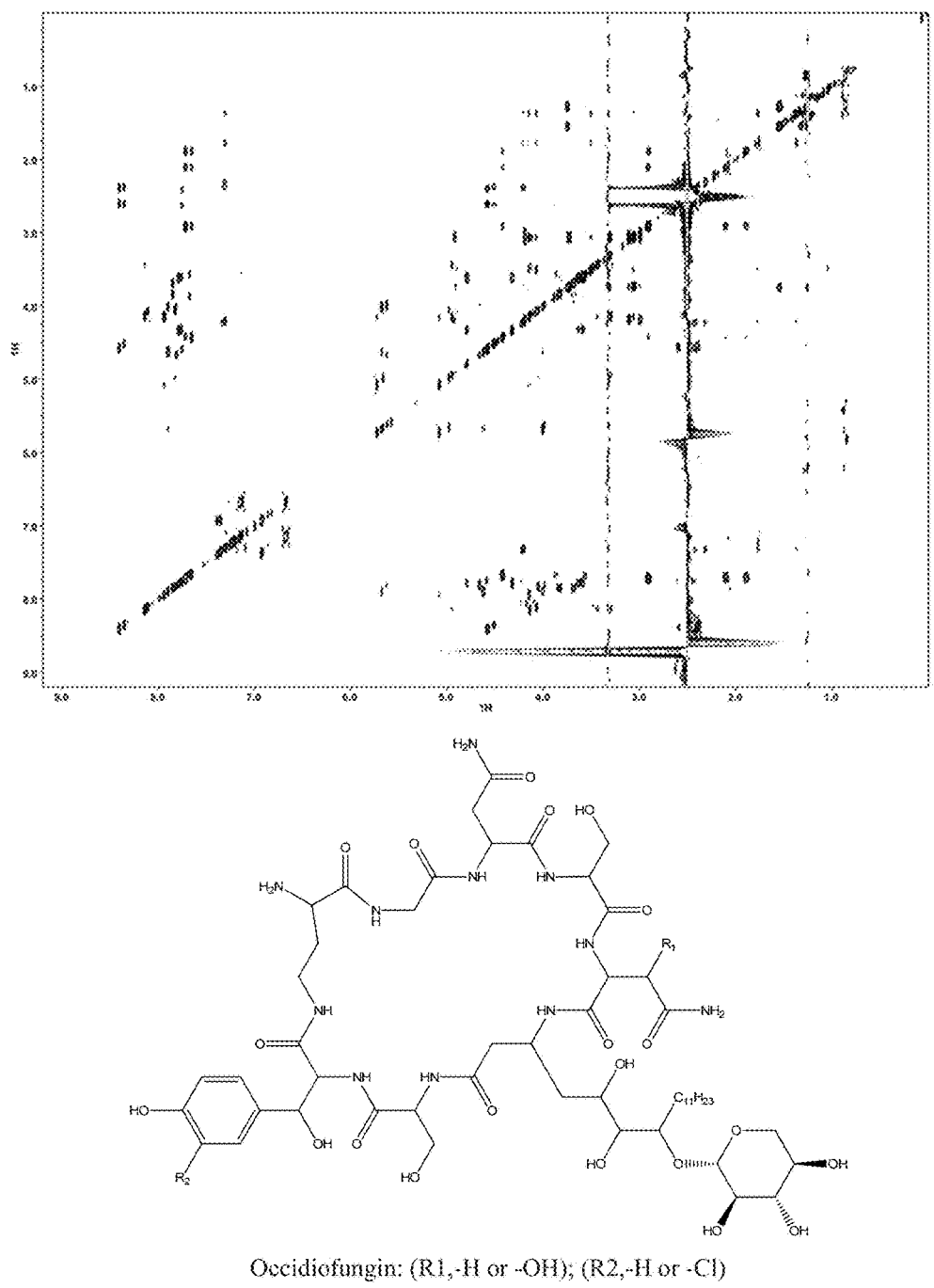

Novel antifungals are needed because of the importance of fungal infections in immunocompromised patients, and the limitations of currently-available antifungal agents regarding their spectra of activity and toxicities. In addition, new antifungals are crucial for food preservation and production of a sufficient and affordable food supply. In this context, this application relates to the disclosure of a composition enriched for occidiofungin diastereomers/conformers having increased antifungal activity as compared to occidiofungin compositions produced by *Burkholderia contaminans* MS14 (disclosed in U.S. Patent Application Publication 2011/0136729, the disclosure of which is hereby incorporated by reference in its entirety). Diastereomers/conformers have been characterized by a number of techniques, including COSY, TOCSY, NOESY, ROESY, and HSQC 2D NMR spectroscopy experiments.

The antifungal activity of the disclosed occidiofungin diastereomers/conformers (diastereomers/conformers having the TOCSY fingerprint identified in FIG. 5C (the green NH correlations)) provides for compositions having greater antifungal activity as compared to as compared to occidiofungin compositions produced by *Burkholderia contaminans* MS 14 when cultured under the same conditions.

The phrase "enriched for the disclosed occidiofungin diastereomers/conformers" is intended to convey that the a composition contains the disclosed occidiofungin diastereomers/conformers (diastereomers/conformers having the TOCSY fingerprint identified in FIG. 5C (the green NH correlations)) in an amount higher/greater than that produced by *Burkholderia contaminans* MS14 as disclosed in the examples provided herein (in which approximately 36% of total amount of occidiofungin corresponds to occidiofungin diastereomers/conformers having the TOCSY fingerprint identified in FIG. 5C (the green NH correlations). Thus, the phrase indicates that at least 37% of the total amount of occidiofungin diastereomers/conformers present within an enriched composition are the disclosed diastereomers/conformers having the TOCSY fingerprint identified in FIG. 5C (the green NH correlations)). In various embodiments, compositions "enriched for the disclosed occidiofungin diastereomers/conformers" contain at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the disclosed diastereomers/conformers in relation to the total amount of occidiofungin diastereomers/conformers in the composition.

The phrase "enriched for a particular occidiofungin diastereomers/conformer" is intended to convey that a composition contains the an occidiofungin diastereomer/conformer that is produced by a microorganism in which the activity of the ocfD and/or ocfN thioesterase has been altered such that the production of a particular conformer is favored.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1. Covalent structure of occidiofungin. R1 and R2 represent the locations where a hydroxyl or chlorine is added, respectively (R1, —H or —OH; R2, —H or —Cl).

FIGS. 2A-2C. RP-HPLC Chromatograms. A. Chromatogram of the final purification step of the wild-type occidiofungin fraction at 220 nm using a 4.6×250 mm C18 column. B. Chromatogram of the final purification step of ocfN mutant occidiofungin fraction at 220 nm using a 4.6×250 mm C18 column. C. Overlay of the wild-type (black) and the mutant (grey) fractions of occidiofungin.

FIG. 3. TOCSY (left panel) and HSQC (right panel) spectra of BHY4 in the wild-type sample. The proportions of Asn1 and BHN1 variants were determined by the measurement of the $^{13}$C-HSQC Ha-Ca cross peak intensities of BHY4 in the HSQC spectra. These values are listed next to their corresponding peaks in the right panel. The peaks in red and green represent the BHY4 peaks associated with BHN1 and Asn1 variants, respectively. Based on the calculation of their relative proportions, i.e. (34.81+87.97 for the BHY4 peaks found in the BHN1 conformational variants) and (32.79+37.61 for the BHY4 peaks found in the Asn1 conformational variants), the approximate proportion of the Asn1 variants could be calculated as (32.79+37.61)/(34.81+87.97)+(32.79+37.61).

FIGS. 4A-4B. ESI mass spectrometry. A. EST mass spectrometry data of purified wild-type occidiofungin fraction. B. ESI mass spectrometry data of purified ocfN mutant occidiofungin fraction.

FIGS. 5A-5C. TOCSY fingerprint region (NH correlations). A. NH correlations in the wild-type sample. The two BHN1 and four Asn1 spin systems present in the wild-type sample are colored red. B. NH correlations in the ocfN mutant sample. C. Overlay of the NH correlations found in the wild-type and ocfN mutant samples. NH correlations that are not present in the ocfN mutant sample are colored green.

FIG. 6. Schematic of occidiofungin ring closure. The completely synthesized eight amino acid linear peptide is bound by a 4-phosphopantetheine cofactor (ppan) linker to the thiolation (T) domain. The peptide varies by the presence or absence of a hydroxyl group on the beta carbon of Asn1. The TE domain of OcfD is capable of forming the cyclic peptide of both variants in the absence of a functional OcfN cyclase thioesterase. However, it is not as efficient at producing the Asn1 cyclic peptide variant as OcfN. In the presence of a functional OcfN cyclase thioesterase, a novel diastereomers of occidiofungin is formed by the selective ring closure of the Asn1 cyclic peptide. R1 and R2 are BHN1 and Asn1, respectively.

FIGS. 7A-7B. Comparison of the bioactivity from the wild-type and ocfN mutant occidiofungin fractions. A. MICs of wild-type and ocfN mutant fraction determined by CLSI M27-A3 method in RPMI 1640. B. Comparison of the CFUs in the MIC wells of wild-type fraction to the corresponding well having the same concentration of the ocfN mutant occidiofungin fraction. Asterisks represent no detectable colonies in the MIC wells of the wild-type occidiofungin fraction. Black and grey bars are ocfN mutant and wild-type fractions, respectively. Standard deviations for the CFU measurements are presented.

FIGS. 8A-8C. Potato dextrose agar plates were inoculated with each of the strains and incubated for 3 days at 28° C. The plates were oversprayed with the indicator fungus *Geotrichum candidum* and incubated overnight. A: The wild-type strain MS14; B: Negative control MS14GG78 (ocfJ::nptII); C: MS14GG88 (ocfN::nptII).

FIG. 9. COSY60 NMR Spectrum of Occidiofungin from ocfN mutant MS14GG88 recorded at 600 MHz in DMSO-d6.

FIG. 10. TOCSY60 NMR Spectrum of Occidiofungin from ocfN mutant MS14GG88 recorded at 600 MHz in DMSO-d6.

Figure 11:
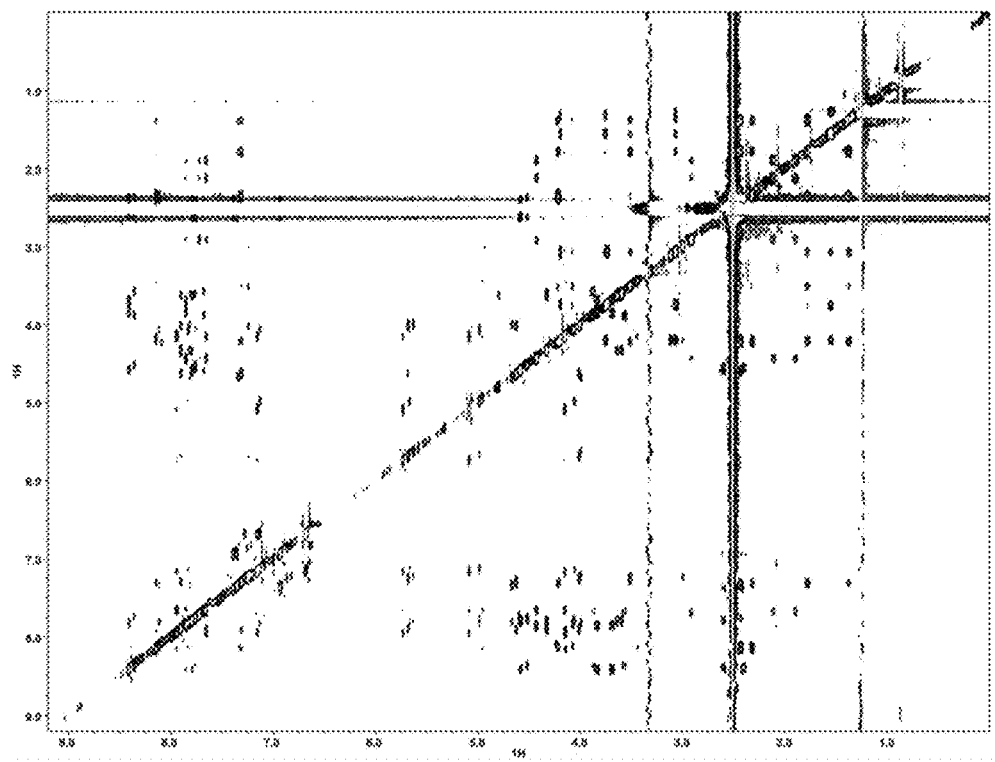
Figure 11:
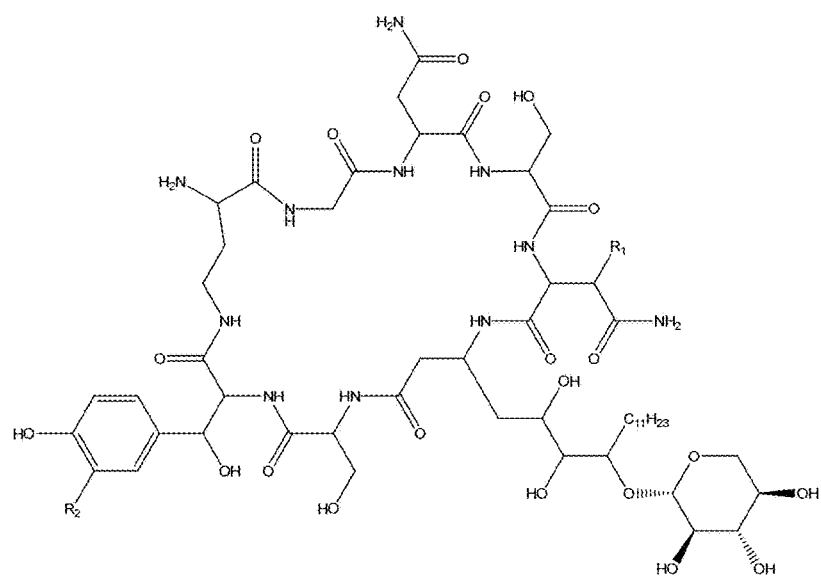

FIG. 11. NOESY400 NMR Spectrum of Occidiofungin from ocfN mutant MS14GG88 recorded at 600 MHz in DMSO-d6.

Figure 12:
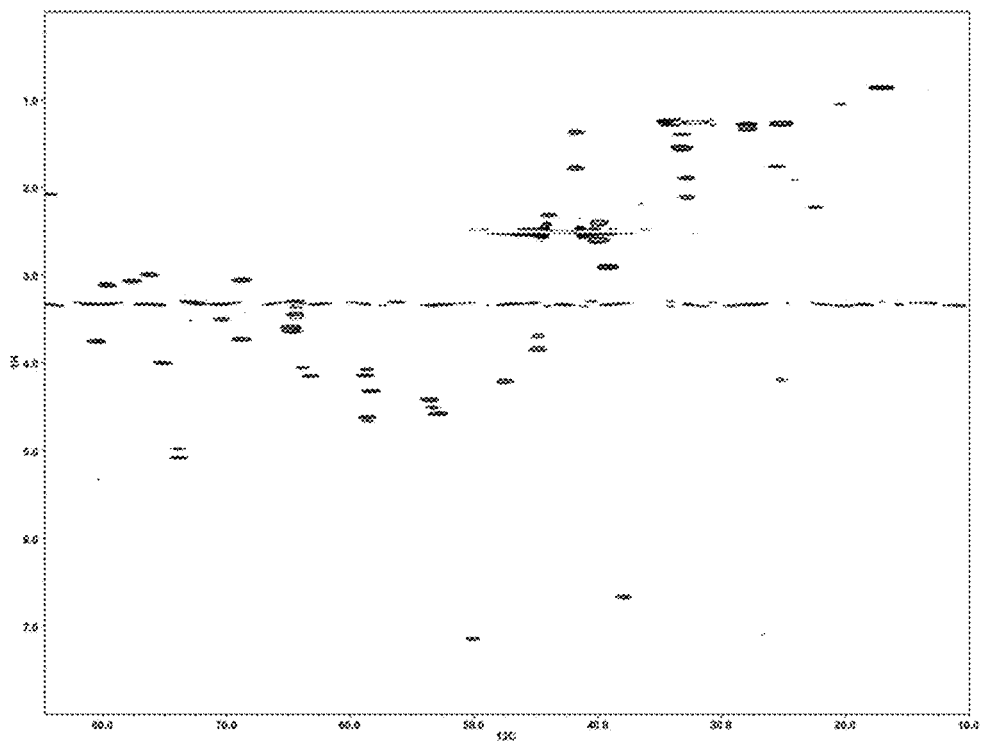
Figure 12:
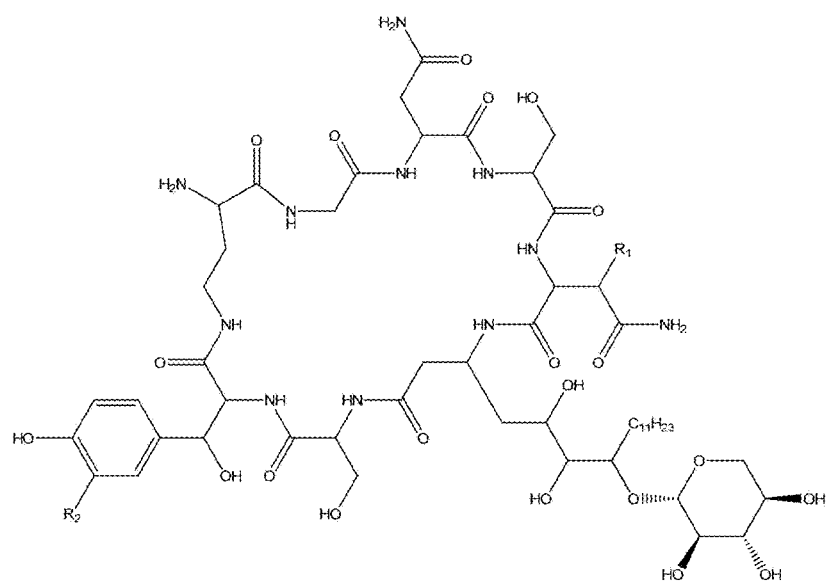

FIG. 12. $^{13}$C-HSQC NMR Spectrum of Occidiofungin from ocfN mutant MS14GG88 recorded at 600 MHz in DMSO-d6.

Figure 13B:
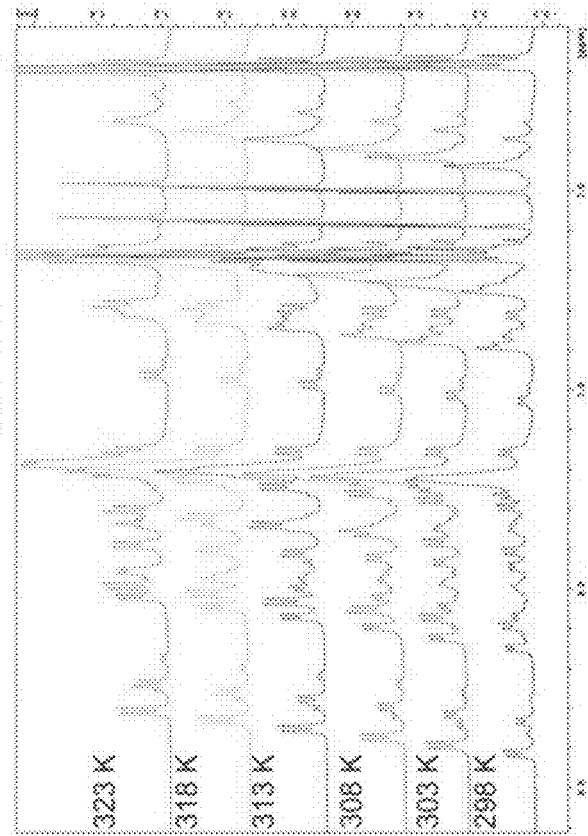
Figure 13A:
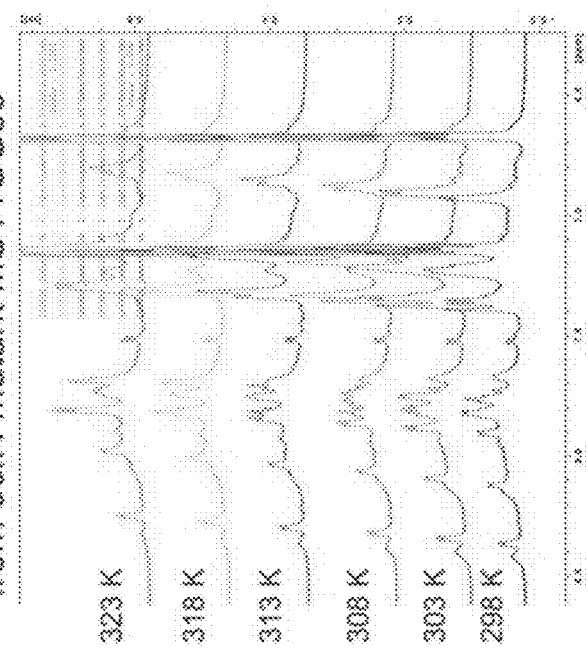

FIGS. 13A-13B. One-dimensional NMR temperature titration curves for occidiofungin derived from ocfN mutant MS14GG88 (FIG. 13A) and wild-type strain MS14 (FIG. 13B).

Figure 14B:
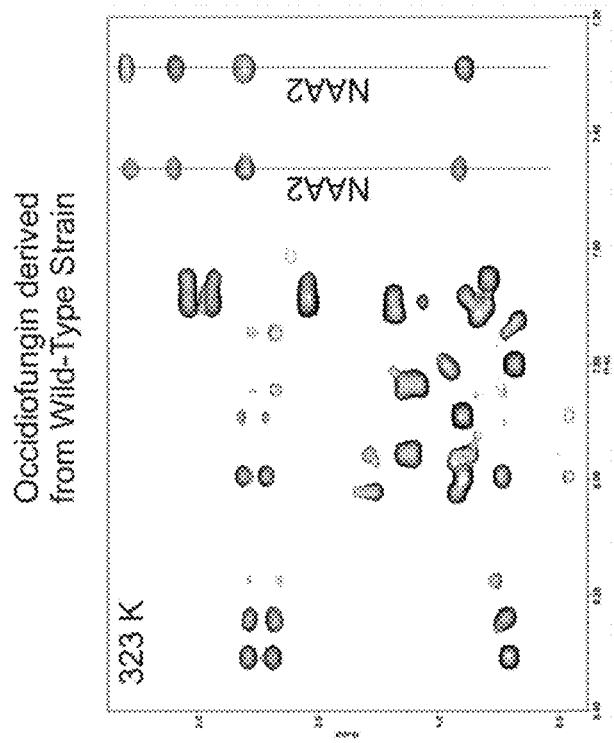
Figure 14A:
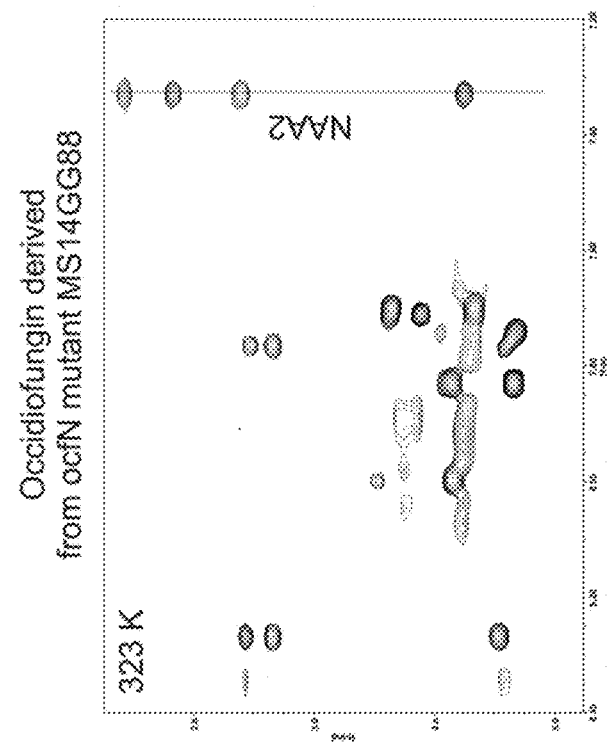

FIGS. 14A-14B. TOCSY fingerprint region (NH correlations) for occidiofungin derived from ocfN mutant MS14GG88 (FIG. 14A) and wild-type strain MS14 (FIG. 14B) at 50° C.

Figure 15:
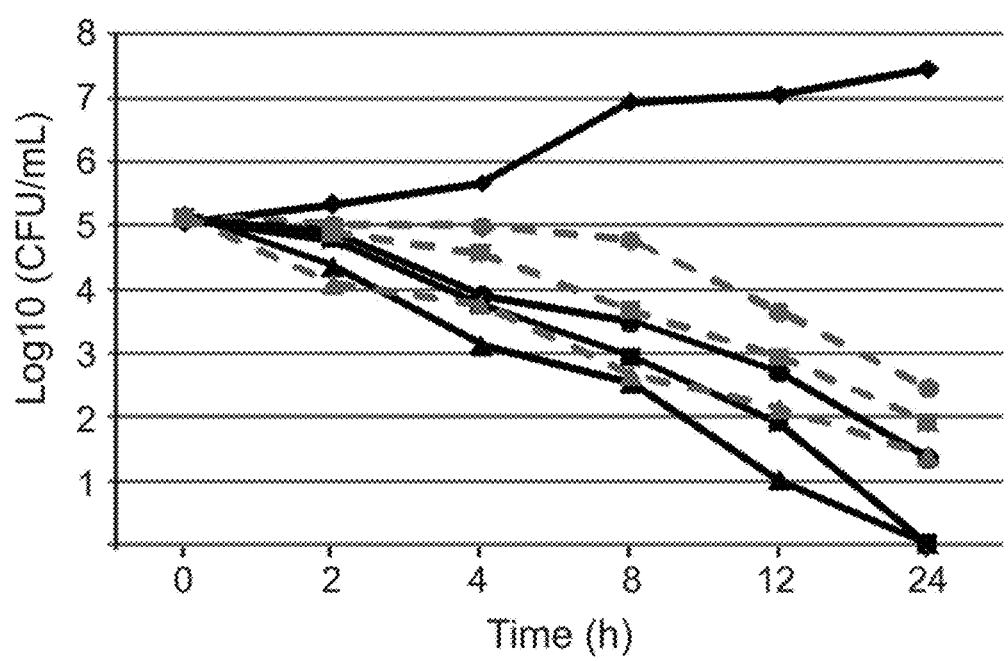

FIG. 15. Time-kill experiments performed against *Candida glabrata* ATCC66032. Solid black lines and dashed grey lines correspond to samples treated with occidiofungin derived from wild-type strain MS14 and ocfN mutant MS14GG88, respectively. Circles, squares, and triangles represent samples treated with 0.5, 1.0, and 2.0 μg/mL of occidiofungin, respectively. The diamond represents the sample treated with the blank control.

BRIEF DESCRIPTION OF THE SEQUENCES

SEQ ID NOs: 1-2: PCR primer sequences
SEQ ID NO: 3: amino acid sequence for OcfN (thioesterase; thioesterase motif of -G-X-S-X-G- underlined (X is any amino acid))

```
MRLICFPYAGGSAAVYRTLQASLPGIEVCRHELAGRGSRLSEPAVRDMA

TLVDTLLCDLDDCFDRPFALLGHSMGAAIAAELALRLPAHARPNLRHLF

VSARAAPGKERHDRRMQALDDRAFIDALREMGGTPKAVLDNSELMALL

MPALRADFTMIENHRPVPGPRLAVDITAFAGRADKEIPVDAVAGWGAAT

TGRFDFHVIEGDHFFLRNEMRTMAGIIAARMRRPEHAASSALQA
```

SEQ ID NO: 4: amino acid sequence for OcfD (thioesterase motif of -G-X-S-X-G-underlined (X is any amino acid))

```
MQDNNVLVTD RESLSRVAGV YGIAAYAPSQ QPGRPLTRSV RLTPASLDLL

RRIGDGELAE FAVAAAGIAF LLWKYFRIPV TVLGTPGLAG HPSARAAIVP

LIIEVRPDER IEDYLSRVAG IVEDSYAEPR FPLETLVRNE KDMALAQLTK

VALADDRVHH APTGRDDDLQ LHLRLARGEI ELRYSGAIEP FIIDGFAGSL

AAVLEAFEHL DGAVGDIEAA PPEQGPLLAA FNETATAGPS HPTVVAMFEA

QVARTPTAPA LVTDSSLMTY ADLNARANSL AHHLREHHGV GPESLVGIML

DRSEWMIVAI LGILKAGAAF VPLDPAYPAE RINHILGDTG LSLLVTQSSQ

LAQWYEFSGV TLLLDQELPG WQPLPDNPPH RAEPAHLAYV LYTSGSTGKP

KGCLLEHRNL AHYIAWAAGY YFPESTTGSF GLYSSLCFDF TLTNIFCPLV

RGKTLRIYPQ SESIDTILAR MFQPGSGVDT LKLTPTHIHL LEYMNLARSG

VRKVIVGGEE LTPQHIATLR KIDPAIEIYN EYGPTEATVG CIVERVEDAP

PTVLIGRPIA DTRVYMLDDA LRPVPLGVPG EICLAGAGLA RGYHQRPDVT

AAKFVEHPFP GEARIYRTGD IGRWLPDGRI QCYGRVDHQV KIRGHRVELG

EIEAAIAAHE DVVGAAVMLR ESAHGVRKLA AYVKGAASLS VPNLRAYLAG

KLPDYMVPSD IIPIAEFPLN ANGKLDRPAL LALEPAAAPE EAPLDATPIQ

RELVRIWRDV LDNPAVDLAG RFFDYGGDSL QAMQLVSRIW SSFSVEIGID

AIFELQTISA VSDLIEASSP HPGSTAGAIP PRSRANDLPL SFPQQRLWFL

AQLEGPSATY NISSALRFEG ELDVARLRFA VSEISRRHEI LRTTFPAVDG

RGVQRIAPPA PVALDVVDVA SESDTLALLA EEADRPFDLA AGPLYRVVLY

RVHERLHVFG IVMHHIVSDA WSSGILIGEL AALYAGESLP ELAVQYADYA

VWQHERLASA DTHRELALLS AALADAPDLI ELPTDRPRPA VQQFRGAVLP

FQLSAERADG LRAIARASGT STFMVVLAAY ALLLSRYSNQ QDLVIGSPIA

NRRSSMTEPL IGFFANMLAL RVDLSGNPTF GDLLARVKRV ALDGYSRQEI

PFEQVVDSLE LERNLGRTPV FQVVFAYEKA QPRAVSFPGL VATPVAVETH

TAKFDLTLHV QDADDGLAGS LEYNLDLFDA ATIDRMAEHF RTLVDAVIAD

PDRPLGALSL SNDAERNLLT VEWNRTDTDF GEDAAQPLHR LFEQQVERTP
```

```
DAVAIVFDDT ALTYAELNLR ANRLAHHLVA LGVGPDSLVG VAMERSLDMS

VALLAILKAG GAYVPVDPDY PAERVRFMID HAQLRWLLTQ QHLHDALPDT

DAHVIVVDRD SLDLDAAATS NPAPALNGDN LAYMIYTSGS TGRPKGALNT

HRAITNRILW MQHAYALDAD DAVLQKTPFS FDVSVWELFW PLVTGARLVF

ARPGGQRETD YLVELIERER ITTIHFVPSM LRAFLDHPDL DAHCASLRRV

VCSGEALPHD LQQRCLERLD VKLYNLYGPT EAAVDVTAWE CRRDDPHRIV

PIGRPIANTR LYIVDAQMQP TPIGVAGELL IGGTPVGRGY HGEPELSAEK

FIADPFSADP LARLYRTGDL ARYRPDGNIE FLGRIDHQIK LRGLRIEPGE

IEAALRAHPS VDDCVVIAKT EGARTFLIAY VATAAPDIAD LRGYLGGKLA

DYMVPSQFFA LESLPMLPNG KINRKALPLP ADRGDAAQPH APAVTPREIL

LASICIDVLQ LPSVGIHDNF FELGGDSILS IQVIARANQA GLRVTAKQLF

QYQTIAQLAA APEERAACAP TLSPLGDAPL TPVQHWFFEQ EIDAPSHYNQ

TVLIQVPADI DASRLADAFR QVYEHHDALR LRFSHDAGRW TQQVVAGGEM

PALFAKQVIA DDAGERLAAM RAAAADAERG IDITHGPLLA ARLFCLADEP

LARLFVSIHH LAVDGVSWRV LLEDLHAAYH GQPLPGKTTS FREWALHLQQ

LARSPAIGDE ARLWQALLAQ PVEPMPVDYP GTGAANNAVD DASSVSFELG

EADTTALLRR LPRAYDTRIN DVLLVALAQA CSMVTGNTRT RIDLESHGRH

VSDAPLDLTR TVGWFTSIYP VVLDADAMHA PEQALRAARQ QLRRIPADGL

GYSLLRYQSP DAAVRDSLAA LPKADILFNY HGQLDTVLRQ SDGWRPAAED

LGSLRAGRSQ RTHAFEIVAA VADGKLQVDW RYGERLHRRQ TVENLAAHFR

DRLLDFAASV PDTAADDIED SYPLSSLQQG ILFHSLYDLD PAAYFQQFSF

VVSGPLQVPA LRQAWANALA RHAVLRTAFA WADRDHPVQT VRHTVDLPWT

FLDWRHRDAS RRAQDFDAFL ADDRRRGFDL QRAPLFRCTL IQETDTRHRF

CWSAHHIILD GWSTATLMKE VFDDYLSLAR TGMPAVAASA PGYRAYIDWL

ARHPRSADET WWRAELAGFK AATPVAASPA RQATGDAPRQ DKRRTQQFLL

DEALAARLQT LTRTHRVTLN VLIRAVWALV LRRHAGTDDV VFGVTVSGRP

PMLDGVESIV GLFINTLPLR LRIAPERPFI EWLAEVHAAQ TAMEPHSYSS

LVDIQSWSEL PAGDSLFDSL LVFENFPVAA APDLGPDDIE ILDTRAFAES

NYPLTLTVHP NERIGFHISH DAHRIAPEVV RQMLDTLRTL LERFAENPGQ

LTGQLADPPA ADGRPSAPRS GAGPAIEAAA GAAAAARAVA HAADESTLLE

IWRRIFKRDD IAVSDNYFDL GGHSIIAIQL MAHVEKAFDR RLPISCLFEN

PTIEKLAAAL AAKEPSAPAG GLVPIRDGGP AAPLFLLPGA GGNVVYFRPL

ANHLSGAHAI HGLEALGLDG ACEPLTRVED IAARHIERIW PLVGAGPYYL

AGHSFGAHVA LEMSRQLVAK GADVKLLAIF DASAPIDSSA ATYWQDWDDT

EWLVAIAHEI GTFLGTDLQV TRADLVHLDP DGQAGLILER IGDRGSWFAD

AGSDRLRAYL RVYQANFKSH YAPHATPLPV PIALFRSTER DPGDYAPSSE

IAQLRLDATW GWSRFSAHPV AVTDVPGDHL TMLLDPHAGV LAAHVNSFLE KTPS
```

SEQ ID NOs: 5-23: polynucleotide and polypeptides associated with GenBank Accession No. EU938698.5.

DETAILED DESCRIPTION OF THE INVENTION

This invention relates to antifungal compounds and their therapeutic use in the prevention or treatment of fungal infections and diseases. Particularly, various aspects of the invention provide compositions enriched for occidiofungin diastereomers/conformers that have higher activity against fungal infections or diseases. Thus, the invention relates to methods of making such occidiofungin diastereomers/conformers, compositions enriched for such diastereomers/conformers and methods of using compositions comprising occidiofungin diastereomers/conformers disclosed herein as fungicides for animals and plants. The invention further relates to the microorganisms that produce compositions enriched for occidiofungin enriched for occidiofungin diastereomers/conformers corresponding to diastereomers/conformers having the TOCSY fingerprint identified in FIG. 5C (the green NH correlations). Methods of increasing the production of occidiofungin diastereomers/conformers corresponding to diastereomers/conformers having the TOCSY fingerprint identified in FIG. 5C (the green NH correlations) in microorganisms and productions systems are also provided.

As discussed above, one aspect of the invention provides compositions enriched for occidiofungin diastereomers/conformers, in particular the occidiofungin diastereomers/conformers corresponding to the diastereomers/conformers having the TOCSY fingerprint identified in FIG. 5C (the green NH correlations observed under the following conditions: 2 mM samples of occidiofungin diasteromers in dimethylsulfoxide (DMSO-d6, Cambridge Isotopes) subjected to 2-D TOCSY, spectra collected at 323 K with a mixing time of 60 milliseconds and data processing using NMRPipe with 45 degree sinebell squared shifts in both dimensions). Thus, the invention provides compositions enriched for such antifungal diastereomers/conformers for treating fungal infection. In certain embodiments of this aspect of the invention, pharmaceutical and agricultural compositions that contain a composition enriched for diastereomers/conformers having the TOCSY fingerprint identified in FIG. 5C (the green NH correlations) are provided.

Another aspect of the invention provides for compositions that are enriched for a particular occidofungin diasteromer/conformer. In this aspect of the invention, the activity of the ocfD and/or ocfN thioesterases is altered such that the activity of one of the thioesterases is decreased (or eliminated) and the activity of the second thioesterase remains functional or is increased. Thus, microorganisms can be genetically manipulated such that OcfD thioesterase activity is decreased or eliminated and the thioesterase activity of OcfN is increased or maintained at unaltered (e.g., levels of activity as observed in *Burkholderia contaminans* MS14 or microorganisms engineered with the biosynthetic pathway for the production of occidiofungin). Alternatively, microorganisms can be genetically manipulated such that OcfN activity is decreased or eliminated and the thioesterase activity of OcfD is increased or unaltered.

Compositions comprising occidiofungin diasteromers/conformers as disclosed herein may be formulated prior to administration in an agriculturally acceptable carrier, for example in an aqueous carrier, medium or suitable diluent, such as saline or other buffer. The formulated compositions may also be in the form of a dust or granular material, or a suspension in oil (vegetable or mineral), water or oil/water emulsions, a wettable powder, or in combination with any other carrier material suitable for agricultural application. Suitable agricultural carriers can be solid or liquid and are well known in the art. The term "agriculturally-acceptable carrier" covers all adjuvants, e.g. inert components, dispersants, surfactants, tackifiers, binders, etc. that are ordinarily used in the formulation of agricultural compositions; these are well known to those skilled in formulation of agricultural compositions.

A pharmaceutical composition contains a desired amount of an occidofungin diastereomers/conformers as disclosed herein. Thus, the pharmaceutical composition can comprise occidofungin diastereomers/conformers having the total correlation spectroscopy (TOCSY) fingerprint identified in FIG. 5C as the green NH correlations or the pharmaceutical composition can comprise a particular occidofungin diastereomer/conformer. Either of these pharmaceutical compositions can be in the form of, for example, a tablet, a caplet, a pill, a hard or soft capsule, a lozenge, a cachet, a dispensable powder, granules, a suspension, an elixir, a dispersion, a liquid, or any other form reasonably adapted for administration. If intended for parenteral administration, it can be in the form, for example, of a suspension or transdermal patch. Presently preferred are oral dosage forms that are discrete dose units each containing a predetermined amount of the disclosed occidofungin diastereomers/con formers.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, ophthalmically, by nasal aerosol or inhalation. Such compositions are prepared according to techniques well-known in the art of pharmaceutical formulation.

Compositions disclosed herein can be used to treat fungal infections in immunocompromised patients or patients having fungal infections. Thus, another aspect of the invention provides for administering compositions enriched for occidiofungin diastereomers/conformers (e.g., those corresponding to the diastereomers/conformers having the TOCSY fingerprint identified in FIG. 5C (the green NH correlations) having increased antifungal activity as compared to occidiofungin compositions produced by *Burkholderia contaminans* MS14 (disclosed in U.S. Patent Application Publication 2011/0136729, the disclosure of which is hereby incorporated by reference in its entirety). These diastereomers/conformers have been characterized by a number of techniques, including COSY, TOCSY, NOESY, ROESY, and HSQC 2D NMR spectroscopy experiments.

The antifungal activity of the disclosed occidiofungin diastereomers/conformers (diastereomers/conformers having the TOCSY fingerprint identified in FIG. 5C (the green NH correlations)) provides for compositions having greater antifungal activity as compared to as compared to occidiofungin compositions produced by *Burkholderia contaminans* MS 14 when cultured under the same conditions. The phrase "enriched for the disclosed occidiofungin diastereomers/conformers" is intended to convey that the composition contains disclosed occidiofungin diastereomers/conformers (diastereomers/conformers having the TOCSY fingerprint identified in FIG. 5C (the green NH correlations)) in amounts higher than that produced by a reference strain (e.g., *Burkholderia contaminans* MS14 as disclosed in the examples provided herein). Thus, the phrase indicates that at least 37% of the total amount of occidiofungin diastereomers/conformers present within an enriched composition are the disclosed diastereomers/conformers having the TOCSY fingerprint identified in FIG. 5C (the green NH correlations)). In various embodiments, compositions "enriched for the disclosed occidiofungin diastereomers/conformers" contain at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the disclosed diastereomers/conformers in relation to the total amount of occidiofungin diastereomers/conformers in a composition.

As discussed above, one aspect of the invention provides microorganisms capable of producing compositions enriched for occidiofungin diastereomers/conformers corresponding to the diastereomers/conformers having the TOCSY fingerprint identified in FIG. 5C (the green NH correlations). In this aspect of the invention, microorganisms are transformed with the genes associated with the biosynthesis of occidiofungin. These genes and open reading frames (ORFs) are disclosed in disclosed in U.S. Patent Application Publication 2011/0136729, the disclosure of which is hereby incorporated by reference in its entirety; Gu et al., *Appl. Environ. Microbiol.,* 2011, 77:(17):6189-6198 which is also incorporated by reference in its entirety and GenBank Accession No. EU938698.5, which is also hereby incorporated by reference in its entirety and is also provided on pages 29-72 (SEQ ID NOs: 5-23). These transformed microorganisms are further manipulated genetically such that the microorganisms exhibit an increase in the level of OcfN thioesterase (SEQ ID NO: 3) activity. An increase in the level of OcfN thioesterase activity can be achieved by means of expressing the ocfN gene in a multicopy plasmid with a native promoter or any other promoter sequence. Another way to increase the expression of the ocfN gene within the cell is to chromosomally integrate additional copies of the ocfN gene using transposons. Yet a further means to increase ocfN thioesterase activity is to substitute the native promoter associated with the ocfN gene with a promoter that increases expression of the gene (relative to the native promoter). In certain embodiments of this aspect of the invention, the thioesterase activity of OcfD can be decreased or eliminated by a point mutation of the catalytic serine at position 2954 of SEQ ID NO: 4, insertional mutation or point mutation of amino acids within the thioesterase motif (in addition to the substitution of the serine residue) found in ocfD to reduce or eliminate its activity, deletion of the catalytic serine or other portions of SEQ ID NO: 4 (e.g., portions or the entirety of the thioesterase motif in SEQ ID NO: 4) or truncation SEQ ID NO: 4 such that thioesterase activity is reduced or eliminated (in addition to increasing the level of OcfN thioesterase activity) within the genetically modified microorganisms.

Another aspect of the invention provides for compositions enriched for a particular Occidiofungin diastereomer/conformer. In this aspect of the invention, transformed microorganisms are manipulated genetically such that the microorganisms exhibit an increase in the level of OcfD thioesterase (SEQ ID NO: 4) activity. An increase in the level of OcfD thioesterase activity can be achieved by means of expressing the ocfD gene in a multicopy plasmid with a native promoter or any other promoter sequence. Another way to increase the expression of the ocfD gene within the cell is to chromosomally integrate additional copies of the ocfD gene using transposons. Yet a further means to increase ocfN thioesterase activity is to substitute the native promoter associated with the ocfD gene with a promoter that increases expression of the gene (relative to the native promoter). In certain embodiments of this aspect of the invention, the thioesterase activity of OcfN can be decreased or eliminated by a point mutation of the catalytic serine at position 73 of SEQ ID NO: 3, insertional mutation or point mutations of other amino acids within the thioesterase motif (in addition to the substitution of the serine residue) of the thioesterase to reduce or eliminate its activity, deletion of the catalytic serine or other portions of SEQ ID NO: 3 (e.g., portions or the entirety of the thioesterase motif in SEQ ID NO: 3), truncation SEQ ID NO: 3 such that thioesterase activity is reduced or eliminated or deletion of ocfN in its entirety (in addition to increasing the level of OcfD thioesterase activity) within the genetically modified microorganisms. Where the biosynthetic pathway for occidiofungin biosynthesis is engineered into a microorganisms, once can, of course, omit ocfN to achieve the same effect as the mutation or deletion of ocfN as discussed above.

Thus, microorganisms such as bacterial cells, fungal cells and yeast can be transformed with genes encoding the occidiofungin biosynthetic pathway and genetically manipulated, as discussed above, such that the cells have increased OcfN activity and/or decreased OcfD activity as compared to reference bacterial, fungal or yeast cells. Alternatively, microorganisms such as bacterial cells, fungal cells and yeast can be transformed with genes encoding the occidiofungin biosynthetic pathway and genetically manipulated, as discussed above, such that the cells have increased OcfD activity and/or decreased OcfN activity as compared to reference bacterial, fungal or yeast cells. Such cells can then be used to produce compositions enriched for occidiofungin diastereomers/conformers corresponding to the diastereomers/conformers having the TOCSY fingerprint identified in FIG. 5C (the green NH correlations) or to produce compositions enriched for a particular occidiofungin diasteromer/conformer. The phrase "reference bacterial, fungal or yeast cells" refers to bacterial, fungal or yeast cells containing the genes associated with the biosynthetic pathway for the production of occidiofungin and where the function/activity of OcfN and/or OcfD has not been altered as disclosed herein. Thus, the phrase "reference bacterial, fungal or yeast cells" refers to cells containing, for example, polynucleotide (SEQ ID NO: 23 encoding the open reading frames (ORFs; SEQ ID NOs: 5-22)) disclosed in GenBank Accession No. EU938698.5. For the comparison of compositions comprising particular occidiofungin conformers (or compositions enriched for occidiofungin diastereomers/conformers corresponding to the diastereomers/conformers having the TOCSY fingerprint identified in FIG. 5C (the green NH correlations)), compositions containing the diastereomers/conformers are obtained from cells genetically manipulated to have increased ocfN activity and/or decreased OcfD activity (or increased OcfD activity and/or decreased ocfN activity) and compared to compositions containing occidiofungin produced by reference bacterial, fungal or yeast cells cultured under similar or the same conditions (e.g., the same temperature and medium).

Bacterial cells can be selected Gram negative bacteria or Gram positive bacteria. In this aspect of the invention, the Gram-negative bacterial cell can be selected from the group consisting of *Escherichia, Zymomonas, Acinetobacter, Gluconobacter, Geobacter, Shewanella, Salmonella, Enterobacter* and *Klebsiella*. Gram-positive bacteria can be selected from the group consisting of *Bacillus, Clostridium, Corynebacterial, Lactobacillus, Lactococcus, Oenococcus, Streptococcus* and *Eubacterial* cells. Various thermophilic bacterial cells, such as *Thermoanaerobes* (e.g., *Thermoanaerobacterium saccharolvticum*). *Bacillus* spp., e.g., *Bacillus coagulans* strains, *Bacillus licheniformis* strains. *Bacillus subtilis* strains, *Bacillus amyloliquifaciens* strains, *Bacillus megaterium* strains, *Bacillus macerans* strains, *Paenibacillus* spp. strains or *Geobacillus* spp. such as *Geobacillus stearothermophilus*.

Yeast cells suitable for use in this aspect of the invention may be a *Candida, Hansenula, Kluveromyces, Pichia, Saccharomyces, Schizosaccharomyvces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell. In this aspect of the invention, the yeast cell must be resistant to the effects of occidiofungin to be a viable production system for compositions enriched for occidiofungin diastereomers/conformers corresponding to the diastereomers/conformers having the TOCSY fingerprint identified in FIG. 5C (the green NH correlations).

In other embodiments of this aspect of the invention, fungal cells can be manipulated to produce compositions enriched for occidiofungin diastereomers/conformers corresponding to the diastereomers/conformers having the TOCSY fingerprint identified in FIG. 5C (the green NH correlations). "Fungi" as used herein includes the phyla *Ascomycota, Basidiomycota, Chytridiomvcota*, and *Zygomycota, Oomycota* and all mitosporic fungi. A fungal cell may be a yeast cell. "Yeast" as used herein includes ascosporogenous yeast (*Endomycetales*), basidiosporogenous yeast, and yeast belonging to the Fungi Imperfecti (*Blastomycetes*). The fungal host cell may be a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. The filamentous fungal host cell may be an *Acremonium, Aspergillus, Aureobasidium, Bjerkandera, Ceriporiopsis, Chrsosporium, Coprinus, Coriolus, Cryptococcus, Filibasidium, Fusarium, Humicola, Magnaporthe, Mucor, Myceliophthora, Neocallimastix. Neurospora, Paecilomyces, Penicillium, Phanerochaete, Phlebia, Piromyces, Pleurotus, Schizophillum, Talaromyces, Thermoascus, Thielavia, Tolypocladium, Trametes*, or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrsosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora ther-* mophila, *Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol, 153: 163; and Hinnen et al., 1978, Proc. Natl. Acad. Sci. USA 75: 1920.

In another embodiment of the present invention, the native promoter of the ocfN gene within *Burkholderia contaminans* MS14 can be replaced by promoter elements known to enhance the level of gene expression, thereby increasing OcfN thioesterase activity within *Burkholderia contaminans* MS14. *Burkholderia contaminans* MS14 can also be genetically modified by other techniques to produce compositions enriched for occidiofungin diastereomers/conformers corresponding to the diastereomers/conformers having the TOCSY fingerprint identified in FIG. 5C (the green NH correlations). Genetic modifications that ocfN thioesterase activity include the introduction of multicopy plasmids comprising a native promoter or any other promoter sequence operably liked to an ocfN gene into *Burkholderia contaminans* MS14, integration of additional copies of the ocfN gene operably linked to a promoter into the chromosome of *Burkholderia contaminans* MS14 using transposon mutagenesis or by replacement of the native ocfN promoter in *Burkholderia contaminans* MS14 with a promoter that increases the expression of ocfN transcripts relative to the native promoter sequence.

Another aspect of the invention provides for the introduction of a point mutation into the nucleotide sequence encoding OcfD, the truncation of ocfD (or introduction of a frameshift mutation) such that the thioesterase activity is reduced or eliminated or the deletion of the segment of the ocfD gene encoding the catalytic serine in order to increase the amounts of occidiofungin diastereomers/conformers corresponding to the diastereomers/conformers having the TOCSY fingerprint identified in FIG. 5C (the green NH correlations) produced by *Burkholderia contaminans* MS14 or by microorganisms genetically modified to produce occidiofungin (e.g., microorganisms into which the biosynthetic pathway for occidiofungin production have been introduced). In this aspect of the invention, a point mutation is introduced into the catalytic serine in the thioesterase domain of ocfD in order to reduce its activity. This amino acid is found at position 2954 of SEQ ID NO: 4. For example, the serine can be mutated into an alanine, glycine or proline residue (with glycine or alanine being preferred in this context). Certain embodiments of this aspect of the invention also provide for genetic modification of the microorganisms such that ocfN activity is increased as well (e.g., the level of OcfN thioesterase activity can be increased by means of expressing the ocfN gene in a multicopy plasmid with a native promoter or any other promoter sequence, chromosomal integration of additional copies of the ocfN gene using transposons or other means or substitution of the native promoter associated with the ocfN gene with a promoter that increases expression of the gene (relative to the native promoter)).

Another aspect of the invention provides for the introduction of a point mutation into the nucleotide sequence encoding OcfN, the truncation of ocfN (or introduction of a frameshift mutation) such that the thioesterase activity is reduced or eliminated, the deletion of the segment of the ocfN gene encoding the catalytic serine or chromosomal deletion of ocfN within a microorganism (e.g., *Burkholderia contaminans* MS14) in order to increase the amounts a particular occidiofungin diastereomer/conformer produced by a microorganism. As would be apparent to one skilled in the art, a similar effect can be obtained by transforming a microorganism with the genes encoding the occidiofungin biosynthetic pathway, with the exception of ocfN gene. In this aspect of the invention, a point mutation is introduced into the catalytic serine in the thioesterase domain of OcfN in order to reduce its activity. This amino acid is found at position 73 of SEQ ID NO: 3. For example, the serine can be mutated into an alanine, glycine or proline residue (with glycine or alanine being preferred in this context). Certain embodiments of this aspect of the invention also provide for genetic modification of the microorganisms such that OcfD activity is increased as well (e.g., the level of OcfD thioesterase activity can be increased by means of expressing the ocfD gene in a multicopy plasmid with a native promoter or any other promoter sequence, chromosomal integration of additional copies of the ocfD gene using transposons or other means or substitution of the native promoter associated with the ocfD gene with a promoter that increases expression of the gene (relative to the native promoter)).

Materials and Methods

Figure 2:
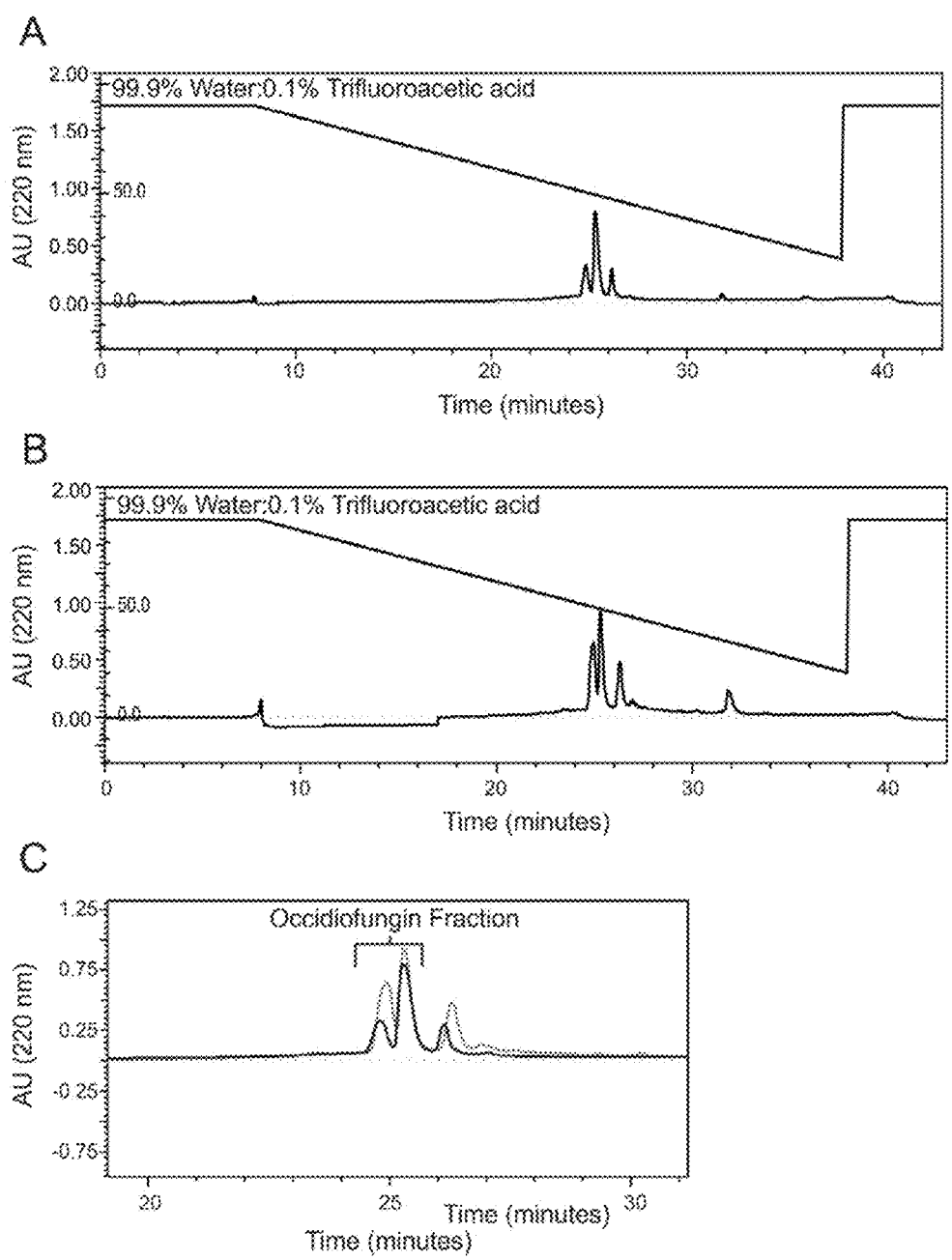

Proportion of Occidiofungin Variants in the Sample. The C-terminal TE domain of OcfD and the OcfN cyclase thioesterase in the occidiofungin biosynthetic gene cluster are both predicted to be involved in the termination of synthesis and formation of the cyclic peptide. Given that the N-terminal end of the linear peptide is an Asn or BHN, we hypothesized that each thioesterase was required for cyclization of the Asn1 and BHN1 variants. The Asn1 and BHN1 variants of occidiofungin are not separable by RP-HPLC (reverse phase high performance liquid phase chromatography), thus, both variants are present in the purified fraction (FIG. 2). The final RP-HPLC step in the purification process reveals the presence of three peaks. Occidiofungin samples elute as a doublet peak before the third peak. Both the wild type strain MS14 and the ocfN mutant MS14GG88 have the same chromatographic profile as observed in the last purification step. Occidiofungin peaks were confirmed by MALDI-TOF and bioassays. It is important to note that the presence of the doublet peak is not associated with the presence of Asn1 or BHN 1. Each peak of the doublet contains both the Asn1 and BHN 1 variants.

Figure 3:
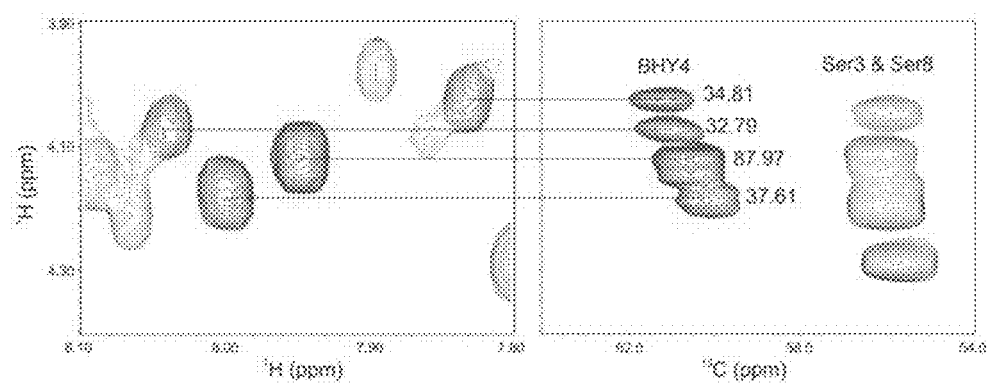
Figure 4:
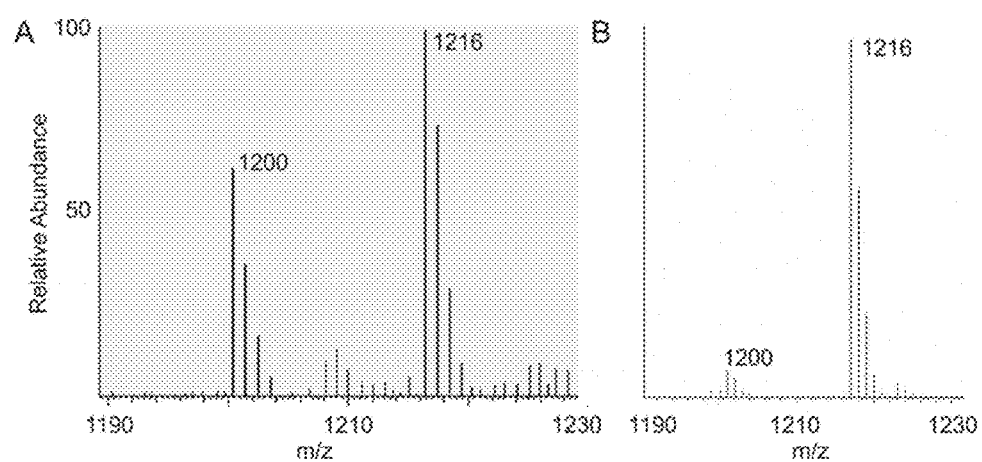

The relative proportion of the Asn1 and BHN1 variants could not be directly compared, because direct measurement of the Asn1 peak intensities could not be done due to the peaks overlapping with Asn7. The relative proportion of the Asn1 and BHN 1 variants in the wild-type fraction was determined by measuring the $^{13}$C-HSQC Ha-Ca cross peak intensities of each BHY4 peak in the data set,[27, 28] given that each of the BHY4 peaks could be attributed to either the Asn1 or BHN1 variant. Based on the Ha-Ca cross peak intensities for BHY4 in HSQC spectrum, the Asn1 and BHN 1 variants was determined by measuring the $^{13}$C-HSQC Ha-Ca cross peak intensities of each BHY4 peak in the data set[27, 28], and was determined to be approximately 36% and 64% of the total amount of occidiofungin, respectively (FIG. 3). The peaks in red and green represent the BHY4 peaks associated with BHN1 and Asn1 variants, respectively. A similar ratio was also observed in the relative abundance of each peak in the ESI-MS spectrum (FIG. 4A). Furthermore, the $^{13}$C-HSQC Ha-Ca cross peak intensities for the BHN1 peaks in the spectra were determined to be 90.50 and 38.65, which support the intensities measured for BHY4 peaks corresponding to the BHN1 conformational variants.

Mutagenesis of the ocfN gene was conducted via a marker exchange procedure as described previously[22], to generate the mutant MS14GG88. The percentage of Asn1 to BHN 1 variants in the ocfN mutant MS14GG88 fraction could be determined by measuring the proportion of each BHN1 variant using the HSQC data set and by the integration of the HN of Asn1 and BHN1 in the $^1$H NMR spectra. Asn1 and BHN1 variants are approximately 20% and 80% of the total amount of occidiofungin, respectively. The ESI-MS spectrum also shows a lower relative abundance for the Asn1 variant (1200.39 Da) compared to the BHN 1 variant (1216.41 Da) (FIG. 4B).

Comparison of Wild-Type and ocfN Mutant NMR Spectra. Occidiofungin has a complex spectrum for a peptide of only eight amino acids (FIG. 5A and Table 1). The NMR spectrum represents an average of the conformers on the NMR time scale. Conformers in slow exchange on the NMR time scale may result in multiple spin systems for each amino acid. In some situations, multiple conformers are known to arise for cyclic peptides due to slow interconverting conformational families.[29, 30] Despite the conformation restrictions brought about by the ring closure, occidiofungin still has a significant amount of conformational freedom. Both Asn1 and BHN1 variants are visibly present in the wild-type fraction, which are colored red in FIG. 5A. The TOCSY fingerprint region (NH correlations) is not as complex for the OcfN thioesterase MS14GG88 mutant spectra (FIG. 5B). A significant number of spin systems found in the wild-type spectra are absent in the ocfN thioesterase mutant spectra. Our experiments show that the TE domain on the C-terminal region of OcfD is able to perform the peptide macrocyclization of both the Asn1 and BHN 1 variants. Although, there is only one amide spin system for Asn1 produced by OcfD. Whereas, the loss of OcfN results in the disappearance of the other three Asn1 amide spin systems.

An overlay of the wild-type and ocfN mutant NMR spectra shows the amino acid spin systems in green that are absent in the mutant spectra (FIG. 5C). These spin systems are for Asn7, Ser8, Asn1, Novel Amino Acid 2 (NAA2), Ser3, BHY4, and Gly6. The loss of these spin systems suggests that the complex spin system observed for the wild-type occidiofungin fraction is not only due to interconverting conformational families, but is the result of distinct diastereomers formed by the regiospecific activity of the OcfN cyclase and OcfD TE domain. Dramatic chemical shifts observed, such as the 2 ppm shift for HN of the NAA2, support the formation of a structurally unique conformer of occidiofungin. A unique conformer is further supported by the subsequent loss of a NAA2 spin system in the ocfN mutant NMR spectra. Furthermore, the presence of both Asn1 and BHN1 spin systems in the mutant spectra along with the absence of the amide spin systems shown in green indicate that the additional spin systems are not due to the presence of the β-hydroxyl on Asn1. The additional spin systems are due to the formation of unique diastereomer produced by OcfN cyclase thioesterase. To further test for the formation of a configurational isomer versus an interchangeable conformational isomer, one dimensional NMR temperature titrations were performed. Amide and aromatic regions revealed little change in the complexity of peaks present with the occidiofungin derived from ocfN mutant MS14GG88 or wild-type strain MS14 (FIGS. 13A-13B). Given that NAA2 spin systems are a good indicator for the presence of both diastereomers in the wild-type spectrum, we collected TOCSY spectra for occidiofungin derived from ocfN mutant MS14GG88 or wild-type strain at 50° C. (FIGS. 14A-14B). There was no loss or addition of a spin system for NAA2 in the mutant spectrum. Furthermore, both spin systems for NAA2 remained in the wild-type spectrum. This data supports that the stereoisomers are non-interchangeable isomers, supporting their classification as a diastereomers (configurational isomers) rather than a conformational isomer.

Figure 6:
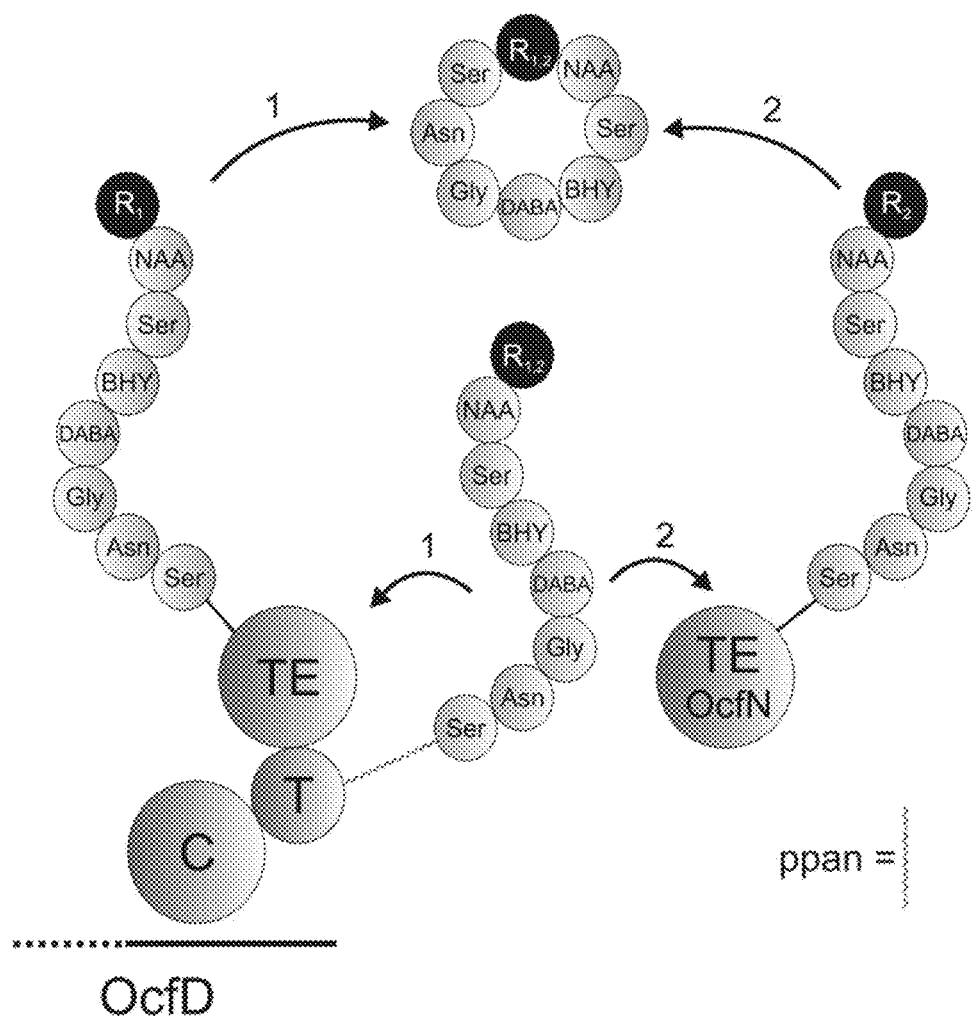

Model for the Coordinated Function of Two Cyclase Thioesterases. There was no loss of an amide spin system for a BHN 1 in the ocfN mutant NMR spectra. This suggests that OcfN thioesterase has a substrate requirement for the peptide containing Asn1, since there is no concomitant loss of a BHN1 spin system with the observed loss of the Asn1 spin systems. The C-terminal TE domain of OcfD has a preference for the peptide containing the BHN1, but is capable, albeit at a lower efficiency of cyclizing the Asn1 variant. This provides an interesting scenario for the activity of the two thioesterases (FIG. 6). Both thioesterases contain the GXSXG motif, which is important for the catalytic transfer of the peptide from the T domain to the cyclase. This suggests that substrate recognition occurs prior to the catalytic transfer of the peptide to the cyclase. Presumably, OcfN cyclase has a higher affinity or better access for the Asn1 peptide product given that the proportion of the Asn1 cyclic peptide product produced by OcfD compared to the BHN1 product is reduced in the wild-type fraction. Therefore the biosynthesis of occidiofungin utilizes the structural differences between Asn and BHN to increase the conformational biodiversity of occidiofungin. The increase in conformational diversity is accomplished by the regiospecific activity of each cyclase, presumably by differences in their binding clefts that helps orientate the peptide before cyclization.

Figure 7:
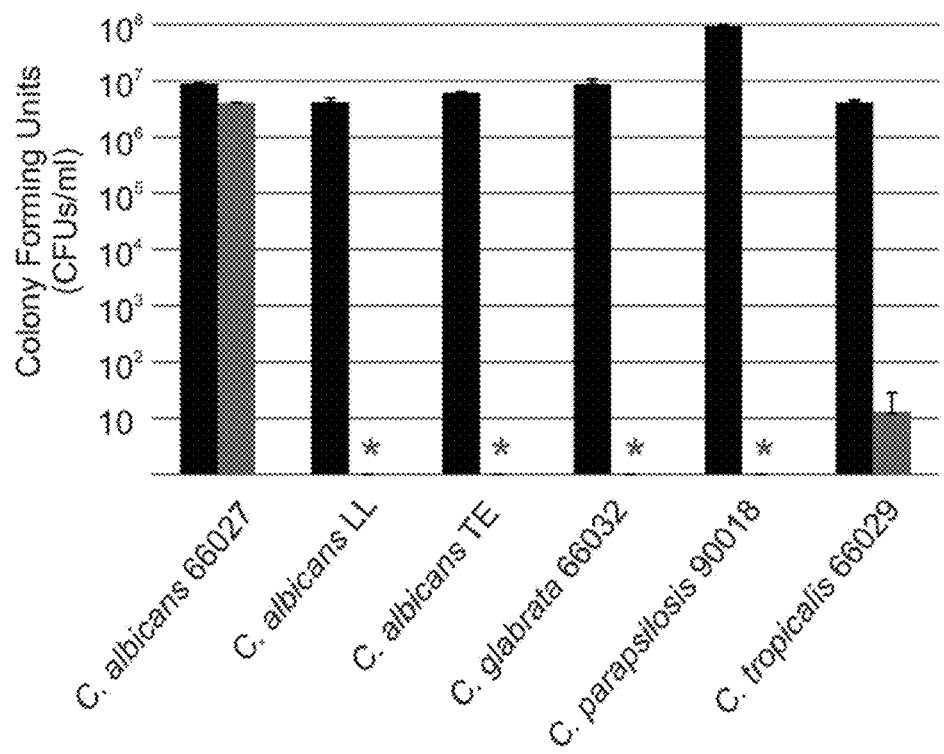
Figure 8:
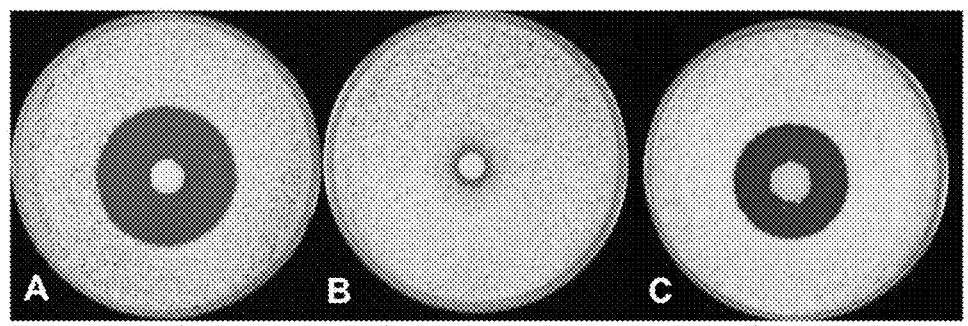
Figure 9:
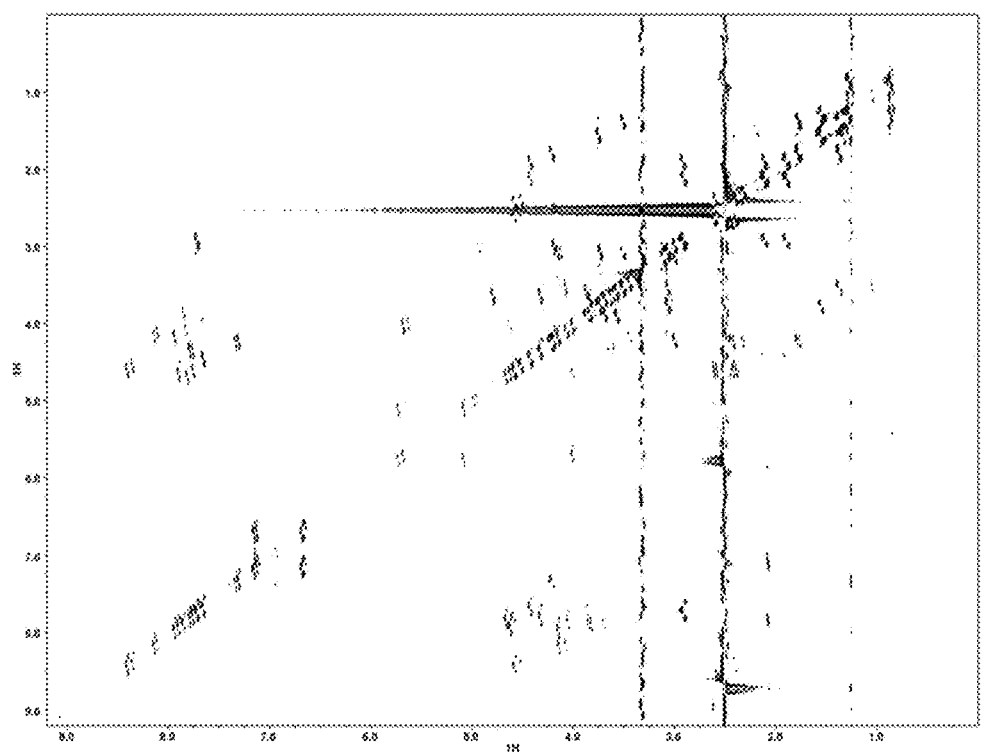
Figure 9:
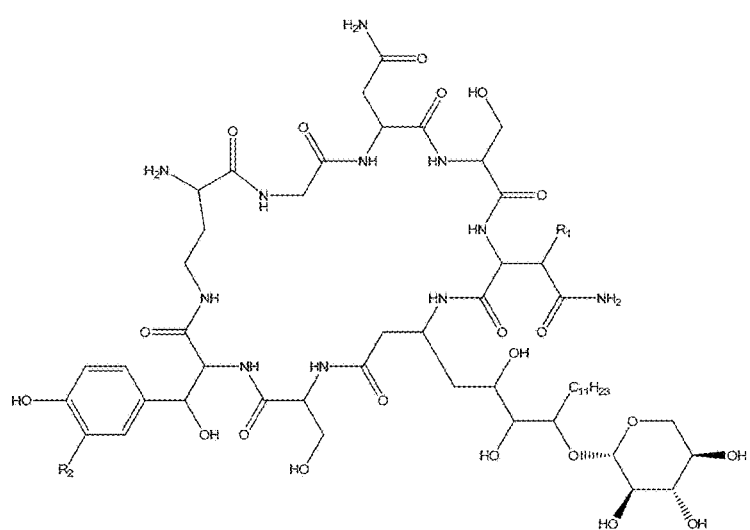

Comparison of the Bioactivity of the Wild-Type and ocfN Mutant Product. To determine whether the increase in conformational diversity is important for bioactivity, minimum inhibitory concentrations were determined against medically relevant *Candida* species (FIG. 7A). There was a 2-fold decrease in the minimum inhibitory concentration (MIC) with the purified ocfN mutant product with respect to the wild-type product against *Candida albicans* LL, *Candida albicans* TE, *Candida glabrata* ATCC66032, *Candida parapsilosis* ATCC90018, and *Candida tropicalis* ATCC66029. There was no difference in the MIC for *Candida albicans* ATCC66027. Colony forming units (CFUs/mL) were determined for the MIC wells of wild-type product for each *Candida* species and compared to the corresponding well containing the same concentration of the ocfN mutant product (FIG. 7B). Following exposure to the same concentration of wild-type and ocfN mutant products, these results show a 5 to 7-log decrease in cell density of the *Candida* species treated with wild-type product. The differences in activity are also visualized by the rate of cell death. Time-kill experiments were performed against *Candida glabrata* ATCC66032. There was a ten-fold difference in yeast present at 4 and 8 hours when cells were treated with 0.5 μg/mL of occidiofungin derived from ocfN mutant MS14GG88 or wild-type strain (FIG. 15). Furthermore, a slower rate of cell death was also observed for yeast treated with occidiofungin derived from ocfN mutant MS14GG88 at 1.0 and 2.0 μg/mL. Given that the cyclic occidiofungin variants produced by OcfN constitute less than half of the total structural variants, a 2-fold loss in activity suggests that the configurational isomer made by OcfN are 4-fold more active than the stereoisomer produced by OcfD against five of the *Candida* species tested. Another possible explanation for the observed differences in activity could be attributed to possible synergism between the configurational isomers produced by each cyclase thioesterase. Furthermore, the antifungal activity of the ocfN mutant (MS14GG88: 8.79±0.38 mm) was also significantly reduced (P<0.05) compared to wild-type activity (inhibitory zone radius±SEM: 13.00±0.58 mm) in an overlay assay against *Geotrichum candidum* (FIG. 8).

General Discussion. The findings from this study include experiments showing the following: the relative proportion of the Asn1 and BHN1 variants in the purified fraction; distinct differences in spin systems for the wild-type and ocfN mutant products: proposed model for the coordinated function of two cyclase thioesterases; and demonstrated differences in biological activity of wild-type and ocfN mutant products against therapeutically relevant *Candida* species. Expanding the conformational repertoire of cyclic peptide natural products can be beneficial to microorganisms. These data suggest that the bacterium *Burkholderia contaminans* MS14 is benefited by maintaining two distinct cyclase thioesterases that improves the spectrum of activity of occidiofungin.

Our data support the observation that cyclase thioesterase substrate recognition occurs prior to the catalytic transfer of the peptide. The presence or absence of a hydroxyl group on the beta carbon of the N-terminal amino acid (Asn1) appears to be important for the substrate recognition by the two cyclase thioesterases. It has also been shown that the N-terminal amino acid is important for substrate recognition for other thioesterases.[4,8] It is possible that the presence of the hydroxyl group promotes a hydrogen bond with the ocfD cyclase thioesterase domain or more likely promotes an interaction within the T domain of the NRPS. Different bound orientations of the peptide to the T domain would establish a basis for the coordinated function of two cyclase thioesterases. It is also possible that the enzymatic conversion of one of the residues between L- and D-isomers is not completed by one of the epimerization domains. A combination of differences in the N-terminal amino acid and a possible difference in amino acid configuration (L or D), may contribute to the selective differences by the cyclase thioesterases that result in the formation of the observed configurational isomers.

The presence of the hydroxyl group on the beta carbon and the bound orientation of the peptide to the T domain may prevent the interaction of the OcfN cyclase, while enabling the continued substrate recognition by OcfD TE domain. There is evidence for the need of a bound orientation of the peptide to the T domain for the successful function of the cyclase thioesterase. Conformational diversity of the T domain has been shown to be important for the directed movement of the peptide substrate bound to the ppan cofactor and its interaction with externally acting enzymes.[3] More specifically, the active site serine of the cyclase thioesterase needs to attack the linear peptide attached by a thioester linkage to the ppan forming an acyl-O-TE intermediate. The position of the peptide bound to the ppan in the T domain will be important for bringing the peptide substrate in proximity of the appropriate cyclase thioesterase.

Furthermore, some cyclase thioesterases are capable of transacylation of the peptide to the active site serine, when the peptide is bound to a biomimetic prosthetic group.[4,16] However, there are several cyclase thioesterases that will not function when the product is bound to a biomimetic group. These data suggest that the interaction of the peptide with the T domain is important for the enzymatic activity of some thioesterases and this interaction cannot be mimicked using a prosthetic group. It is conceivable that the coordinated function of the two cyclase thioesterases, involved in the synthesis of occidiofungin, utilize differences in the interaction of the ppan bound peptide within the T domain.

Presumably, ocfN was integrated into the occidiofungin biosynthetic gene cluster to improve its spectrum of activity against fungi. Given the broad spectrum of antifungal activity associated with occidiofungin, the molecular target is likely to be highly conserved. However, there must be some variation among fungal species to account for the differences in biological activity. Increasing the conformational repertoire must be a selective advantage to the bacterium for it to maintain the two functional cyclase thioesterases. The microbial environment is considerably different than how we intend to apply the natural products produced by microorganisms. For instance, the bacterium *Streptomyces roseosporus* is a soil saprotroph responsible for the production of daptomycin.[31,32] The microbial community that this bacterium encounters is far more diverse than the group of bacteria that cause human infection. Thus, evolutionary pressures that selected for the current conformers of daptomycin may not necessarily be the best conformers for treating a *Staphylococcus aureus* infection. It is very likely that the therapeutic application of daptomycin or other cyclic peptide drugs could be improved by engineering novel conformational or configurational isomers.

Creating novel diastereomers of other cyclic peptide drugs using new or engineered cyclase thioesterases may lead to improvements in their therapeutic activity against clinically relevant pathogens. This is true for occidiofungin produced by the bacterium *Burkholderia contaminans* MS14, which accomplishes this goal by the evolutionary integration of an additional cyclase thioesterase into the occidiofungin biosynthetic gene cluster.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Experimental Section

Materials. Occidiofungin produced by both the wild type strain MS14 and the ocfN mutant MS14GG88 were purified as previously described for the wild-type sample. Chemicals were purchased from Sigma-Aldrich (St. Louis, Mo.) and were the highest grade, unless otherwise stated. Media were purchased from Fisher Scientific, enzymes were purchased from New England BioLabs, and primers were purchased from Integrated DNA Technologies (IDT) unless otherwise stated. *Candida* strains used were purchased from the ATCC biological resource center and were a gift from Thomas Edlind (Drexel University College of Medicine).

Site Directed Mutagenesis. A nonpolar mutation was constructed in the open reading frame of wild-type ocfN by the insertion of a kanamycin resistance gene, nptII.[33] To mutate ocfN, a 1-kb fragment containing ocfN was obtained by PCR using primers MocfNF (5'-CGCCACCCGTTAC-GAGGATTC, SEQ ID NO: 1) and MocfNR (5'-ACGCGTC-CCCTCTTCCTACG, SEQ ID NO: 2). The 1-kb PCR product was cloned into the pGEM-T Easy Vector System I (Promega Corporation, Madison. WI) resulting in plasmid pGG30. The nptII gene was inserted into the cloned ocfN at SmaI, generating plasmid pGG31. The ~2-kb EcoRI fragment of pGG31 harboring the ocfN gene disrupted by insertion of nptII was cloned into pBR325[34] at the EcoRI site to generate pGG32. Mutagenesis of the ocfN gene was conducted via a marker exchange procedure as described previously[35], to generate the mutant MS 14GG88. PCR analysis and sequencing were used to verify the double crossover mutants. Production and purification of the antifungal were done as previously described.[23]

NMR Spectroscopy. A 2 mM sample of ocfN thioesterase mutant fraction of occidiofungin was prepared in dimethyl sulfoxide (DMSO-d6, Cambridge Isotopes) and data were collected as previously described for the wild-type fraction.[22] The NMR data were collected on a Bruker Advance DRX spectrometer, equipped with a CryoProbe, operating at a proton frequency of 600 MHz. The $^1$H resonances were assigned according to standard methods[36] using COSY (correlation spectroscopy), TOCSY (total correlation spectroscopy), NOESY (nuclear overhauser effect spectroscopy) and $^{13}$C-HSQC (heteronuclear single quantum coherence) experiments. NMR experiments were collected at 25° C. The carrier frequency was centered on the residual water resonance (3.333 ppm), which was suppressed minimally using standard presaturation methods. A 2.0 s relaxation delay was used between scans. The TOCSY experiment was acquired with a 60 ms mixing time using the Bruker DIPSI-2 spinlock sequence. The NOESY experiment was acquired with 400 ms mixing time. The parameters for collecting the HSQC spectrum were optimized to observe aliphatic and aromatic CH groups. The spectral sweep width for the TOCSY and NOESY was 11.35 ppm in both dimensions. The spectral sweep widths for HSQC were 11.35 ppm in the proton dimensions and 0 and 85 ppm for the carbon dimension. All 2D data were collected with 2048 complex points in the acquisition dimension and 256 complex points for the indirect dimensions, except for the HSQC which was collected with 2048 and 128 complex points in the direct and indirect dimension, respectively. Phase sensitive indirect detection for NOESY, TOCSY, and COSY experiments was achieved using the standard Bruker pulse sequences. $^1$H chemical shifts were referenced to the residual water peak (3.33 ppm). Data were processed with nmrPipe[37] by first removing the residual water signal by deconvolution, multiplying the data in both dimensions by a squared sinebell function with 45 or 60 degree shifts (for the $^1$H dimension of HSQC), zerofilling once, Fourier transformation, and baseline correction. Data were analyzed with the interactive computer program NMRView.[38] One-dimensional NMR temperature titrations were collected on the wild type and mutant peptides, using a Bruker AVANCE III HD 600 MHz spectrometer equipped with a cryoprobe. Eight scans were collected in each 1-D experiment, using 32K points, at a temperature of 298 K. The experiments were repeated using higher temperatures for both samples in 5 degrees K increments, up to a temperature of 323 K. 2-D TOCSY spectra were collected at a temperature of 323 K, using a mixing time of 60 milliseconds. Eight scans and 256 indirect points were used for both the wild type and mutant peptides. The 2-D spectra were processed using NMRPipe, with 45 degree sinebell squared shifts in both dimensions.

Mass Spectrometry. The wild-type occidiofungin and the ocfN mutant sample (10 μg) were evaporated to dryness in a Speed Vac Concentrator (ThermoScientific, San Jose, Calif.) and the residue was taken up in 50 μl methanol and analyzed by direct infusion at 3 μl/minutes into an LCQ DecaXP (ThermoScientific. San Jose, Calif.). Data were acquired over a mass range of m/z 200 to 2000.

In Vitro Susceptibility Testing. Microdilution broth susceptibility testing was performed in triplicate according to the CLSI M27-A3 method in RPMI (Roswell Park Memorial Institute) 1640 [buffered to a pH of 7.0 with MOPS (morpholinepropanesulfonic acid)] growth medium. 100× stock solutions of occidiofungin were prepared in dimethyl sulfoxide (DMSO). MIC endpoints for occidiofungin were determined by visual inspection and were based on the wells that had no visible growth (an optically clear well) after 24 hours of incubation. DMSO containing no antifungal agent was used as a negative control. Colony forming units (CFUs) were determined in triplicate by plating 100 μl from the MIC wells onto a Yeast Peptone Dextrose (YPD) plate as well as plating 100 μl from 10-fold serial dilutions of the cell suspension in Yeast Peptone Dextrose (YPD) Broth. Colony counts were performed and reported as CFUs/ml. Time-kill experiments were performed as previously reported.[19] *Candida glabrata* (ATCC 66032) colonies on 24-h-old YPD plates were suspended in 9 ml of sterile water. The density was adjusted to a 0.5 McFarland standard and was diluted 10-fold with RPMI 1640 medium to a final volume of 10 ml containing a final concentration of 2, 1, 0.5 and 0 μg/ml of occidiofungin from wild type strain MS14 and the ocfN mutant MS14GG88. The cultures were incubated at 35° C. with agitation. Samples were drawn, serially diluted, and plated on YPD medium for colony counts.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Chemical Shift Values for Occidiofungin derived from the ocfN mutant MS14GG88[a]

| Unit | No. | $\delta_C$ | $\delta_H$ |
|------|-----|------------|------------|
| Asn1 | 2 | 52.71, CH | 4.59 |
| | 2-NH | | 7.75 |
| | 3 | 39.91, CH2 | 2.62, 2.41 |
| | 4 | — | |
| | 4-NH2 | | 7.39, 6.93 |
| BHN1 | 2 | 58.47, CH | 4.66, 4.61 |
| | 2-NH | | 7.81, 7.9 |
| | 3 | 75.01, C | 3.98, 4.02 |
| | 3-OH | | 4.66 |
| | 4 | — | |
| | 4-NH2 | | 7.24 |

TABLE 1-continued

Chemical Shift Values for Occidiofungin
derived from the ocfN mutant MS14GG88[a]

| Unit | No. | $\delta_C$ | $\delta_H$ |
|---|---|---|---|
| NAA2 | 2 | 43.88, CH2 | 2.34, 2.36 |
|  | 3 | 47.25, CH | 4.23 |
|  | 3-NH |  | 7.31, 7.34 |
|  | 4 | 41.57, CH2 | 1.39, 1.76 |
|  | 5 | 66.36, CH | 3.50 |
|  | 6 | 76.07, CH | 3.08 |
|  | 7 | 79.61, CH | 3.72 |
|  | 8 | 33.19, CH2 | 1.54 |
|  | 9-17 | 25.14-28.02, CH2 | 1.27 |
|  | 18 | 16.94, CH3 | 0.86 |
| Ser3 | 2 | 58.59, CH | 4.07, 4.15 |
|  | 2-NH |  | 8.11, 8.14 |
|  | 3 | 70.23, 64.29 | 3.49, 3.45 |
|  | 3-OH |  | 4.95 |
| BHY4 | 2 | 58.71, CH | 4.06, 4.15 |
|  | 2-NH |  | 7.83, 7.94 |
|  | 3 | 73.75, CH | 4.98, 5.08 |
|  | 3-OH |  | 5.66, 5.73 |
|  | 4 | — |  |
|  | 5, 6 | — | 7.15 |
|  | 8, 9 | — | 6.67 |
| DABA5 | 2 | 53.49, CH | 4.43 |
|  | 2-NH |  | 7.66 |
|  | 3 | 32.68, CH2 | 1.88, 2.11 |
|  | 4 | 39.17, CH2 | 2.92 |
|  | 4, NH |  | 7.71 |
| Gly6 | 2 | 44.76, CH2 | 3.87, 3.58, 3.84, 3.70 |
|  | 2-NH |  | 7.68, 7.85 |
| Asn7 | 2 | 53.25, CH | 4.51, 4.58 |
|  | 2-NH |  | 8.35, 8.41 |
|  | 3 | 40.03, CH2 | 2.61, 2.38 |
|  | 4 | — |  |
|  | 4-NH2 |  | 7.39, 6.93 |
| Ser8 | 2 | 58.11, CH | 4.33, 4.32 |
|  | 2-NH |  | 7.76, 7.78 |
|  | 3 | 64.59 | 3.61, 3.62 |
|  | 3-OH |  | 4.79 |

[a]Proton chemical shift values are from a TOCSY and NOESY experiments. Chemical shifts in brackets are $^{13}$C values from the HSQC experiment.

```
GenBank: EU938698.5
Go to:
LOCUS       EU938698 58101 by DNA linear BCT 13-DEC-2010
DEFINITION  Burkholderia contaminans strain MS14 putative FAD linked
            oxidase
            domain protein gene, partial cds; and putative LuxR-type
            egulator
            (ambR1), putative LuxR-type regulator (ambR2), putative cyclic
            peptide transporter, hypothetical protein, putative glycosyl
            transferase, putative nonribosomal peptide synthetases,
            putative
            beta-lactamase domain protein, putative beta-ketoacyl synthase
            nonribosomal peptide synthetase, putative short chain
            dehydrogenase/reductase SDR, putative beta-ketoacyl synthetase,
            putative taurine catabolism dioxygenase, putative transaminase,
            putative epemerase/dehydratase, putative thioesterase, and
            hypothetical protein genes, complete cds.
ACCESSION   EU938698
VERSION     EU938698.5 GI: 314950578
KEYWORDS    .
SOURCE      Burkholderia contaminans
  ORGANISM  Burkholderia contaminans
            Bacteria; Proteobacteria; Betaproteobacteria; Burkholderiales;
            Burkholderiaceae; Burkholderia; Burkholderia cepacia complex.
REFERENCE   1 (bases 1 to 58101)
  AUTHORS   Gu, G., Smith, L., Wang, N., Wang, H. and Lu, S. E.
  TITLE     Biosynthesis of an antifungal oligopeptide in Burkholderia
            contaminans strain MS14
  JOURNAL   Biochem. Biophys. Res. Commun. 380 (2), 328-332 (2009)
   PUBMED   19167363
REFERENCE   2 (bases 1 to 58101)
  AUTHORS   Gu, G., Wang, N., Chaney, N., Smith, L. and Lu, S. E.
  TITLE     AmbR1 is a key transcriptional regulator for production of
            antifungal activity of Burkholderia contaminans strain MS14
  JOURNAL   FEMS Microbiol. Lett. 297 (1), 54-60 (2009)
   PUBMED   19500142
REFERENCE   3 (bases 1 to 58101)
  AUTHORS   Gu, G., Smith, L., Wang, N., Wang, H. and Lu, S.
  TITLE     Direct Submission
  JOURNAL   Submitted (01-AUG-2008) Entomology and Plant Pathology,
            Mississippi
            State University, 32 Creelman St., Mississippi State, MS 39762,
            USA
REFERENCE   4 (bases 1 to 58101)
  AUTHORS   Gu, G., Smith, L., Wang, N., Wang, H. and Lu, S.
  TITLE     Direct Submission
  JOURNAL   Submitted (12-NOV-2008) Entomology and Plant Pathology,
            Mississippi
            State University, 32 Creelman St., Mississippi State, MS 39762,
            USA
  REMARK    Sequence update by submitter
```

```
                                              -continued
REFERENCE   5  (bases 1 to 58101)
AUTHORS        Gu, G., Smith, L., Wang, N., Wang, H. and Lu, S.
TITLE          Direct Submission
JOURNAL        Submitted (15-JAN-2009) Entomology and Plant Pathology,
               Mississippi
               State University, 32 Creelman St., Mississippi State, MS 39762,
               USA
REMARK         Sequence update by submitter
REFERENCE   6  (bases 1 to 58101)
AUTHORS        Gu, G., Smith, L., Wang, N., Wang, H. and Lu, S.
TITLE          Direct Submission
JOURNAL        Submitted (24-FEB-2009) Entomology and Plant Pathology,
               Mississippi
               State University, 32 Creelman St., Mississippi State, MS 39762,
               USA
REMARK         Sequence update by submitter
REFERENCE   7  (bases 1 to 58101)
AUTHORS        Gu, G., Smith, L., Wang, N., Wang, H. and Lu, S.
TITLE          Direct Submission
JOURNAL        Submitted (13-DEC-2010) Entomology and Plant Pathology,
               Mississippi
               State University, 32 Creelman St., Mississippi State, MS 39762,
               USA
REMARK         Sequence update by submitter
COMMENT        On Dec 13, 2010 this sequence version replaced gi: 224016442.
FEATURES       Location/Qualifiers
source 1 . . . 58101
        /organism = "Eurkholderia contaminans"
        /mol_type = "genomic DNA"
        /strain = "MS14"
        /db_xref = "taxon: 488447"
CDS     complement(<1 . . . 1175)
        /note = "ORF1"
        /codon_start = 1
        /transl_table = 11
        /product = "putative FAD linked oxidase domain protein"
        /protein_id = "ACN32485.1"
        /db_xref = "GI: 224016443"

(SEQ ID NO: 5)
/translation = "MSHDFRDEPAPRRAFLADMAKLAAAGIVTGWTPLYQVAAHARTA

GETPPGFPADIQLYKQAFLNWSGEIAVQDVWTAAPRSADDVVATVNWARANGYRIRPR

GYTHNWSPLTLDPGAGAANLVLLDTTKSLTAVSVDTSARPARVTAQTGVSLESLLATL

EQVGLGVIAAPAPGDITLGGALIDAHGTAVPAAGETLQPGHTYGSLSNLVVALTAVV

FDPARQQYVLRRFERSDPEIGAFLAHIGRALVVEVTLTAGPNQRLRCQSYVDIPASEL

FAAPGTTGRTIASFLDGSGRVEAIWFPFTTKPWLKWTPTPSKPFLSRAVTQPYNYPF

SDSISQSISDLVKRIVIGGEGALTPLFGQTQLAITTAGLALTLSGDIWGWSRTVLQE"

gene 2480 . . . 3301
        /gene = "ambR1"
CDS     2480 . . . 3301
        /gene = "ambR1"
        /note = "AmbR1"
        /codon_start = 1
        /transl_table = 11
        /product = "putative LuxR-type regulator"
        /protein_id = "ACN32486.1"
        /db_xref = "GI: 224016444"

(SEQ ID NO: 6)
/translation = "MFAKLGKVISSAGSERFASDMHALLVESIPLTITRMTEWTLDEP

AGEVVRVQSLGADGAPGDDGRGAPAAHGEREPAAHPPLNRILAACDRQLIHINPLMRR

GNGGEVAPSRGPGGGFQCHLVSGKANRRYVISLHRTASHRDFSLREMSFLKNFADTLL

PLVEWHASTCRHGEREGATAPGATAGMPGVEALRHEFESRLARARVVLSARENEVCLG

LLAGKMLREMAGELGVKESTIETYIKPAAVKLGISGRHGLTKWMIDDSVPCASAA"

gene complement(3372 . . . 4262)
        /gene = "ambR2"
CDS     complement(3372 . . . 4262)
        /gene = "ambR2"
        /note = "AmbR2"
```

```
       /codon_start = 1
       /transl_table = 11
       /product = "putative LuxR-type regulator"
       /protein_id = "ACI01437.2"
       /db_xref = "GI: 212381179"
```

(SEQ ID NO: 7)

/translation = "MEFSRLFAHVGEAISSSGSRRFPRMMYNLIAAAVPVDEIRISEL

AIDDVPDGPPEVRSLGAVGAALAKTGAAAVCCGPQMPPRPGTSPLHVDDTLAGHGPIH

AQLDRFILMQAAIVSPRYAQFHLVTRKRGHCYVISLYRTCTFDDFSPQERTFLKELSH

VLFPIVESHVAALDSAPPAARVTTAAPPATQSGRERVARRFADRLQQAGVKLSTREIE

ACTALLAGDTVPAIAMRFALRESTVETYLKRAAVKLGFSGRHGLTRWMLDETAGAATE

AAGGDMRSMRRDYASPRLGT"

```
CDS complement(4466 . . . 6169)
       /note = "ORF2"
       /codon_start = 1
       /transl_table = 11
       /product = "putative cyclic peptide transporter"
       /protein_id = "ACJ24909.2"
       /db_xref = "GI: 220898663"
```

(SEQ ID NO: 8)

/translation = "MDSAQSKSPPWHSAATLMWRSHPWLTLGTVVTGLVSGIASIAGV

GLISTVLHDQDDRQTLLLLFIAVNVVAVVCRSCAAVMPSYACMKVMTRLRVNLCKRIL

ATPLDEIDRRGAPNVLTMLTQDIPQLSQTLLTIPTIIVQSVVLICSIAYLAYLSWIVF

ASTIILTLVGLVLYLFFYRKAVNFTERVRDEFVQFNEYTHGLVFGIKELKLNRARRRW

FTRAAIELSSKRVAGFNYIERFWFMSGDSIGQITVAVLLGCLLFGVPSLGVVDPSVLT

ASILAVLYMMGPLTMLINVLPVVAEGKTALARLAEFGFLIDDTQASHEEPRPAGNVET

LSAKSWKVIELKDVTMNYRDNEASVDFVLGPIDMTIHAGELVYVIGGNGSGKSTLGKV

LSGLYAPTGGTISLDGKVVDDAARERYRNLFSAVFTDFHLFNRIIGPDRGNESIELAR

KYLATLKLADKIEISGRTYSTTRALSTGQRKRLALLCAYIEDRPIYILDEWAADQDPV

FKRFSYEVLVPDLKSRGKCVVIITHDDQYFKLADPVIRLDSGRIFSDTAMCAVRAEAA

G"

```
CDS complement(6186 . . . 6668)
       /note = "ORF3"
       /codon_start = 1
       /transl_table = 11
       /product = "hypothetical protein"
       /protein_id = "ACL81525.1"
       /db_xref = "GI: 220898664"
```

(SEQ ID NO: 9)

/translation = "MQLTTVDLEAAFVKAALDALHRDCKLGDAISLAYGKCESTAGVI

DLIFPLITKKLRIDYILMYSIESNPRTLLQFLRQIESGLARSEDWTAASVEAALRSVA

DSPDGVGWERAQRLLKCCILFSDSPLGIVESITFLGKHETSSRLRSAASNVELSHLIN"

```
CDS complement: (672 . . . 7378)
       /note = "ORF4"
       /codon_start = 1
       /transl_table = 11
       /product = "putative glycosyl transferase"
       /protein_id = "ACL81526.1"
       /db_xref = "GI: 220898665"
```

(SEQ ID NO: 10)

/translation = "MKSTPTIDNTFAPKVCINLDRRPDRWEAMQRKFAEQNILTVERL

PAVDARLVSVPESLSHMRAQDYGCTMSHLAAVKQAKAAGAREVLIFEDDAFFDADFAA

RFPEFIAQVPDDWHMLFLGAYHFTPPIPVAPNIVKAVETLTAHAYVVRNSLYDAFIAI

NENPPAINDRNNLVLQQTFNCYCFEPNLVGQESGYSDIMDEVMPEKPLTYSMPIPDGW"

```
CDS complement(7375 . . . 16869)
    /note = "ORF5"
    /codon_start = 1
    /transl_table = 11
    /product = "putative nonribosomal peptide synthetase"
    /protein_id = "ACL81527.1"
    /db_xref = "GI: 220898666"
```

(SEQ ID NO: 11)

/translation = "MQDNNVLVTDHRYAATARFWRESLSRVAGVYGIAAYAPSQQPGR

PLTRSVRLTPASLDLLRRIGDGELAEFAVAAAGIAFLLWKYFRIPVTVLGTPGLAGHP

SARAAIVPLIIEVRPDERIEDYLSRVAGIVEDSYAEPRFPLETLVRNEKDMALAQLTK

VALADDRVHHAPTGRDDDLQLHLRLARGEIELRYSGAIEPFIIDGFAGSLAAVLEAFE

HLDGAVGDIEAAPPEQGPLLAAFNETATAGPSHPTVVAMFEAQVARTPTAPALVTDSS

LMTYADLNARANSLAHHLREHHGVGPESLVGIMLDRSEWMIVAILGILKAGAAFVPLD

PAYPAERINHILGDTGLSLLVTQSSQLAQWYEFSGVTLLLDQELPGWQPLPDNPPHRA

EPAHLAYVLYTSGSTGKPKGCLLEHRNLAHYIAWAAGYYFPESTTGSFGLYSSLCFDF

TLTNIFCPLVRGKTLRIYPQSESIDTILARMFQPGSGVDTLKLTPTHIHLLEYMNLAR

SGVRKVIVGGEELTPQHIATLRKIDPAIEIYNEYGPTEATVGCIVERVEDAPPTVLIG

RPIADTRVYMLDDALRPVPLGVPGEICLAGAGLARGYHQRPDVTAAKFVEHPFPGEAR

IYRTGDIGRWLPDGRIQCYGRVDHQVKIRGHRVELGEIEAAIAAHEDVVGAAVMLRES

AHGVRKLAAYVKGAASLSVPNLRAYLAGKLPDYMVPSDIIPIAEFPLNANGKLDRPAL

LALEPAAAPEEAPLDATPIQRELVRIWRDVLDNPAVDLAGRFFDYGGDSLQAMQLVSR

IWSSFSVEIGIDAIFELQTISAVSDLIEASSPHPGSTAGAIPPRSRANDLPLSFPQQR

LWFLAQLEGPSATYNISSALRFEGELDVARLRFAVSEISRRHEILRTTFPAVDGRGVQ

RIAPPAPVALDVVDVASESDTLALLAEEADRPFDLAAGPLYRVVLYRVHERLHVFGIV

MHHIVSDAWSSGILIGELAALYAGESLPELAVQYADYAVWQHERLASADTHRELALLS

AALADAPDLIELPTDRPRPAVQQFRGAVLPFQLSAERADGLRAIARASGTSTFMVVLA

AYALLLSRYSNQQDLVIGSPIANRRSSMTEPLIGFFANMLALRVDLSGNPTFGDLLAR

VKRVALDGYSRQEIPFEQVVDSLELERNLGRTPVFQVVFAYEKAQPRAVSFPGLVATP

VAVETHTAKFDLTLHVQDADDGLAGSLEYNLDLFDAATIDRMAEHFRTLVDAVIADPD

RPLGALSLSNDAERNLLTVEWNRTDTDFGEDAAQPLHRLFEQQVERTPDAVAIVFDDT

ALTYAELNLRANRLAHHLVALGVGPDSLVGVAMERSLDMSVALLAILKAGGAYVPVDP

DYPAERVRFMIDHAQLRWLLTQQHLHDALPDTDAHVIVVDRDSLDLDAAATSNPAPAL

NGDNLAYMIYTSGSTGRPKGALNTHRAITNRILWMQHAYALDADDAVLQKTPFSFDVS

VWELFWPLVTGARLVFARPGGQRETDYLVELIERERITTIHFVPSMLRAFLDHPDLDA

HCASLRRVVCSGEALPHDLQQRCLERLDVKLYNLYGPTEAAVDVTAWECRRDDPHRIV

PIGRPIANTRLYIVDAQMQPTPIGVAGELLIGGTPVGRGYHGEPELSAEKFIADPFSA

DPLARLYRTGDLARYRFDGNIEFLGRIDHQIKLRGLRIEPGEIEAALRAHPSVDDCVV

IAKTEGARTFLIAYVATAAPDIADLRGYLGGKLADYMVPSQFFALESLPMLPNGKINR

KALPLPADRGDAAQPHAPAVTPREILLASICIDVLQLPSVGIHDNFFELGGDSILSIQ

VIARANQAGLRVTAKQLFQYQTIAQLAAAPEERAACAPTLSPLGDAPLTPVQHWFFEQ

EIDAPSHYNQTVLIQVPADIDASRLADAFRQVYEHHDALRLRFSHDAGRWTQQVVAGG

EMPALFAKQVIADDAGERLAAMRAAAADAERGIDITHGPLLAARLFCLADEPLARLFV

SIHHLAVDGVSWRVLLEDLHAAYHGQPLFGKTTSFREWALHLQQLARSPAIGDEARLW

-continued

QALLAQPVEPMPVDYPGTGAANNAVDDASSVSFELGEADTTALLRRLPRAYDTRINDV

LLVALAQACSMVTGNTRTRIDLESHGRHVSDAPLDLTRTVGWFTSIYPVVLDADAMHA

PEQALRAARQQLRRIPADGLGYSLLRYQSPDAAVRDSLAALPKADILFNYHGQLDTVL

RQSDGWRPAAEDLGSLRAGRSQRTHAFEIVAAVADGKLQVDWRYGERLHRRQTVENLA

AHFRDRLLDFAASVPDTAADDIEDSYPLSSLQQGILFHSLYDLDPAAYFQQFSFVVSG

PLQVPALRQAWANALARHAVLRTAFAWADRDHPVQTVRHTVDLPWTFLDWRHRDASRR

AQDFDAFLADDRRRGFDLQRAPLFRCTLIQETDTRHRFCWSAHHIILDGWSTATLMKE

VFDDYLSLARTGMPAVAASAPGYRAYIDWLARHPRSADETWWRAELAGFKAATPVAAS

PARQATGDAPRQDKRRTQQFLLDEALAARLQTLTRTHRVTLNVLIRAVWALVLRRHAG

TDDVVFGVTVSGRPPMLDGVESIVGLFINTLPLRLRIAPERPFIEWLAEVHAAQTAME

PHSYSSLVDIQSWSELPAGDSLFDSLLVFENFPVAAAPDLGPDDIEILDTRAFAESNY

PLTLTVHPNERIGFHISHDAHRIAPEVVRQMLDTLRTLLERFAENPGQLTGQLADPPA

ADGRPSAPRSGAGPAIEAAAGAAAAARAVAHAADESTLLEIWRRIFKRDDIAVSDNYF

DLGGHSIIAIQLMAHVEKAFDRRLPISCLFENPTIEKLAAALAAKEPSAPAGGLVPIR

DGGPAAPLFLLPGAGGNVVYFRPLANHLSGAHAIHGLEALGLDGACEPLTRVEDIAAR

HIERIWPLVGAGPYYLAGHSFGAHVALEMSRQLVAKGADVKLLAIFDASAPIDSSAAT

YWQDWDDTEWLVAIAHEIGTFLGTDLQVTRADLVHLDPDGQAGLILERIGDRGSWFAD

AGSDRLRAYLRVYQANFKSHYAQHATPLPVPIALFRSTERDPGDYAPSSEIAQLRLDA

TWGWSRFSAHPVAVTDVPGDHLTMLLDPHAGVLAAHVNSFLEKTPS"

```
CDS  complement (16957 . . . 26022)
     /note = "ORF6"
     /codon_start = 1
     /transl_table = 11
     /product = "putative nonribosomal peptide synthetase"
     /protein_id = "ACL81528.1"
     /db_xref = "GI:220898667"
```

(SEQ ID NO: 12)

/translation = "MQEGMLFHAVHEPGSRSSFNQLSCRITGSLDPALFHAAWQQLID

RHPVMRTSFHWEEFDKPMQVVHARATLPWVQDDWLDLPEHEQRSRWRAHLDNDLAEGF

ALDRAPLVRCRLVRVAADAYLFSWSHHHILADGWCLSLVIEEIFEVYGALARGVSPAL

PPVRPYRDYIQWLQQHEPQAAQQYWTRYLEGFRTPTPLPTAARAGADERFGQGLAQVQ

ADLSADLSARLRQFAARHHVTLNTLAQAAWALVLSRYSGETDVVFGAVVSGRGANLPG

IETMLGLFINTVPVRVRVDPRQPLVPWLKMIQARVAARAPFEHTPLPDIQRCSDVPPT

APLFESNITFMNYPLDASLTHGAHGLAVDEVQLYNRADIPLEFVVTARDDWKMELSFD

PRRFDEDTMQRMLGHVAATLDAFAADPNRLLGRVPILPDAERRQLLETFNDTAVPFDA

ALTVVHRLEQAAADHPERPAVEYEDGVLSAGELNARANBIAHRLLAAADLGPDALVAI

CMHRSAQLMEAILAVWKCGAAYIPVDPNYPVARIRTILEDSGAALVITCDGLLPPELA

GIALVVSLDAATDAVDDSNPGRPVSPDSLAYVIYTSGSTGKPKGAMVEHAGMLNHMLA

EIDEFSISASSVIAQTAPHCFDISVWQFFTAPLVGGKTVIVDDDCIRDPARFVAYLET

TRISILELVPSYLSAVLDRASERPALMRHLRHLLVTGEMVSPALVKQWFDVFPAIPLV

NAYGPAEASDDVAQHRMTGAPSTPYVPVGKPIRNVRLYVVDPQMNLCPIGIPGELCVS

GVAVGRGYLNNEAATQDAFVEDPFHPQRGVRLYRTRDIGCYLPDGTIVLHGRKDHQLK

IRGYRIELGEIDQRRLADHSRKLRQAAALDYRDEAGRAALCAYVAFRDGASLSDAGIA

AALSATLPDYMVPGIYVVLDALPLSGNGKIDRNALPPLDRARLAATAHAPTPPRTPTE

-continued

TLLCRIWGEALGIPSPGIHDNLFALGGDSILSMRIVSLAAKAGLKLTTRLIFQHPTVA

ELAAVATRGTVGAAAFVASSGPLPLTPIQKRFFAQGKHDPDQYNQAVLLDVPADLDPV

LLRQALRHAVKWHDALRLRFREGESGWTQEVVDDPEIPVVVSDIARDQLAQYVAQSHA

SLNLADGPVVRADLFRVDEGRSLRLLLVAHHLVVDGVSWGALLETVYDAYTRLRNGKA

PEFAGGSATWTAWTRAISTWAGSGAADADLAHWQALARAALPGLPLDRDAPADANTVS

SADTIVVELGHAATTALLGAAPRAYDAQVNDVLLAALAHAVSEWSGCADVLLDLEAHG

REELIDALDISRTVGWFTSVFPVLLTVDAGSHDPASLVASVRTRLRAVPNAGITYGLL

LDRLDGPLPQPRLQFNYLGQTDQLFTAAHDWKQAAHPSGDGRNANQLHEHLLDINAYV

TGNRLHVAWEFSRACHDTATILRVAQAYIAALETLVAGHAVPSASTRPATALPQAPAP

ASVSPDEIADVYPLTPTQQGMLFHSLYEFASDAYFSSLNFRIDGALDVERFRRAWETV

AHRHDILRTSFHWEDIESPVQVVHRRIDLPWHDEDLRAASAAEAEQRWEAYVAQDRAR

GFDFTRAPLMRLALFRVGEHAWRFHWSHHHILLDGWSSARLLSDVAAAYQAPPAEGAP

QRDAPPAFAGYVRWLARQDAAAAQRFWKTKLADFPATTPLVLGRPELDGTAAPGAYVE

EPLLLSESDTQRLVAFAQSRRLTLNTLAQGAWAQLLSRYSGESDVVFGTIVSGRPASL

PASDEMVGLFINTLPVRVRIDARPTSAWLAQLQMDLAQQEDYAHYPLADIQKFAGLPP

GVPLFESLLIFQNYPVEEALADALPGLRIGAFEVSDPNNYPLTLVVTPGKRLSLQVLY

DDGRFDRDTIVRLLRHVETLLTGLAGAEDRPNRSVPLLAAAERDAILLGWNDTFAPVP

SDRTLPELIEAVAAAHPERVAVRCGTEVRTYRDLVEGANRIAAHLLQTAFLQPDDRIA

VWMPRSPLMLETILAIWKCGAAYVPVDPAYPAQRVETILTLARPAVIVTTDCVPPPAL

ASIPLVDPARLPDRRGAEAPAPVTPRCRPADLAYVIFTSGSTGQPKGAMVEHRGMLNH

VLAMARRVGLGAQSAVAQTASHCSDISVWQCFAALASGGTTVIYPDAVILEPARLIDS

LHRDRITAMQFVPSYLATFLGELERHAAPAFPHLDTLLTIGETLQPATAQAWFRLNPA

VRLINAYGPTEASDSVAHYCLTRAPDGPAIPIGRPIENLRLYVVDADMNPCPAGVHGE

ICIGGVGVGRGYLFDEARTRAVFRDDPFSPEPGARLYRTGDIGCFGADGNLHFFGRRD

FQVKIRGYRIELGEIEAALTSLAGISHAVVVARETSDAEMTLCGYASGTGWTPQRVRD

ALRDTLPAHMVPDTVMLLPALPVMPNGKINRAALPLPDAASVPDGVRAEPRTPVEAAL

LRLFAEVLGRRENGVDDDFFEHGGQSLKAIQMVSRIPHAALNVAVADIFHAPTPRALA

QRLAAMPVDGAADDDAIIPALAAQPSYAVSRAQKRIWLASRGADPSTYNMAGALQLDG

AVDTARLVRAFDTLVDRHESLRTVFAMIEGELRQRVLSREASGFRVEQHDLADDAGFQ

AIDALIRAECEQPFDLASGPLFRVKLVRLSQEKHLLLLNMHHVISDAWSIRVLTDDLH

ALYAGRDLPPLSIQYRDYAAWHNASLAGPRAAAHRAYWLEQLAPPLPRLQLASDFPRP

ERLGHAGQTLEVELPQPHAAELATLARAHHTSLHAVLLASFCVLMHRYTGREDIVIGS

VSAGRDSEQLESQVGVYLNTVVLRVPVRKSATVAEVIDGVAKASAQALEHASYPFDVL

LEDLKIETPANHFPIFDIQVNHVSMPAPQPGLRITDISPADTTAKFDLSFQVVESEGR

HLIQFIYNTHLFRPSTIAAMRDRLLAIHDVFRRDPATPVDRIPLSDEAPAAGPRVRVG

LRLKRAPAVTADDALEEKT"

```
CDS complement(26061 . . . 29981)
    /note = "ORF7"
    /codon_start = 1
    /transl_table = 11
    /product = "putative nonribosomal peptide synthetase"
    /protein_id = "ACN32478.1"
    /db_xref = "GI: 224016445"
```

(SEQ ID NO: 13)

/translation = "MSELNLNALSTSGQYQEHVAFWNDALGRIDEDFRLQQAWQAYAL

PLGPEPALTFALDGDAAQVLERLAAGNELGAFVVLLAALFRVLGRYNGAAGLFVASPQ

LIVEPASGCAEPVPLLDAGEPGPTVRAYLNQLRDSVQRSYSYQDFPIAALAHKLHGER

RATNVGVRFDGLHEAWAAADYDLSIEIRHRERYEIVLTGRQTVFTLHYLQHVARHLRN

VVAGFGALDAPLDTVSLLDDEERARLRSHAAFVAVQGTFLEQFAQRVAAAPDSVAVVT

ADASLTYAELDDQASRLASFLLAEYAIERGDVVGVVADRSERWIVGMLGALKAGAVYL

PLDPEFPRERLRFMIEDAKVKALLTHSEHLPLLADFWAIPMFALDFQLDTLAPASASA

QVEVRPDDAAYIIYTSGSTGVPKGVVLEHAGLLNMAQYHVDAFGFDSADRFVQFYSPG

FDGSIMEIFVTLLAGARLVLAKTAVIRDVPRFVDYIAQQGVTTVNATPAYLAALDWHA

LGAVKRVISAGDSARVADLRELARTRTCHNSYGPTEATVCIADYVVDPAITYGARLPV

GRPIHNTHLYLLDEHGALAPEGCAGEICVSGIALARGYVGRDDLTAAAFVAHPFEAGE

RLYRTGDLGVWLPDGNLEVTGRRDTQVKIRGYRIEMGEIEAALRQHAGVADAIVFVRE

DTPQHKQLVACVATATASVASLREHLKERLPEFMVPASIVTLERLPLTPNGKPDRKAL

AALELAFAPSETAYVAPANDVEARLGRIWCDVLGREPIGVHDNFFELGGDSILIIQVM

SLAQQVGLKFTADQFFAHPTIAELAQVATEAPSIRIAQEPVVGPAPLTPIQHWFFAQD

VADPHHYNQSTMIEVPASLRPDTIERALAAVATHHDALRLSFACVAGVWQQSHAAPPL

AIPLGVTSLADAAPAARQAAMLATATGMQESFTLSAPPLLRAHLFQFGPDAPQRLLAV

AHHLVIDGVSWRILFEDLYTACRQLEAGDAVQLPARTTAWRDWSTRLSGLGATALDGL

GLDYWLQGNAGEPACFDDMPAGTVAEAGSTIVEFDAQQTLALLQDVPRAFNTQINEVL

LTALLLAFGDWTGNASLVVDLEGHGREDIFDGVDTSRTIGWFTTHYPVCLNAGDATVA

VDALRHVKEQLRAVPMRGLGYGIARYLGEDAGIAAALERQPPAPVRFNYLGQVDRVLP

DDTGWKPVLDFQSPEHSPRARRGHLFEIDGMVFDGRLRLTWHYNREACAPGVIEQLTQ

CYRSRLLSIVAAGGDGPRALSPSDFPAARISQEALDALVSRIKS"

```
CDS complement(29969 . . . 31585)
    /note = "ORF8"
    /codon_start = 1
    /transl_table = 11
    /product = "putative beta-lactamase domain protein"
    /protein_id = "ACN32488.1"
    /db_xref = "GI: 224016446"
```

(SEQ ID NO: 14)

/translation = "MTISSSAQVYLRQNIQFEPLINSWYAWYHTLPPLTAALNVAERF

LPLLKSYAASPMMHAAACKDPAMRGGPFLDLGGQRVDEIRTLIHQTTQRATRQLELAK

AYKAFSTLLLERATGMASDPLYPEIPEVLKGYVEIYYDLNHNPSFRVFESLLYASPFY

ARDAQSIALSAIEEHTPRPFILSTPRLRDERTVFSNMAFDDRALDTLFRMRDTFGSYA

KIVDLMRVEEKDEPLFRSFFVEEAPAPKPDRSFDGDDIRIRYYGHACVLIQSRGVSIL

IDPVISYGYDTALPRYTFADLPDQIDYVLITHSHHDHIVLETLLQLRHKVKTVVVGRN

LDGFPQDPSMELALRKLGFDDVLEVRDAQEIKVPGGAITAIPFMGEHNDLAIHSKQSF

MIRFGSRSVLCIADSCNLDPRLYEHVFRLAGKPDTLFVGMETEGAPPSWVYGPLFPKA

-continued
LPRDIDQSRRARGCQFGEAAALVDDFAFNAAYVYAMGQEPWLNHLLDNTFDENSPSHI

QSTQFVAHCKAKGIASEILYATREIVLCQN"

```
CDS complement(31596 . . . 45005)
    /note = "ORF9"
    /codon_start = 1
    /transl_table = 11
    /product = "putative beta-ketoacyl synthase nonribosomal
    peptide synthetase"
    /protein_id = "ACN32489.1"
    /dp_xref = "GI: 224016447"
```

(SEQ ID NO: 15)

/translation = "MNAKATHALKAALDELRLRRAEIAALRSDRNEPIAVIGMACRFP

GRSDTPDAFWQLLDGAHDAVTEVPGERWDIDRYYDPDPSTPGKMATRHGAFLERVDQF

DAAFFGIAPREATYLDPQQRLLLEVAWEALENAHLAPERFRQSATGVYVGITCFDHAI

QVSNASMPSSSYAGTGSALNMAAGRLSFVLGLTGPSMAIDTACSSSLVCLHLACESLR

SRESNMALAGGVNLMLSPEVMVSFSQARMLSPDGRCKTFDAAADGYVRGEGCGMVVLK

RLADALADGDRVLGIVRGTAVDQGGAGGGLTVPSRDSQERVIRRALNQAGLAPGDVSY

VEAHGTGTSLGDPIEVEALAGVYGPGRAANEPLVIGSVKTNIGHLESASGIAGLIKVL

LSFEHDRIPAHLHFTQPNPHTPWQDIPIRVAADPVAWRRGERRIAGVSAFGFSGTNA

HAIVEEPPVAPAHAAQRALLLLSARSEAALAALVPRYERAIAGATPQELAAICRAAAT

GRSHYPFRAAYVSGARVASAAAPRTGKALRMGFGFGVPDTGVAHALHASEPLFRDAFA

RCSVPLDALETDAGRFAIQFAWAELWKGWGLRPAVVSGHGIGEYVAACVAGVVSVADA

LRLVAARSDAEALRAVLRDMPLARPSVRLISGYLGTDVTDEVTHPQYWLQLAGASDQA

DASHPPEGLADGWLPPPCAGDALERALAALYVQGAQFDWRALFPAPAQPATTLPNYPF

ERQRFSLEKIPSPIVGMDAGSIDAALRHLKSSGKYPEDMLNAFPDLLRTAFAAAETVA

SNAHPLYHVVWEQQAAMPAAPAAADASPWLIFADASGVGERLAALLRARGASCSLVRP

GIDYVTGAEAGWQVAPERPDDFVRLLNETAASGQRIVFLWALDEAVGETRMSAALLHL

VHALVGSEREWTPSTRPRISVVTRDAVEAGEAPHVSGLAQAALSGLARGAMIEHPEWF

GTAIDLDPAAPENETQALLQEMLGESREEQVALRHGARHVARLSPLAPAETAALPVDP

DAAYLITGGFGALGLHTARWLAARGAGTLILVGRQGAASDESQRAIAELRERNVTLRC

ERLDIADPAAVAAFFAALRRDGVPLKGIVHAAGIVGYKPIMQVERDELDAVLQPKVAG

AWLLHQQSEHFPLDFFLLFSSIASAWGSREQAHYSAANRFLDALAHHRRGQGLPALSV

NWGPWAEGGMTFPEAEALLRRVGIRSLAADRALDVLNRLPAVPQVAVVDIDLALFQGS

YEARGPKPFLDHVRVAKSAPSAPAMPALSDASPRERKRLLADSIDRAVAQVLGYDAGT

LDRDLGFFEMGMDSLMALDVRTHLENALGIPLSVALLFDHPTVNALADFLAEQASGTA

QAQTVPPQQQPRPIAPAIEARDAGTPEPIAIVGMSCRFPGAAHDLDAYWNLLNDGVDA

ISEVPRERWDVDAYYDPDPEAPGRMYSRFGGFLDDVDQFDPAFFRITPREAAAMDPQQ

RLLLEVSHEALEHAGIPVDSLKGSRTGVFVGITTNDYANLQLRNGGGSGIDGYFFTGN

PLNTAAGRISYGLGVQGPSMAIDTACSSSLTAIHTASQNLRSGECDLAIAGGVNLILS

PDNSIAVSRTRALAPDGRCKTFDAAADGFVRSEGCGALVLKRLSDALAAGDRVLAVLR

GSAVNHDGASSGFTAPNGRAQEAVIRQALGGLPAASIDYVEAHGTGTPLGDPVELQAL

ATVFGAGRDAGRRLRVGSVKTNIGHTESAAGIAGVIKVVLSLNHDRLPAHLHFRQPSP

LVQWDAMPVEICAEASAWPRGERPRRAGVSAFGASGTNAHLVLEEAPAPARQATPSRH

KVHPLVLSAKTPAALRELAGRYQRRLEAEPGLDIAAVAFSAATGRSHFAHRLAWPVTS

LDDAIDKLRAFHAKEPAGAAQPAPRVKMAFLFTGQGSQYAGMGRRLYDAYPVFRDAID

-continued

RCRAVADPLLDKPLLEVLSAQGEDIHQTGYSQPALFSLQYALTTLLASFGVVPDAVMG

HSVGEYAAACAAGVFSPEDGLRLIAERGRLMQALPRDGEMAAIFTDLATVERAIDAW

HEVAVAAVNGPASIVISGKRERIAMLVDAFAARDIRSVPLNTSHAFHSPLLEPMLDSF

QLAAKTVPVARPAIPFYSNLTGAVMDEAPTDTYWRRHCREPVQFASSVERLAEAGFNV

LVEIGPKPVLVNLARACCAPDAGIQFLALQRPQVEQQALIETLSSLYARGVDVDWAPT

ETPAPARIALPSYPFQRSRTWFQKADTSMTQTSASPIAAAPTHNRSGEILEWLRGKIG

ELIQADPATINIELPFLEMGADSIVLIEAIRHIEAEYGVKLAMRRFFEDLATVQALAE

YVADNLPAAAAPSGAEAVAVAVAAAEPSTPAVAVTPSAAGLAPLAAAPAEWVAAEGGS

TVERVLREQNQLLSHVMSQQMELLRTSLTGQPGVRPATAAVQAVASTASVAPKAASAA

PAAAPAAKPAPAAAAAPAADNPPPKPMMPWGSPVQQRARGLSAAQQEHLEALIVRYTT

RTRKSKDSVQASRPVLADSRATVGFRFSTKEMLYPIVGDRAAGSRLWDIDGNEYIDFT

MGFGVHLFGHTPDFIQQQVTREWQRPLELGARSSLVGEVAARFARVTGLDRVAFSNTG

TEAVMTAMRLARAVTGRDKIVMFTHSYHGHADGTLAAANAEGVTETIAPGVPFGSVEN

MILLDYGSDAALEAIRGMASTLAAVMVEPVQSRNPSLQPVAFLKELRRITEEAGVALI

FDEMITGFRVHPGGSQAMFGIRADLATYGKIIGGGLPLGVIAGTSRFMDAIDGGMWTY

GDHSFPAADRTAFGGTFCQYPLAMAAALAVLEKIEQEGPALQAALNERTAQIAGTLNA

FFAEAEAPIKVTWFGSMFRFEFTENLDLFFYHMLEKGIYIWEWRTCFLSTAHTDADID

RFIRAVKDSVADLRRGGFIRPHSKHGTVAALSEAQRQLWVLSEIDPEGSLAYNVNTTL

ELNGRLDEAAMRAAVQSLVDRHEALRTTVMADGSGQIVHPSLTLEIPLIDTDPNAWRE

QESRQPFDLVNGPLFRAALVRLGSERHLLVMTAHHIICDGSTFGVLLEDLARAYAGAA

PADAPLQFRAYLKQLDGQRHSPETKANREYWLAQCARQAAPLNLPVDYPRPAVKTFHG

ERVSLHLDAATAATLRTAARQNGCTLYMVLLAGFNLFLHRVAGQQEIVTGIPVTGRSV

AGSDRLAGYCTHLLPLHSTLPEQATVASFLAGTRQNLLDALEHQDYPFAELVREIGAQ

RDLNAAPLVSAVFNLEPVSALPELPGLTVGLVAPLIRHTAFDLNVNVLDAGQALLIDC

DYNTDLFDASTVQRFLDIYRTLLTHLADDASAAVARLPLSSDAERNLLTVEWNRTDTD

FGEDAAQPLHRLFEQQVERTPDAVAIVFDDTALTYAELNLRANRLAHHLVALGVGPDS

LVGVAMERSLDMSVALLAILKAGGAYVPVDPDYPAERVRFMIDHAQLRWLLTQQHLHD

ALPDTDAHVIVVDRDSLDLDAAATSNPAPALNGDNLAYMIYTSGSTGRPKGALNTHRA

ITNRILWMQHAYALGADDAVLQKTPFSFDVSVWELFWPLVTGARLVFARPGGQRETDY

LVELIERERITTIHFVPSMLRAFLDHPDLDAHCASLRRVVCSGEALPHDLQQRCLERL

DVELYNLYGPTEAAVDVTAWECRRDDPHRIVPIGRPIANTRLYIVDAQMQPTPIGVAG

ELLIGGTPVGRGYHGEPELSAEKFIADPFSADFLARLYRTGDLARYRPDGNIEFLGRI

DHQIKLRGLRIEPGEIEAALTSHPLVDAAVVALRGVDDGARLVGWLCSSHPEAELIEA

VRGHLRQRLPDYMVPSAFVVVSAFEHLPNGKLDRTRLPEPGDGLDHVAPVNALEAQLA

AIWQEVLGQARISTTGNFFDLGGNSLLATKVVARIRRDLHVKLEIRSLFALPTISSLA

KRIADTQPIDYAPVTPLPAQASYALSPAQTRLWVQDRLHAAQAEGPLPTSLLFEGVLD

VDALVRAFRALSERHEILRTRFVLEGNQPVQHVLPPGEAAFPVEIVDLQDAEDRDAQA

AAIQASERLVPMDLATGPLFRVKLLRLSEVRHVCLCTMHHIVSDGWSTEVLLDDLSAL

YDAFVQRRDDPLPALPIQYKDYAGWLNRLLAGPDGARMKDYWLTKLGGGLRALELPGD

VEQPAAPSWKSWRFDLPAAETAALESLGKRHGATLFIALLSAIKALFYRRSGQEDIVV

-continued

GTPVAGRELPELESQVGPYLNVLALRDRVAGDDRFDTLLTRVRDTTLEAFSHPLYPLD

RLLDELHIKRVAGRNPLFDIGLTLQNQRHGPVDRYAGQVHIAELPDHDPQRADTEAAT

DFWFLAEPHAEGLAIRVVYHAGRFSEALVQGLANELTSVIGEVLANPGVRIRNLTLGQ

RALHAEARQPTVELSAF"

```
CDS complement(45002 . . . 48325)
    /note = "ORF10"
    /codon_start = 1
    /transl_table = 11
    /product = "putative short chain dehydrogenase/reductase
    SDR"
    /protein_id = "ACT64845.1"
    /dp_xref = "GI: 314954101"
```

(SEQ ID NO: 16)

/translation = "MKFGLMFFASSEEALSGNKYQLVMESARFADANGFSSVWVPERH

FTEFGSLYPNPAVLHAALAAATQRVKLVAGSVVAALHNPIRIAEEWSMVDNLSNGRVG

VSFASGWNPDDFVFAPDKYATRQDDMLTTMRAVQHLWRGGTLDATNGVGKPVRLRVYP

TPVQPELPVWVTAASNPQTFVRAGEAGANLLTHVLDQDRDQLAHKIALYREARAKHGF

DPAAGTVSVMLHTFVGDDAAQAREQARVPFCNYIRSNIGLLNGLAQSRGQSVDVRAMG

ARELDEFVEFLYERFAQSRGLIGTPETCVELVRDLESIGVDEVACLLDFGPPVERILG

NLPQLRRLREMCAPRRSAAPTRFDAAEVQARCTETTSGADFNGEIRQHGVQIDGVFDA

IRQIWRTTGEALGKISLPADALASSPYQVHPAFLDACSRVLAAAIDPDALESGDLYLP

SSIGAVRVHQPPASTEAWSHATLRTPIGQGALEGDIRVHDLAGRLLIEIDALRLQQVR

AARAVERHDFAALLYQRVWRPSNVDAATGGSAHGEWLILADRGGVGAQLSALLEAHGD

TCTLRFADATPELPAADRPLKGVIHLWSLDLAPSDIAARRRASASVLHLVRALASRAP

SARQARLWLVTSGAMNVLDGESIAVAQAPLWGLGRAIAVEHAALWGGLVDLDPEQPSA

ADIMQAVQAGGREDMIAFRRDQHYVARIARDNREYVSHRPIRFHGDATYLVTGGLGGL

GLRLASWLADNGAGKIVLLGRGEPSAAAGKILRTLDARFIRADLSRREDVGQALGEIA

HSMPPLKGIFHLAGALDDALLTRQDDDFFHRAGSGKADGAWYLHELTAGLPLDHFVLF

SSMAALITMFGQGNYAAANSFLDALAQHRRAQGKPGLSVNWGFWAEIGHAATDYGRRA

HEQLGALGVGTLPPELAIATLERLMASGVAQSGVARIDWPTLFRVDAPAAGSALFSEL

TQPAAQPAQQETALLRQLHACAPRERVERITDTLAAMLAETLRLSGPDAIAPEQSLLD

LGLDSLVALELTDRLTKVFGRPFRATLFFSYPNLQTLAQYVLNELSPSLPAPVVDEAS

DDLDEDDLSELIAQEIGAQ"

```
CDS complement(48322 . . . 52749)
    /note = "ORF11"
    /codon_start = 1
    /transl_table = 11
    /product = "putative beta-ketoacyl synthetase"
    /protein_id = "ADT64846.1"
    /db_xref = "GI: 314954102"
```

(SEQ ID NO: 17)

/translation = "MLPDTKERTVTEILLFRGKVEPEKTAFIFLENGEAELTRLTFGD

LDKRARGIAARLQAIAQPGDRVLLVYPPGLEFICAWVGCLYAGLIGVPAYPPRRHRPA

DRLKAIVADATPVVALTDAATLDGIAHHADGYSDTLELKILATDQRFDAPAEQWRAPD

ITPQTLALLQYTSGSTGTPKGVMISHANILSNMAVIAEASDADASTVFVSWLPVFHDM

GFFGKVLLPIYLGVLSVLMAPAAFVQKPVRWLQAITKYRGTHCAAPDFAYDLCARKIA

DEARAQLDLSSWRVAFNGAEPVRAESVARFSRAFAACGFHAHTMRPVYGMAEATLFIS

GQPARSLPRVADYDADALAQGVATRNDSGKRHALVSCGRTWAEHRVRIVNPDTGERCA

-continued

PGRIGEIWLTGPSVGVGYWNRIDETERTFRAKLDGDDARYLRTGDLGFVDGEDLFVTG

RLKDLIIVAGRNHYPQDLEQSAEGSHPALAPNASAAFSIHVDNVERVVVACEVRREAL

NTLDAEAVAAEIRHTLAEVHDVDLYAAVLLKPATILRTSSGKIQRSRIRQAFLDEQGL

AIAGEWRRAFSAPPAPPQTAEPRDTQALVQWCIERVSRLSGIASGKIDPDAPFSVHGL

DSKDAIMLSGELQDWLGRPVSPTVVYDFPSISLLARHLSGTGSAMPDQAPGSAEARAD

IAIVGMGCRFPGAGNPDAFWQLLLEGRDAVGAATQRAADLPLAGLLDQVDQFDAAFFG

ISAREAESMDPQQRLLLEVAWETLEHAGIAPRSLAGGRTAVIVGISNSDYIRLAQDEV

ADVGPYVATGNALSVAANRISYALDLRGPSWAVDTACSSSLVAVHQACRALQRGESDA

ALAGGVNLILAPQLSASFTQAGMLSPDGRCKAFDAAANGYVRGEGVGMVLLKRLDDAL

ENGDTVFAVIRGSAVNQDGRSNGLTAPNGPAQQAVIHGALRDAGVRAQDIGFVETHGT

GTPLGDPIELNSLAAVLNESRRPDDLCWIGSVKTNIGHLESAAGIASLIKTALALHHR

AIPPNLHFRSINPQIALDGTPFRIPRQVTPWNSEHGPRLAGVSSFGFGGTNAHLILSE

APGLPEIEAEPVAPAARVVTLSARTPDALQALAASYAAYLDAHPEAGVRDVAFTANTG

RTHFTQRAAIVAPSRDSLRAQLDSVSSGEPAETPPAVTFHFCADDGASADAVRQLRAA

SPAFDALMQRQSDASGAPALAPDEAGFTRFQRALAQLWMSFGIAPDAVSSTGDGQRAA

AAWAGVPQAPDSGAAGHPGIVIDIGAHTAAWDAILHTLAALYVRGASIDWDAVEQGAP

HRRLALPTYPFERRGFWIRPHARRHPLLGRLMEQHAHAPATWIWQSRLDAPATNFLDG

HRVKGSPVLPYSAFVEMALSATSEIGAAGHTTLKDLALHAPLPLHPHESHTVQTVLSR

RSWGPFSFAVYHRIDDTRAAATWQMCASAEIHESDRSHA"

```
CDS complement (52936 . . . 53922)
    /note = "ORF12"
    /codon_start = 1
    /transl_table = 11
    /product = "putative taurine catabolism dioxygenase"
    /protein_id = "ADT64847.1"
    /db_xref = "GI: 314954103"
```

(SEQ ID NO: 18)

/translation = "MEGMTERKLLAEGSTPWLLEPVSNGRDLAQAVNDNRAALESRLL

EHGVLLFRGEDVSSVGGFEAFARAISAHQSDYVYRSTPRTSIGNGIFTATEYPPSETI

ALHCENAYQRSWPLRVAFCCLTPAATGGETPIADMREVSRRIGPRILDHFEARQVRYV

RHYRRHVDIPWETVFQTSDRNQVAAFCADNGIALEWLDDDTLRTAQINQGVAYHPVTG

ERVFFNQAHLFHISNLEASLASSIVSLFGEDRIPRNACHGDGSPFDLADLEQIRHAFR

ECAITFPWQRGDVLLVDNMRFAHGRNPFEGERKVVVSLLDPYTPDIEGIADR"

```
CDS complement (53999 . . . 55369)
    /note = "ORF13"
    /codon_start = 1
    /transl_table = 11
    /product = "putative transaminase"
    /protein_id = "ADT64848.1"
    /db_xref = "GI: 314954104"
```

(SEQ ID NO: 19)

/translation = "MKRFSCASVHQSALQAGSARMEKLEYLKQVESNARTYATSFPRL

FTHAKGIRVRDADGQEYIDCLSNAGTLALGHNHPEVNEAVMRFLSSDQMQQALDLATP

AKHAFVEQLFSLLPGKIAESGKIQFCSPSGADGVEAAIKLTRHYTGRPTIMAFHGAYH

GMTSGALAASGNLTPKSAGGNGRDVHFLPYPYAFRCPFGTDGSATDQLSINYIRTVLS

DPESGITKPAAIIVEVVQGEGGCIPAPDTWLIELRELTLRHEIPLIVDEVQTGLGRTG

ALFAIEHSGIRPDVLVLSKAFGGGYPLSVVVYDERLDTWPPGAHAGTFRGNQIAMVAG

LSTMRIVEREDLSAHADRVGKLLVAGLEELAERFPCLGQIRGRGLMIGAEVVVPGTHG

RAGPPHTERARAIKQNCLRNGLIVETGGRNGAVLRFLPPLIVSEADIHDILNRFEHAV

ETACRA"

```
CDS complement (55516 . . . 56466)
    /note = "ORF14"
    /codon_start = 1
    /transl_table = 11
    /product = "putative epemerase/dehydratase"
    /protein_id = "ADT64849.1"
    /db_xref = "GI: 314954105"
```

(SEQ ID NO: 20)

/translation = "MQRNRKRILVTGGAGFLGSHLCERLVELGHDVLCVDNYFTGTKQ

NVATLLGNPSFEALRHDVTFPLYVEVDEIYNLACPASPIHYQFDPVQTTKTSVMGAIN

MLGLAKRTHARVLQTSTSEVYGDPDVHPQPESYRGNVNPLGPRACYDEGKRCAETLFF

DYHRQQNVRIKVVRIFNTYGPRMHPNDGRVVSNFIVQALRGEDITLYGDGSQTRAFCY

VDDMVDGLIRMMATPAELTGPINLGNPHEIAVSELAQIILRLTGSKSRLVFRPLPKDD

PTQRCPDISLARTHLDWEPTIGLEAGLQRTIDYFCSTLAA"

```
CDS complement (56622 . . . 57341)
    /note = "ORF15"
    /codon_start = 1
    /transl_table = 11
    /product = "putative thioesterase"
    /protein_id = "ADT64850.1"
    /db_xref = "GI: 314954106"
```

(SEQ ID NO: 21)

/translation = "MRLICFPYAGGSAAVYRTLQASLPGIEVCRHELAGRGSRLSEPA

VRDMATLVDTLLCDLDDCFDRPFALLGHSMGAAIAAELALRLPAHARPNLRHLFVSAR

AAPGKERHDRRMQALDDRAFIDALREMGGTPKAVLDNSELMALLMPALRADFTMIENH

RPVPGPRLAVDITAFAGRADKEIPVDAVAGWGAATTGRFDFHVIEGDHFFLRNEMRTM

AGIIAARMRRPEHAASSALQA"

```
CDS 57710 . . . 57997
    /note = "ORF16"
    /codon_start = 1
    /transl_table = 11
    /product = "hypothetical protein"
    /protein_id = "ADT64851.1"
    /db_xref = "GI: 314954107"
```

(SEQ ID NO: 22)

/translation = "MQHRQKAVPTQQVANERVIVTEWRFAPGAETGWHVHRHDYVVVP
QTDGQLLLETAQGNRESQLHAGRSYAGLKGVEHNVVNATDHEVVFVEVEIL"

ORIGIN (SEQ ID NO: 23)

```
  1 aattcctgca gcacggtgcg cgaccagccc cagatgtccc cgctgagcgt gagtgcgaga
 61 ccggccgtcg tgatggccag ctgcgtctgg ccgaacagcg gcgtcaatgc gccttcgccg
121 ccgatcacga tccgcttgac gagatccgag atggactgcg agatcgaatc ggagaacgga
181 tagttgtacg gctgcgtgac ggcgcgcgac aggaacggct tgctgggcgt cggcgtccag
241 accttgagcc acggcttggt cgtgaacggg aaccagatgg cttccacccg gcccgagccg
301 tcgagaaacg atgcgatcgt gcggccgtc gtgccgggcg cggcgaacga ttcggaggcc
361 ggaatatcga cgtagctctg gcagcgtagc cgctggttcg gccctgccgt cagcgtgact
421 tcgacgacga gcgctcgccc gatgtgcgcg aggaacgcgc cgatctcggg atcgctgcgc
481 tcgaaccggc gcagcacgta ttgctgccgg gccggatcga acacgaccgc cgtgagcgcg
541 accacgagat tgctcagcga gccgtaggta tggcccggtt gcaaggtttc accggccgcg
601 ggcacggcgg tgccgtgtgc atcgatcgcg agcgcgccgc cgagcgtgat gtcgcccggt
```

-continued

```
 661 gccggcgcgg caatcacgcc gaggccaacc tgctcgagcg tcgcgagcag cgactccagc
 721 gagacgcccg tttgggcggt gacgcgcgcc ggacgcgccg acgtgtcgac ggagacggcc
 781 gtcagcgact tcgtcgtatc gagcagcacg aggttcgcgg cgccggcgcc cgggtccagc
 841 gtcagcggcg accagttgtg cgtgtagccg cgcgggcgta tccgatagcc gtttgcgcgc
 901 gcccagttga cggttgcgac gacgtcgtcg gcggagcgcg gcgcggcggt ccatacgtcc
 961 tgcacggcga tctcgccgct ccagttcagg aacgcctgct tgtaaagctg gatgtcggcc
1021 gggaagccgg gcggtgtctc gccggccgtt cgcgcgtgcg ccgcaacctg gtagagcggt
1081 gtccagccgg tgacgatgcc ggccgccgcg agcttcgcca tgtcggccag gaaggcgcga
1141 cgcggcgcag gttcgtctct gaagtcgtga ctcatggtgt gctccaattt ttcggaattg
1201 ttttgcagat tggaaagacg acaaatgacg cgttgagact cgtgtggcaa ttcgagcagg
1261 tgcgacgcgc gggaagtgtt gcgcgtgggt gggccaggat tgaaaaaaga cggtgcgttc
1321 ggcaatgcgc ggccgcacat catcacggac gtctaatagg aaatcggaaa accgcctggc
1381 gattgcttta attggccgtc ggccggttct gtcggcaagc agatagggag attcgacgga
1441 atcgcgcgcg gcgaagcgct agccgtggcg atcgataaaa gatgatttca cgtgaatatt
1501 aatcttcatg tttcgatttt taaataaacc cggccgcagt tcaaggttga ttgacgatgc
1561 gtcatgcatt tcggtcgaaa gcgtagcaat ttatctatcg ggtgacaagc ggcggagttg
1621 acgaattccg agtcatttaa tatggaaatt ttatgacggg aaatggcttc gtccgttgtg
1681 ggtattttgc aacgcggctg ccggtgtcgc gccacgtggg cttggagcgc aaattatgct
1741 ttgccgtcgc gtatattgaa tcgattgttg agcgaatcga ataacgtcc ggaagacaat
1801 agctgaagcc gggtcgatga gcgggaggta gggtgaaatc cgataattcc tctctcgaat
1861 aacgctcctg gatgaaaatt cgtggtatgc gtcgcccggg tgattattac aaaagttcgt
1921 ggtaaacgga tgtcgattta tcggtgtatt cataataatg ccaatgagcg gctcgcgaat
1981 tgattgattt ccggttcgtg aaagatgtgt tttaaaaaaa tagatgtcgg gctgactgca
2041 aatgtctgaa tcgtcgctat catacgcggc tgggatatac atggatcaaa ttcaatggaa
2101 agaatcgttt cgcttttga tcgcgatttt tctttgaatt cgccgggaac gcgcccgctt
2161 cgagccggcg ccgggttttc cgattcaggt ttcaggcacg tccggcggcg gcgcgttttc
2221 atccggcaac gcgaatcggc cgaaatggac gtttcagcct tttgcggctt cgcgagtcgc
2281 ccgcatcggg ctgaactggg aacggcacgc cgtcgtctcg catgagccgg acgcatcggc
2341 gcgcgctggc ggcggcgcgt tgcccgcctg aaaaaggcgc gcgacgcagc gcgacccgac
2401 gcgcgccgcg caaaccgtgc cggttcgccg gcgcttgcgt tgtgccaggt cctcaagcac
2461 gcacaacaag gagagtcaga tgttcgcgaa gctcgggaag gtgatttcga gcgcaggcag
2521 tgagcggttc gcatccgaca tgcatgcatt gctggtcgag tcgattccgc tcacgatcac
2581 ccggatgact gaatggacgc tcgacgagcc ggcgggcgaa gtcgtccgcg tgcaatcgct
2641 cggcgcggac ggcgcgccgg gcgatgacgg gcgcggcgcg ccggccgcgc acggcgagcg
2701 ggaaccggca gcgcatccgc cgttgaaccg gatcctggcg gcctgcgacc ggcagctcat
2761 tcacatcaat ccgctgatgc ggcgcggcaa tggcggcgaa gtcgcgccgt cgcgcgggcc
2821 gggcggcgga tttcagtgcc atctcgtgtc gggcaaggcg aatcgccgtt acgtgatctc
2881 gctgcatcgc acggcatcgc atcgcgactt ctcgttgcgt gagatgtcgt tcctgaagaa
2941 tttcgccgat acgctgctgc cgctcgtcga gtggcatgcg tcgacgtgcc ggcacggcga
3001 gcgggaaggt gcgacggcac ccggtgcgac ggcaggcatg cccggcgtcg aggcgctgcg
```

-continued

```
3061 ccacgagttc gaatcgcggc tcgcgcgcgc gagggtcgtg ttgtcggcgc gtgaaaacga
3121 agtgtgcctc ggcctgctcg cgggcaagat gctgcgcgaa atggccggcg agctcggtgt
3181 gaaggagagc acgatcgaga cgtacatcaa gcgagccgcg gtgaagctcg gcatcagcgg
3241 ccggcacggg ctcacgaaat ggatgatcga cgattccgta ccgtgcgcgt cggcggcgtg
3301 acaccgtcac gccatcacgc cgcggacgcg cgacgcatgc cgccgggcat gcgcgttcgg
3361 gccgcgggcc ctcaggttcc gaggcgcggc gacgcgtagt cgcgccgcat gcttctcatg
3421 tcgcccccag cagcttccgt cgcggccccg gccgtctcgt cgagcatcca gcgcgtcagg
3481 ccatgacgcc cgctgaagcc cagcttgacg gccgcccgct tcaggtaggt ttcgacggtg
3541 ctttcgcgca gcgcgaagcg catggcgatg gcaggcaccg tgtcaccggc caggagtgcc
3601 gtgcatgcct cgatctcgcg cgtcgacagc ttgacgcccg cttgctgcag gcgatcggcg
3661 aatcgccgcg ccacgcgctc ccggcccgat tgcgtcgccg gcggcgcggc ggtcgtcaca
3721 cgagcggccg gcggagccga atcgagcgcc gcgacatggc tctcgacgat cggaaacagc
3781 acgtgcgaga gttccttgag gaaggtccgc tcctgcggcg agaaatcgtc gaacgtacag
3841 gtgcgataca acgagatcac gtaacagtgg ccccgcttgc gggtcacgag gtggaattgc
3901 gcgtagcgcg gcgacacgat cgccgcctgc atgaggatga agcggtcgag ctgcgcgtgg
3961 atcgggccgt ggccggcgag cgtgtcgtcg acgtgcaggg ggctcgtgcc cgggcgcggc
4021 ggcatctgcg gcccgcaaca gacagcggcc gcgccggtct tcgcgagcgc cgcgccgacc
4081 gcgccgaggc tgcgcacctc gggagggccg tccggcacgt cgtcgatcgc aagctccgaa
4141 atgcggatct cgtcgacggg gaccgccgcg gcgatcaggt tgtacatcat ccggggaaaa
4201 cgtcggctcc cgctgctcga gatcgcttcg ccgacgtgtg cgaacaatct gctgaactcc
4261 atgaagggat tcctgatgag acgttgaagc tgcgcttgtg cgcatgaatg ccgacatgat
4321 ttaaacaccc ggttgcgaac gcgtctgtaa cggattgccg ggacagacgc aacattgccg
4381 gccgtcgaag ccggtacggc gcacgcgac cgttgcgccc gtctgcgacg gatggcgcgc
4441 accttgtccg agtccggatc gctgctcatc cggctgcctc ggcccggacg gcacacatgg
4501 ccgtatcgga gaagatgcgg ccgctatcca ggcgaatgac ccgatccgcc agcttgaagt
4561 actgatcgtc gtgggtgatg atgacaacgc atttcccgcg tgatttcaga tcgggaacca
4621 gcacttcata ggaaaatcgc ttgaacaccg gatcctgatc ggcggcccat tcgtccagga
4681 tataaatcgg acgatcctcg atgtacgcgc aaagcagcgc caagcgcttg cgttgccctg
4741 tcgataacgc gcggtggtc gagtaggtcc ggccggaaat ctcgatcttg tccgccagtt
4801 tcagggtggc gaggtatttc cgggcaagct cgatgctttc attgccccga tccggtccga
4861 tgatgcgatt gaacaaatgg aaatcggtga agacggcgga aaacaggttt cggtagcgtt
4921 ccctcgcagc gtcgtcaacg acttttccgt cgagggaaat cgtgccgccg gtaggcgcat
4981 agaggccgct gaggaccttg ccaagcgtgc tcttgccgct gccgtttccg ccgatcacgt
5041 agacgagttc tccggcatga atcgtcatgt cgatggggcc gagcacgaag tcgaccgatg
5101 cttcattgtc acggtagttc atcgtcacgt ctttcaactc gatgaccttc catgacttgg
5161 ccgacagggt ttccacgttg cccgcagggc gcggttcctc gtgtgaggcc tgcgtgtcgt
5221 cgatcagaaa gccgaattcc gccagccggg cgagcgcggt cttgccttcg gccaccaccg
5281 gcagaacatt gatcagcatg gtcaagggcc ccatcatgta gagcacggcc agaatgctcg
5341 ccgtgagtac ggagggatcc acgacgccca gagaaggtac gccgaacagc aggcatccga
5401 gcaggaccgc tacggtgatc tggccgatgc tgtcgccgct catgaaccag aagcgttcta
5461 tgtaattgaa tcccgccacg cgcttcgacg acaattcgat cgcggcgcgg gtaaaccagc
```

```
-continued 5521  gtcgcctggc ccggttgagc ttgagctcct tgatgccgaa cacgaggcca tgtgtgtatt
5581  cgttgaactg gacgaattca tcgcgaaccc gctccgtaaa attgaccgcc ttccgataga
5641  aaaacagata aagcaccagg ccgacgaggg tcaggatgat cgtcgacgcg aacacgatcc
5701  acgagagata ggcgagatag gcgatgctgc agatcaggac gactgattga acgatgatcg
5761  tcgggatggt cagcagggtc tggctcagtt gcggaatgtc ctgtgtcagc atggtcagca
5821  cattgggggc gccgcgtctg tcgatttcat ccagcggggt tgccaggatc cgtttgcaca
5881  ggttgacgcg caacctcgtc atgactttca tgcaggcata ggagggcatc acggcggcgc
5941  agctcctgca gaccaccgcg acgacattca ccgcgatgaa cagcagcaac agcgtctggc
6001  gatcatcctg gtcgtgcagc acggtgctga tcaacccgac gcccgcgatc gacgcgatgc
6061  cgctgacgag gcccgtcacg accgtgccca gcgtcagcca gggatgactg cgccacatca
6121  gggtggcggc ggaatgccat ggcggcgatt tgctttgagc ggaatccatg agtggccaat
6181  aggtctcagt tgatcaggtg gctgagttcg acattgcttg ccgctgatct caacctcgac
6241  gaggtttcgt gcttgcccag gaacgtgatg ctttccacga ttcccagcgg cgaatcggaa
6301  aacaggatgc agcacttcag caggcgctgc gcacgctccc agccgacgcc gtccggtgaa
6361  tcggccacgc ttcgcaacgc ggcctcgacc gaggcggccg tccagtcttc gctccgtgcc
6421  agccccgact cgatctgccg aagaaattgc aggagcgtgc ggggattgct ttcgatgctg
6481  tacatgagga tgtaatcgat ccgcagtttc ttcgtgatca gcggaaaaat caggtcgatc
6541  acgccggcgg tcgattcgca tttcccatat gccagtgaaa tcgcgtcgcc gagcttgcag
6601  tcccggtgaa gcgcatccag cgcggccttg acgaacgccg cttcgaggtc aacggtggtg
6661  agttgcatga tgttcagtgg cctgtcgagt gttggatcgc ggcgagcacg ggcggcaggc
6721  gttaccagcc gtccggaatg ggcatggaat aggtcagcgg cttctccggc atcacttcgt
6781  ccatgatgtc ggagtagccg gactcctgtc cgaccagatt cggctcgaag cagtagcaat
6841  tgaacgtctg ctgcaggacg aggttgttgc ggtcgttgat cgccggcggg ttttcgttga
6901  tcgcgatgaa tgcgtcgtaa agcgagttcc tgacgacgta cgcgtgcgcg gtgagcgtct
6961  ccacggcctt gacgatgttc ggcgcgacgg gaatcggcgg cgtgaagtga tacgcgccca
7021  ggaacagcat gtgccagtcg tccggcactt gcgcgatgaa ctcgggaaag cgcgcggcga
7081  aatcggcgtc gaagaacgcg tcgtcctcga agatcaggac ttctctcgca ccggcggcct
7141  tcgcctgtttt caccgcggcg agatggctca tcgtgcagcc gtagtcctgc gcacgcatat
7201  ggctcaacga ttccggcacg ctcaccagcc ttgcatcgac ggcaggcagc cgttccaccg
7261  tgaggatgtt ctgctctgcg aattttcgtt gcatcgcttc ccagcggtcg gggcgccggt
7321  ccaggttgat gcagaccttg cgggcaaaag tattgtcgat cgtcggcgtt gatttcatga
7381  gggcgttttt tccagaaacg aattgacatg gcggcgagg acaccggcat gcggatcgag
7441  cagcatggtc aggtggtcgc cggggacgtc cgtcaccgcg acggggtgcg ccgagaagcg
7501  agaccatccc caggtcgcgt ccaggcgaag ctgcgcgatc tcggacgacg gcgcgtagtc
7561  gccgggatcg cgctcggtgc tgcggaacaa cgcgatcggc acgggcagcg gggtggcgtg
7621  cggcgcgtag tgcgacttga agttggcctg atagacgcgc aggtaggcgc gcaggcggtc
7681  ggacccggcg tccgcgaacc agctgccgcg gtcgccgatc cgttcgagga tcaggccggc
7741  ctggccgtcg ggatcgagat ggacgaggtc cgctcgcgtc acctgaaggt cggtcccgag
7801  gaaggtgccg atttcgtggg cgatcgcgac cagccattcg gtgtcgtccc agtcctgcca
7861  gtaagtggcg gccgagctgt cgatgggcgc ggacgcgtcg aagatcgcca gcaatttcac
```

```
7921  gtcggcgccc ttggcgacca gttgcctgct catttcgagc gccacgtgcg cgccgaacga 7981  gtggcccgcc aggtagtacg gacccgcgcc caccagcggc cagatgcgtt cgatatgacg 8041  ggccgcgatg tcttccacgc gggtgagcgg ctcgcacgcg ccgtcgaggc cgagcgcttc 8101  cagcccgtga atcgcgtgag cgccgctcag gtggttcgcg agcgggcgga agtagaccac 8161  gttcccgccg gcgcccggca gcaggaagag cggcgcggcg gggccgccgt cgcgaatcgg 8221  cacgagcccg ccggcgggcg cggacggttc tttcgcggcc agcgccgccg ccagtttctc 8281  gatcgtcgga ttctcgaaga gacaggaaat cggcagcctg cgatcgaacg ccttctcgac 8341  atgggccatc agctggatcg cgatgatcga gtggccgccc aggtcgaaat agttgtcgct 8401  gaccgcgatg tcgtctcttt tgaagatccg ccgccagatc tccagcaacg tgctttcgtc 8461  cgccgcatgc gcgacggcgc gcgccgccgc ggccgcaccg gcagcggctt cgatggccgg 8521  cccggccccg ctgcgcggcg cgctcggccg gccgtcggcg gccggcggat cggcgagctg 8581  gccggtcaac tggcccgggt tctcggcgaa tcgctcgagc aacgtgcgga gggtatcgag 8641  catctgccgc acgacctccg gcgcgatgcg gtgggcatcg tgcgaaatat ggaagccgat 8701  gcgctcgttc gggtgcacgg tcagggtcag cgggtagttc gattccgcga acgcgcgggt 8761  gtcgaggatc tcgatgtcgt ccgcccgag atcggggcg cggcaaccg ggaagttctc 8821  gaagaccagc aggctgtcga acagactgtc gccggcgggc agttcgctcc acgactggat 8881  atcgaccagc gagctgtacg aatgcggctc catcgccgtc tgggctgcgt ggacctctgc 8941  cagccattcg atgaacgggc gctcgggcgc gatccgcagg cgcagcggca gcgtgttgat 9001  gaacagcccc acgatcgact cgacgccgtc gagcatcggc gggcgaccgg acacggtgac 9061  gccgaagacg acgtcgtccg ttccggcgtg gcgccgcagc accaacgccc agaccgcgcg 9121  gatcagcacg ttgagggtga cgcgatgcgt gcgcgtgagc gtttgcagcc gcgcggccag 9181  cgcctcgtcc agcaggaatt gctgggtccg gcgcttgtcc tgccgcgggg catcgccggt 9241  cgcctgccgg gccggactgg ccgcgaccgg cgtggcggcc ttgaagccgg ccagttcggc 9301  gcgccaccac gtttcgtcgg ccgagcgagg atgacgcgcg agccagtcga tgtacgcgcg 9361  gtatcccggc gccgacgccg cgaccgcggg catgccggtg cgggcgagcg acaggtagtc 9421  gtcgaacacc tccttcatca gggtcgcggt gctccagccg tcgaggatga tgtggtgcgc 9481  gctccagcag aagcgatggc gcgtgtccgt ttcctggatc agcgtgcagc ggaacaacgg 9541  cgcgcgctgc agatcgaagc cgcgccgccg gtcgtcggcg aggaacgcat cgaaatcctg 9601  cgcgcggcgg gacgcatcgc ggtgccgcca gtcaaggaac gtccatggca ggtcgaccgt 9661  gtgccgtacg gtctggacgg gatggtcgcg atcggccac gcgaacgcgg tgcgcagcac 9721  ggcatggcgc gcgagcgcat tggcccacgc ctgccggagc gccggcacct ggagcgggcc 9781  gctgacgaca aagctgaact gctggaagta ggcggcagga tccaggtcgt acagcgaatg 9841  gaacaggatg ccctgttgca gcgacgagag cggatagctg tcctcgatat cgtccgctgc 9901  ggtgtcgggg accgacgccg cgaagtcgag caaccggtcc ctgaagtgcg cggccaggtt 9961  ctcgaccgtc tgccgccggt ggagccgctc gccgtagcgc cagtccacct ggagcttgcc 10021 gtcggcaacg gccgcgacga tctcgaaggc atgcgtgcgc tgcgaccgcc cggcgcgcag 10081 cgaaccgagg tcttcggccg ccgggcgcca gccatcggat tgccgcaata cggtatcgag 10141 ctgcccgtga tagttgaaga ggatatcggc cttcggcaac gcggcgagac tgtcgcgcac 10201 ggcggcgtcg gggctctggt agcggagcag cgaataaccg agaccgtcgg ccggaatccg 10261 gcgcagctgc tgccgtgcgc cacgcagcgc ttgctccggc gcgtgcatcg cgtcggcgtc 10321 gagcacgacg gggtagatgg acgtgaacca gcccaccgtc cgggtgaggt cgagcggcgc
```

```
10381 atccgacacg tggcggccgt gactctcgag atcgatccgc gtgcgggtgt tacccgtgac 10441 catgctgcag gcttgcgcga gcgcgacgag caggacgtcg ttgatgcggg tgtcgtaggc 10501 ccgcggcagc cggcgcagca acgcggtggt atcggcttcg cccagctcga atgaaacgga 10561 cgacgcgtcg tcgactgcgt tgttggccgc gcccgtgcct ggatagtcaa ccggcatcgg 10621 ctcgacgggc tgcgcgagga gggcttgcca cagccgtgct tcgtcgccga tggcgggcga 10681 ccgggccagt tgctgcagat gcaacgccca ttcgcggaac gaagtcgtct tcccgggcaa 10741 cggctggccg tggtaagcgg catgcaggtc ctcgagaagc acgcgccatg acacgccgtc 10801 caccgccagg tgatggatcg acacgaacag gcgggcgagc ggctcgtcgg ccaggcagaa 10861 gagccgggcc gccagcaacg ggccatgcgt gatgtcgatg ccgcgctccg cgtcagcggc 10921 ggcggcacgc atcgccgcca ggcgctcgcc tgcgtcgtcg gcgatcacct gtttcgcaaa 10981 gagcgccggc atctcgccgc cggcgacgac ctgctgggtc cagcggcccg catcgtgcga 11041 gaaacgcagt cgcaacgcat cgtgatgttc gtagacctgc cggaacgcgt cggccagcct 11101 cgatgcgtcg atatccgccg gcacctggat caggaccgtc tggttgtagt gcgacggcgc 11161 atcgatctcc tgttcgaaga accagtgctg caccggcgta agcggcgcat cgcccagcgg 11221 gctcaaggtc ggcgcgcagg ctgcccgctc ctcgggcgcg gcggccagct gcgcgatcgt 11281 ctgatactgg aacagctgct tcgccgtcac gcgcagccct gcctgattgg cgcgcgcgat 11341 cacctggatg ctcaggatcg agtcgccgcc gagttcgaag aaattgtcgt ggatgccgac 11401 ggaaggcaac tgcagcacgt ctatgcagat cgacgccagc aggatttccc gcggcgtgac 11461 ggcaggtgca tgcggctggg ccgcgtcgcc ccgatccgcc ggaagcggca gcgccttgcg 11521 gttgatcttg ccgttgggca gcatcggcaa ggattcaagg gcgaagaact gcgacggcac 11581 catgtagtcg gcgagcttgc cgcccagata gccgcgcaga tcggcgatgt ccggcgcggc 11641 ggtcgcgaca taggcgatca ggaacgttcg ggctccttcg gttttcgcga tcacgacgca 11701 gtcgtcgacc gacggatgcg cgcgcagcgc cgcctcgatt tcaccgggtt cgatgcgcag 11761 gccgcgcagc ttgatctggt gatcgatgcg ccgaggaac tcgatgttgc cgtcgggccg 11821 gtagcgcgcg aggtcgccgg tgcggtagag gcgcgcgagc gggtcggccg agaacggatc 11881 ggcgatgaac ttttcggcgc tcagttcggg ttcgccgtgg tagccgcgcc cgaccggtgt 11941 gccgccgatc agcaattcgc cggccacgcc gatcggcgtg gctgcatct gcgcgtcgac 12001 gatgtagagg cgggtgttgg cgatgggccg gccgatcggc acgatgcggt gcggatcgtc 12061 gcgccggcat tcccacgcgg tcacgtcgac ggcggcctcg gtggggccgt agaggttgta 12121 gagcttgacg tccaggcgct cgaggcaacg ctgctgcagg tcatggggca aggcctcgcc 12181 gctgcacacg acgcggcgca gcgacgcgca gtgcgcgtcg aggtccggat gatcgaggaa 12241 cgcgcgcagc atcgacggca cgaaatggat cgtggtgatg cgttcgcgct cgatgagctc 12301 gaccaggtag tcggtctcgc gctggccgcc ggggcgggcg aacacgaggc gcgcgccggt 12361 gacgagcggc cagaagagtt cccagaccga gacgtcgaag ctgaacgggg tcttctgcag 12421 cacggcatcg tcggcgtcga gcgcataggc gtgctgcatc cagaggatgc ggttggtgat 12481 cgcgcgatgg gtgttgagcg cgcccttggg gcggccggtc gagccggacg tgtagatcat 12541 gtaggcgagg ttgtcgccgt tcagcgcggg tgcggggttg gacgtcgccg cggcgtcgag 12601 gtcgagcgag tcgcgatcga cgacgatcac gtgcgcgtcg gtgtcgggca gcgcgtcgtg 12661 cagatgctgc tgggtgagga gccagcgcaa ctgcgcgtgg tcgatcatga agcgcacgcg 12721 ctcggcgggg tagtcggggt cgacggggac gtaggcgccg ccggccttga ggatcgcgag
```

```
12781  cagggcaacg ctcatgtcga gcgaacgctc catggcgacg ccgacgagcg agtcggggcc 12841  gacgccgagc gcgacgaggt ggtgggcgag gcggttggcg cgcaggttga gttcggcgta 12901  ggtgagcgcg gtgtcatcga agacgatcgc gacggcatcg ggcgtgcgct cgacctgctg 12961  ctcgaacagg cggtgcagcg gttgcgcggc gtcctcgccg aaatccgtgt cggtgcggtt 13021  ccactcgacg gtcagcaggt tccgctccgc gtcattcgac aacgacagcg cgccgagcgg 13081  ccggtccgga tcggcgatca cggcatcgac gagcgtgcgg aagtgttccg ccatgcgatc 13141  gatcgtggcg gcgtcgaaca gatccaggtt gtattccagc gagcccgcga ggccgtcgtc 13201  ggcatcctga acatgaagcg tgaggtcgaa cttcgcggtg tgggtctcca ccgccaccgg 13261  cgtggccacg agaccgggga agctcactgc ccggggttgc gctttctcgt atgcgaacac 13321  gacctggaac accggcgtgc ggcccaggtt gcgttcgagc tcgagcgagt ccaccacctg 13381  ctcgaacgga atctcctggc ggctgtagcc gtccagcgcg acgcgcttca cgcgcgccag 13441  caggtcgccg aaggtcggat tgcccgacag gtccacgcgc agcgcgagca tgttcgcgaa 13501  gaagccgatc agcggctcgg tcatgctgga acgccgattg gcgatcgggg agccgatgac 13561  gaggtcctgc tggttgctgt atcgcgacag gagcagcgca tacgcggcga gcacgaccat 13621  gaacgtgctg gtgccggacg cacgggcaat cgcgcgcagg ccgtcggcgc gttcggcgct 13681  cagctggaac ggcaggaccg cgccgcggaa ctgctggacg gcgggccggg ggcggtcggt 13741  gggcagttcg atcaggtccg gcgcgtccgc cagcgcggcg ctcaggagcg ccagctcccg 13801  atgcgtgtcg gcggacgcca ggcgctcgtg ctgccacacg gcgtagtccg cgtactgcac 13861  ggccagttcc ggcagcgact cgccggcata gagcgcggcc agttcgccga tgaggatgcc 13921  tgacgaccat gcatcggaaa cgatgtgatg catcacgatg ccgaagacgt gcaggcgctc 13981  atggacgcga tacagcacga cgcgatagag cggcccgcg gcgagatcga acgggcggtc 14041  ggcttcctcc gcgagcagcg cgagcgtgtc ggattcgctg gcgacgtcga cgacgtcgag 14101  cgcgaccggc gccggcggcc caatgcgttg aaccccgcgg ccgtcgacgg cgggaaacgt 14161  cgtgcgcagg atctcgtgac gccggctgat ctcggacacg gcaaaccgca ggcgcgcgac 14221  gtcgagttcg ccttcgaagc gcagcgcgct cgagatgttg taggtggccg acgggccttc 14281  cagttgcgcg aggaaccaca gccgctgctg cggaaaggac agcggcaggt cgttcgcgcg 14341  cgagcggggc gggatgcgcg cggccgtcga gccggggtgg ggcgacgacg cttcgatcag 14401  gtcggacacc gcgctgatgg tctggagttc gaagatcgcg tcgatgccga tctcgacgga 14461  gaagctgctc cagatccgcg agaccagttg catggcttgc agcgaatcgc cgccgtagtc 14521  gaagaagcgg ccggcgagat cgacggccgg attgtcgagc acgtcgcgcc agatgcgcac 14581  cagttcgcgc tgaatcggcg tggcgtcgag aggggcttcc tcgggcgcgg cggcaggctc 14641  cagggccagg agcgccgggc gatccagctt gccgttggcg ttgagcggga attcggcgat 14701  cgggatgatg tcggacggga ccatgtagtc cggcagcttc ccggccaggt aggcccgcag 14761  gttcggcacg ctcaggctcg cggcgcccttg acgtaggcc gccagcttgc gcaccccgtg 14821  ggcggattcg cgcagcatga ccgccgcgcc gacgacgtcc tcgtgcgcgg cgatcgcggc 14881  ctcgatctcg ccgagttcga cacggtgccc gcggatcttg acctggtggt cgacgcgtcc 14941  gtagcactgg atacgtccgt cgggcagcca ccggccgatg tcgccggtgc gatagatgcg 15001  cgcttcgccg ggaaacggat gctcgacgaa tttcgcgcg gtgacgtcgg gccgctggtg 15061  gtagccgcgt gcaaggccgg cgccggcgag gcagatttcc ccgggcacgc cgagcggaac 15121  cggccgcagc gcgtcgtcga gcatgtacac ccgggtgtcg gcgatgggac ggccgatcag 15181  caccgtgggc ggcgcgtcct cgacgcgctc gacgatgcag ccgaccgtcg cctcggtggg
```

```
15241 accgtactcg ttgtagattt cgatcgcggg atcgatcttg cgcagcgtgg cgatgtgctg
15301 gggcgtcagt tcctcgccgc ccacgatcac cttgcgcacg ccggagcgtg ccaggttcat
15361 gtattccagc aggtgaatgt gggtgggcgt gagcttgagg gtgtcgacgc cgctgccggg
15421 ctggaacatc cgggccagga tggtgtcgat gctttccgac tgcggataga tgcgcagcgt
15481 cttgccgcgc accagcgggc agaagatgtt ggtgagcgtg aagtcgaagc agagcgagct
15541 gtacaggccg aaactgccgg tcgtgctttc cggaaagtaa tacccggcgg cccacgcgat
15601 gtagtgggcc aggttccggt gttcgagcag gcagcctttg ggtttcccgg tcgagcccga
15661 cgtgtagagc acgtaggcca ggtgcgccgg ttcggcacgg tgcggcgggt tgtccggcag
15721 cggctgccag ccggggagtt cctggtccag cagcagcgtc acgccggaga attcatacca
15781 ctgcgcgagc tgactcgact gggtcaccag cagcgacagg cccgtgtcgc cgaggatgtg
15841 attgatccgc tcggccggat acgcggggtc cagcggaacg aacgccgccc ccgccttcag
15901 gatgccgaga atcgcgacga tcatccattc ggaacggtcg agcatgatgc cgaccagcga
15961 ttccggcccg acgccgtggt gttcgcgcaa gtgatgcgcg aggctgttgg cccgcgcgtt
16021 caggtcggcg taggtcatca gcgaactgtc ggtgaccagg gccggcgccg tcggcgtgcg
16081 tgcgacctgg gcttcgaaca tggcgacgac cgtcgggtgg ctggggccgg ccgtcgcggt
16141 ttcgttgaac gcggccagca gcgggccctg ttccggcggg gccgcttcga tgtcgccgac
16201 ggcgccgtcg aggtgttcga atgcctccag caccgcggcg aggctgccgg cgaaaccgtc
16261 gatgatgaaa ggctcgatgg ccccgctgta acgaagctcg atttcgccgc gcgcgagccg
16321 caggtgcaac tgcagatcgt cgtcccgacc ggtcggtgcg tggtgcacgc ggtcgtccgc
16381 cagcgcgact ttcgtgagct gcgcgagcgc catgtccttt tcgttgcgca cgagcgtttc
16441 cagcgggaat cgaggctcgg cgtagctgtc ttccacgatc ccggccacgc gcgacaggta
16501 gtcctcgatg cgctcgtcgg ggcggacctc gatgatcagc ggaacgatgg cggcccgggc
16561 cgacggatgc ccggccagcc ccggcgtgcc gagcaccgtg accggaatcc ggaagtattt
16621 ccagagcagg aacgcgatgc ccgccgccgc gacggcgaat tcgcaagct cgccgtcgcc
16681 gatgcgccgc aacaggtcga gcgacgcggg cgtgagccgc accgagcggg tcagcgggcg
16741 acccggctgc tggctcgggg cgtacgccgc gattccgtac acgccggcga cccgggaaag
16801 gctttcgcgc cagaaacgcg cggtggctgc atagcgatgg tcggtgacca gcacgttatt
16861 gtcttgcaca ggaaactcct tgagacgttt tgttcacctg aaacaacctg aagcagcacg
16921 cacggcgcgc gccgctcgaa ccccggcggg cgcgcatcac gtcttctcct cgagcgcgtc
16981 gtcggccgtg accgcgggcg cgcgcttcag gcgcaggccg acccggactc gcgggccggc
17041 ggcgggcgcc tcgtcggaga gcgggatgcg atcgaccggc gtggccggat cgcgacggaa
17101 gacgtcgtgg atcgcgagca gtcgatcgcg catcgcggcg atggtcgacg ggcggaacag
17161 gtgggtgttg tagatgaact ggatcaggtg ccggccttcg ctttccacga cctggaagga
17221 caggtcgaac ttggccgtcg tgtccgccgg cgagatgtcc gtgatgcgaa ggcctggctg
17281 cggcgccggc atcgacacgt ggttcacctg aatgtcgaag atcgggaaat ggttcgccgg
17341 cgtgcggatc ttcaggtctt ccagcaacac gtcgaacgga taggacgcat gctccagcgc
17401 ttgcgcggag gctttcgcca ccccgtcgat cacctccgcg accgtcgcgg atttccgcac
17461 cggcacgcgc agcacgacgg tgttgaggta cacgccgacc tgcgattcga gctgctcgct
17521 gtcgcgcccg gccgacacgc tgccgatgac gatgtcctca cgccccgtgt agcggtgcat
17581 cagcacgcag aacgacgcca gtagcaccgc gtggagcgac gtgtggtgag cgcggggccag
```

```
17641 cgtcgcgagt tccgccgcgt gcggctgcgg cagttcgact tcgagcgtct gcccggcatg 17701 accgagccgc tcgggacgcg ggaagtcgga tgccagttgc aggcggggca gcggcggcgc 17761 cagttgctcg agccagtacg cgcgatgcgc ggcggcgcgc ggacccgcga ggctcgcgtt 17821 gtgccacgcg gcgtagtcgc gatactggat cgacagcggc ggcaggtcgc gccccgcata 17881 cagcgcatgc aggtcgtcgg tcagcacgcg gatcgaccat gcatccgaga tcacgtggtg 17941 catgttcagc agcaacagat gcttctcctg cgacagccgg accagcttga cgcgaaagag 18001 cgggcccgac gcgagatcga acggctgctc gcattccgcg cgaatcagcg catcgatcgc 18061 ttgcggcccg gcatcgtccg cgagatcgcg ctgctcgacc cggaatccgg acgcttcgcg 18121 gctgaggacg cgttgccgca actcgccttc gatcatcgcg aacacggtgc gcaggctctc 18181 gtggcgatcg accagcgtgt cgaatgcacg gacgaggcgc gccgtatcga cggcgccgtc 18241 cagctgcagc gcgcccgcca tgttgtacgt ggacggatcc gcgccgcggc tggcgagcca 18301 gatccgcttc tgtgcacgag acaccgcgta ggacggttgc gcggccagcg ccgggatgat 18361 cgcgtcgtcg tcggcggcgc cgtcgacggg catggcagcc agcctttgtg cgagcgcgcg 18421 cggcgtcggc gcatggaaga tgtcggcgac cgcgacgttc agtgcagccc ggggatccg 18481 gctgaccatc tggatcgcct tgaggctttg gcctccgtgc tcgaagaaat cgtcgtcgac 18541 gccgttcggc cggcggccga gcacctcggc gaagaggcgc agcagcgccg cttcgaccgg 18601 cgtgcgcggt tcggcccgca cgccgtcggg cacggacgcg gcatccggca gcggcagcgc 18661 ggcgcggttg atcttgccgt tcggcatgac gggcagcgcc ggcagcagca tcacggtgtc 18721 gggcaccatg tgcgccggca gcgtgtcgcg cagtgcgtcg cgcacgcgct ggggcgtcca 18781 gccggttccc gacgcgtagc cgcacagggt catttcggca tccgacgttt cccgggcgac 18841 caccacggcg tgggaaatgc cggcaagact ggtcagcgcg gcttcgattt ccccgagctc 18901 gatgcggtag ccacggatct tgacctggaa gtcgcggcgg ccgaagaagt gcagattgcc 18961 gtccgccccg aagcagccga tgtcgccggt gcgatacagg cgcgcgcctg gttccggact 19021 gaacggatcg tcgcggaaca ccgcccgggt gcgggcttcg tcgaacaggt agccgcgccc 19081 gacgccgacg cccccgatgc agatctcgcc cttgacgccg gccgggcacg gattcatgtc 19141 ggcatccacg acgtagaggc gcaggttctc gatcggccgg ccgatcggaa tcgccggccc 19201 atccggcgcg cgcgtcaggc agtaatgcgc gacggagtcc gacgcttcgg tcggcccata 19261 ggcgttgatg agccggacgg ccggattcag gcggaaccac gcttgcgcgg tggcgggctg 19321 cagcgtttcg ccgatcgtca gcaacgtgtc gaggtgaggg aaggccggtg ccgcgtgccg 19381 ttccagttcg ccgagaaagg tcgcgagata ggacggtacg aattgcattg ccgtgatgcg 19441 gtcgcggtgc aggctgtcga tcaggcgcgc gggctcgagg atcacggcat cgggatagat 19501 caccgtcgtg ccgcccgacg ccagcgccgc gaagcattgc cagaccgaaa tatcggagca 19561 gtgcgaagcg gtctgggcga ccgcgctctg cgcgccgagc ccgacccggc gcgccatcgc 19621 gagcacgtga ttgagcatgc cgcgatgttc gaccatcgcg cccttcggct ggccggtcga 19681 acccgacgtg aagatcacgt aggcgaggtc cgcgggccgg cagcgcggcg tcaccggcgc 19741 cggcgcttcg gcgccgcgac ggtcgggcag gcgggccgga tcgaccagcg ggatcgacgc 19801 cagcgccggc ggcggcacgc agtccgtcgt gacgatgacg gccggccgcg ccagcgtcag 19861 gatggtctcg acccgctggg ccgggtaggc cggatcgacc ggaacgtacg ccgcgccgca 19921 cttccagatg gccaggatcg tttccagcat cagcggcgag cgcggcatcc agacggcgat 19981 ccggtcgtcc ggctgcagcg gcgccgtctg cagaagatgc gcggcgatcc ggttggcgcc 20041 ttcgacgagg tcacggtagg tgcgaaccct cgtgccgcag cgaaccgcca cgcgctcggg
```

-continued

```
20101  gtgcgctgcg gcgacggcct cgatcagttc gggcagcgtc cggtcggacg gaaccggcgc 20161  gaacgtgtcg ttccagccga gcaggatggc gtcccgctcg gcggcagcga gaagcggcac 20221  gctgcggttc gggcgatctt ccgcgccggc caggccggtg agcagggtct cgacatggcg 20281  cagcaggcgg acgatcgtgt cgcgatcgaa ccggccgtcg tcgtacagca cctgcagcga 20341  caggcgcttg cccggcgtca cgaccagcgt cagcgggtaa ttgttcggat cggacacctc 20401  gaatgcgccg atccgcaggc cgggcagcgc atcggccagc gcttcttcca ccggataatt 20461  ctggaagatg agcaggcttt cgaagagcgg cacgccgggt ggcaggccgg cgaatttctg 20521  gatgtcggcc agcggatagt gcgcatagtc ctcctgctgc gcgagatcca tctgcaattg 20581  cgccagccac gctgacgtcg ggcgtgcgtc gatgcgcacc cgcaccggca gcgtgttgat 20641  gaacagcccg accatttcgt cggatgccgg cagcgacgcc gggcggccgg aaacgatcgt 20701  gccgaacacg acgtccgatt cgccgctgta gcggctcagc aactgcgccc atgcgccctg 20761  cgcgagcgtg ttcagggtga ggcggcggga ttgcgcgaat gcgacgagcc gttgcgtgtc 20821  gctttcggag agcagcagcg gctcttccac gtaggcgccc ggcgcggccg tgccgtcgag 20881  ttcggggcgg cccagcacga gcggcgtcgt cgccgggaaa tccgccagct tcgtcttcca 20941  gaaacgttgc gcggcggcgg cgtcctggcg tgccagccag cgcacgtaac cggcgaaggc 21001  aggcggcgcg tcccgctgcg gcgcgccttc ggccggcggc gcctgatagg cggcggccac 21061  gtcgctcagc aaccgggcgg agctccaccc gtcgagcagg atgtggtgat ggctccaatg 21121  gaagcgccat gcgtgctcgc ccacgcggaa cagcgcgagc cgcatcagcg gcgcgcgggt 21181  aaagtcgaag ccgcgcgccc ggtcttgcgc cacgtaggct tcccagcgct gttcggcctc 21241  cgcggcggac gccgcgcgca gatcctcgtc gtgccacggc aagtcgatcc ggcgatgcac 21301  gacctgcacg gggctttcga tgtcttccca gtgaaacgac gtacgcagga tgtcgtgccg 21361  gtgcgccacg gtctcccacg cgcggcggaa ccgttcgacg tcgagcgccc cgtcgatacg 21421  gaaattcagg ctgctgaagt acgcatccga cgcgggttcg tacaggctgt ggaacagcat 21481  gccctgctgg gtcggcgtca gcgggtagac gtcggcgatc tcgtccggac tcaccgacgc 21541  cggcgccggc gcctgcggca acgcagtcgc gggccgggtc gatgcggacg ggacagcgtg 21601  gccggcgacc agggtttcga gcgccgcgat gtaggcttgc gcgacgcgca ggatggtggc 21661  cgtgtcgtgg caggcccggc tgaattccca cgcaacgtgc aggcgattac cggtcacgta 21721  cgcgttgatg tcgagcaggt gctcgcgcaa ctggttcgcg ttgcggccgt ccccgctcgg 21781  ctccgcggcc tgtttccagt cgcgtgcggc ggtgaacagc tggtcggtct gccccaggta 21841  gttgaactgc agtcgcggct gcggaagcgg gccgtcgagc cggtctagca gcaggccgta 21901  ggtgatgccc gcgttcggca ccgcgcgcag ccgcgtcctg accgatgcga cgaggctggc 21961  cggatcgtgc gaaccggcat cgaccgtcag caagaccggg aaaaccgacg taaaccagcc 22021  caccgtgcgc gagatgtcga gcgcgtcgat cagttcctcg cgcccgtgcg cttcgagatc 22081  cagcagcacg tcggcgcatc cgctccattc gctgacggca cgcgcgagcg cggcgagcag 22141  cacgtcgttg acctgcgcgt cgtaggcgcg gggcgcggcg cccagcaagg ccgtcgtcgc 22201  ggcttcgccc aactcgacga cgatcgtgtc ggcggacgac acggtattgg cgtcggcagg 22261  cgcatcgcga tcgagcggca ggccgggcag ggcggcacgc gcgagggcct gccaatgggc 22321  gaggtcggcg tcggcggcgc cggagccggc ccaggtcgag atcgcccggg tccatgcggt 22381  ccaggtcgcg ctgccgcctg cgaattcggg cgccttgccg ttgcgcagcc gggtataggc 22441  gtcgtacacg gtttcgagca gcgcgcccca cgacacgccg tcgacgacca gatgatgggc
```

```
22501 gaccagcagc aggcggagcg aacggccttc gtcgacgcgg aacaggtccg cgcgcacgac 22561 ggggccgtcc gcgagattca ggctcgcatg cgactgcgcg acgtactgcg cgagctgatc 22621 gcgcgcaatg tcggacacga cgacggggat ctccgggtcg tcgacgactt cctgggtcca 22681 gccgctctcg ccctcgcgaa agcgcagccg cagcgcgtca tgccatttga ccgcatgccg 22741 cagcgcctgg cgcagcaaga ccggatcgag gtcggccggc acgtcgagca ggaccgcctg 22801 gttgtactgg tccgggtcgt gcttgccctg cgcgaagaaa cgcttctgga tgggcgtcag 22861 cggcagcggg ccggacgatg cgacgaacgc cgccgcgccg accgtgccgc gcgtcgccac 22921 ggcggcgagt tcggccaccg tcggatgctg gaagatgagc cgggtggtga gcttcaggcc 22981 cgccttcgcg gccagcgaca cgatgcgcat gctcagaatc gaatcgccgc ccagcgcgaa 23041 gaggttgtcg tggatgccgg gcgacggaat gcccagcgct tcgccccaga tgcggcacag 23101 cagcgtctcg gtaggcgtgc ggggcggcgt cggcgcgtgt gccgtggcgg cgagtcgcgc 23161 gcggtccagc ggcggcagcg cgttgcggtc gatcttgccg ttgccgctca ggggcagcgc 23221 gtcgagcacc acgtagatgc cgggcaccat gtagtccggc agcgtggcgg acagcgcggc 23281 ggcgatcccg gcgtcgctca gcgacgcgcc gtcgcggaac gcgacgtacg cgcacagcgc 23341 ggcgcggccg gcctcgtcgc gatagtcgag gcgcggcgcc tggcggagtt ccgcgaatg 23401 gtcggccagt cgtcgttggt cgatctcccc gagctcgatg cggtagccgc ggatcttcag 23461 ctggtggtcc ttgcggccgt gcagcacgat cgttccgtcg ggcaggtagc agccgatgtc 23521 gcgggtgcgg tacaggcgga cgccgcgctg aggatggaac ggatcctcga cgaacgcgtc 23581 ctgcgtggcg gcttcattgt tcagatagcc gcgaccgacg gcgacgccgg acacgcacag 23641 ctcgccggga atcccgatcg ggcacaggtt catctgcggg tcgacgacgt agaggcgaac 23701 gttgcggatc ggcttgccga ccggtacgta aggcgtggac ggcgcgcccg tcatgcggtg 23761 ctgtgcgacg tcgtcgacg cttcggccgg gccgtacgcg ttcaccagcg ggatcgccgg 23821 gaacacgtcg aaccactgtt tcaccagcgc cgggctgacc atctcgccgg tgacgagcag 23881 gtgccgcaga tgccgcatca gcgccggccg ttccgacgcg cggtcgagca cggcggacag 23941 ataggacggc accagttcga ggatgctgat ccgggtggtt tccaggtacg cgacgaaacg 24001 cgcgggatcg cgaatgcagt cgtcgtcgac gatcacggtc ttgccgccga cgagcggcgc 24061 cgtgaaaaat tgccagaccg aaatatcgaa gcaatgcggc gcggtttgcg cgatcaccga 24121 cgacgccgag atcgagaact cgtcgatctc ggcgagcatg tggttcagca tgccggcgtg 24181 ctcgaccatc gcgcctttgg gcttgccggt ggagccggac gtgtagatca cgtaggcgag 24241 gctgtcgggc gacacggggc ggccgggatt ggagtcgtcg acggcgtcgg tggcggcgtc 24301 gagcgacacg accagcgcga tcccggccag ctccgggggc aggagcccgt cgcaggtgat 24361 cacgagggcg gcgccggaat cctcgaggat ggtgcggatg cgggccaccg gataattcgg 24421 gtcgaccgga atataggcgg cgccgcactt ccagaccgcg aggatcgcct ccatcagctg 24481 ggcggaccgg tgcatgcaga ttgcgaccag cgcgtccggg cccaggtcgg cggcggcgag 24541 caggcggtgc gcgatgcgt tggcgcgcgc gttcagttcg cccgcgctca ggacgccatc 24601 ccggtactcg accgcgggcc gctcggggtg gtccgcgcg cctgctcca ggcgatgcac 24661 cacggtgagc gcggcgtcga acggcacggc ggtgtcgttg aaggtctcca gcaactgccg 24721 gcgttccgcg tcgggcaaga tcggcacgcg gccgagcagc cggttcggat cggccgcgaa 24781 cgcgtcgagc gtcgcggcca cgtggcccag catccgctgc atcgtgtctt catcgaagcg 24841 ccgcgggtcg aacgacagtt ccatcttcca gtcgtcgcgc gccgtcacca cgaattcgag 24901 cggaatgtcg gcgcggttgt agagctgcac ctcgtcgacc gccagcccgt gcgcgccatg
```

-continued

```
24961 cgtgagcgac gcgtcgagcg ggtaattcat gaacgtgatg ttgctctcga acagcggcgc
25021 cgtcggcggc acgtcgctgc agcgctgaat gtcgggcaac ggggtgtgct cgaacggcgc
25081 gcgggcggcc acgcgcgcct ggatcatctt cagccacggc accagcggct gcctcgggtc
25141 gacccgcacc cgcaccggca ccgtattgat gaacaggccg agcatggttt cgatccccgg
25201 caggttggcg ccccgcccgg acacgacggc gccgaacacc acgtcggttt ccccgctgta
25261 acgcgacagc acgagcgccc acgccgcttg cgcgagggta ttgagggtga cgtgatggcg
25321 ggccgcgaat tgccgcaggc gcgcgctcag gtcggccgac aggtcggcct gcacttgcgc
25381 gaggccctgg ccgaagcgtt cgtccgcgcc cgcgcgcgcg gccgtgggca gcggggtcgg
25441 tgtgcggaac ccttcgagat agcgcgtcca gtattgctgc gcggcttgcg gctcgtgctg
25501 ctgcagccac tggatatagt cgcgataggg gcgcaccggc gggagcgccg gcgacacgcc
25561 gcgcgcgagc gcgccataga cctcgaagat ctcctcgatg acgagcgaca ggcaccagcc
25621 atcggccagg atgtgatggt ggctccagct gaacaggtag gcgtcggcgg cgacgcgcac
25681 caggcgacag cgcacgagcg gcgcgcgatc gagcgcgaag ccctcggcca ggtcgttgtc
25741 gagatgcgcg cgccaccgtg agcgctgttc gtgttccggc aggtcgagcc agtcgtcctg
25801 cacccacggc agcgtggcgc gcgcgtgcac gacctgcatc ggcttgtcga actcctccca
25861 atggaacgac gtgcgcatca ccggatgccg atcgatgagc tgctgccacg cggcatgaaa
25921 cagcgcggga tcgaggctgc cggtgatccg gcaactgagc tggttgaagc tgcttctcga
25981 gccgggctcg tgcacggcat gaaagagcat cccctcctgc atcggggaga gctcgtagat
26041 atcggcgatg gtgggggatg tcacgatttg atccttgaga caagggcgtc cagcgcttcc
26101 tggctgatgc gcgcggccgg aaagtccgac gggctcagcg cgcgcgggcc gtcgccgccg
26161 gccgcgacga tcgacagcag gcggctgcgg tagcactgcg tcagctgttc gatgacgccg
26221 ggtgcgcagg cctcgcggtt gtagtgccag gtcaggcgca gacggccgtc gaacaccatc
26281 ccgtcgatct cgaacagatg gccgcgacgt gcgcgcgggc tgtgctcggg gctctggaag
26341 tcgagtaccg gcttccagcc cgtgtcgtcg ggcagcacgc gatcgacctg gccgagatag
26401 ttgaagcgca ccggcgccgg cggctgccgt tcgagcgccg ccgcgatgcc ggcgtcgtgg
26461 ccgaggtagc gggcgatgcc gtagccgagc ccgcgcatcg gaaccgcgcg cagctgctcc
26521 ttgacgtggc gcagcgcgtc gaccgccacg gtggcgtcgc cggcgttcag gcacaccgga
26581 tagtgggtgg tgaaccagcc gatcgtgcgc gacgtatcga cgccgtcgaa aatgtcctcg
26641 cggccgtggc cttcgagatc gacgaccagc gacgcgttgc cggtccagtc gccgaacgcg
26701 agcagcaggg ccgtcagcag gacttcgttg atctgcgtgt tgaacgcacg cggcacgtcc
26761 tgcaacagcg cgagtgtctg ctgcgcatcg aactcgacga tcgtcgagcc cgcttcggcg
26821 acggtgccgg ccggcatgtc gtcgaagcac gccggctcgc cggcgttgcc ctggagccag
26881 tagtccagcc ccaggccgtc gagcgcggtc gcgccgagtc cggacaggcg cgtcgaccag
26941 tcgcgccagg ccgtcgtcct ggccgggagc tgtaccgcgt cgcccgcttc gagctggcga
27001 catgcggtgt acaggtcttc gaacaggatg cgccacgaca cgccgtcgat caccaggtga
27061 tgcgcgaccg cgagcaggcg ctgcggcgcg tcgggaccga actggaacag gtgcgcgcgc
27121 agcagcggcg cgccgacacg cgtgaagctt tcctgcatgc cggtggcggt cgcgagcatc
27181 gcggcctgcc gtgcggcagg cgccgcgtcc gccagcgacg tgacgccgag cggaatggcc
27241 agcggcggcg cggcatgcga ttgctgccac acgccggcga cgcacgcgaa actcagccgc
27301 agcgcgtcgt gatgcgtcgc gacggccgcc agcgcgcgct cgatcgtgtc cggccgcagc
```

```
27361 gatgcgggca cctcgatcat cgtcgactgg ttgtagtggt gcggatcggc gacgtcttgc 27421 gcgaagaacc agtgctggat cggcgtcagc ggggcggggc cgaccaccgg ctcctgcgcg 27481 atccggatcg acggcgcctc cgtcgcgacc tgggcgagct cggcgatggt cgggtgtgcg 27541 aagaactggt cggcggtgaa cttgagcccg acttgctggg ccagcgacat cacctggatg 27601 atcaggatcg agtcgccgcc cagttcgaag aaattgtcgt gcacgccgat cggctcgcgg 27661 cccagcacgt cgcaccagat cctgcccagg cgcgcctcga cgtcattggc cggtgcgacg 27721 taggcggttt cgctcggcgc gggcgccagt ccagcgcgg cgagcgcctt gcgtcgggc 27781 ttgccgttcg gcgtcagcgg caggcgttcg agcgtcacga tcgacgccgg caccatgaac 27841 tcgggcaggc gttccttcag gtgttcccgc aggctggcga cgctggccgt cgccgtcgcg 27901 acgcaggcca ccagctgctt gtgctgcggc gtgtcctcgc gcacgaacac gatcgcgtcg 27961 gcgacgccgg cgtgctgcct gagccgccgcc tcgatctcgc ccatttcgat ccggtagccg 28021 cgaatcttca cctgcgtgtc gcgccgcccg gtgacttcca ggttgccgtc cggcagccag 28081 acgccgaggt cgccggtgcg atagaggcgc tcgcccgcct cgaacgggtg ggcgacgaac 28141 gcggcggccg tcaggtcgtc gcggccgaca tagccgcgcg ccagcgcgat gccggacacg 28201 cagatctcgc ccgcgcaacc ctcgggggcc agcgccccgt gctcgtcgag caggtacagg 28261 tgcgtgttgt ggatcgggcg gcccaccggc agacgggcgc cgtaggtgat ggccgggtcg 28321 accacgtagt ccgcgatgca cacggttgcc tcggtcgggc cgtacgagtt gtggcacgtg 28381 cgggtccggg ccagctcgcg cagatccgcc acgcgggcgc tgtcgcccgc gctgatgacc 28441 cgtttcacgg cgccgagcgc atgccagtcg agcgcggcaa gtaggccgg cgtcgcgttg 28501 acggtggtga cgccctgctg tgcgatgtag tcgacgaaac gcggcacgtc ccggatcacg 28561 gcggtctttg ccagcaccag gcgggcgccc gcgagcagcg tgacgaagat ttccatgatc 28621 gagccgtcga agcccgggga gtagaactgg acgaagcggt cggcggaatc gaaaccgaat 28681 gcgtccacgt ggtactgcgc catgttcagg agccctgcgt gttcgagcac gacgcccttg 28741 ggcacgcccg tggagccgga cgtgtagatg atgtatgccg cgtcgtccgg ccgcacctcg 28801 acctgcgccg atgccgacgc gggtgccagc gtgtcgagct ggaagtcgag ggcgaacatc 28861 gggatcgccc agaaatcggc gagcaacggc aggtgttccg agtgcgtcag cagcgccttg 28921 accttcgcgt cctcgatcat gaagcgcagg cgctcccgcg gaaattccgg gtcgagcggc 28981 agatacaccg cgcccgcctt gagggcgccg agcatgccga cgatccagcg ctcggaacgg 29041 tcggccacca cgcccaccac gtcgccgcgt tcgatcgcgt attccgcgag caggaagctc 29101 gccagccggg acgcctggtc gtcgagttcg gcataggtca gcgatgcgtc ggcggtcacc 29161 accgcgacgc tgtccggcgc ggccgcgacc cgttgcgcga actgctccag gaaggtgccc 29221 tgtaccgcga cgggcgccgc atgcgaacgc aggcgcgcgc gctcttcgtc gtcgagcagc 29281 gagacggtgt cgagcggcgc atccagtgcg ccgaagccgg ccacgacgtt gcgcaggtgc 29341 cgtgcgacat gctggagata gtgcagcgtg aacaccgtcg gccggcccgt cagcacgatc 29401 tcgtagcgct cccgatgccg gatctcgatc gacaggtcgt agtcggccgc tgcccaggct 29461 tcgtgaaggc cgtcgaagcg cacgccgacg ttggtcgcgc gccgttcgcc atgcagcttg 29521 tgcgcgaggg cggcgatcgg gaaatcctgg tacgaatagc tgcgctgcac gctgtcgcgc 29581 agctggttca ggtacgcgcg aaccgtgggg ccgggctcgc cggcgtcgag cagcgggaca 29641 ggctcggcgc agccgctcgc gggttcgacg atcagctgcg gcgacgccac gaacaggccg 29701 gccgcgccgt tgtagcgccc cagcacgcgg aacagcgcgg ccagcagcac gacgaacgcg 29761 cccagctcgt tgccggcggc gagccgctcc agcacctgcg ccgcgtcgcc gtcgagcgcg
```

```
29821 aacgtcagtg ccggctcggg gccgagcggc agcgcatacg cctgccacgc ctgctgaagg
29881 cggaaatctt catcgatgcg accgagcgcg tcgttccaga acgccacgtg ttcctggtat
29941 tgcccgctgg tcgagagcgc gttgagattc agttctgaca aagcacgatc tccctcgtcg
30001 cgtacaggat ttcggaagcg atgcccttgg ccttgcagtg cgcgacgaac tgggtggact
30061 ggatgtggct gggcgagttt tcgtcgaagg tgttgtcgag gaggtggttc agccagggct
30121 cctgacccat cgcatagaca tacgccgcgt tgaacgcgaa atcgtccacc agcgcggcgg
30181 cctcgccgaa ctggcagccg cgcgcccggc gtgattgatc gatgtcgcgc ggcagcgcct
30241 tgggaaacag cgggccgtag acccatgacg gcggcgcgcc ctcggtttcc atcccgacga
30301 acagggtgtc cggcttgccg gcgaggcgga agacatgctc gtagaggcgc gggtccaggt
30361 tgcacgaatc ggcgatgcac agcaccgagc gcgagccgaa gcggatcatg aagctctgct
30421 tgctgtggat cgccaggtcg ttgtgttcgc ccatgaacgg aatggcggtg atggcgccgc
30481 cgggcacctt gatttcctgc gcatcccgaa cttccagcac gtcgtcgaag ccgagcttgc
30541 gcaacgccag ctccatcgac ggatcttgcg gaaagccgtc gagattcctg ccgaccacca
30601 cggtcttgac cttgtggcga agctgcagca gcgtttcgag gacgatgtga tcgtgatggc
30661 tgtgcgtgat cagcacgtag tcgatctggt ccggcaggtc ggcgaacgta tagcgcggca
30721 gcgcggtgtc gtagccgtag ctgatcaccg gatcgatcag gatgctcacg ccccggctct
30781 ggatcagcac gcacgcgtgg ccgtagtagc ggatgcggat gtcgtcgccg tcgaacgaac
30841 gatccggttt cggcgccggc gcctcctcga cgaagaacga gcggaacagc ggctcgtcct
30901 tctcctccac gcgcatcagg tcgacgatct tcgcgtagct gccgggcgtg tcgcgcatgc
30961 ggaacagcgt gtcgagcgcg cggtcgtcga aggccatgtt gctgaacacc gtgcgctcgt
31021 cgcggagccg gggcgtgctg aggatgaacg gccgcggcgt gtgctcctcg atcgccgaca
31081 gcgcgatgct ctgcgcatcg cgcgcataga acgggctcgc gtacagcagg cttttcgaaca
31141 cccggaagga cgggttgtgg ttcaggtcgt agtagatctc gacatagccc ttcagcacct
31201 ccggaatctc ggggtagagc gggtccgacg ccatccccgt ggcccgttcc agcagcagcg
31261 tggagaacgc cttgtatgcc ttcgccagtt ccagttgccg ggtcgcgcgt tgggtggtct
31321 gctcgatcag cgtgcggatt tcgtcgacgc gctggccgcc caggtcgagg aacggcccgc
31381 cgcgcatcgc gggatccttg caggccgccg catgcatcat cggcgatgcg gcataggact
31441 tcagcagcgg caggaaccgc tccgccacgt tgagggcggc ggtcaacggc ggaagcgtgt
31501 gataccacgc gtaccagctg ttgatcagcg gttcgaactg gatgttttgg cgcaggtaga
31561 cctgcgcgct ggacgaaata gtcaacgaag gctccttaga atgcgctgag ttcgacggtg
31621 ggctggcggg cttcggcgtg cagcgcgcgt tgtcccaggg tcaggttccg gatgcgaacg
31681 cccggattgg cgagcacctc gccgatgacg gacgtcagct cgttggcgag gccttgcacc
31741 agggcttcgc tgaaccgccc cgcgtgatag acgacgcgga tcgcgagacc ctcggcgtgc
31801 ggctcggcca ggaaccagaa atcggttgcg gcttccgtgt ccgcgcgctg cgggtcgtgg
31861 tccggcagct cggcgatatg cacttgtccc gcgtagcgat cgacggggcc gtgtcgctgg
31921 ttctgcagcg tcaggccgat gtcgaagagc ggattgcgtc ccgccacgcg tttgatgtgc
31981 agctcgtcga gcaggcgatc cagcgggtac agcgggtgcg agaacgcttc gagcgtggtg
32041 tcccgcaccc gggtcagcag cgtgtcgaac cggtcgtcgc ccgcgacacg atcgcgcagc
32101 gccagcacgt tcaggtaggg gccgacctgc gactcgagtt cgggcagttc gcggcccgcg
32161 accggcgtgc cgacgacgat gtcctcctgg ccggagcggc ggtagaacag cgccttgatg
```

-continued

```
32221 gcggacagca gcgcgatgaa caaggtcgcg ccgtggcgct tgccgagcga ttccagcgcg
32281 gccgtctcgg cggcgggcag gtcgaatcgc caggatttcc agctcggcgc ggccggctgc
32341 tcgacgtcgc ccggcagttc cagtgcgcgc aggccgccgc ccagtttggt cagccagtag
32401 tccttcatgc gcgcgccgtc cggcccggcg agcaggcggt tcagccagcc ggcgtaatcc
32461 ttgtactgga tcgggagggc gggcagcgga tcgtcgcgac gctggacgaa tgcgtcatag
32521 agcgcggaca ggtcgtcgag cagtacctcc gtggaccagc cgtcgctcac gatgtgatgc
32581 atcgtgcaga ggcagacgtg acggacttcg gagagcctca gcagcttgac gcggaacagc
32641 gggccggtcg cgagatccat cggcacgagc cgttcgctcc cctggatcgc cgctgcctgg
32701 gcatcgcggt cctcggcatc ctgcagatcc acgatctcga ccgggaacgc ggcttcgccg
32761 ggcggcagca cgtgctggac cggctggttg ccttccagca cgaaacgcgt gcgcaggatc
32821 tcgtgacgct cgctcaacgc gcggaacgcc cgcacgagcg catccacgtc cagcacgccc
32881 tcgaacagca gcgacgtggg cagcggcccc tcggcttgcg ccgcatggag acgatcctgg
32941 acccacagcc gcgtctgtgc gggagagagc gcgtagcttg cctgcgccgg cagcggcgtc
33001 accggcgcgt aatcgatcgg ctgcgtatcg gcgatgcgct tcgcgaggct cgagatggtt
33061 gggagtgcga acaggctgcg gatttccagc ttcacatgca gatcgcgccg gatgcgcgcg
33121 acgaccttcg tcgccagcag cgaattgccg cccagatcga agaaattgcc ggtcgtgctg
33181 atccgcgcct ggccgagcac ttcctgccag atggcagcca actgcgcttc gagtgcgttg
33241 acgggcgcaa cgtggtccag gccgtcgccg ggttcgggca gcctggtgcg atcgagcttg
33301 ccgttgggca gatgctcgaa cgcgctcacg acgacgaacg cggagggcac catgtaatcc
33361 ggcagccgct gccgcaggtg gccgcgcacc gcttcgatca gttctgcttc ggggtgcgac
33421 gagcacagcc atccgaccag tctcgcgccg tcgtccacgc cgcgcagcgc gacgacggcg
33481 gcatcgacca gcgggtgcga cgtcagcgcc gcctcgattt caccgggttc gatgcgcagg
33541 ccgcgcagct tgatctggtg atcgatgcgg ccgaggaact cgatgttgcc gtcgggccgg
33601 tagcgcgcga ggtcgccggt gcggtagagg cgcgcgagcg ggtcggccga gaacggatcg
33661 gcgatgaact tttcggcgct cagttcgggt tcgccgtggt agccgcgccc gaccggtgtg
33721 ccgccgatca gcaattcgcc ggccacgccg atcggcgtgg gctgcatctg cgcgtcgacg
33781 atgtagaggc gggtgttggc gatgggccgg ccgatcggca cgatgcggtg cggatcgtcg
33841 cgccggcatt cccacgcggt cacgtcgacg gcggcctcgg tggggccgta gaggttgtag
33901 agctcgacgt ccaggcgctc gaggcaacgc tgctgcaggt catgggcaa ggcctcgccg
33961 ctgcacacga cgcggcgcag cgacgcgcag tgcgcgtcga ggtccggatg atcgaggaac
34021 gcgcgcagca tcgacggcac gaaatggatc gtggtgatgc gttcgcgctc gatgagctcg
34081 accaggtagt cggtctcgcg ctggccgccg gggcgggcga acacgaggcg cgcgccggtg
34141 acgagcggcc agaagagttc ccagaccgag acgtcgaagc tgaacgggt cttctgcagc
34201 acggcatcgt cggcgccgag ggcgtaggcg tgctgcatcc agaggatgcg gttggtgatc
34261 gcgcgatggg tgttgagcgc gcccttgggg cggccggtcg agccggacgt gtagatcatg
34321 taggcgaggt tgtcgccgtt cagcgcgggt gcggggttgg acgtcgccgc ggcgtcgagg
34381 tcgagcgagt cgcgatcgac gacgatcacg tgcgcgtcgg tgtcgggcag cgcgtcgtgc
34441 agatgctgct gggtgaggag ccagcgcaac tgcgcgtggt cgatcatgaa gcgcacgcgc
34501 tcggcggggt agtcggggtc gacggggacg taggcgccgc cggccttgag gatcgcgagc
34561 agggcaacgc tcatgtcgag cgaacgctcc atggcgacgc cgacgagcga gtcggggccg
34621 acgccgagcg cgacgaggtg gtgggcgagg cggttggcgc gcaggttgag ttcggcgtag
```

```
34681 gtgagcgcgg tgtcatcgaa gacgatcgcg acggcatcgg gcgtgcgctc gacctgctgc
34741 tcgaacaggc ggtgcagcgg ttgcgcggcg tcctcgccga aatccgtgtc ggtgcggttc
34801 cactcgacgg tcagcaggtt ccgctccgca tcgctcgaca acggcagacg ggcaacggcg
34861 gccgacgcat cgtccgcgag atgcgtcagt agggtccggt agatgtcgag gaaacgctgc
34921 accgtgctcg cgtcgaacag atcggtgttg tagtcgcaat cgatcaggag tgcttgcccc
34981 gcgtcgagca cgttgacgtt caggtcgaac gcggtatggc ggatcagcgg cgccacgagg
35041 ccgaccgtca ggccgggcag ttcgggcagc gccgacacgg gttcgaggtt gaagaccgcc
35101 gataccagcg gcgcggcgtt gagatcgcgc tgtgcgccga tttcgcggac cagttcggcg
35161 aacggataat cctggtgctc gagcgcgtcg agcaggttct gccgggtgcc ggccaggaaa
35221 ctggccacgg tggcctgctc cggcagcgtg gagtgcagcg gcagcagatg cgtgcagtag
35281 ccggcgaggc gatcgctgcc ggccaccgag cggccggtca ccggaatgcc ggtgacgatc
35341 tcctgctggc cggcgacgcg gtgcaggaac agattgaagc cggcgagcag caccatgtag
35401 agcgtgcagc cgttctgacg ggccgcggtg cgcagcgtcg cggccgtcgc cgcgtccaga
35461 tgcagggaca cgcgctcgcc gtgaaacgtc ttcaccgcgg gccgcgggta gtccaccgga
35521 agattcagcg gtgcggcctg acgcgcgcat gcgccagcc agtactcgcg attcgccttc
35581 gtttccgggc tgtggcgctg gccgtcgagc tgcttcaggt acgcgcgaaa ctgcagcggc
35641 gcgtcggccg gcgccgcacc ggcatacgcg cgggccagat cctcgagcag cacgccgaac
35701 gtcgagccgt cacagatgat gtgatgggcc gtcatccacca gcaggtgacg ctcgctgccg
35761 aggcgcacga gcgcggcccg aaagagcggc ccgttcacca ggtcgaacgg ctggcggctt
35821 tcctgctccc gccacgcgtt cgggtccgtg tcgatcagcg gaatctcgag tgtcagcgac
35881 gggtgcacga tctggcccga cccgtccgcc atcaccgtgg tgcgcagtgc ctcgtgccga
35941 tcgacgaggc tctggacggc cgcgcgcatc gcggcttcgt cgagccggcc gttcagttcg
36001 agcgtggtgt tgacgttgta ggcgagcgat ccttcgggat cgatttccga caacacccac
36061 agctggcgtt gcgcttcgct cagcgcggcc accgtgccgt gtttcgagtg cggccggatg
36121 aagccgcccc ggcgcaggtc ggcgacgctg tccttcaccg cccggatgaa gcggtcgata
36181 tcggcatcgg tatgcgcggt ggacaggaag caggtgcgcc attcccagat gtagatgccc
36241 ttttcgagca tgtgatagaa gaacaggtcg aggttctcgg tgaattcgaa gcggaacatc
36301 gagccgaacc acgtgaacctt gatcggcgcc tcggcctccg cgaagaatgc attcagcgtg
36361 ccggcgatct gcgcggtgcg ttcgttgagc gcggcctgca gcgccggccc ctcctgttcg
36421 atcttctcga gcacggccag cgccgccgcc atcgcgagcg gatactggca gaaggtgccg
36481 ccgaacgcgg tgcggtccgc cgcggggaac gagtggtcgc cgtaggtcca catgccgccg
36541 tcgatggcat ccatgaagcg gctggtgccg gcgatcacgc ccagcggcag gccgccgccg
36601 atgatcttgc cgtacgtcgc gagatcggcc ctgatgccga acatggcttg cgagccgccc
36661 ggatggacgc ggaaaccggt gatcatttcg tcgaagatca gtgcgacgcc ggcctcctcg
36721 gtgatgcgac gcagttcctt gaggaatgcg acgggctgca gggaagggtt gcggctctgc
36781 accggctcca ccatcacggc ggcgagggtc gacgccatcc cgcgaatggc ctcgagcgcg
36841 gcgtcgctgc cgtagtcgag caggatcatg ttctcgacgg agccgaacgg tacgcccggg
36901 gcgatggttt ccgtcacgcc ttccgcgttc gccgcggcga gcgtgccgtc ggcatggccg
36961 tgatacgaat gcgtgaacat cacgatcttg tcgcgcccgg tcacggcgcg cgcgagccgc
37021 atcgcggtca tgacggcctc ggtgccggtg ttcgagaacg ccacgcgatc gaggccggtc
```

```
37081 acgcgggcaa agcgcgcggc gacttcgccg acgaggctgg agcgcgcacc cagttcgagc 37141 gggcgctgcc attcccgcgt gacctgctgc tggatgaaat ccggcgtgtg gccgaacagg 37201 tgcacgccga agcccatcgt gaaatcgatg tactcgttgc cgtcgatgtc ccacagccgc 37261 gaaccggccg cgcgatcgcc gacgatcgga tacagcatct ccttggtcga aaagcggaag 37321 ccgaccgtgg cgcggctgtc ggccagcacc gggcgcgacg cctgcaccga gtccttcgat 37381 ttccgggtgc gcgtcgtgta gcgcacgatc agcgcctcga gatgctcctg ctgcgcggcg 37441 gacagcccgc gcgcccgctg ctggaccggg ctgccccacg gcatcatcgg cttgggcggc 37501 gggttgtcgg ccgcgggcgc ggcggcagct gcaggcgcgg gcttcgccgc gggtgcggcg 37561 gccggggccg cgctcgccgc tttgggtgcg acgctcgccg tgctcgcgac ggcttgcacg 37621 gcggccgtcg ccggccggac gccgggctgg ccggtcagcg acgtgcgcag cagttccatc 37681 tgctggctca tcacgtgcga cagcagctga ttctgctccc gcagcacgcg ctcgaccgtc 37741 gagccgcctt cggccgccac ccattccgcg ggggcggccg cgagcggcgc aagccccgcc 37801 gcggacggcg tgaccgcgac cgccggcgtg gacggttccg ccgcggccac ggctacggct 37861 acggcctcgg ccccggacgg tgcggcggct gccggcaggt tgtccgcgac atattcggcg 37921 agcgcctgca ccgtcgcgag gtcttcgaag aagcggcgca tggccagctt cacgccgtac 37981 tccgcctcga tgtgccggat ggcctcgatc agcacgatcg agtcggcgcc catctcgagg 38041 aagggcagtt cgatgttgat ggtggcggga tcggcctgga tcaattcgcc gatcttgccg 38101 cgaagccatt cgagaatctc gccgctgcga ttgtgcgtcg gtgctgcggc gatgggtgat 38161 gcgcttgtct gagtcatgga cgtgtccgct ttctggaacc aggtacggct gcgttggaag 38221 ggataggacg gcaatgcgat gcgcgcgggc gcgggtgttt cggtcggggc ccagtcgaca 38281 tcgacgccgc gggcatacag gctcgacagc gtttcgatca gcgcttgctg ctcgacttgc 38341 ggccgctgca gggcaaggaa ctggatcccg cgtccggcg cacagcacgc gcgggccagg 38401 ttgacagcag accggcttcgg gccgatttcg accagcacgt tgaaaccggc ttcggcgagg 38461 cgctcgacgc tgctcgcgaa ctgcactggc tcccggcagt ggcggcgcca gtacgtgtcg 38521 gtgggtgcct cgtccatcac ggcgcccgtg agattcgaat agaacgggat cgccgggcgt 38581 gcgacgggca cggttttcgc cgcgagctgg aagctgtcca gcatcggctc gagcagcggc 38641 gagtgaaacg cgtgcgacgt attgagcggc acggaccgga tgtcccgcgc ggcgaacgca 38701 tcgaccagca tcgcgatgcg ctcgcgcttg ccggaaatca cgatgctcgc cgggccgttg 38761 acggccgcca ccgcgacctc gtgcggccac gcgtcgatcg cgcgctcgac cgtggcgagg 38821 tcggtgaaaa tcgccgccat ctcgccgtcg cggggcaacg cctgcatcag ccggccgcgt 38881 tcggcgatca gccgcaggcc gtcttccggc gagaagacgc cggccgcgca agccgccgcg 38941 tactcgccga cgctgtggcc catcacggcg tcgggcacca cgccgaacga cgccagcaac 39001 gtggtgagcg cgtactgcag cgagaacagg gccggctggc tgtagccggt ctggtggatg 39061 tcctcgccct gggccgacag cacttcgagc aacgcttgt cgagcaacgg atcggccacc 39121 gcgcggcaac ggtcgatggc gtctcggaac accggatacg cgtcgtacag gcggcggccc 39181 atgccggcgt attgcgagcc ctgccggtg aacaggaagg ccatcttcac gcggggggcg 39241 ggctgcgccg ccgcggccgg ttccttcgcg tggaaggcgc gcagcttgtc gatggcgtcg 39301 tcgagcgacg tcaccggcca tgccagccga tgcgcgaaat gcgagcggcc ggtcgccgcc 39361 gaaaaggcca cggccgcgat gtcgagaccg ggttcggctt cgagccgccg ctgatagcgc 39421 ccggccagct cgcgcaacgc cgcggggtc ttggccgaca gcaccagcgg atgcaccttg 39481 tgtctcgacg gcgtcgcctg ccgcgccggc gccggcgctt cttccagcac caggtgggca
```

-continued

```
39541 ttggtgccgc tcgcgccgaa cgcgctgacg ccggctcgcc gtggccgttc gccacgcggc
39601 cacgcgctcg cctcggcgca gatctcgacg ggcattgcgt cccactgcac cagcgggctc
39661 ggctggcgga aatgcaggtg ggcgggcagg cggtcgtggt tcagcgacag cacgaccttg
39721 atgacgcccg cgatgccggc ggcggactcc gtgtggccga tgttggtttt caccgagccg
39781 acgcgcagcc gccggcccgc gtcgcggcct cgccgaaca ccgtcgccag cgcctgcaac
39841 tcgacgggat cgcccagcgg ggtgccggtg ccgtgcgctt ccacgtaatc gatggacgcg
39901 gcgggcaacc cgcccagcgc ctggcggatc acggcttcct gcgcacgacc gttcggcgcg
39961 gtaaagccgc tcgacgcgcc gtcgtggttg accgccgaac cccgcagcac ggccagcacg
40021 cgatcgcccg cggcgagcgc atcggacagg cgcttgagca ccagcgcgcc gcagccttcg
40081 ctgcgtacga agccgtccgc cgccgcgtcg aaggtcttgc agcggccgtc cggcgccagc
40141 gcccgcgtgc gcgagacggc gatggagttg tccggcgaca ggatcaggtt gacgccgccc
40201 gcgatggcga gatcgcactc gccgctgcgc aggttctggc tggcggtatg gatcgccgtg
40261 agcgacgacg agcaggcggt gtcgatcgcc atgcttggcc cctgcacgcc gagtccgtag
40321 gagatgcggc cggccgccgt gttcagcggg ttgccggtga agaaatagcc gtcgatgccg
40381 ctgccgccgc cgttgcgaag ctgcaggttc gcgtaatcgt tggtggtgat gccgacgaac
40441 acgccggtgc ggctgccctt gagactgtcg accggaatgc cggcatgctc cagcgcttcg
40501 tgactgacct cgagcaacag gcgctgctgc gggtccatcg cggccgcttc gcgcggcgtg
40561 atgcggaaga acgccggatc gaactggtcg acgtcgtcga gaaaaccgcc gaagcggctg
40621 tacatacgcc ccggcgcttc cggatcggga tcgtagtacg cgtcgacatc ccagcgctcg
40681 cgcggcactt cggagatcgc atccacgccg tcgttcagca ggttccagta ggcgtcgaga
40741 tcgtgcgcgg cgcccggaaa ccggcagctc atgccgacga tcgcgatcgg ctccggcgtg
40801 ccggcgtcgc gggcctcgat ggccgcgcg atcggccgcg gctgctgctg cggcggcacg
40861 gtctgcgcct gcgccgtgcc ggacgcctgc tccgccagga aatccgcgag ggcgttgacc
40921 gtcggatgat cgaacaacag cgcgaccgac agcgggatgc ccagcgcatt ttcgaggtgc
40981 gtgcgcacgt ccagtgccat cagcgaatcc atgcccatct cgaagaagcc gagatcgcga
41041 tccagcgtcc ccgcgtcgta gcccagcacc tgggccaccg cgcgatcgat gctgtccgcc
41101 agcagccgct ttcgctcgcg cggcgatgcg tcgctcagcg ccggcattgc cggcgcgctc
41161 ggcgcgcttt tggccacccg cacgtggtcg aggaacggct tgggtccgcg cgcctcgtag
41221 gagccctgga acagcgccag gtcgatatcg acgaccgcga cctggggcac ggcggggaga
41281 cgattcagca cgtcgagcgc gcgatccgcc gccagcgacc ggatgccgac acgccgcagc
41341 agcgcttccg cctcggggaa cgtcatgccg ccttccgccc agggcccccca gttcacgctc
41401 agcgccggca ggccctggcc gcggcgatga tgcgcgagcg cgtcgaggaa acggttcgct
41461 gcactgtagt gcgcctgctc acgcgagccc cacgcggacg cgatcgacga aaacaggagg
41521 aagaaatcga gcgggaagtg ctcgctctgc tgatggagca gccacgcgcc ggcgaccttc
41581 ggttgcagga ccgcgtccag ttcgtcgcgc tcgacctgca tgatcggctt gtagccgacg
41641 atgccggccg cgtgcacgat gcctttcagc ggcacgccgt cgcgccgcag cgcggcgaag
41701 aaagcggcga ccgctgcggg gtcggcgata tcgaggcgct cgcagcgcag cgtgacgttc
41761 cgctcacgca gctcggcgat cgcccgctgg ctctcgtcgc tcgcggcccc ttgccggccg
41821 accaggatca gcgtgcccgc accgcgcgcc gccagccatc gggcggtgtg cagcccgagc
41881 gcgccgaacc cgccggtgat caggtaggcc gcgtccgggt cgaccggcag cgcggccgtt
```

```
41941 tcggctggcg cgagcgggct caggcgcgcg acatggcgcg cgccgtgccg caacgccacc
42001 tgctcctcgc ggctctcgcc gagcatctcc tgaagcagtg cctgcgtctc gttctccggc
42061 gcggccggat cgagatcgat cgcggtgccg aaccattccg gatgctcgat cattgccccg
42121 cgtgcgaggc ccgacagcgc agcctgggcg agcccggata cgtgcggcgc ttcgccggct
42181 tccaccgcgt cgcgcgtgac caccgagatc ctgggccggg tcgaaggcgt ccactcgcgc
42241 tcgctgccga ccagcgcgtg cacgagatgc agcagggcgg cggacatgcg cgtttcgccg
42301 acggcttcgt ccagcgccca taaaaagacg atgcgctggc cggaagcggc ggtttcgttc
42361 agcaagcgga cgaaatcgtc cggccgctcg ggcgcgacct gccagcccgc ttccgcgccg
42421 gtgacatagt cgatgccggg gcggaccagc gagcaggatg cgccgcgcgc gcgcagcagc
42481 gctgcaagcc gctcgccgac accgctcgca tccgcgaaga tcagccacgg ggacgcgtcg
42541 gcggcggccg gtgccgccgg catcgcggcc tgctgctccc acaccacgtg atagagcggg
42601 tgtgcgttcg acgcgacggt ctcggcggcg gcgaatgcag tcctgagcag gtccggaaac
42661 gcgttcagca tgtcctccgg gtacttgccg gacgacttga ggtgccgcaa cgctgcgtcg
42721 atgctgccgg catccatgcc gacgatcggc gacggaatct tctccaggct gaagcgctgc
42781 cgctcgaacg ggtagttcgg cagggtcgtg gcgggctggg cgggcgccgg aaacagcgcg
42841 cgccagtcga actgcgcgcc ctgcacgtac agcgccgcga gtgcgcgctc cagtgcatcg
42901 cccgcgcagg gcggcggcag ccagccgtcg gcgagcccct ccggcgggtg cgatgcgtcg
42961 gcctgatccg acgcgccagc cagttgcaac cagtactgcg ggtgcgtcac ctcgtcggtc
43021 acgtcggtgc cgagatagcc cgaaatcagg cggaccgacg gccgtgcgag cggcatgtcc
43081 cgaagcacgg cgcgcaacgc ttcggcatcc gaacgggcgg ccacgaggcg cagcgcgtcg
43141 gccacgctca cgacgcccgc cacgcaggcc gcgacatatt cgccgatgcc atggcccgac
43201 acgacggccg ggcggaggcc ccatcccttc cacagttccg cccacgcgaa ctggatcgcg
43261 aaccggcccg cgtcggtctc gagtgcgtcc agcggcaccg agcaacgcgc gaacgcgtcg
43321 cggaacagcg gttccgacgc gtggagcgcg tgcgcgacgc cggtgtccgg cacaccgaac
43381 ccgaagccca tgcgcaacgc cttgcccgtg cgcggcgcgg ccgccgacgc taccctcgcg
43441 cccgatacat aggcggcgcg aaacggatag tgactccgcc cggtggcggc ggcacggcag
43501 atcgcggcta gctcctgcgg cgtcgcgccg gcgatcgcgc gctcgtagcg tggcacgagc
43561 gccgccagcg ccgcttcgga ccttgccgac agcagcagca acgcgcgctg cgcggcgtgt
43621 gccggcgcga cgggcggttc ctcgacgatg gcgtgggcat tggtgccgct gaatccgaac
43681 gcgctcaccc cggcgatgcg cctgcgttcc ccgcgccgcc acgcgaccgg atcggccgcg
43741 acgcggatcg ggatgtcctg ccacggcgta tgcggattgg gttgcgtgaa atgcaggtgc
43801 gccggaatcc ggtcgtgctc gaacgacagc agcaccttga tcaggccggc gatgccggag
43861 gccgactcca gatgcccgat attggtcttg accgaaccga tcacgagcgg ctcgttcgcc
43921 gcgcgcccgg ggccatagac gccggccagc gcttcgacct cgatcgggtc gccgagggac
43981 gtgccggtgc cgtgggcctc gacgtaggac acgtcgccgg gcgcgaggcc ggcctggttc
44041 agtgcgcggc ggatcacccg ttcctgcgaa tcgcggctcg gcacggtcag cccgccgccc
44101 gcgccgccct ggtcgaccgc cgtgccgcgc acgatgccga gcaccggtc gccgtcggcg
44161 agcgcgtcgg cgaggcgctt gagcaccacc atgccgcacc cttcgccgcg cacatagccg
44221 tccgccgccg cgtcgaaggt cttgcagcgt ccgtccggcg acagcatgcg cgcctgcgag
44281 aagctgacca tgacctcggg cgacagcatc aggttgacgc cgcccgcgag cgccatgttc
44341 ctttcgcgcg agcgcaggct ttcgcaggcg aggtgcaggc acaccagcga agacgagcag
```

```
44401 gcggtgtcga tcgccatgct cgggccggtg aggcccagca cgaacgacag ccggcccgcg 44461 gccatgttca gcgcgctgcc cgtgccggca tagctgctcg acggcatcga cgcattggac 44521 acctggatcg cgtggtcgaa gcaggtgatg ccgacgtaca cgcccgtggc ggactgccgg 44581 aagcgttcgg gcgcgagatg ggcgttctcg agcgcctccc acgccacttc gagcaggagc 44641 cgttgttgcg gatcgaggta ggtcgcttcg cgcggcgcga tcccgaagaa cgccgcgtcg 44701 aattgatcca cgcgttcgag aaaggcgccg tggcgggtcg ccatcttgcc gggcgtggac 44761 ggatcggggt cgtagtagcg atcgatgtcc cagcgttcgc cgggcacttc ggtgacggca 44821 tcgtgcgcgc cgtcgagcaa ttgccagaac gcgtccggcg tatcgctgcg tccggggaag 44881 cggcaagcca tgccgatgac ggcgatcggc tcgttgcggt cagaacgcag cgccgcgatt 44941 tccgcgcgcc gcaggcgcag ttcgtcgagc gcggctttca gtgcatgcgt ggccttggcg 45001 ttcattgggc gccgatctcc tgggcgatca gttcggaaag gtcgtcctcg tcgaggtcgt 45061 cggatgcttc gtcgacgacc ggcgcgggga cgacggcga cagttcgttg agcacgtact 45121 gggcgagcgt ctgcaggttc ggataggaaa agaacaacgt cgcgcgaaac ggtcttccga 45181 ataccttggt gaggcggtcc gtcagttcga gcgcgaccag cgaatccagg ccgagatcga 45241 gcagcgattg ctcgggcgcg atggcatcgg ggccggaaag gcgcaaggtt tcagccagca 45301 tcgccgcgag cgtgtcggtg atgcgctcga cccgttcgcg cggcgcgcac gcatgcagct 45361 ggcgcagcaa cgccgtctcc tgctgcgccg gctgcgcggc cggttgcgtc agctcggaaa 45421 acagcgcgga cccggcggcc ggcgcatcga cccggaacag ggtcggccag tcgatccgcg 45481 cgactccgga ctgggcgacg ccggacgcca tcagccgttc cagcgtcgcg atggccagtt 45541 cgggcggcag cgtgccgacg ccgagcgcgc cgagttgttc gtgcgcgcgc cgtccgtagt 45601 cggtggcggc gtggccgatc tccgcccacg gcccccaatt gacgctgagc cccggtttcc 45661 cctgcgcgcg ccgatgctgg gcgagcgcgt cgaggaagct gttcgccgcc gcgtagttgc 45721 cctggcccgg catggtgatc agcgcggcca tcgacgagaa caggacgaaa tggtccagcg 45781 gcaagccggc cgtcagctcg tgcagatacc acgcgccgtc ggccttgccg ctgccggcgc 45841 gatggaagaa gtcgtcgtcc tggcgtgtca gcagcgcatc gtcgagcgcg ccggcgaggt 45901 gaaagatccc tttgagcggc ggcatcgaat gcgcgatttc accgagcgcc tgcccgacgt 45961 cctcgcgacg cgacaagtcg gcgcgaatga accgtgcgtc gagcgtgcgc aggatttttcc 46021 cggctgcggc ggaaggttcg ccgcgcccca gcagcacgat tttcccggcg ccgttgtcgg 46081 caagccagga cgcgagccgc aggccgagcc cgccgagccc gccggtcaca agataggtcg 46141 cgtcaccgtg gaaccggatc ggccggtggc tgacgtattc gcgattgtcg cgggcgatgc 46201 gcgcgacgta gcgctggtcg cggcgaaacg cgatcatgtc ttcacggccg ccagcctgta 46261 ccgcttgcat gatgtccgct gccgacggct gctcgggatc gaggtcgacg agcccgcccc 46321 acagcgccgc atgctccacc gcgatcgcgc ggcccaatcc ccacagcggc gcctgtgcca 46381 ccgcgatcga ttcgccatcc agaacattca tcgcacccga cgtcaccagc cacaggcgag 46441 cctgccgggc cgacggcgcg cgtgacgcaa gcgccctgac caggtgcagc acgctcgcgc 46501 tggcacgccg tctcgccgcg atgtcagagg gtgcgagatc gagactccac aggtggatga 46561 cgcccttcag cgggcggtcg gccgcgggca gttccggcgt cgcgtcggcg aagcgcagcg 46621 tgcacgtatc gccgtgggct tccagcagag ctgacagctg ggcgcccacg ccgccgcggt 46681 ccgcgagaat cagccactcg ccgtgcgccg aaccgccggt tgccgcgtcg acgttcgacg 46741 gtctccagac gcgttgataa agcagcgcgg cgaagtcgtg ccgctcgacg gcgcgcgccg
```

```
46801 cgcgaacctg ttgcaaccgc agtgcatcga tctcgatcag cagtcggcca gcaaggtcat
46861 ggacgcggat gtcgccctcc agcgcgccct gtccgatcgg cgtgcgcagc gtggcgtgac
46921 tccatgcctc ggtcgacgcc ggcggctgat ggaccgtac cgcgccgatc gagctgggca
46981 ggtacaggtc gcccgactcc agcgcgtccg gatcgatggc ggcggcgagc acgcggctgc
47041 atgcgtcgag aaaggcgggg tgtacctggt acggcgacga cgccagcgca tctgccggca
47101 ggctgatttt ccccagcgcc tcgccggtcg tgcgccagat ctgccggatc gcgtcgaaca
47161 cgccgtcgat ctgcacgccg tgctgccgaa tttcgccgtt gaagtccgcg cccgacgtcg
47221 tttcggtgca gcgggcctgc acctcggcgg catcgaatcg cgtcggcgcg gcggatcgcc
47281 gggggcaca catttcccgg agccggcgca gctgcggaag attgccgagg atccgctcga
47341 ccggcggacc gaaatcgagc aggcaggcca cttcatccac gccgatcgac tcgagatccc
47401 gcaccagttc gacgcaggtt tccggcgtgc cgatgagccc gcgcgattgc gcgaagcgtt
47461 catagagaaa ctcgacgaac tcgtccagct cgcgtgcgcc catcgcgcgc acgtcgaccg
47521 actggccgcg actctgcgcg agcccgttca atagcccgat attgctgcgg atgtagttgc
47581 agaacggcac acgcgcctgt tcgcgcgcct gcgccgcatc gtcgccgacg aacgtatgca
47641 gcatcacgga aacggtgccg gccgccggat cgaagccatg cttcgcacgc gcctcgcggt
47701 agagcgcgat cttgtgcgcg agctggtcac gatcctggtc gagcacgtgg gtcagcaggt
47761 tggcgccggc ttcgccggca cgcacgaatg tctgcggatt gctcgcggcg gtcacccaga
47821 cgggcagctc cggctgcacc ggcgtcggat agacacgcaa ccgcaccggc ttgccgacac
47881 cgttcgtcgc atccagcgtg ccgccgcgcc acagatgctg gacggcgcgc atcgtggtca
47941 gcatgtcgtc ctgccgggtc gcatatttgt ccggggcaaa cacgaagtcg tcaggattcc
48001 atccggaggc gaacgacacg cccacgcggc cgttcgacag gttgtccacc atcgaccatt
48061 cttccgcgat ccggatcggg ttgtgcagcg ccgcgaccac gctgcccgcg accagcttca
48121 cgcgctgggt ggccgcggcg agcgcggcgt gcaggacggc gggattcggg taaagcgagc
48181 cgaattcggt gaaatggcgc tccggcaccc agacgctgga gaacccgttc gcatcggcga
48241 aacgcgcgct ctccatcacg agctggtact tgttgccgga cagcgcctct tcactgctgg
48301 cgaagaacat cagtccgaat tcatgcgtg ctccgatcc gattcgtgaa tttcggcact
48361 cgcgcacatc tgccacgtcg cggcggcgcg ggtgtcgtcg atccggtgat agacggcaaa
48421 cgaaaacggt ccccaggacc ggcggctcag cacggtctgc acggtgtgcg attcgtgcgg
48481 atgcagcggc aacggcgcat gcagtgcgag gtccttcaac gtcgtatggc cggctgcgcc
48541 gatttccgac gttgccgaca gcgccatttc cacgaaggcg gaatagggca ggacgggcga
48601 ccccttgacg cgatgaccgt cgagaaagtt ggttgccggc gcatcgagac gcgattgcca
48661 gatccacgtg gccggcgcat gcgcgtgctg ctccatgagg cgcccgagca acggatgccg
48721 acgcgcatgt ggcctgatcc agaagccgcg ccgctcgaac gggtaggtcg gcagggcgag
48781 ccggcggtgc ggtgcacctt gctccacggc atcccagtcg atggatgcgc cgcgtacgta
48841 gagcgcgcg agcgtgtgca ggatcgcgtc ccacgcggcc gtgtgcgcgc cgatgtcgat
48901 cacgatgccg gggtgtcctg ccgcaccgct gtccggcgcc tgcggcacgc cggcccacgc
48961 ggctgcggcg cgctgcccgt cgccggtgct gctgaccgca tccggtgcga tgccgaagga
49021 catccacagt tgcgcgagcg cgcgctggaa tctcgtgaac ccggcttcgt cggggggcgag
49081 cgcgggcgcg ccggatgcgt cggactgccg ctgcatcagc gcgtcgaaag cggggctggc
49141 cgcgcgcaat tgccgaaccg cgtcggcgct ggcgccgtcg tcggcgcaaa agtggaacgt
49201 caccgcgggc ggtgtttcgg caggctcccc ggacgaaacg gaatcaagtt gcgcacgcaa
```

```
49261 cgaatcgcga ctcggtgcga cgatggccgc gcgctgcgtg aagtgggtgc gcccggtatt
49321 ggccgtgaac gcgacatccc gcacaccggc ctcgggatgg gcgtcgagat aggccgcata
49381 ggacgcagcg agcgcttgca acgcgtccgg cgtgcgcgcg gagagcgtca cgacgcgcgc
49441 cgcgggtgca accggttcgg cttcgatctc cgggagcccg ggtgcttctg acaggatcag
49501 gtgcgcgttg gtgccgccga agccgaacga gctcacccct gccaggcgcg gcccgtgttc
49561 cgaatgccag ggcgtgacct gccgaggaat ccggaagggc gtgccgtcga gcgcgatttg
49621 cggattgatc gaccggaaat ggaggttcgg cggaatcgcg cgatggtgta gtgcaagggc
49681 ggtcttgatc aggctggcga tgcccgcggc cgattccagg tggccgatgt tggtcttgac
49741 cgacccgatc cagcagagat cgtccgggcg gcgggattcg ttcaggacgg ccgccagcga
49801 gttcaactcg atcgggtcgc cgagcggcgt gcccgtcccg tgcgtctcga cgaagccgat
49861 gtcctgcgcg cgtacaccgg catcgcgcag cgcgccgtga atcacggcct gctgggccgg
49921 gccattcggc gcggtcaggc cgttgctgcg cccatcctga ttcaccgcgg agccgcggat
49981 cacggcgaac acggtgtcgc cgttctcgag cgcatcgtcg agccgcttga gcagcaccat
50041 gcccacgcct tcgccgcgaa cataaccgtt cgctgccgcg tcgaacgcct tgcatcggcc
50101 gtccggcgac agcatgcccg cttgcgtgaa ggacgcgctc aattgcggcg ccagaatcag
50161 gttgaccccg ccggccagcg ccgcatcgga ctcgccgcgc tgcagcgcgc ggcacgcctg
50221 gtgaaccgcg acgagcgagg acgaacacgc ggtgtcgacc gcccagctcg ggccgcgcaa
50281 atcgagcgcg taggaaatgc ggttggcggc gacgctgagc gcattgcccg tcgcgacata
50341 agggccgacg tccgcgactt cgtcctgcgc cagacggatg tagtccgaat tgctgatgcc
50401 gacgatgacc gcggtgcgtc cgccggcgag gctgcggggt gcgatccccg catgctcgag
50461 cgtctcccag gccacctcca gcagcaggcg ctgttgcgga tccatcgatt cggcttcgcg
50521 ggcgctgatg ccgaagaaag ccgcatcgaa ttgatcgacc tgatccagca gtccggcgag
50581 cggaaggtcg gccgcgcgct gcgtcgccgc accgaccgcg tcccggccct ccagcagaag
50641 ctgccagaat gcgtcgggat tgccggcgcc ggggaagcgg catcccatcc cgacgatcgc
50701 gatatccgcg cgtgcttcgg ccgagcccgg cgcctggtcc ggcatggcac tcccggtgcc
50761 gctcaaatgg cgcgccagca gggaaatact cggaaaatca tagacgacgg tcggggaaac
50821 cggccgcccg agccagtcct gcagctcgcc cgagagcatg atggcgtcct tcgaatcgag
50881 cccgtggacg ctgaacggcg cgtcggggtc gatcttgccg gaagcgattc ccgacagacg
50941 cgagacacgc tcgatgcacc attgcaccag cgcttgcgtg tcgcgtggct cggcagtctg
51001 cgggggggct ggcggcgcgg agaacgcacg ccgccattcg cccgcgatcg cgagcccctg
51061 ttcatcgagg aatgcctgcc tgatccggct ccgctggatt tttccgctgg acgtgcgcag
51121 gatcgtggca ggtttcaaca ggactgccgc atacagatcg acgtcgtgca cttcggcgag
51181 cgtgtgccgg atctcggcgg ccacggcttc cgcgtccagc gtgttgagcg cttcccggcg
51241 cacttcacag gcgacgacga cccgctccac gttatcgacg tggatcgaga aagccgccga
51301 tgcgttcggc gccagcgcgg ggtggctgcc ctccgcggat tgctcgagat cctgcgggta
51361 gtgattgcgg ccggcgacga tgatgaggtc tttcaagcgg ccggtaacga agagatcctc
51421 gccatcgacg aagccgagat cgcccgtgcg caggtaacgc gcgtcatcgc cgtccagctt
51481 cgcgcggaag gtgcgctccg tttcgtcgat acggttccag tagccgacgc cgacactcgg
51541 gccggtcagc cagatttcgc cgatccggcc gggcgcgcag cgctcaccgg tatccggatt
51601 cacgatgcgc acgcggtgct cagcccaggt ccggccgcat gagaccagcg cgtggcgctt
```

```
51661 gccggagtcg tttctcgtcg ccacgccttg tgccagcgcg tcggcatcgt agtccgccac 51721 gcgcggcagc gagcgtgccg gctggccgga gatgaacaag gtcgcctcgg ccatcccgta 51781 gacggggcgc atggtgtgcg cgtggaagcc gcacgcgcg aatgcgcgcg aaaaacgcgc 51841 caccgactcc gcgcgcaccg gttccgcgcc gttgaatgca acccgccagc tgctcaggtc 51901 cagctgcgcg cgcgcttcat cggcgatttt gcgagcacac aggtcatacg cgaaatccgg 51961 cgcggcacaa tgcgtgccgc gatacttcgt gatggcctgc agccagcgca cgggtttctg 52021 cacgaatgcc gcgggcgcca tcagcaccga cagcacgccg agatagatcg gcagcaacac 52081 cttcccgaag aaacccatgt cgtgaaacac cgggagccag ctgacgaaca ccgtcgacgc 52141 atcggcatcg ctcgcctcgg cgatgaccgc catattgctc aggatgttcg cgtggctgat 52201 catcacgcct ttgggcgtac cggtggagcc tgacgtgtat tgcagaagcg ccagcgtctg 52261 cggcgtgatg tccgtgcgc gccattgttc ggccggggcg tcgaagcgct ggtccgtcgc 52321 caggatcttc agttccagcg tgtcggaata accgtccgcg tgatgcgcga tgccgtcgag 52381 cgtcgcggcg tccgtcagcg cgacgaccgg cgtggcgtcg gcgacgatgg ccttgagacg 52441 atcggcggga cgatgcctgc gcggtggata cgcgggtacg ccgatcaggc cggcgtacag 52501 gcatcccacc catgcgcaga tgaattccag cccgggcgga taaaccagaa ggacgcgatc 52561 gcccggttga gcgatggctt gcagcctggc ggcgatgccg cgagcccgct tgtccaggtc 52621 gccgaacgtg aggcgggtca gctccgcttc gccgttctcg agaaaaatga atgcggtctt 52681 ctccggttcg accttgccgc gaaacaacaa aatttctgta acagtcctga attttgtatc 52741 gggaagcatg ctcaaccttc gttgtcttct aaacgttgaa tatctcagga ccggttgtgg 52801 cgatcccgcc aagcgtgctt catcggacgg tatcgaaatt agagcattgc tctaatccgg 52861 cgtctgcccc gtaatccaag gacacggcgt ttcgcgcact ggatcaatac ggcttgtcat 52921 tgatgtgcac gctcgctaac gatcggcgat tccttcgatg tcgggcgtgt acgggtccag 52981 cagcgacacg acgaccttgc gctcgccttc gaacgggttg cggccatgcg cgaagcgcat 53041 gttgtcgacc agcaggacgt cgcctcgttg ccacggaaac gtgatcgcgc attcgcggaa 53101 cgcgtggcgg atctgctcga ggtcggcgag atcgaacgga ctcccgtcgc catggcaggc 53161 attgcgcgga atgcgatcct cgccgaacag gctgacgatc gaactggcga gcgatgcttc 53221 caggttcgag atatggaaca gatgggcctg attgaagaac acccgctcgc cggtgaccgg 53281 atggtaggcc acgccctggt tgatctgcgc ggtgcgcaac gtgtcgtcgt cgagccattc 53341 gagcgcgatg ccgttatccg cgcagaaggc tgcaacctgg ttgcggtcgc tggtctggaa 53401 cacggtctcc cacggaatgt cgacgtgccg ccggtagtgc ctgacatagc ggacctgtct 53461 cgcctcgaag tgatccagga tgcgcggtcc gatcctgcgg ctcacctccc gcatgtcggc 53521 aatcggcgtt tcgccgccgg tcgcggccgg cgtcaggcaa cagaaggcca ctcgcagcgg 53581 ccagcttcgt tgatacgcgt tttcgcaatg aagggcgatc gtctcgctcg gcggatactc 53641 ggttgcggtg aagatgccgt tgccgatcga ggtgcgcggc gtggaacggt aaacgtagtc 53701 ggactgatgg gccgaaatcg cgcgagcaaa cgcttcgaag ccgcccacgg atgaaacgtc 53761 gaagccacga aacaggagta cgccgtgttc cagaagccgg gattcgagtg ccgcccggtt 53821 gtcgttcacc gcctgcgcca gatcgcgtcc attcgataca ggctccagca gccacggcgt 53881 gcttccctcg gcaagcaact tgcgttccgt catgcccagc atcgtcaata gtcctttcct 53941 gtacgtggat cacggcgaag ccgaacgggt cggcccgcgt ggtcgcgccg cggtgcggct 54001 atgcgcggca ggccgttttc acggcatgct cgaagcgatt gagaatgtcg tggatgtccg 54061 cttccgaaac gatcagcggc ggcaggaacc ggagcaccgc gccgttgcgg ccgccggttt
```

```
54121  cgacgatgag cccgtttcgc aggcagttct gcttgatggc tcttgcccgt tccgtgtggg 54181  gcgggccggc tcggccgtgg gtgccgggca cgacgacttc ggcgccgatc atcaggccgc 54241  ggccgcgtat ctggcccagg caggggaagc gttcggcaag ctcctcgagg ccggcaacca 54301  ggagtttgcc gaccctgtcc gcgtgcgccg acagatcttc tctctcgacg atgcgcatgg 54361  tcgacaagcc ggccaccatc gcaatctggt tgcctcgaaa ggtgccggca tgcgcgccgg 54421  gcggccaggt gtccaggcgc tcgtcataga ccaccaccga taacggatag ccgccgccga 54481  atgccttcga cagcaccagt acgtccggcc ggatgccgga atgttcgatc gcgaacaggg 54541  cgccggtgcg accgagtccg gtctgcactt catcgacgat caacgggatt tcatgccgca 54601  gcgtcagctc gcgcaactcg atcaaccagg tgtcgggagc ggggatgcag cctccttcgc 54661  cttgcacgac ttcgacgatg atggccgccg gcttcgtgat cccgctctcg ggatcggaca 54721  ggacggtccg gatgtagttg atgctgagtt gatcggtcgc cgagccgtcg gtgccgaacg 54781  ggcagcgaaa ggcgtaggga tagggcagga aatgaacgtc gcgtccgttg ccgccggccg 54841  acttgggcgt gaggtttccc gacgcggcga gtgcgccgga cgtcatgccg tggtaggcgc 54901  cgtggaacgc catgatcgtc ggccggccgg tatagtgccg ggtcagcttg atcgccgctt 54961  cgacgccatc cgcgccactg gggctgcaaa actggatctt gccggattcg gcgatcttcc 55021  cgggcagaag cgagaaaagc tgctcgacga atgcgtgctt ggccggcgtc gccagatcga 55081  gtgcctgttg catctgatcg gacgacagaa accgcatcac ggcttcattg acttccgggt 55141  gattgtgtcc gagcgcgagc gtgcccgcat tcgacaggca gtcgatgtat tcctgcccgt 55201  cggcgtcgcg tacgcgtatg cctttcgcat gggtaaacag ccgcgggaag gaggttgcgt 55261  aggttcgcgc gttcgattcg acctgcttca gatactcgag ttttttccatg cgcgcagatc 55321  cggcttgcaa ggcggattga tggacactgg cgcacagaaa tcgcttcatc ctggccaatg 55381  gtgttttaacg gtacgaccgg attggagcat ggtctccgta tcgcgtctgt cacgtaaaaa 55441  tgggacatcg gccatgcgac gtcaccacgt catgccgttg ccttccgatc atcgaagcgg 55501  tttccgggcg cgacgtcagg cagcgagggt cgagcagaaa taatcgatgg tccgttggag 55561  acccgcttcg agcccgatcg tcggctccca gtcgaggtgg gtgcgtgcga ggctgatgtc 55621  ggggcaacgt tgcgtcggat cgtccttcgg cagcggacgg aatacgagcc gcgacttcga 55681  gccggtcagg cgcaagatga tctgcgccag ttcgctgacc gcgatctcgt gcggattgcc 55741  gaggttgatc gggccggtga gctccgcggg cgtggccatc atccggatca aaccgtcgac 55801  catgtcgtcg acatagcaga atgcccgggt ctggctgccg tcgccataca gcgtgatgtc 55861  ctcgccccgc agcgcctgca cgatgaagtt ggacacgacg cggccgtcgt tgggatgcat 55921  gcgcggcccg tacgtgttga agatgcgtac caccttgatt cgtacgttct gctggcggtg 55981  atagtcgaag aacagggtct ccgcgcaacg cttgccttcg tcgtagcagg cgcgcggccc 56041  gagcgggttg acgttgcccc ggtaactctc cggttgcgga tgcacatcgg ggtcgccgta 56101  cacctcgctc gtcgacgttt gcagaacgcg tgcatgcgtg cgcttggcga gcccgagcat 56161  gttgatcgcg cccatcacac tggtcttggt ggtctgcacg ggatcgaatt gatagtggat 56221  gggcgaagcc gggcaggcga ggttgtagat ctcgtccacc tccacgtaca acggaaaagt 56281  gacgtcgtgg cgcagcgcct cgaagctcgg gttgccgagc agcgtagcca cgttctgctt 56341  cgtgccggtg aaatagttgt cgacgcacaa tacgtcgtga ccgagttcga cgagacgctc 56401  gcaaagatgc gaaccgagga aacccgcgcc acccgttacg aggattcgct ttcgattacg 56461  ttgcacaatt gcactccaag tatcgcgcgc tgggaagcga cgcggcctcc ccgcacgctt
```

-continued

```
56521 gaccggcccg cggcaccggc aggggagcgg atcaggcgcg cgggcgtttg cattcgacga
56581 tcacggcgcc ggccggcacg ccgatcgcga ggatcggccc gtcatgcctg cagtgcgctc
56641 gacgcggcgt gctccgggcg ccgcatgcgc gccgcgatga tgccggccat cgttcgcatt
56701 tcgtttctca aaaagaaatg atcccttcg atgacgtgaa aatcgaagcg cccggtcgtc
56761 gcggcgcccc agcctgcaac ggcatcgacg gggatctctt tatccgcccg gcccgcgaac
56821 gcggtgatgt ccaccgccag cctgggcccg ggcacgggcc ggtggttttc gatcatcgtg
56881 aaatccgcac gcagcgccgg catcagcagc gccatcagtt cgctgttgtc cagcaccgcc
56941 ttcggtgtgc cgcccatttc gcgcagcgca tcatgaagg cgcggtcgtc cagcgcctgc
57001 atgcgccgat cgtggcgctc cttgcccggt gcggcacgcg cgctcacgaa cagatgccgc
57061 aggttcggtc gtgcgtgggc gggaagccgc agggccagtt cggccgcaat ggccgcgccc
57121 atgctgtgtc cgagcagtgc gaagggacga tcgaagcagt cgtccaggtc gcacagcaac
57181 gtgtcgacca gcgtcgccat gtctcggacg gcaggctcgg acaggcggct gcctcggcct
57241 gcaagttcat gacggcacac ttcgatgccc ggtaacgacg cttgcagcgt gcgatagacg
57301 gcggccgagc cgcccgcata gggaaaacag atcagacgca tgcgggcggg tactcgagcg
57361 gctcatctgc tgccggcgcg caggcgatgg cgctgtgaa attcatgtgt tcggcgtttt
57421 tcaccattca ggttccagat ccggttgggc gtgagttaaa cacgaggctg cgtggatgta
57481 tgtcgtagga agagggacg cgttgtcggc catgtcgaag cggttcgtct ctgaatggat
57541 cccggcgcgg acacggtatc ggcgaaaaca gatgcgcggg aaatcgcgac gcatctgagt
57601 gtgtcgaacg atgcgcttcg tctttagaat gggcagcgag catggcgagc catcagaatt
57661 gcggcatccg atggtgccgc cgcgctaccc gataagttgg agacatacta tgcaacaccg
57721 tcagaaagcc gtcccgaccc agcaagtcgc gaacgagcgc gtgatcgtca ccgaatggcg
57781 attcgcgccc ggcgccgaga ccggctggca tgttcaccgg catgactatg tcgtggtgcc
57841 gcaaacggac ggtcagcttc tcctcgaaac cgcacaaggc aaccgcgagt cgcaattgca
57901 cgccgggcgc agctatgcgg ggctgaaggg cgtcgagcat aacgtcgtca acgcgacgga
57961 ccacgaagtg gtgttcgtcg aagtcgagat tctctaaggg gcgtcaggcc ccgcgagcaa
58021 ggccacgaca gggagcagca ggatgaaaat gaccgacatc ccgtttggca cgaccgactg
58081 gcgcaccgtt gaaccgaccg a
```

REFERENCES (1) Fischbach, M. A.; Walsh, C. T. *Chem. Rev.* 2006, 106, 3468-3496.
(2) Koglin, A.; Löhr, F.; Bernhard, F.; Rogov, V. V.; Frueh, D. P.; Stricter, E. R.; Mofid, M. R.; Güntert, P.; Wagner, G.; Walsh. C. T.; Marahiel, M. A.; Dötsch, V. *Nature* 2008, 454, 907-911.
(3) Koglin, A.; Mofid, M. R.; Löhr, F.; Schäfer. B.; Rogov, V. V.; Blum, M.-M.; Mittag, T.; Marahiel, M. A.; Bernhard, F.; Dötsch, V. *Science* 2006, 312, 273-276.
(4) Kohli, R. M.; Takagi, J.; Walsh, C. T. *PNAS* 2002, 99, 1247-1252.
(5) Lautru, S.; Challis, G. L. *Microbiology* 2004, 150, 1629-1636.
(6) Samel, S. A.; Wagner, B.; Marahiel, M. A.; Essen, L.-O. *J. Mol. Biol.* 2006, 359, 876-889.
(7) Walsh, C. T. *Science* 2004, 303, 1805-1810.
(8) White, C. J.; Yudin, A. K. *Nat. Chem.* 2011, 3, 509-524.
(9) Yeh, E.; Kohli. R. M.; Bruner. S. D.: Walsh. C. T. *Chembiochem* 2004, 5, 1290-1293.
(10) Boddy, C. N. *Chem. Biol.* 2004, 11, 1599-1600.
(11) Boguslavsky, V.; Hruby, V. J.; O'Brien. D. F.: Misicka, A.; Lipkowski, A. W. *J. Pept. Res.* 2003, 61, 287-297.
(12) Fernandez-Lopez, S.; Kim, H. S.; Choi, E. C.; Delgado, M.; Granja, J. R.; Khasanov, A.; Kraehenbuehl. K.; Long, G.: Weinberger, D. A.; Wilcoxen, K. M.; Ghadiri, M. R. *Nature* 2001, 412, 452-455.
(13) Fridkin, G.; Gilon, C. *J. Pept. Res.* 2002, 60, 104-111.
(14) Jelokhani-Niaraki, M.; Hodges, R. S.; Meissner, J. E.; Hassenstein, U. E.; Wheaton. L. *Biophys. J.* 2008, 95, 3306-3321.
(15) Jelokhani-Niaraki, M.; Prenner, E. J.; Kondejewski, L. H.; Kay, C. M.; McElhaney, R. N.; Hodges, R. S. *J. Pept. Res.* 2001, 58, 293-306.
(16) Kohli, R. M.; Walsh. C. T.; Burkart. M. D. *Nature* 2002, 418, 658-661.
(17) Rayan, A.; Senderowitz, H.; Goldblum, A. *J. Mol. Graph. Model.* 2004, 22, 319-333.
(18) Schwarzer. D.; Mootz, H. D.: Marahiel, M. A., *Chem. Biol.* 2001, 8, 997-1010.
(19) Ellis, D.; Gosai, J.; Emrick, C.; Heintz, R.; Romans, L.; Gordon, D.; Lu, S.-E.; Austin. F.; Smith, L. *Antimicrob. Agents Ch.* 2012, 56, 765-769.

(20) Sieber, S. A.; Marahiel, M. A. *J. Bacteriol.* 2003, 185, 7036-7043.
(21) Tseng, C. C.; Bruner, S. D.; Kohli, R. M.; Marahici, M. A.; Walsh, C. T.; Sieber, S. A. *Biochemistry* 2002, 41, 13350-13359.
(22) Gu, G.; Smith, L.; Liu, A.; Lu, S.-E. *Appl. Environ. Microbiol.* 2011, 77, 6189-6198.
(23) Gu, G.; Smith. L.; Wang, N.; Wang. H.; Lu. S.-E. *Biochem. Bioph. Res. Co.* 2009, 380, 328-332.
(24) Gu, G.; Wang, N.; Chancy, N.; Smith, L.; Lu, S.-E. *FEMS Microbiol. Lett.* 2009, 297, 54-60.
(25) Lu. S.-E.; Novak. J.; Austin, F. W.; Gu, G.; Ellis, D.; Kirk. M.; Wilson-Stanford, S.; Tonelli. M.; Smith, L. *Biochemistry* 2009, 48, 8312-8321.
(26) Tan, W.; Cooley, J.; Austin. F.; Lu, S.-E.; Smith, L.; Pruett, S. *Int. J. Toxicol.* 2012, 31, 326-336.
(27) Heikkinen, S.; Toikka, M. M.; Karhunen, P. T.; Kilpeläinen, I. A. *JACS* 2003, 125, 4362-4367.
(28) Rai, R. K.; Tripathi, P.; Sinha, N. *Anal. Chem.* 2009, 81, 10232-10238.
(29) Baysal, C.; Meirovitch, H. *Biopolymers* 1999, 50, 329-344.
(30) Bonmatin, J.-M.; Laprévote. O.; Peypoux, F. *Com. Chem. High T. Scr.* 2003, 6, 541-556.
(31) Liao. G.; Shi, T.; Xie. J. *J. Cell. Biochem.* 2012, 113, 735-741.
(32) Vilhena, C.; Bettencourt. A. *Mini Rev. Med. Chem.* 2012, 12, 202-209.
(33) Alexeyev, M. F. *Biotechniques* 1995, 18, 52.
(34) Prentki, P.; Karch, F.; Iida, S.; Meyer, J. *Gene* 1981, 14, 289-299.
(35) Lu, S.-E.; Scholz-Schroeder, B. K.; Gross, D. C. *MPMI* 2002, 15, 43-53.
(36) Wüthrich, K., *NMR of Proteins and Nucleic Acids*; Wiley. New York, 1986.
(37) Delaglio, F.; Grzesiek, S.; Vuister, G. W.; Zhu, G.; Pfeifer, J.; Bax, A. *J. Biomol. NMR* 1995, 6, 277-293.
(38) Johnson, B. A.; Blevins, R. A. *J. Biomol. NMR* 1994, 4, 603-614.

We claim:

1. A method of increasing production of occidiofungin diastereomers/conformers corresponding to the diastereomers/conformers having the total correlation spectroscopy (TOCSY) fingerprint set forth in FIG. 5C as the green NH correlations in a microorganism producing occidiofungin comprising:

decreasing the thioesterase activity of an occidiofungin gene D (ocfD) product (OcfD) in said microorganism, wherein said OcfD thioesterase activity is decreased by the introduction of a point mutation at the serine in position 2954 of the amino acid sequence of SEQ ID NO: 4, said point mutation replaces said serine with an alanine, glycine or proline, and culturing said microorganism under conditions to produce said occidiofungin diastereomers/conformers, wherein said increase in production of occidiofungin diastereomers/conformers is as compared to a reference microorganism without said decrease in OcfD thioesterase activity cultured under the same conditions.

* * * * *

SEQUENCE LISTING

```
<160> NUMBER OF SEQ ID NOS: 23

<210> SEQ ID NO 1
<211> LENGTH: 21
<212> TYPE: DNA
<213> ORGANISM: Artificial sequence
<220> FEATURE:
<223> OTHER INFORMATION: primer

<400> SEQUENCE: 1
cgccacccgt tacgaggatt c                                              21

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
acgcgtcccc tcttcctacg                                                20

<210> SEQ ID NO 3
<211> LENGTH: 239
<212> TYPE: PRT
<213> ORGANISM: Burkholderia contaminans MS14

<400> SEQUENCE: 3

Met Arg Leu Ile Cys Phe Pro Tyr Ala Gly Gly Ser Ala Ala Val Tyr
1               5                   10                  15

Arg Thr Leu Gln Ala Ser Leu Pro Gly Ile Glu Val Cys Arg His Glu
            20                  25                  30

Leu Ala Gly Arg Gly Ser Arg Leu Ser Glu Pro Ala Val Arg Asp Met
        35                  40                  45

Ala Thr Leu Val Asp Thr Leu Leu Cys Asp Leu Asp Asp Cys Phe Asp
    50                  55                  60

Arg Pro Phe Ala Leu Leu Gly His Ser Met Gly Ala Ala Ile Ala Ala
65                  70                  75                  80

Glu Leu Ala Leu Arg Leu Pro Ala His Ala Arg Pro Asn Leu Arg His
                85                  90                  95

Leu Phe Val Ser Ala Arg Ala Ala Pro Gly Lys Glu Arg His Asp Arg
```

```
            100                 105                 110
Arg Met Gln Ala Leu Asp Asp Arg Ala Phe Ile Asp Ala Leu Arg Glu
            115                 120                 125

Met Gly Gly Thr Pro Lys Ala Val Leu Asp Asn Ser Glu Leu Met Ala
        130                 135                 140

Leu Leu Met Pro Ala Leu Arg Ala Asp Phe Thr Met Ile Glu Asn His
145                 150                 155                 160

Arg Pro Val Pro Gly Pro Arg Leu Ala Val Asp Ile Thr Ala Phe Ala
                165                 170                 175

Gly Arg Ala Asp Lys Glu Ile Pro Val Asp Ala Val Ala Gly Trp Gly
            180                 185                 190

Ala Ala Thr Thr Gly Arg Phe Asp Phe His Val Ile Glu Gly Asp His
        195                 200                 205

Phe Phe Leu Arg Asn Glu Met Arg Thr Met Ala Gly Ile Ile Ala Ala
210                 215                 220

Arg Met Arg Arg Pro Glu His Ala Ala Ser Ser Ala Leu Gln Ala
225                 230                 235

<210> SEQ ID NO 4
<211> LENGTH: 3154
<212> TYPE: PRT
<213> ORGANISM: Burkholderia contaminans MS14

<400> SEQUENCE: 4

Met Gln Asp Asn Asn Val Leu Val Thr Asp Arg Glu Ser Leu Ser Arg
1               5                   10                  15

Val Ala Gly Val Tyr Gly Ile Ala Ala Tyr Ala Pro Ser Gln Gln Pro
            20                  25                  30

Gly Arg Pro Leu Thr Arg Ser Val Arg Leu Thr Pro Ala Ser Leu Asp
        35                  40                  45

Leu Leu Arg Arg Ile Gly Asp Gly Glu Leu Ala Glu Phe Ala Val Ala
    50                  55                  60

Ala Ala Gly Ile Ala Phe Leu Leu Trp Lys Tyr Phe Arg Ile Pro Val
65                  70                  75                  80

Thr Val Leu Gly Thr Pro Gly Leu Ala Gly His Pro Ser Ala Arg Ala
                85                  90                  95

Ala Ile Val Pro Leu Ile Ile Glu Val Arg Pro Asp Glu Arg Ile Glu
            100                 105                 110

Asp Tyr Leu Ser Arg Val Ala Gly Ile Val Glu Asp Ser Tyr Ala Glu
        115                 120                 125

Pro Arg Phe Pro Leu Glu Thr Leu Val Arg Asn Glu Lys Asp Met Ala
    130                 135                 140

Leu Ala Gln Leu Thr Lys Val Ala Leu Ala Asp Asp Arg Val His His
145                 150                 155                 160

Ala Pro Thr Gly Arg Asp Asp Asp Leu Gln Leu His Leu Arg Leu Ala
                165                 170                 175

Arg Gly Glu Ile Glu Leu Arg Tyr Ser Gly Ala Ile Glu Pro Phe Ile
            180                 185                 190

Ile Asp Gly Phe Ala Gly Ser Leu Ala Ala Val Leu Glu Ala Phe Glu
        195                 200                 205

His Leu Asp Gly Ala Val Gly Asp Ile Glu Ala Ala Pro Pro Glu Gln
    210                 215                 220

Gly Pro Leu Leu Ala Ala Phe Asn Glu Thr Ala Thr Ala Gly Pro Ser
225                 230                 235                 240
```

-continued

```
His Pro Thr Val Val Ala Met Phe Glu Ala Gln Val Ala Arg Thr Pro
                245                 250                 255

Thr Ala Pro Ala Leu Val Thr Asp Ser Ser Leu Met Thr Tyr Ala Asp
            260                 265                 270

Leu Asn Ala Arg Ala Asn Ser Leu Ala His His Leu Arg Glu His His
        275                 280                 285

Gly Val Gly Pro Glu Ser Leu Val Gly Ile Met Leu Asp Arg Ser Glu
    290                 295                 300

Trp Met Ile Val Ala Ile Leu Gly Ile Leu Lys Ala Gly Ala Ala Phe
305                 310                 315                 320

Val Pro Leu Asp Pro Ala Tyr Pro Ala Glu Arg Ile Asn His Ile Leu
                325                 330                 335

Gly Asp Thr Gly Leu Ser Leu Leu Val Thr Gln Ser Ser Gln Leu Ala
            340                 345                 350

Gln Trp Tyr Glu Phe Ser Gly Val Thr Leu Leu Asp Gln Glu Leu
        355                 360                 365

Pro Gly Trp Gln Pro Leu Pro Asp Asn Pro Pro His Arg Ala Glu Pro
    370                 375                 380

Ala His Leu Ala Tyr Val Leu Tyr Thr Ser Gly Ser Thr Gly Lys Pro
385                 390                 395                 400

Lys Gly Cys Leu Leu Glu His Arg Asn Leu Ala His Tyr Ile Ala Trp
                405                 410                 415

Ala Ala Gly Tyr Tyr Phe Pro Glu Ser Thr Thr Gly Ser Phe Gly Leu
            420                 425                 430

Tyr Ser Ser Leu Cys Phe Asp Phe Thr Leu Thr Asn Ile Phe Cys Pro
        435                 440                 445

Leu Val Arg Gly Lys Thr Leu Arg Ile Tyr Pro Gln Ser Glu Ser Ile
    450                 455                 460

Asp Thr Ile Leu Ala Arg Met Phe Gln Pro Gly Ser Gly Val Asp Thr
465                 470                 475                 480

Leu Lys Leu Thr Pro Thr His Ile His Leu Leu Glu Tyr Met Asn Leu
                485                 490                 495

Ala Arg Ser Gly Val Arg Lys Val Ile Val Gly Gly Glu Glu Leu Thr
            500                 505                 510

Pro Gln His Ile Ala Thr Leu Arg Lys Ile Asp Pro Ala Ile Glu Ile
        515                 520                 525

Tyr Asn Glu Tyr Gly Pro Thr Glu Ala Thr Val Gly Cys Ile Val Glu
    530                 535                 540

Arg Val Glu Asp Ala Pro Pro Thr Val Leu Ile Gly Arg Pro Ile Ala
545                 550                 555                 560

Asp Thr Arg Val Tyr Met Leu Asp Asp Ala Leu Arg Pro Val Pro Leu
                565                 570                 575

Gly Val Pro Gly Glu Ile Cys Leu Ala Gly Ala Gly Leu Ala Arg Gly
            580                 585                 590

Tyr His Gln Arg Pro Asp Val Thr Ala Ala Lys Phe Val Glu His Pro
        595                 600                 605

Phe Pro Gly Glu Ala Arg Ile Tyr Arg Thr Gly Asp Ile Gly Arg Trp
    610                 615                 620

Leu Pro Asp Gly Arg Ile Gln Cys Tyr Gly Arg Val Asp His Gln Val
625                 630                 635                 640

Lys Ile Arg Gly His Arg Val Glu Leu Gly Glu Ile Glu Ala Ala Ile
                645                 650                 655

Ala Ala His Glu Asp Val Val Gly Ala Ala Val Met Leu Arg Glu Ser
```

```
                660             665             670
Ala His Gly Val Arg Lys Leu Ala Ala Tyr Val Lys Gly Ala Ala Ser
            675             680             685
Leu Ser Val Pro Asn Leu Arg Ala Tyr Leu Ala Gly Lys Leu Pro Asp
        690             695             700
Tyr Met Val Pro Ser Asp Ile Ile Pro Ile Ala Glu Phe Pro Leu Asn
705             710             715             720
Ala Asn Gly Lys Leu Asp Arg Pro Ala Leu Leu Ala Leu Glu Pro Ala
            725             730             735
Ala Ala Pro Glu Glu Ala Pro Leu Asp Ala Thr Pro Ile Gln Arg Glu
        740             745             750
Leu Val Arg Ile Trp Arg Asp Val Leu Asp Asn Pro Ala Val Asp Leu
        755             760             765
Ala Gly Arg Phe Phe Asp Tyr Gly Gly Asp Ser Leu Gln Ala Met Gln
        770             775             780
Leu Val Ser Arg Ile Trp Ser Ser Phe Ser Val Glu Ile Gly Ile Asp
785             790             795             800
Ala Ile Phe Glu Leu Gln Thr Ile Ser Ala Val Ser Asp Leu Ile Glu
            805             810             815
Ala Ser Ser Pro His Pro Gly Ser Thr Ala Gly Ala Ile Pro Pro Arg
            820             825             830
Ser Arg Ala Asn Asp Leu Pro Leu Ser Phe Pro Gln Gln Arg Leu Trp
        835             840             845
Phe Leu Ala Gln Leu Glu Gly Pro Ser Ala Thr Tyr Asn Ile Ser Ser
850             855             860
Ala Leu Arg Phe Glu Gly Glu Leu Asp Val Ala Arg Leu Arg Phe Ala
865             870             875             880
Val Ser Glu Ile Ser Arg Arg His Glu Ile Leu Arg Thr Thr Phe Pro
            885             890             895
Ala Val Asp Gly Arg Gly Val Gln Arg Ile Ala Pro Ala Pro Val
            900             905             910
Ala Leu Asp Val Val Asp Val Ala Ser Glu Ser Asp Thr Leu Ala Leu
            915             920             925
Leu Ala Glu Glu Ala Asp Arg Pro Phe Asp Leu Ala Ala Gly Pro Leu
        930             935             940
Tyr Arg Val Val Leu Tyr Arg Val His Glu Arg Leu His Val Phe Gly
945             950             955             960
Ile Val Met His His Ile Val Ser Asp Ala Trp Ser Ser Gly Ile Leu
            965             970             975
Ile Gly Glu Leu Ala Ala Leu Tyr Ala Gly Glu Ser Leu Pro Glu Leu
        980             985             990
Ala Val Gln Tyr Ala Asp Tyr Ala Val Trp Gln His Glu Arg Leu Ala
        995             1000            1005
Ser Ala Asp Thr His Arg Glu Leu Ala Leu Leu Ser Ala Ala Leu
        1010            1015            1020
Ala Asp Ala Pro Asp Leu Ile Glu Leu Pro Thr Asp Arg Pro Arg
        1025            1030            1035
Pro Ala Val Gln Gln Phe Arg Gly Ala Val Leu Pro Phe Gln Leu
        1040            1045            1050
Ser Ala Glu Arg Ala Asp Gly Leu Arg Ala Ile Ala Arg Ala Ser
        1055            1060            1065
Gly Thr Ser Thr Phe Met Val Val Leu Ala Ala Tyr Ala Leu Leu
        1070            1075            1080
```

```
Leu Ser Arg Tyr Ser Asn Gln Gln Asp Leu Val Ile Gly Ser Pro
    1085                1090                1095

Ile Ala Asn Arg Arg Ser Ser Met Thr Glu Pro Leu Ile Gly Phe
    1100                1105                1110

Phe Ala Asn Met Leu Ala Leu Arg Val Asp Leu Ser Gly Asn Pro
    1115                1120                1125

Thr Phe Gly Asp Leu Leu Ala Arg Val Lys Arg Val Ala Leu Asp
    1130                1135                1140

Gly Tyr Ser Arg Gln Glu Ile Pro Phe Glu Gln Val Val Asp Ser
    1145                1150                1155

Leu Glu Leu Glu Arg Asn Leu Gly Arg Thr Pro Val Phe Gln Val
    1160                1165                1170

Val Phe Ala Tyr Glu Lys Ala Gln Pro Arg Ala Val Ser Phe Pro
    1175                1180                1185

Gly Leu Val Ala Thr Pro Val Ala Val Glu Thr His Thr Ala Lys
    1190                1195                1200

Phe Asp Leu Thr Leu His Val Gln Asp Ala Asp Gly Leu Ala
    1205                1210                1215

Gly Ser Leu Glu Tyr Asn Leu Asp Leu Phe Asp Ala Ala Thr Ile
    1220                1225                1230

Asp Arg Met Ala Glu His Phe Arg Thr Leu Val Asp Ala Val Ile
    1235                1240                1245

Ala Asp Pro Asp Arg Pro Leu Gly Ala Leu Ser Leu Ser Asn Asp
    1250                1255                1260

Ala Glu Arg Asn Leu Leu Thr Val Glu Trp Asn Arg Thr Asp Thr
    1265                1270                1275

Asp Phe Gly Glu Asp Ala Ala Gln Pro Leu His Arg Leu Phe Glu
    1280                1285                1290

Gln Gln Val Glu Arg Thr Pro Asp Ala Val Ala Ile Val Phe Asp
    1295                1300                1305

Asp Thr Ala Leu Thr Tyr Ala Glu Leu Asn Leu Arg Ala Asn Arg
    1310                1315                1320

Leu Ala His His Leu Val Ala Leu Gly Val Gly Pro Asp Ser Leu
    1325                1330                1335

Val Gly Val Ala Met Glu Arg Ser Leu Asp Met Ser Val Ala Leu
    1340                1345                1350

Leu Ala Ile Leu Lys Ala Gly Gly Ala Tyr Val Pro Val Asp Pro
    1355                1360                1365

Asp Tyr Pro Ala Glu Arg Val Arg Phe Met Ile Asp His Ala Gln
    1370                1375                1380

Leu Arg Trp Leu Leu Thr Gln Gln His Leu His Asp Ala Leu Pro
    1385                1390                1395

Asp Thr Asp Ala His Val Ile Val Val Asp Arg Asp Ser Leu Asp
    1400                1405                1410

Leu Asp Ala Ala Ala Thr Ser Asn Pro Ala Pro Ala Leu Asn Gly
    1415                1420                1425

Asp Asn Leu Ala Tyr Met Ile Tyr Thr Ser Gly Ser Thr Gly Arg
    1430                1435                1440

Pro Lys Gly Ala Leu Asn Thr His Arg Ala Ile Thr Asn Arg Ile
    1445                1450                1455

Leu Trp Met Gln His Ala Tyr Ala Leu Asp Ala Asp Asp Ala Val
    1460                1465                1470
```

-continued

| | | | | | | | | | | | | | |
|---|---|---|---|---|---|---|---|---|---|---|---|---|---|
|Leu|Gln|Lys|Thr|Pro|Phe|Ser|Phe|Asp|Val|Ser|Val|Trp|Glu|Leu|
| |1475| | | |1480| | | |1485| | | | | |
|Phe|Trp|Pro|Leu|Val|Thr|Gly|Ala|Arg|Leu|Val|Phe|Ala|Arg|Pro|
| |1490| | | |1495| | | |1500| | | | | |
|Gly|Gly|Gln|Arg|Glu|Thr|Asp|Tyr|Leu|Val|Glu|Leu|Ile|Glu|Arg|
| |1505| | | |1510| | | |1515| | | | | |
|Glu|Arg|Ile|Thr|Thr|Ile|His|Phe|Val|Pro|Ser|Met|Leu|Arg|Ala|
| |1520| | | |1525| | | |1530| | | | | |
|Phe|Leu|Asp|His|Pro|Asp|Leu|Asp|Ala|His|Cys|Ala|Ser|Leu|Arg|
| |1535| | | |1540| | | |1545| | | | | |
|Arg|Val|Val|Cys|Ser|Gly|Glu|Ala|Leu|Pro|His|Asp|Leu|Gln|Gln|
| |1550| | | |1555| | | |1560| | | | | |
|Arg|Cys|Leu|Glu|Arg|Leu|Asp|Val|Lys|Leu|Tyr|Asn|Leu|Tyr|Gly|
| |1565| | | |1570| | | |1575| | | | | |
|Pro|Thr|Glu|Ala|Ala|Val|Asp|Val|Thr|Ala|Trp|Glu|Cys|Arg|Arg|
| |1580| | | |1585| | | |1590| | | | | |
|Asp|Asp|Pro|His|Arg|Ile|Val|Pro|Ile|Gly|Arg|Pro|Ile|Ala|Asn|
| |1595| | | |1600| | | |1605| | | | | |
|Thr|Arg|Leu|Tyr|Ile|Val|Asp|Ala|Gln|Met|Gln|Pro|Thr|Pro|Ile|
| |1610| | | |1615| | | |1620| | | | | |
|Gly|Val|Ala|Gly|Glu|Leu|Leu|Ile|Gly|Gly|Thr|Pro|Val|Gly|Arg|
| |1625| | | |1630| | | |1635| | | | | |
|Gly|Tyr|His|Gly|Glu|Pro|Glu|Leu|Ser|Ala|Glu|Lys|Phe|Ile|Ala|
| |1640| | | |1645| | | |1650| | | | | |
|Asp|Pro|Phe|Ser|Ala|Asp|Pro|Leu|Ala|Arg|Leu|Tyr|Arg|Thr|Gly|
| |1655| | | |1660| | | |1665| | | | | |
|Asp|Leu|Ala|Arg|Tyr|Arg|Pro|Asp|Gly|Asn|Ile|Glu|Phe|Leu|Gly|
| |1670| | | |1675| | | |1680| | | | | |
|Arg|Ile|Asp|His|Gln|Ile|Lys|Leu|Arg|Gly|Leu|Arg|Ile|Glu|Pro|
| |1685| | | |1690| | | |1695| | | | | |
|Gly|Glu|Ile|Glu|Ala|Ala|Leu|Arg|Ala|His|Pro|Ser|Val|Asp|Asp|
| |1700| | | |1705| | | |1710| | | | | |
|Cys|Val|Val|Ile|Ala|Lys|Thr|Glu|Gly|Ala|Arg|Thr|Phe|Leu|Ile|
| |1715| | | |1720| | | |1725| | | | | |
|Ala|Tyr|Val|Ala|Thr|Ala|Ala|Pro|Asp|Ile|Ala|Asp|Leu|Arg|Gly|
| |1730| | | |1735| | | |1740| | | | | |
|Tyr|Leu|Gly|Gly|Lys|Leu|Ala|Asp|Tyr|Met|Val|Pro|Ser|Gln|Phe|
| |1745| | | |1750| | | |1755| | | | | |
|Phe|Ala|Leu|Glu|Ser|Leu|Pro|Met|Leu|Pro|Asn|Gly|Lys|Ile|Asn|
| |1760| | | |1765| | | |1770| | | | | |
|Arg|Lys|Ala|Leu|Pro|Leu|Pro|Ala|Asp|Arg|Gly|Asp|Ala|Ala|Gln|
| |1775| | | |1780| | | |1785| | | | | |
|Pro|His|Ala|Pro|Ala|Val|Thr|Pro|Arg|Glu|Ile|Leu|Leu|Ala|Ser|
| |1790| | | |1795| | | |1800| | | | | |
|Ile|Cys|Ile|Asp|Val|Leu|Gln|Leu|Pro|Ser|Val|Gly|Ile|His|Asp|
| |1805| | | |1810| | | |1815| | | | | |
|Asn|Phe|Phe|Glu|Leu|Gly|Gly|Asp|Ser|Ile|Leu|Ser|Ile|Gln|Val|
| |1820| | | |1825| | | |1830| | | | | |
|Ile|Ala|Arg|Ala|Asn|Gln|Ala|Gly|Leu|Arg|Val|Thr|Ala|Lys|Gln|
| |1835| | | |1840| | | |1845| | | | | |
|Leu|Phe|Gln|Tyr|Gln|Thr|Ile|Ala|Gln|Leu|Ala|Ala|Ala|Pro|Glu|
| |1850| | | |1855| | | |1860| | | | | |
|Glu|Arg|Ala|Ala|Cys|Ala|Pro|Thr|Leu|Ser|Pro|Leu|Gly|Asp|Ala|

-continued

```
            1865                1870                1875
Pro Leu Thr Pro Val Gln His Trp Phe Glu Gln Glu Ile Asp
            1880                1885                1890
Ala Pro Ser His Tyr Asn Gln Thr Val Leu Ile Gln Val Pro Ala
            1895                1900                1905
Asp Ile Asp Ala Ser Arg Leu Ala Asp Ala Phe Arg Gln Val Tyr
            1910                1915                1920
Glu His His Asp Ala Leu Arg Leu Arg Phe Ser His Asp Ala Gly
            1925                1930                1935
Arg Trp Thr Gln Gln Val Val Ala Gly Gly Glu Met Pro Ala Leu
            1940                1945                1950
Phe Ala Lys Gln Val Ile Ala Asp Ala Gly Glu Arg Leu Ala
            1955                1960                1965
Ala Met Arg Ala Ala Ala Ala Asp Ala Glu Arg Gly Ile Asp Ile
            1970                1975                1980
Thr His Gly Pro Leu Leu Ala Ala Arg Leu Phe Cys Leu Ala Asp
            1985                1990                1995
Glu Pro Leu Ala Arg Leu Phe Val Ser Ile His His Leu Ala Val
            2000                2005                2010
Asp Gly Val Ser Trp Arg Val Leu Leu Glu Asp Leu His Ala Ala
            2015                2020                2025
Tyr His Gly Gln Pro Leu Pro Gly Lys Thr Thr Ser Phe Arg Glu
            2030                2035                2040
Trp Ala Leu His Leu Gln Gln Leu Ala Arg Ser Pro Ala Ile Gly
            2045                2050                2055
Asp Glu Ala Arg Leu Trp Gln Ala Leu Leu Ala Gln Pro Val Glu
            2060                2065                2070
Pro Met Pro Val Asp Tyr Pro Gly Thr Gly Ala Ala Asn Asn Ala
            2075                2080                2085
Val Asp Asp Ala Ser Ser Val Ser Phe Glu Leu Gly Glu Ala Asp
            2090                2095                2100
Thr Thr Ala Leu Leu Arg Arg Leu Pro Arg Ala Tyr Asp Thr Arg
            2105                2110                2115
Ile Asn Asp Val Leu Leu Val Ala Leu Ala Gln Ala Cys Ser Met
            2120                2125                2130
Val Thr Gly Asn Thr Arg Thr Arg Ile Asp Leu Glu Ser His Gly
            2135                2140                2145
Arg His Val Ser Asp Ala Pro Leu Asp Leu Thr Arg Thr Val Gly
            2150                2155                2160
Trp Phe Thr Ser Ile Tyr Pro Val Val Leu Asp Ala Asp Ala Met
            2165                2170                2175
His Ala Pro Glu Gln Ala Leu Arg Ala Ala Arg Gln Gln Leu Arg
            2180                2185                2190
Arg Ile Pro Ala Asp Gly Leu Gly Tyr Ser Leu Leu Arg Tyr Gln
            2195                2200                2205
Ser Pro Asp Ala Ala Val Arg Asp Ser Leu Ala Ala Leu Pro Lys
            2210                2215                2220
Ala Asp Ile Leu Phe Asn Tyr His Gly Gln Leu Asp Thr Val Leu
            2225                2230                2235
Arg Gln Ser Asp Gly Trp Arg Pro Ala Ala Glu Asp Leu Gly Ser
            2240                2245                2250
Leu Arg Ala Gly Arg Ser Gln Arg Thr His Ala Phe Glu Ile Val
            2255                2260                2265
```

-continued

Ala Ala Val Ala Asp Gly Lys Leu Gln Val Asp Trp Arg Tyr Gly
    2270            2275            2280

Glu Arg Leu His Arg Arg Gln Thr Val Glu Asn Leu Ala Ala His
    2285            2290            2295

Phe Arg Asp Arg Leu Leu Asp Phe Ala Ala Ser Val Pro Asp Thr
    2300            2305            2310

Ala Ala Asp Asp Ile Glu Asp Ser Tyr Pro Leu Ser Ser Leu Gln
    2315            2320            2325

Gln Gly Ile Leu Phe His Ser Leu Tyr Asp Leu Asp Pro Ala Ala
    2330            2335            2340

Tyr Phe Gln Gln Phe Ser Phe Val Val Ser Gly Pro Leu Gln Val
    2345            2350            2355

Pro Ala Leu Arg Gln Ala Trp Ala Asn Ala Leu Ala Arg His Ala
    2360            2365            2370

Val Leu Arg Thr Ala Phe Ala Trp Ala Asp Arg Asp His Pro Val
    2375            2380            2385

Gln Thr Val Arg His Thr Val Asp Leu Pro Trp Thr Phe Leu Asp
    2390            2395            2400

Trp Arg His Arg Asp Ala Ser Arg Arg Ala Gln Asp Phe Asp Ala
    2405            2410            2415

Phe Leu Ala Asp Asp Arg Arg Arg Gly Phe Asp Leu Gln Arg Ala
    2420            2425            2430

Pro Leu Phe Arg Cys Thr Leu Ile Gln Glu Thr Asp Thr Arg His
    2435            2440            2445

Arg Phe Cys Trp Ser Ala His His Ile Ile Leu Asp Gly Trp Ser
    2450            2455            2460

Thr Ala Thr Leu Met Lys Glu Val Phe Asp Asp Tyr Leu Ser Leu
    2465            2470            2475

Ala Arg Thr Gly Met Pro Ala Val Ala Ala Ser Ala Pro Gly Tyr
    2480            2485            2490

Arg Ala Tyr Ile Asp Trp Leu Ala Arg His Pro Arg Ser Ala Asp
    2495            2500            2505

Glu Thr Trp Trp Arg Ala Glu Leu Ala Gly Phe Lys Ala Ala Thr
    2510            2515            2520

Pro Val Ala Ala Ser Pro Ala Arg Gln Ala Thr Gly Asp Ala Pro
    2525            2530            2535

Arg Gln Asp Lys Arg Arg Thr Gln Gln Phe Leu Leu Asp Glu Ala
    2540            2545            2550

Leu Ala Ala Arg Leu Gln Thr Leu Thr Arg Thr His Arg Val Thr
    2555            2560            2565

Leu Asn Val Leu Ile Arg Ala Val Trp Ala Leu Val Leu Arg Arg
    2570            2575            2580

His Ala Gly Thr Asp Asp Val Val Phe Gly Val Thr Val Ser Gly
    2585            2590            2595

Arg Pro Pro Met Leu Asp Gly Val Glu Ser Ile Val Gly Leu Phe
    2600            2605            2610

Ile Asn Thr Leu Pro Leu Arg Leu Arg Ile Ala Pro Glu Arg Pro
    2615            2620            2625

Phe Ile Glu Trp Leu Ala Glu Val His Ala Ala Gln Thr Ala Met
    2630            2635            2640

Glu Pro His Ser Tyr Ser Ser Leu Val Asp Ile Gln Ser Trp Ser
    2645            2650            2655

```
Glu Leu Pro Ala Gly Asp Ser Leu Phe Asp Ser Leu Val Phe
2660             2665             2670

Glu Asn Phe Pro Val Ala Ala Ala Pro Asp Leu Gly Pro Asp Asp
2675             2680             2685

Ile Glu Ile Leu Asp Thr Arg Ala Phe Ala Glu Ser Asn Tyr Pro
2690             2695             2700

Leu Thr Leu Thr Val His Pro Asn Glu Arg Ile Gly Phe His Ile
2705             2710             2715

Ser His Asp Ala His Arg Ile Ala Pro Glu Val Val Arg Gln Met
2720             2725             2730

Leu Asp Thr Leu Arg Thr Leu Leu Glu Arg Phe Ala Glu Asn Pro
2735             2740             2745

Gly Gln Leu Thr Gly Gln Leu Ala Asp Pro Pro Ala Ala Asp Gly
2750             2755             2760

Arg Pro Ser Ala Pro Arg Ser Gly Ala Gly Pro Ala Ile Glu Ala
2765             2770             2775

Ala Ala Gly Ala Ala Ala Ala Ala Arg Ala Val Ala His Ala Ala
2780             2785             2790

Asp Glu Ser Thr Leu Leu Glu Ile Trp Arg Arg Ile Phe Lys Arg
2795             2800             2805

Asp Asp Ile Ala Val Ser Asp Asn Tyr Phe Asp Leu Gly Gly His
2810             2815             2820

Ser Ile Ile Ala Ile Gln Leu Met Ala His Val Glu Lys Ala Phe
2825             2830             2835

Asp Arg Arg Leu Pro Ile Ser Cys Leu Phe Glu Asn Pro Thr Ile
2840             2845             2850

Glu Lys Leu Ala Ala Ala Leu Ala Ala Lys Glu Pro Ser Ala Pro
2855             2860             2865

Ala Gly Gly Leu Val Pro Ile Arg Asp Gly Gly Pro Ala Ala Pro
2870             2875             2880

Leu Phe Leu Leu Pro Gly Ala Gly Gly Asn Val Val Tyr Phe Arg
2885             2890             2895

Pro Leu Ala Asn His Leu Ser Gly Ala His Ala Ile His Gly Leu
2900             2905             2910

Glu Ala Leu Gly Leu Asp Gly Ala Cys Glu Pro Leu Thr Arg Val
2915             2920             2925

Glu Asp Ile Ala Ala Arg His Ile Glu Arg Ile Trp Pro Leu Val
2930             2935             2940

Gly Ala Gly Pro Tyr Tyr Leu Ala Gly His Ser Phe Gly Ala His
2945             2950             2955

Val Ala Leu Glu Met Ser Arg Gln Leu Val Ala Lys Gly Ala Asp
2960             2965             2970

Val Lys Leu Leu Ala Ile Phe Asp Ala Ser Ala Pro Ile Asp Ser
2975             2980             2985

Ser Ala Ala Thr Tyr Trp Gln Asp Trp Asp Asp Thr Glu Trp Leu
2990             2995             3000

Val Ala Ile Ala His Glu Ile Gly Thr Phe Leu Gly Thr Asp Leu
3005             3010             3015

Gln Val Thr Arg Ala Asp Leu Val His Leu Asp Pro Asp Gly Gln
3020             3025             3030

Ala Gly Leu Ile Leu Glu Arg Ile Gly Asp Arg Gly Ser Trp Phe
3035             3040             3045

Ala Asp Ala Gly Ser Asp Arg Leu Arg Ala Tyr Leu Arg Val Tyr
```

```
            3050                3055                3060

Gln Ala Asn Phe Lys Ser His Tyr Ala Pro His Ala Thr Pro Leu
        3065                3070                3075

Pro Val Pro Ile Ala Leu Phe Arg Ser Thr Glu Arg Asp Pro Gly
    3080                3085                3090

Asp Tyr Ala Pro Ser Ser Glu Ile Ala Gln Leu Arg Leu Asp Ala
        3095                3100                3105

Thr Trp Gly Trp Ser Arg Phe Ser Ala His Pro Val Ala Val Thr
    3110                3115                3120

Asp Val Pro Gly Asp His Leu Thr Met Leu Leu Asp Pro His Ala
    3125                3130                3135

Gly Val Leu Ala Ala His Val Asn Ser Phe Leu Glu Lys Thr Pro
    3140                3145                3150

Ser
```

<210> SEQ ID NO 5
<211> LENGTH: 391
<212> TYPE: PRT
<213> ORGANISM: Burkholderia contaminans
<220> FEATURE:
<221> NAME/KEY: MISC_FEATURE
<222> LOCATION: (1)..(391)
<223> OTHER INFORMATION: putative FAD linked oxidase domain protein

<400> SEQUENCE: 5

```
Met Ser His Asp Phe Arg Asp Glu Pro Ala Pro Arg Arg Ala Phe Leu
1               5                   10                  15

Ala Asp Met Ala Lys Leu Ala Ala Ala Gly Ile Val Thr Gly Trp Thr
            20                  25                  30

Pro Leu Tyr Gln Val Ala Ala His Ala Arg Thr Ala Gly Glu Thr Pro
        35                  40                  45

Pro Gly Phe Pro Ala Asp Ile Gln Leu Tyr Lys Gln Ala Phe Leu Asn
    50                  55                  60

Trp Ser Gly Glu Ile Ala Val Gln Asp Val Trp Thr Ala Ala Pro Arg
65                  70                  75                  80

Ser Ala Asp Asp Val Val Ala Thr Val Asn Trp Ala Arg Ala Asn Gly
                85                  90                  95

Tyr Arg Ile Arg Pro Arg Gly Tyr Thr His Asn Trp Ser Pro Leu Thr
            100                 105                 110

Leu Asp Pro Gly Ala Gly Ala Ala Asn Leu Val Leu Leu Asp Thr Thr
        115                 120                 125

Lys Ser Leu Thr Ala Val Ser Val Asp Thr Ser Ala Arg Pro Ala Arg
    130                 135                 140

Val Thr Ala Gln Thr Gly Val Ser Leu Glu Ser Leu Leu Ala Thr Leu
145                 150                 155                 160

Glu Gln Val Gly Leu Gly Val Ile Ala Ala Pro Ala Pro Gly Asp Ile
                165                 170                 175

Thr Leu Gly Gly Ala Leu Ala Ile Asp Ala His Gly Thr Ala Val Pro
            180                 185                 190

Ala Ala Gly Glu Thr Leu Gln Pro Gly His Thr Tyr Gly Ser Leu Ser
        195                 200                 205

Asn Leu Val Val Ala Leu Thr Ala Val Val Phe Asp Pro Ala Arg Gln
    210                 215                 220

Gln Tyr Val Leu Arg Arg Phe Glu Arg Ser Asp Pro Glu Ile Gly Ala
225                 230                 235                 240
```

```
Phe Leu Ala His Ile Gly Arg Ala Leu Val Val Glu Val Thr Leu Thr
                245                 250                 255

Ala Gly Pro Asn Gln Arg Leu Arg Cys Gln Ser Tyr Val Asp Ile Pro
            260                 265                 270

Ala Ser Glu Leu Phe Ala Ala Pro Gly Thr Thr Gly Arg Thr Ile Ala
        275                 280                 285

Ser Phe Leu Asp Gly Ser Gly Arg Val Glu Ala Ile Trp Phe Pro Phe
    290                 295                 300

Thr Thr Lys Pro Trp Leu Lys Val Trp Thr Pro Thr Pro Ser Lys Pro
305                 310                 315                 320

Phe Leu Ser Arg Ala Val Thr Gln Pro Tyr Asn Tyr Pro Phe Ser Asp
                325                 330                 335

Ser Ile Ser Gln Ser Ile Ser Asp Leu Val Lys Arg Ile Val Ile Gly
            340                 345                 350

Gly Glu Gly Ala Leu Thr Pro Leu Phe Gly Gln Thr Gln Leu Ala Ile
        355                 360                 365

Thr Thr Ala Gly Leu Ala Leu Thr Leu Ser Gly Asp Ile Trp Gly Trp
    370                 375                 380

Ser Arg Thr Val Leu Gln Glu
385                 390
```

<210> SEQ ID NO 6
<211> LENGTH: 273
<212> TYPE: PRT
<213> ORGANISM: Burkholderia contaminans
<220> FEATURE:
<221> NAME/KEY: MISC_FEATURE
<222> LOCATION: (1)..(273)
<223> OTHER INFORMATION: putative LuxR-type regulator

<400> SEQUENCE: 6

```
Met Phe Ala Lys Leu Gly Lys Val Ile Ser Ser Ala Gly Ser Glu Arg
1               5                   10                  15

Phe Ala Ser Asp Met His Ala Leu Val Glu Ser Ile Pro Leu Thr
            20                  25                  30

Ile Thr Arg Met Thr Glu Trp Thr Leu Asp Glu Pro Ala Gly Glu Val
        35                  40                  45

Val Arg Val Gln Ser Leu Gly Ala Asp Gly Ala Pro Gly Asp Asp Gly
    50                  55                  60

Arg Gly Ala Pro Ala Ala His Gly Glu Arg Glu Pro Ala Ala His Pro
65                  70                  75                  80

Pro Leu Asn Arg Ile Leu Ala Ala Cys Asp Arg Gln Leu Ile His Ile
                85                  90                  95

Asn Pro Leu Met Arg Arg Gly Asn Gly Gly Glu Val Ala Pro Ser Arg
            100                 105                 110

Gly Pro Gly Gly Gly Phe Gln Cys His Leu Val Ser Gly Lys Ala Asn
        115                 120                 125

Arg Arg Tyr Val Ile Ser Leu His Arg Thr Ala Ser His Arg Asp Phe
    130                 135                 140

Ser Leu Arg Glu Met Ser Phe Leu Lys Asn Phe Ala Asp Thr Leu Leu
145                 150                 155                 160

Pro Leu Val Glu Trp His Ala Ser Thr Cys Arg His Gly Glu Arg Glu
                165                 170                 175

Gly Ala Thr Ala Pro Gly Ala Thr Ala Gly Met Pro Gly Val Glu Ala
            180                 185                 190

Leu Arg His Glu Phe Glu Ser Arg Leu Ala Arg Ala Arg Val Val Leu
```

```
            195                 200                 205
Ser Ala Arg Glu Asn Glu Val Cys Leu Gly Leu Leu Ala Gly Lys Met
            210                 215                 220

Leu Arg Glu Met Ala Gly Glu Leu Gly Val Lys Glu Ser Thr Ile Glu
225                 230                 235                 240

Thr Tyr Ile Lys Arg Ala Ala Val Lys Leu Gly Ile Ser Gly Arg His
                245                 250                 255

Gly Leu Thr Lys Trp Met Ile Asp Asp Ser Val Pro Cys Ala Ser Ala
                260                 265                 270

Ala
```

<210> SEQ ID NO 7
<211> LENGTH: 296
<212> TYPE: PRT
<213> ORGANISM: Burkholderia contaminans
<220> FEATURE:
<221> NAME/KEY: MISC_FEATURE
<222> LOCATION: (1)..(296)
<223> OTHER INFORMATION: putative LuxR-type regulator

<400> SEQUENCE: 7

```
Met Glu Phe Ser Arg Leu Phe Ala His Val Gly Glu Ala Ile Ser Ser
1               5                   10                  15

Ser Gly Ser Arg Arg Phe Pro Arg Met Met Tyr Asn Leu Ile Ala Ala
                20                  25                  30

Ala Val Pro Val Asp Glu Ile Arg Ile Ser Glu Leu Ala Ile Asp Asp
            35                  40                  45

Val Pro Asp Gly Pro Pro Glu Val Arg Ser Leu Gly Ala Val Gly Ala
        50                  55                  60

Ala Leu Ala Lys Thr Gly Ala Ala Ala Val Cys Cys Gly Pro Gln Met
65                  70                  75                  80

Pro Pro Arg Pro Gly Thr Ser Pro Leu His Val Asp Asp Thr Leu Ala
                85                  90                  95

Gly His Gly Pro Ile His Ala Gln Leu Asp Arg Phe Ile Leu Met Gln
            100                 105                 110

Ala Ala Ile Val Ser Pro Arg Tyr Ala Gln Phe His Leu Val Thr Arg
        115                 120                 125

Lys Arg Gly His Cys Tyr Val Ile Ser Leu Tyr Arg Thr Cys Thr Phe
    130                 135                 140

Asp Asp Phe Ser Pro Gln Glu Arg Thr Phe Leu Lys Glu Leu Ser His
145                 150                 155                 160

Val Leu Phe Pro Ile Val Glu Ser His Val Ala Ala Leu Asp Ser Ala
                165                 170                 175

Pro Pro Ala Ala Arg Val Thr Thr Ala Ala Pro Pro Ala Thr Gln Ser
            180                 185                 190

Gly Arg Glu Arg Val Ala Arg Arg Phe Ala Asp Arg Leu Gln Gln Ala
        195                 200                 205

Gly Val Lys Leu Ser Thr Arg Glu Ile Glu Ala Cys Thr Ala Leu Leu
    210                 215                 220

Ala Gly Asp Thr Val Pro Ala Ile Ala Met Arg Phe Ala Leu Arg Glu
225                 230                 235                 240

Ser Thr Val Glu Thr Tyr Leu Lys Arg Ala Ala Val Lys Leu Gly Phe
                245                 250                 255

Ser Gly Arg His Gly Leu Thr Arg Trp Met Leu Asp Glu Thr Ala Gly
            260                 265                 270
```

```
Ala Ala Thr Glu Ala Ala Gly Gly Asp Met Arg Ser Met Arg Arg Asp
            275                 280                 285

Tyr Ala Ser Pro Arg Leu Gly Thr
    290                 295

<210> SEQ ID NO 8
<211> LENGTH: 567
<212> TYPE: PRT
<213> ORGANISM: Burkholderia contaminans
<220> FEATURE:
<221> NAME/KEY: MISC_FEATURE
<222> LOCATION: (1)..(567)
<223> OTHER INFORMATION: putative cyclic peptide transporter

<400> SEQUENCE: 8

Met Asp Ser Ala Gln Ser Lys Ser Pro Pro Trp His Ser Ala Ala Thr
1               5                   10                  15

Leu Met Trp Arg Ser His Pro Trp Leu Thr Leu Gly Thr Val Val Thr
            20                  25                  30

Gly Leu Val Ser Gly Ile Ala Ser Ile Ala Gly Val Gly Leu Ile Ser
        35                  40                  45

Thr Val Leu His Asp Gln Asp Asp Arg Gln Thr Leu Leu Leu Leu Phe
    50                  55                  60

Ile Ala Val Asn Val Val Ala Val Val Cys Arg Ser Cys Ala Ala Val
65                  70                  75                  80

Met Pro Ser Tyr Ala Cys Met Lys Val Met Thr Arg Leu Arg Val Asn
                85                  90                  95

Leu Cys Lys Arg Ile Leu Ala Thr Pro Leu Asp Glu Ile Asp Arg Arg
            100                 105                 110

Gly Ala Pro Asn Val Leu Thr Met Leu Thr Gln Asp Ile Pro Gln Leu
        115                 120                 125

Ser Gln Thr Leu Leu Thr Ile Pro Thr Ile Ile Val Gln Ser Val Val
    130                 135                 140

Leu Ile Cys Ser Ile Ala Tyr Leu Ala Tyr Leu Ser Trp Ile Val Phe
145                 150                 155                 160

Ala Ser Thr Ile Ile Leu Thr Leu Val Gly Leu Val Leu Tyr Leu Phe
                165                 170                 175

Phe Tyr Arg Lys Ala Val Asn Phe Thr Glu Arg Val Arg Asp Glu Phe
            180                 185                 190

Val Gln Phe Asn Glu Tyr Thr His Gly Leu Val Phe Gly Ile Lys Glu
        195                 200                 205

Leu Lys Leu Asn Arg Ala Arg Arg Arg Trp Phe Thr Arg Ala Ala Ile
    210                 215                 220

Glu Leu Ser Ser Lys Arg Val Ala Gly Phe Asn Tyr Ile Glu Arg Phe
225                 230                 235                 240

Trp Phe Met Ser Gly Asp Ser Ile Gly Gln Ile Thr Val Ala Val Leu
                245                 250                 255

Leu Gly Cys Leu Leu Phe Gly Val Pro Ser Leu Gly Val Val Asp Pro
            260                 265                 270

Ser Val Leu Thr Ala Ser Ile Leu Ala Val Leu Tyr Met Met Gly Pro
        275                 280                 285

Leu Thr Met Leu Ile Asn Val Leu Pro Val Val Ala Glu Gly Lys Thr
    290                 295                 300

Ala Leu Ala Arg Leu Ala Glu Phe Gly Phe Leu Ile Asp Asp Thr Gln
305                 310                 315                 320

Ala Ser His Glu Glu Pro Arg Pro Ala Gly Asn Val Glu Thr Leu Ser
```

```
                    325                 330                 335

Ala Lys Ser Trp Lys Val Ile Glu Leu Lys Asp Val Thr Met Asn Tyr
                340                 345                 350

Arg Asp Asn Glu Ala Ser Val Asp Phe Val Leu Gly Pro Ile Asp Met
                355                 360                 365

Thr Ile His Ala Gly Glu Leu Val Tyr Val Ile Gly Asn Gly Ser
370                 375                 380

Gly Lys Ser Thr Leu Gly Lys Val Leu Ser Gly Leu Tyr Ala Pro Thr
385                 390                 395                 400

Gly Gly Thr Ile Ser Leu Asp Gly Lys Val Val Asp Ala Ala Arg
                405                 410                 415

Glu Arg Tyr Arg Asn Leu Phe Ser Ala Val Phe Thr Asp Phe His Leu
                420                 425                 430

Phe Asn Arg Ile Ile Gly Pro Asp Arg Gly Asn Glu Ser Ile Glu Leu
                435                 440                 445

Ala Arg Lys Tyr Leu Ala Thr Leu Lys Leu Ala Asp Lys Ile Glu Ile
                450                 455                 460

Ser Gly Arg Thr Tyr Ser Thr Thr Arg Ala Leu Ser Thr Gly Gln Arg
465                 470                 475                 480

Lys Arg Leu Ala Leu Leu Cys Ala Tyr Ile Glu Asp Arg Pro Ile Tyr
                485                 490                 495

Ile Leu Asp Glu Trp Ala Ala Asp Gln Asp Pro Val Phe Lys Arg Phe
                500                 505                 510

Ser Tyr Glu Val Leu Val Pro Asp Leu Lys Ser Arg Gly Lys Cys Val
                515                 520                 525

Val Ile Ile Thr His Asp Asp Gln Tyr Phe Lys Leu Ala Asp Arg Val
                530                 535                 540

Ile Arg Leu Asp Ser Gly Arg Ile Phe Ser Asp Thr Ala Met Cys Ala
545                 550                 555                 560

Val Arg Ala Glu Ala Ala Gly
                565

<210> SEQ ID NO 9
<211> LENGTH: 160
<212> TYPE: PRT
<213> ORGANISM: Burkholderia contaminans
<220> FEATURE:
<221> NAME/KEY: MISC_FEATURE
<222> LOCATION: (1)..(160)
<223> OTHER INFORMATION: hypothetical protein

<400> SEQUENCE: 9

Met Gln Leu Thr Thr Val Asp Leu Glu Ala Ala Phe Val Lys Ala
1               5                   10                  15

Leu Asp Ala Leu His Arg Asp Cys Lys Leu Gly Asp Ala Ile Ser Leu
                20                  25                  30

Ala Tyr Gly Lys Cys Glu Ser Thr Ala Gly Val Ile Asp Leu Ile Phe
                35                  40                  45

Pro Leu Ile Thr Lys Lys Leu Arg Ile Asp Tyr Ile Leu Met Tyr Ser
            50                  55                  60

Ile Glu Ser Asn Pro Arg Thr Leu Leu Gln Phe Leu Arg Gln Ile Glu
65              70                  75                  80

Ser Gly Leu Ala Arg Ser Glu Asp Trp Thr Ala Ala Ser Val Glu Ala
                85                  90                  95

Ala Leu Arg Ser Val Ala Asp Ser Pro Asp Gly Val Gly Trp Glu Arg
                100                 105                 110
```

```
Ala Gln Arg Leu Leu Lys Cys Cys Ile Leu Phe Ser Asp Ser Pro Leu
        115                 120                 125

Gly Ile Val Glu Ser Ile Thr Phe Leu Gly Lys His Glu Thr Ser Ser
    130                 135                 140

Arg Leu Arg Ser Ala Ala Ser Asn Val Glu Leu Ser His Leu Ile Asn
145                 150                 155                 160

<210> SEQ ID NO 10
<211> LENGTH: 218
<212> TYPE: PRT
<213> ORGANISM: Burkholderia contaminans
<220> FEATURE:
<221> NAME/KEY: MISC_FEATURE
<222> LOCATION: (1)..(218)
<223> OTHER INFORMATION: putative glycosyl transferase

<400> SEQUENCE: 10

Met Lys Ser Thr Pro Thr Ile Asp Asn Thr Phe Ala Arg Lys Val Cys
1               5                   10                  15

Ile Asn Leu Asp Arg Arg Pro Asp Arg Trp Glu Ala Met Gln Arg Lys
            20                  25                  30

Phe Ala Glu Gln Asn Ile Leu Thr Val Glu Arg Leu Pro Ala Val Asp
        35                  40                  45

Ala Arg Leu Val Ser Val Pro Glu Ser Leu Ser His Met Arg Ala Gln
    50                  55                  60

Asp Tyr Gly Cys Thr Met Ser His Leu Ala Ala Val Lys Gln Ala Lys
65                  70                  75                  80

Ala Ala Gly Ala Arg Glu Val Leu Ile Phe Glu Asp Asp Ala Phe Phe
                85                  90                  95

Asp Ala Asp Phe Ala Ala Arg Phe Pro Glu Phe Ile Ala Gln Val Pro
            100                 105                 110

Asp Asp Trp His Met Leu Phe Leu Gly Ala Tyr His Phe Thr Pro Pro
        115                 120                 125

Ile Pro Val Ala Pro Asn Ile Val Lys Ala Val Glu Thr Leu Thr Ala
    130                 135                 140

His Ala Tyr Val Val Arg Asn Ser Leu Tyr Asp Ala Phe Ile Ala Ile
145                 150                 155                 160

Asn Glu Asn Pro Pro Ala Ile Asn Asp Arg Asn Asn Leu Val Leu Gln
                165                 170                 175

Gln Thr Phe Asn Cys Tyr Cys Phe Glu Pro Asn Leu Val Gly Gln Glu
            180                 185                 190

Ser Gly Tyr Ser Asp Ile Met Asp Glu Val Met Pro Glu Lys Pro Leu
        195                 200                 205

Thr Tyr Ser Met Pro Ile Pro Asp Gly Trp
    210                 215

<210> SEQ ID NO 11
<211> LENGTH: 3164
<212> TYPE: PRT
<213> ORGANISM: Burkholderia contaminans
<220> FEATURE:
<221> NAME/KEY: MISC_FEATURE
<222> LOCATION: (1)..(3164)
<223> OTHER INFORMATION: putative nonribosomal peptide synthetase

<400> SEQUENCE: 11

Met Gln Asp Asn Asn Val Leu Val Thr Asp His Arg Tyr Ala Ala Thr
1               5                   10                  15
```

-continued

```
Ala Arg Phe Trp Arg Glu Ser Leu Ser Arg Val Ala Gly Val Tyr Gly
             20                  25                  30
Ile Ala Ala Tyr Ala Pro Ser Gln Gln Pro Gly Arg Pro Leu Thr Arg
             35                  40                  45
Ser Val Arg Leu Thr Pro Ala Ser Leu Asp Leu Leu Arg Arg Ile Gly
 50                  55                  60
Asp Gly Glu Leu Ala Glu Phe Ala Val Ala Ala Gly Ile Ala Phe
 65                  70                  75                  80
Leu Leu Trp Lys Tyr Phe Arg Ile Pro Val Thr Val Leu Gly Thr Pro
             85                  90                  95
Gly Leu Ala Gly His Pro Ser Ala Arg Ala Ala Ile Val Pro Leu Ile
            100                 105                 110
Ile Glu Val Arg Pro Asp Glu Arg Ile Glu Asp Tyr Leu Ser Arg Val
            115                 120                 125
Ala Gly Ile Val Glu Asp Ser Tyr Ala Glu Pro Arg Phe Pro Leu Glu
            130                 135                 140
Thr Leu Val Arg Asn Glu Lys Asp Met Ala Leu Ala Gln Leu Thr Lys
145                 150                 155                 160
Val Ala Leu Ala Asp Asp Arg Val His His Ala Pro Thr Gly Arg Asp
            165                 170                 175
Asp Asp Leu Gln Leu His Leu Arg Leu Ala Arg Gly Glu Ile Glu Leu
            180                 185                 190
Arg Tyr Ser Gly Ala Ile Glu Pro Phe Ile Ile Asp Gly Phe Ala Gly
            195                 200                 205
Ser Leu Ala Ala Val Leu Glu Ala Phe Glu His Leu Asp Gly Ala Val
            210                 215                 220
Gly Asp Ile Glu Ala Ala Pro Pro Glu Gln Gly Pro Leu Leu Ala Ala
225                 230                 235                 240
Phe Asn Glu Thr Ala Thr Ala Gly Pro Ser His Pro Thr Val Val Ala
            245                 250                 255
Met Phe Glu Ala Gln Val Ala Arg Thr Pro Thr Ala Pro Ala Leu Val
            260                 265                 270
Thr Asp Ser Ser Leu Met Thr Tyr Ala Asp Leu Asn Ala Arg Ala Asn
            275                 280                 285
Ser Leu Ala His His Leu Arg Glu His His Gly Val Gly Pro Glu Ser
            290                 295                 300
Leu Val Gly Ile Met Leu Asp Arg Ser Glu Trp Met Ile Val Ala Ile
305                 310                 315                 320
Leu Gly Ile Leu Lys Ala Gly Ala Ala Phe Val Pro Leu Asp Pro Ala
            325                 330                 335
Tyr Pro Ala Glu Arg Ile Asn His Ile Leu Gly Asp Thr Gly Leu Ser
            340                 345                 350
Leu Leu Val Thr Gln Ser Ser Gln Leu Ala Gln Trp Tyr Glu Phe Ser
            355                 360                 365
Gly Val Thr Leu Leu Asp Gln Glu Leu Pro Gly Trp Gln Pro Leu
            370                 375                 380
Pro Asp Asn Pro Pro His Arg Ala Glu Pro Ala His Leu Ala Tyr Val
385                 390                 395                 400
Leu Tyr Thr Ser Gly Ser Thr Gly Lys Pro Lys Gly Cys Leu Leu Glu
            405                 410                 415
His Arg Asn Leu Ala His Tyr Ile Ala Trp Ala Ala Gly Tyr Tyr Phe
            420                 425                 430
Pro Glu Ser Thr Thr Gly Ser Phe Gly Leu Tyr Ser Ser Leu Cys Phe
```

```
            435                 440                 445
Asp Phe Thr Leu Thr Asn Ile Phe Cys Pro Leu Val Arg Gly Lys Thr
450                 455                 460

Leu Arg Ile Tyr Pro Gln Ser Glu Ser Ile Asp Thr Ile Leu Ala Arg
465                 470                 475                 480

Met Phe Gln Pro Gly Ser Gly Val Asp Thr Leu Lys Leu Thr Pro Thr
                    485                 490                 495

His Ile His Leu Leu Glu Tyr Met Asn Leu Ala Arg Ser Gly Val Arg
                500                 505                 510

Lys Val Ile Val Gly Gly Glu Leu Thr Pro Gln His Ile Ala Thr
            515                 520                 525

Leu Arg Lys Ile Asp Pro Ala Ile Glu Ile Tyr Asn Glu Tyr Gly Pro
530                 535                 540

Thr Glu Ala Thr Val Gly Cys Ile Val Glu Arg Val Glu Asp Ala Pro
545                 550                 555                 560

Pro Thr Val Leu Ile Gly Arg Pro Ile Ala Asp Thr Arg Val Tyr Met
                565                 570                 575

Leu Asp Asp Ala Leu Arg Pro Val Pro Leu Gly Val Pro Gly Glu Ile
                580                 585                 590

Cys Leu Ala Gly Ala Gly Leu Ala Arg Gly Tyr His Gln Arg Pro Asp
            595                 600                 605

Val Thr Ala Ala Lys Phe Val Glu His Pro Phe Pro Gly Glu Ala Arg
610                 615                 620

Ile Tyr Arg Thr Gly Asp Ile Gly Arg Trp Leu Pro Asp Gly Arg Ile
625                 630                 635                 640

Gln Cys Tyr Gly Arg Val Asp His Gln Val Lys Ile Arg Gly His Arg
                645                 650                 655

Val Glu Leu Gly Glu Ile Glu Ala Ile Ala Ala His Glu Asp Val
            660                 665                 670

Val Gly Ala Ala Val Met Leu Arg Glu Ser Ala His Gly Val Arg Lys
            675                 680                 685

Leu Ala Ala Tyr Val Lys Gly Ala Ala Ser Leu Ser Val Pro Asn Leu
            690                 695                 700

Arg Ala Tyr Leu Ala Gly Lys Leu Pro Asp Tyr Met Val Pro Ser Asp
705                 710                 715                 720

Ile Ile Pro Ile Ala Glu Phe Pro Leu Asn Ala Asn Gly Lys Leu Asp
                725                 730                 735

Arg Pro Ala Leu Leu Ala Leu Glu Pro Ala Ala Pro Glu Glu Ala
                740                 745                 750

Pro Leu Asp Ala Thr Pro Ile Gln Arg Glu Leu Val Arg Ile Trp Arg
            755                 760                 765

Asp Val Leu Asp Asn Pro Ala Val Asp Leu Ala Gly Arg Phe Phe Asp
            770                 775                 780

Tyr Gly Gly Asp Ser Leu Gln Ala Met Gln Leu Val Ser Arg Ile Trp
785                 790                 795                 800

Ser Ser Phe Ser Val Glu Ile Gly Ile Asp Ala Ile Phe Glu Leu Gln
                805                 810                 815

Thr Ile Ser Ala Val Ser Asp Leu Ile Glu Ala Ser Ser Pro His Pro
                820                 825                 830

Gly Ser Thr Ala Gly Ala Ile Pro Pro Arg Ser Arg Ala Asn Asp Leu
            835                 840                 845

Pro Leu Ser Phe Pro Gln Gln Arg Leu Trp Phe Leu Ala Gln Leu Glu
850                 855                 860
```

Gly Pro Ser Ala Thr Tyr Asn Ile Ser Ser Ala Leu Arg Phe Glu Gly
865                 870                 875                 880

Glu Leu Asp Val Ala Arg Leu Arg Phe Ala Val Ser Glu Ile Ser Arg
            885                 890                 895

Arg His Glu Ile Leu Arg Thr Thr Phe Pro Ala Val Asp Gly Arg Gly
        900                 905                 910

Val Gln Arg Ile Ala Pro Pro Ala Pro Val Ala Leu Asp Val Val Asp
    915                 920                 925

Val Ala Ser Glu Ser Asp Thr Leu Ala Leu Leu Ala Glu Glu Ala Asp
930                 935                 940

Arg Pro Phe Asp Leu Ala Ala Gly Pro Leu Tyr Arg Val Val Leu Tyr
945                 950                 955                 960

Arg Val His Glu Arg Leu His Val Phe Gly Ile Val Met His His Ile
                965                 970                 975

Val Ser Asp Ala Trp Ser Ser Gly Ile Leu Ile Gly Glu Leu Ala Ala
            980                 985                 990

Leu Tyr Ala Gly Glu Ser Leu Pro Glu Leu Ala Val Gln Tyr Ala Asp
        995                 1000                1005

Tyr Ala Val Trp Gln His Glu Arg Leu Ala Ser Ala Asp Thr His
    1010                1015                1020

Arg Glu Leu Ala Leu Leu Ser Ala Ala Leu Ala Asp Ala Pro Asp
    1025                1030                1035

Leu Ile Glu Leu Pro Thr Asp Arg Pro Arg Pro Ala Val Gln Gln
    1040                1045                1050

Phe Arg Gly Ala Val Leu Pro Phe Gln Leu Ser Ala Glu Arg Ala
    1055                1060                1065

Asp Gly Leu Arg Ala Ile Ala Arg Ala Ser Gly Thr Ser Thr Phe
    1070                1075                1080

Met Val Val Leu Ala Ala Tyr Ala Leu Leu Leu Ser Arg Tyr Ser
    1085                1090                1095

Asn Gln Gln Asp Leu Val Ile Gly Ser Pro Ile Ala Asn Arg Arg
    1100                1105                1110

Ser Ser Met Thr Glu Pro Leu Ile Gly Phe Phe Ala Asn Met Leu
    1115                1120                1125

Ala Leu Arg Val Asp Leu Ser Gly Asn Pro Thr Phe Gly Asp Leu
    1130                1135                1140

Leu Ala Arg Val Lys Arg Val Ala Leu Asp Gly Tyr Ser Arg Gln
    1145                1150                1155

Glu Ile Pro Phe Glu Gln Val Val Asp Ser Leu Glu Leu Glu Arg
    1160                1165                1170

Asn Leu Gly Arg Thr Pro Val Phe Gln Val Val Phe Ala Tyr Glu
    1175                1180                1185

Lys Ala Gln Pro Arg Ala Val Ser Phe Pro Gly Leu Val Ala Thr
    1190                1195                1200

Pro Val Ala Val Glu Thr His Thr Ala Lys Phe Asp Leu Thr Leu
    1205                1210                1215

His Val Gln Asp Ala Asp Asp Gly Leu Ala Gly Ser Leu Glu Tyr
    1220                1225                1230

Asn Leu Asp Leu Phe Asp Ala Ala Thr Ile Asp Arg Met Ala Glu
    1235                1240                1245

His Phe Arg Thr Leu Val Asp Ala Val Ile Ala Asp Pro Asp Arg
    1250                1255                1260

```
Pro Leu Gly Ala Leu Ser Leu Ser Asn Asp Ala Glu Arg Asn Leu
    1265                1270                1275

Leu Thr Val Glu Trp Asn Arg Thr Asp Thr Asp Phe Gly Glu Asp
    1280                1285                1290

Ala Ala Gln Pro Leu His Arg Leu Phe Glu Gln Gln Val Glu Arg
    1295                1300                1305

Thr Pro Asp Ala Val Ala Ile Val Phe Asp Asp Thr Ala Leu Thr
    1310                1315                1320

Tyr Ala Glu Leu Asn Leu Arg Ala Asn Arg Leu Ala His His Leu
    1325                1330                1335

Val Ala Leu Gly Val Gly Pro Asp Ser Leu Val Gly Val Ala Met
    1340                1345                1350

Glu Arg Ser Leu Asp Met Ser Val Ala Leu Leu Ala Ile Leu Lys
    1355                1360                1365

Ala Gly Gly Ala Tyr Val Pro Val Asp Pro Asp Tyr Pro Ala Glu
    1370                1375                1380

Arg Val Arg Phe Met Ile Asp His Ala Gln Leu Arg Trp Leu Leu
    1385                1390                1395

Thr Gln Gln His Leu His Asp Ala Leu Pro Asp Thr Asp Ala His
    1400                1405                1410

Val Ile Val Val Asp Arg Asp Ser Leu Asp Leu Asp Ala Ala Ala
    1415                1420                1425

Thr Ser Asn Pro Ala Pro Ala Leu Asn Gly Asp Asn Leu Ala Tyr
    1430                1435                1440

Met Ile Tyr Thr Ser Gly Ser Thr Gly Arg Pro Lys Gly Ala Leu
    1445                1450                1455

Asn Thr His Arg Ala Ile Thr Asn Arg Ile Leu Trp Met Gln His
    1460                1465                1470

Ala Tyr Ala Leu Asp Ala Asp Asp Ala Val Leu Gln Lys Thr Pro
    1475                1480                1485

Phe Ser Phe Asp Val Ser Val Trp Glu Leu Phe Trp Pro Leu Val
    1490                1495                1500

Thr Gly Ala Arg Leu Val Phe Ala Arg Pro Gly Gly Gln Arg Glu
    1505                1510                1515

Thr Asp Tyr Leu Val Glu Leu Ile Glu Arg Glu Arg Ile Thr Thr
    1520                1525                1530

Ile His Phe Val Pro Ser Met Leu Arg Ala Phe Leu Asp His Pro
    1535                1540                1545

Asp Leu Asp Ala His Cys Ala Ser Leu Arg Arg Val Val Cys Ser
    1550                1555                1560

Gly Glu Ala Leu Pro His Asp Leu Gln Gln Arg Cys Leu Glu Arg
    1565                1570                1575

Leu Asp Val Lys Leu Tyr Asn Leu Tyr Gly Pro Thr Glu Ala Ala
    1580                1585                1590

Val Asp Val Thr Ala Trp Glu Cys Arg Arg Asp Asp Pro His Arg
    1595                1600                1605

Ile Val Pro Ile Gly Arg Pro Ile Ala Asn Thr Arg Leu Tyr Ile
    1610                1615                1620

Val Asp Ala Gln Met Gln Pro Thr Pro Ile Gly Val Ala Gly Glu
    1625                1630                1635

Leu Leu Ile Gly Gly Thr Pro Val Gly Arg Gly Tyr His Gly Glu
    1640                1645                1650

Pro Glu Leu Ser Ala Glu Lys Phe Ile Ala Asp Pro Phe Ser Ala
```

```
                1655                1660                1665

Asp Pro Leu Ala Arg Leu Tyr Arg Thr Gly Asp Leu Ala Arg Tyr
    1670                1675                1680

Arg Pro Asp Gly Asn Ile Glu Phe Leu Gly Arg Ile Asp His Gln
    1685                1690                1695

Ile Lys Leu Arg Gly Leu Arg Ile Glu Pro Gly Glu Ile Glu Ala
    1700                1705                1710

Ala Leu Arg Ala His Pro Ser Val Asp Asp Cys Val Val Ile Ala
    1715                1720                1725

Lys Thr Glu Gly Ala Arg Thr Phe Leu Ile Ala Tyr Val Ala Thr
    1730                1735                1740

Ala Ala Pro Asp Ile Ala Asp Leu Arg Gly Tyr Leu Gly Gly Lys
    1745                1750                1755

Leu Ala Asp Tyr Met Val Pro Ser Gln Phe Phe Ala Leu Glu Ser
    1760                1765                1770

Leu Pro Met Leu Pro Asn Gly Lys Ile Asn Arg Lys Ala Leu Pro
    1775                1780                1785

Leu Pro Ala Asp Arg Gly Asp Ala Ala Gln Pro His Ala Pro Ala
    1790                1795                1800

Val Thr Pro Arg Glu Ile Leu Leu Ala Ser Ile Cys Ile Asp Val
    1805                1810                1815

Leu Gln Leu Pro Ser Val Gly Ile His Asp Asn Phe Phe Glu Leu
    1820                1825                1830

Gly Gly Asp Ser Ile Leu Ser Ile Gln Val Ile Ala Arg Ala Asn
    1835                1840                1845

Gln Ala Gly Leu Arg Val Thr Ala Lys Gln Leu Phe Gln Tyr Gln
    1850                1855                1860

Thr Ile Ala Gln Leu Ala Ala Ala Pro Glu Glu Arg Ala Ala Cys
    1865                1870                1875

Ala Pro Thr Leu Ser Pro Leu Gly Asp Ala Pro Leu Thr Pro Val
    1880                1885                1890

Gln His Trp Phe Phe Glu Gln Glu Ile Asp Ala Pro Ser His Tyr
    1895                1900                1905

Asn Gln Thr Val Leu Ile Gln Val Pro Ala Asp Ile Asp Ala Ser
    1910                1915                1920

Arg Leu Ala Asp Ala Phe Arg Gln Val Tyr Glu His His Asp Ala
    1925                1930                1935

Leu Arg Leu Arg Phe Ser His Asp Ala Gly Arg Trp Thr Gln Gln
    1940                1945                1950

Val Val Ala Gly Gly Glu Met Pro Ala Leu Phe Ala Lys Gln Val
    1955                1960                1965

Ile Ala Asp Asp Ala Gly Glu Arg Leu Ala Ala Met Arg Ala Ala
    1970                1975                1980

Ala Ala Asp Ala Glu Arg Gly Ile Asp Ile Thr His Gly Pro Leu
    1985                1990                1995

Leu Ala Ala Arg Leu Phe Cys Leu Ala Asp Glu Pro Leu Ala Arg
    2000                2005                2010

Leu Phe Val Ser Ile His His Leu Ala Val Asp Gly Val Ser Trp
    2015                2020                2025

Arg Val Leu Leu Glu Asp Leu His Ala Ala Tyr His Gly Gln Pro
    2030                2035                2040

Leu Pro Gly Lys Thr Thr Ser Phe Arg Glu Trp Ala Leu His Leu
    2045                2050                2055
```

```
Gln Gln Leu Ala Arg Ser Pro Ala Ile Gly Asp Glu Ala Arg Leu
2060                2065                2070

Trp Gln Ala Leu Leu Ala Gln Pro Val Glu Pro Met Pro Val Asp
    2075                2080                2085

Tyr Pro Gly Thr Gly Ala Ala Asn Asn Ala Val Asp Asp Ala Ser
2090                2095                2100

Ser Val Ser Phe Glu Leu Gly Glu Ala Asp Thr Thr Ala Leu Leu
2105                2110                2115

Arg Arg Leu Pro Arg Ala Tyr Asp Thr Arg Ile Asn Asp Val Leu
2120                2125                2130

Leu Val Ala Leu Ala Gln Ala Cys Ser Met Val Thr Gly Asn Thr
2135                2140                2145

Arg Thr Arg Ile Asp Leu Glu Ser His Gly Arg His Val Ser Asp
2150                2155                2160

Ala Pro Leu Asp Leu Thr Arg Thr Val Gly Trp Phe Thr Ser Ile
2165                2170                2175

Tyr Pro Val Val Leu Asp Ala Asp Ala Met His Ala Pro Glu Gln
2180                2185                2190

Ala Leu Arg Ala Ala Arg Gln Gln Leu Arg Arg Ile Pro Ala Asp
2195                2200                2205

Gly Leu Gly Tyr Ser Leu Leu Arg Tyr Gln Ser Pro Asp Ala Ala
2210                2215                2220

Val Arg Asp Ser Leu Ala Ala Leu Pro Lys Ala Asp Ile Leu Phe
2225                2230                2235

Asn Tyr His Gly Gln Leu Asp Thr Val Leu Arg Gln Ser Asp Gly
2240                2245                2250

Trp Arg Pro Ala Ala Glu Asp Leu Gly Ser Leu Arg Ala Gly Arg
2255                2260                2265

Ser Gln Arg Thr His Ala Phe Glu Ile Val Ala Ala Val Ala Asp
2270                2275                2280

Gly Lys Leu Gln Val Asp Trp Arg Tyr Gly Glu Arg Leu His Arg
2285                2290                2295

Arg Gln Thr Val Glu Asn Leu Ala Ala His Phe Arg Asp Arg Leu
2300                2305                2310

Leu Asp Phe Ala Ala Ser Val Pro Asp Thr Ala Ala Asp Asp Ile
2315                2320                2325

Glu Asp Ser Tyr Pro Leu Ser Ser Leu Gln Gln Gly Ile Leu Phe
2330                2335                2340

His Ser Leu Tyr Asp Leu Asp Pro Ala Ala Tyr Phe Gln Gln Phe
2345                2350                2355

Ser Phe Val Val Ser Gly Pro Leu Gln Val Pro Ala Leu Arg Gln
2360                2365                2370

Ala Trp Ala Asn Ala Leu Ala Arg His Ala Val Leu Arg Thr Ala
2375                2380                2385

Phe Ala Trp Ala Asp Arg Asp His Pro Val Gln Thr Val Arg His
2390                2395                2400

Thr Val Asp Leu Pro Trp Thr Phe Leu Asp Trp Arg His Arg Asp
2405                2410                2415

Ala Ser Arg Arg Ala Gln Asp Phe Asp Ala Phe Leu Ala Asp Asp
2420                2425                2430

Arg Arg Arg Gly Phe Asp Leu Gln Arg Ala Pro Leu Phe Arg Cys
2435                2440                2445
```

Thr Leu Ile Gln Glu Thr Asp Thr Arg His Arg Phe Cys Trp Ser
2450                2455                2460

Ala His His Ile Ile Leu Asp Gly Trp Ser Thr Ala Thr Leu Met
2465                2470                2475

Lys Glu Val Phe Asp Asp Tyr Leu Ser Leu Ala Arg Thr Gly Met
2480                2485                2490

Pro Ala Val Ala Ala Ser Ala Pro Gly Tyr Arg Ala Tyr Ile Asp
2495                2500                2505

Trp Leu Ala Arg His Pro Arg Ser Ala Asp Glu Thr Trp Trp Arg
2510                2515                2520

Ala Glu Leu Ala Gly Phe Lys Ala Ala Thr Pro Val Ala Ala Ser
2525                2530                2535

Pro Ala Arg Gln Ala Thr Gly Asp Ala Pro Arg Gln Asp Lys Arg
2540                2545                2550

Arg Thr Gln Gln Phe Leu Leu Asp Glu Ala Leu Ala Ala Arg Leu
2555                2560                2565

Gln Thr Leu Thr Arg Thr His Arg Val Thr Leu Asn Val Leu Ile
2570                2575                2580

Arg Ala Val Trp Ala Leu Val Leu Arg Arg His Ala Gly Thr Asp
2585                2590                2595

Asp Val Val Phe Gly Val Thr Val Ser Gly Arg Pro Pro Met Leu
2600                2605                2610

Asp Gly Val Glu Ser Ile Val Gly Leu Phe Ile Asn Thr Leu Pro
2615                2620                2625

Leu Arg Leu Arg Ile Ala Pro Glu Arg Pro Phe Ile Glu Trp Leu
2630                2635                2640

Ala Glu Val His Ala Ala Gln Thr Ala Met Glu Pro His Ser Tyr
2645                2650                2655

Ser Ser Leu Val Asp Ile Gln Ser Trp Ser Glu Leu Pro Ala Gly
2660                2665                2670

Asp Ser Leu Phe Asp Ser Leu Leu Val Phe Glu Asn Phe Pro Val
2675                2680                2685

Ala Ala Ala Pro Asp Leu Gly Pro Asp Asp Ile Glu Ile Leu Asp
2690                2695                2700

Thr Arg Ala Phe Ala Glu Ser Asn Tyr Pro Leu Thr Leu Thr Val
2705                2710                2715

His Pro Asn Glu Arg Ile Gly Phe His Ile Ser His Asp Ala His
2720                2725                2730

Arg Ile Ala Pro Glu Val Val Arg Gln Met Leu Asp Thr Leu Arg
2735                2740                2745

Thr Leu Leu Glu Arg Phe Ala Glu Asn Pro Gly Gln Leu Thr Gly
2750                2755                2760

Gln Leu Ala Asp Pro Pro Ala Ala Asp Gly Arg Pro Ser Ala Pro
2765                2770                2775

Arg Ser Gly Ala Gly Pro Ala Ile Glu Ala Ala Ala Gly Ala Ala
2780                2785                2790

Ala Ala Ala Arg Ala Val Ala His Ala Ala Asp Glu Ser Thr Leu
2795                2800                2805

Leu Glu Ile Trp Arg Arg Ile Phe Lys Arg Asp Asp Ile Ala Val
2810                2815                2820

Ser Asp Asn Tyr Phe Asp Leu Gly Gly His Ser Ile Ile Ala Ile
2825                2830                2835

Gln Leu Met Ala His Val Glu Lys Ala Phe Asp Arg Arg Leu Pro

```
            2840                2845                2850
Ile Ser Cys Leu Phe Glu Asn Pro Thr Ile Glu Lys Leu Ala Ala
    2855                2860                2865

Ala Leu Ala Ala Lys Glu Pro Ser Ala Pro Ala Gly Gly Leu Val
    2870                2875                2880

Pro Ile Arg Asp Gly Gly Pro Ala Ala Pro Leu Phe Leu Leu Pro
    2885                2890                2895

Gly Ala Gly Gly Asn Val Val Tyr Phe Arg Pro Leu Ala Asn His
    2900                2905                2910

Leu Ser Gly Ala His Ala Ile His Gly Leu Gly Ala Leu Gly Leu
    2915                2920                2925

Asp Gly Ala Cys Glu Pro Leu Thr Arg Val Glu Asp Ile Ala Ala
    2930                2935                2940

Arg His Ile Glu Arg Ile Trp Pro Leu Val Gly Ala Gly Pro Tyr
    2945                2950                2955

Tyr Leu Ala Gly His Ser Phe Gly Ala His Val Ala Leu Glu Met
    2960                2965                2970

Ser Arg Gln Leu Val Ala Lys Gly Ala Asp Val Lys Leu Leu Ala
    2975                2980                2985

Ile Phe Asp Ala Ser Ala Pro Ile Asp Ser Ser Ala Ala Thr Tyr
    2990                2995                3000

Trp Gln Asp Trp Asp Thr Glu Trp Leu Val Ala Ile Ala His
    3005                3010                3015

Glu Ile Gly Thr Phe Leu Gly Thr Asp Leu Gln Val Thr Arg Ala
    3020                3025                3030

Asp Leu Val His Leu Asp Pro Asp Gly Gln Ala Gly Leu Ile Leu
    3035                3040                3045

Glu Arg Ile Gly Asp Arg Gly Ser Trp Phe Ala Asp Ala Gly Ser
    3050                3055                3060

Asp Arg Leu Arg Ala Tyr Leu Arg Val Tyr Gln Ala Asn Phe Lys
    3065                3070                3075

Ser His Tyr Ala Pro His Ala Thr Pro Leu Pro Val Pro Ile Ala
    3080                3085                3090

Leu Phe Arg Ser Thr Glu Arg Asp Pro Gly Asp Tyr Ala Pro Ser
    3095                3100                3105

Ser Glu Ile Ala Gln Leu Arg Leu Asp Ala Thr Trp Gly Trp Ser
    3110                3115                3120

Arg Phe Ser Ala His Pro Val Ala Val Thr Asp Val Pro Gly Asp
    3125                3130                3135

His Leu Thr Met Leu Leu Asp Pro His Ala Gly Val Leu Ala Ala
    3140                3145                3150

His Val Asn Ser Phe Leu Glu Lys Thr Pro Ser
    3155                3160

<210> SEQ ID NO 12
<211> LENGTH: 3021
<212> TYPE: PRT
<213> ORGANISM: Burkholderia contaminans
<220> FEATURE:
<221> NAME/KEY: MISC_FEATURE
<222> LOCATION: (1)..(3021)
<223> OTHER INFORMATION: putative nonribosomal peptide synthetase

<400> SEQUENCE: 12

Met Gln Glu Gly Met Leu Phe His Ala Val His Glu Pro Gly Ser Arg
1               5                   10                  15
```

```
Ser Ser Phe Asn Gln Leu Ser Cys Arg Ile Thr Gly Ser Leu Asp Pro
            20                  25                  30

Ala Leu Phe His Ala Ala Trp Gln Gln Leu Ile Asp Arg His Pro Val
        35                  40                  45

Met Arg Thr Ser Phe His Trp Glu Glu Phe Asp Lys Pro Met Gln Val
50                  55                  60

Val His Ala Arg Ala Thr Leu Pro Trp Val Gln Asp Asp Trp Leu Asp
65                  70                  75                  80

Leu Pro Glu His Glu Gln Arg Ser Arg Trp Arg Ala His Leu Asp Asn
                85                  90                  95

Asp Leu Ala Glu Gly Phe Ala Leu Asp Arg Ala Pro Leu Val Arg Cys
            100                 105                 110

Arg Leu Val Arg Val Ala Ala Asp Ala Tyr Leu Phe Ser Trp Ser His
        115                 120                 125

His His Ile Leu Ala Asp Gly Trp Cys Leu Ser Leu Val Ile Glu Glu
130                 135                 140

Ile Phe Glu Val Tyr Gly Ala Leu Ala Arg Gly Val Ser Pro Ala Leu
145                 150                 155                 160

Pro Pro Val Arg Pro Tyr Arg Asp Tyr Ile Gln Trp Leu Gln Gln His
                165                 170                 175

Glu Pro Gln Ala Ala Gln Gln Tyr Trp Thr Arg Tyr Leu Glu Gly Phe
            180                 185                 190

Arg Thr Pro Thr Pro Leu Pro Thr Ala Ala Arg Ala Gly Ala Asp Glu
        195                 200                 205

Arg Phe Gly Gln Gly Leu Ala Gln Val Gln Ala Asp Leu Ser Ala Asp
210                 215                 220

Leu Ser Ala Arg Leu Arg Gln Phe Ala Ala Arg His His Val Thr Leu
225                 230                 235                 240

Asn Thr Leu Ala Gln Ala Ala Trp Ala Leu Val Leu Ser Arg Tyr Ser
                245                 250                 255

Gly Glu Thr Asp Val Val Phe Gly Ala Val Val Ser Gly Arg Gly Ala
            260                 265                 270

Asn Leu Pro Gly Ile Glu Thr Met Leu Gly Leu Phe Ile Asn Thr Val
        275                 280                 285

Pro Val Arg Val Arg Val Asp Pro Arg Gln Pro Leu Val Pro Trp Leu
290                 295                 300

Lys Met Ile Gln Ala Arg Val Ala Arg Ala Pro Phe Glu His Thr
305                 310                 315                 320

Pro Leu Pro Asp Ile Gln Arg Cys Ser Asp Val Pro Thr Ala Pro
                325                 330                 335

Leu Phe Glu Ser Asn Ile Thr Phe Met Asn Tyr Pro Leu Asp Ala Ser
            340                 345                 350

Leu Thr His Gly Ala His Gly Leu Ala Val Asp Glu Val Gln Leu Tyr
        355                 360                 365

Asn Arg Ala Asp Ile Pro Leu Glu Phe Val Val Thr Ala Arg Asp Asp
370                 375                 380

Trp Lys Met Glu Leu Ser Phe Asp Pro Arg Arg Phe Asp Glu Asp Thr
385                 390                 395                 400

Met Gln Arg Met Leu Gly His Val Ala Thr Leu Asp Ala Phe Ala
                405                 410                 415

Ala Asp Pro Asn Arg Leu Leu Gly Arg Val Pro Ile Leu Pro Asp Ala
            420                 425                 430
```

Glu Arg Arg Gln Leu Leu Glu Thr Phe Asn Asp Thr Ala Val Pro Phe
            435                 440                 445

Asp Ala Ala Leu Thr Val Val His Arg Leu Glu Gln Ala Ala Ala Asp
    450                 455                 460

His Pro Glu Arg Pro Ala Val Glu Tyr Arg Asp Gly Val Leu Ser Ala
465                 470                 475                 480

Gly Glu Leu Asn Ala Arg Ala Asn Arg Ile Ala His Arg Leu Leu Ala
                485                 490                 495

Ala Ala Asp Leu Gly Pro Asp Ala Leu Val Ala Ile Cys Met His Arg
            500                 505                 510

Ser Ala Gln Leu Met Glu Ala Ile Leu Ala Val Trp Lys Cys Gly Ala
            515                 520                 525

Ala Tyr Ile Pro Val Asp Pro Asn Tyr Pro Val Ala Arg Ile Arg Thr
            530                 535                 540

Ile Leu Glu Asp Ser Gly Ala Ala Leu Val Ile Thr Cys Asp Gly Leu
545                 550                 555                 560

Leu Pro Pro Glu Leu Ala Gly Ile Ala Leu Val Val Ser Leu Asp Ala
                565                 570                 575

Ala Thr Asp Ala Val Asp Asp Ser Asn Pro Gly Arg Pro Val Ser Pro
            580                 585                 590

Asp Ser Leu Ala Tyr Val Ile Tyr Thr Ser Gly Ser Thr Gly Lys Pro
            595                 600                 605

Lys Gly Ala Met Val Glu His Ala Gly Met Leu Asn His Met Leu Ala
            610                 615                 620

Glu Ile Asp Glu Phe Ser Ile Ser Ala Ser Ser Val Ile Ala Gln Thr
625                 630                 635                 640

Ala Pro His Cys Phe Asp Ile Ser Val Trp Gln Phe Thr Ala Pro
                645                 650                 655

Leu Val Gly Gly Lys Thr Val Ile Val Asp Asp Cys Ile Arg Asp
                660                 665                 670

Pro Ala Arg Phe Val Ala Tyr Leu Glu Thr Thr Arg Ile Ser Ile Leu
            675                 680                 685

Glu Leu Val Pro Ser Tyr Leu Ser Ala Val Leu Asp Arg Ala Ser Glu
            690                 695                 700

Arg Pro Ala Leu Met Arg His Leu Arg His Leu Leu Val Thr Gly Glu
705                 710                 715                 720

Met Val Ser Pro Ala Leu Val Lys Gln Trp Phe Asp Val Phe Pro Ala
                725                 730                 735

Ile Pro Leu Val Asn Ala Tyr Gly Pro Ala Glu Ala Ser Asp Asp Val
            740                 745                 750

Ala Gln His Arg Met Thr Gly Ala Pro Ser Thr Pro Tyr Val Pro Val
            755                 760                 765

Gly Lys Pro Ile Arg Asn Val Arg Leu Tyr Val Val Asp Pro Gln Met
            770                 775                 780

Asn Leu Cys Pro Ile Gly Ile Pro Gly Glu Leu Cys Val Ser Gly Val
785                 790                 795                 800

Ala Val Gly Arg Gly Tyr Leu Asn Asn Glu Ala Ala Thr Gln Asp Ala
                805                 810                 815

Phe Val Glu Asp Pro Phe His Pro Gln Arg Gly Val Arg Leu Tyr Arg
            820                 825                 830

Thr Arg Asp Ile Gly Cys Tyr Leu Pro Asp Gly Thr Ile Val Leu His
            835                 840                 845

Gly Arg Lys Asp His Gln Leu Lys Ile Arg Gly Tyr Arg Ile Glu Leu

-continued

```
            850                 855                 860
Gly Glu Ile Asp Gln Arg Arg Leu Ala Asp His Ser Arg Lys Leu Arg
865                 870                 875                 880

Gln Ala Ala Ala Leu Asp Tyr Arg Asp Glu Ala Gly Arg Ala Ala Leu
                885                 890                 895

Cys Ala Tyr Val Ala Phe Arg Asp Gly Ala Ser Leu Ser Asp Ala Gly
                900                 905                 910

Ile Ala Ala Ala Leu Ser Ala Thr Leu Pro Asp Tyr Met Val Pro Gly
            915                 920                 925

Ile Tyr Val Val Leu Asp Ala Leu Pro Leu Ser Gly Asn Gly Lys Ile
            930                 935                 940

Asp Arg Asn Ala Leu Pro Pro Leu Asp Arg Ala Arg Leu Ala Ala Thr
945                 950                 955                 960

Ala His Ala Pro Thr Pro Pro Arg Thr Pro Thr Glu Thr Leu Leu Cys
                965                 970                 975

Arg Ile Trp Gly Glu Ala Leu Gly Ile Pro Ser Pro Gly Ile His Asp
                980                 985                 990

Asn Leu Phe Ala Leu Gly Gly Asp Ser Ile Leu Ser Met Arg Ile Val
            995                 1000                1005

Ser Leu Ala Ala Lys Ala Gly Leu Lys Leu Thr Thr Arg Leu Ile
        1010                1015                1020

Phe Gln His Pro Thr Val Ala Glu Leu Ala Ala Val Ala Thr Arg
        1025                1030                1035

Gly Thr Val Gly Ala Ala Ala Phe Val Ala Ser Ser Gly Pro Leu
        1040                1045                1050

Pro Leu Thr Pro Ile Gln Lys Arg Phe Phe Ala Gln Gly Lys His
        1055                1060                1065

Asp Pro Asp Gln Tyr Asn Gln Ala Val Leu Leu Asp Val Pro Ala
        1070                1075                1080

Asp Leu Asp Pro Val Leu Leu Arg Gln Ala Leu Arg His Ala Val
        1085                1090                1095

Lys Trp His Asp Ala Leu Arg Leu Arg Phe Arg Glu Gly Glu Ser
        1100                1105                1110

Gly Trp Thr Gln Glu Val Val Asp Asp Pro Glu Ile Pro Val Val
        1115                1120                1125

Val Ser Asp Ile Ala Arg Asp Gln Leu Ala Gln Tyr Val Ala Gln
        1130                1135                1140

Ser His Ala Ser Leu Asn Leu Ala Asp Gly Pro Val Val Arg Ala
        1145                1150                1155

Asp Leu Phe Arg Val Asp Glu Gly Arg Ser Leu Arg Leu Leu Leu
        1160                1165                1170

Val Ala His His Leu Val Val Asp Gly Val Ser Trp Gly Ala Leu
        1175                1180                1185

Leu Glu Thr Val Tyr Asp Ala Tyr Thr Arg Leu Arg Asn Gly Lys
        1190                1195                1200

Ala Pro Glu Phe Ala Gly Gly Ser Ala Thr Trp Thr Ala Trp Thr
        1205                1210                1215

Arg Ala Ile Ser Thr Trp Ala Gly Ser Gly Ala Ala Asp Ala Asp
        1220                1225                1230

Leu Ala His Trp Gln Ala Leu Ala Arg Ala Ala Leu Pro Gly Leu
        1235                1240                1245

Pro Leu Asp Arg Asp Ala Pro Ala Asp Ala Asn Thr Val Ser Ser
        1250                1255                1260
```

```
Ala Asp Thr Ile Val Val Glu Leu Gly Glu Ala Thr Thr Ala
1265                 1270             1275

Leu Leu Gly Ala Ala Pro Arg Ala Tyr Asp Ala Gln Val Asn Asp
    1280             1285             1290

Val Leu Leu Ala Ala Leu Ala Arg Ala Val Ser Glu Trp Ser Gly
    1295             1300             1305

Cys Ala Asp Val Leu Leu Asp Leu Glu Ala His Gly Arg Glu Glu
    1310             1315             1320

Leu Ile Asp Ala Leu Asp Ile Ser Arg Thr Val Gly Trp Phe Thr
    1325             1330             1335

Ser Val Phe Pro Val Leu Leu Thr Val Asp Ala Gly Ser His Asp
    1340             1345             1350

Pro Ala Ser Leu Val Ala Ser Val Arg Thr Arg Leu Arg Ala Val
    1355             1360             1365

Pro Asn Ala Gly Ile Thr Tyr Gly Leu Leu Leu Asp Arg Leu Asp
    1370             1375             1380

Gly Pro Leu Pro Gln Pro Arg Leu Gln Phe Asn Tyr Leu Gly Gln
    1385             1390             1395

Thr Asp Gln Leu Phe Thr Ala Ala Arg Asp Trp Lys Gln Ala Ala
    1400             1405             1410

Glu Pro Ser Gly Asp Gly Arg Asn Ala Asn Gln Leu Arg Glu His
    1415             1420             1425

Leu Leu Asp Ile Asn Ala Tyr Val Thr Gly Asn Arg Leu His Val
    1430             1435             1440

Ala Trp Glu Phe Ser Arg Ala Cys His Asp Thr Ala Thr Ile Leu
    1445             1450             1455

Arg Val Ala Gln Ala Tyr Ile Ala Ala Leu Glu Thr Leu Val Ala
    1460             1465             1470

Gly His Ala Val Pro Ser Ala Ser Thr Arg Pro Ala Thr Ala Leu
    1475             1480             1485

Pro Gln Ala Pro Ala Pro Ala Ser Val Ser Pro Asp Glu Ile Ala
    1490             1495             1500

Asp Val Tyr Pro Leu Thr Pro Thr Gln Gln Gly Met Leu Phe His
    1505             1510             1515

Ser Leu Tyr Glu Pro Ala Ser Asp Ala Tyr Phe Ser Ser Leu Asn
    1520             1525             1530

Phe Arg Ile Asp Gly Ala Leu Asp Val Glu Arg Phe Arg Arg Ala
    1535             1540             1545

Trp Glu Thr Val Ala His Arg His Asp Ile Leu Arg Thr Ser Phe
    1550             1555             1560

His Trp Glu Asp Ile Glu Ser Pro Val Gln Val Val His Arg Arg
    1565             1570             1575

Ile Asp Leu Pro Trp His Asp Glu Asp Leu Arg Ala Ala Ser Ala
    1580             1585             1590

Ala Glu Ala Glu Gln Arg Trp Glu Ala Tyr Val Ala Gln Asp Arg
    1595             1600             1605

Ala Arg Gly Phe Asp Phe Thr Arg Ala Pro Leu Met Arg Leu Ala
    1610             1615             1620

Leu Phe Arg Val Gly Glu His Ala Trp Arg Phe His Trp Ser His
    1625             1630             1635

His His Ile Leu Leu Asp Gly Trp Ser Ser Ala Arg Leu Leu Ser
    1640             1645             1650
```

-continued

| | | | | | | | | | | |
|---|---|---|---|---|---|---|---|---|---|---|
| Asp | Val | Ala | Ala | Tyr | Gln | Ala | Pro | Pro | Ala | Glu | Gly | Ala | Pro |
| 1655 | | | | | 1660 | | | | | 1665 | | | |

Gln Arg Asp Ala Pro Pro Ala Phe Ala Gly Tyr Val Arg Trp Leu
1670                1675                1680

Ala Arg Gln Asp Ala Ala Ala Gln Arg Phe Trp Lys Thr Lys
1685                1690                1695

Leu Ala Asp Phe Pro Ala Thr Thr Pro Leu Val Leu Gly Arg Pro
1700                1705                1710

Glu Leu Asp Gly Thr Ala Ala Pro Gly Ala Tyr Val Glu Glu Pro
1715                1720                1725

Leu Leu Leu Ser Glu Ser Asp Thr Gln Arg Leu Val Ala Phe Ala
1730                1735                1740

Gln Ser Arg Arg Leu Thr Leu Asn Thr Leu Ala Gln Gly Ala Trp
1745                1750                1755

Ala Gln Leu Leu Ser Arg Tyr Ser Gly Glu Ser Asp Val Val Phe
1760                1765                1770

Gly Thr Ile Val Ser Gly Arg Pro Ala Ser Leu Pro Ala Ser Asp
1775                1780                1785

Glu Met Val Gly Leu Phe Ile Asn Thr Leu Pro Val Arg Val Arg
1790                1795                1800

Ile Asp Ala Arg Pro Thr Ser Ala Trp Leu Ala Gln Leu Gln Met
1805                1810                1815

Asp Leu Ala Gln Gln Glu Asp Tyr Ala His Tyr Pro Leu Ala Asp
1820                1825                1830

Ile Gln Lys Phe Ala Gly Leu Pro Pro Gly Val Pro Leu Phe Glu
1835                1840                1845

Ser Leu Leu Ile Phe Gln Asn Tyr Pro Val Glu Glu Ala Leu Ala
1850                1855                1860

Asp Ala Leu Pro Gly Leu Arg Ile Gly Ala Phe Glu Val Ser Asp
1865                1870                1875

Pro Asn Asn Tyr Pro Leu Thr Leu Val Val Thr Pro Gly Lys Arg
1880                1885                1890

Leu Ser Leu Gln Val Leu Tyr Asp Asp Gly Arg Phe Asp Arg Asp
1895                1900                1905

Thr Ile Val Arg Leu Leu Arg His Val Glu Thr Leu Leu Thr Gly
1910                1915                1920

Leu Ala Gly Ala Glu Asp Arg Pro Asn Arg Ser Val Pro Leu Leu
1925                1930                1935

Ala Ala Ala Glu Arg Asp Ala Ile Leu Leu Gly Trp Asn Asp Thr
1940                1945                1950

Phe Ala Pro Val Pro Ser Asp Arg Thr Leu Pro Glu Leu Ile Glu
1955                1960                1965

Ala Val Ala Ala Ala His Pro Glu Arg Val Ala Val Arg Cys Gly
1970                1975                1980

Thr Glu Val Arg Thr Tyr Arg Asp Leu Val Glu Gly Ala Asn Arg
1985                1990                1995

Ile Ala Ala His Leu Leu Gln Thr Ala Pro Leu Gln Pro Asp Asp
2000                2005                2010

Arg Ile Ala Val Trp Met Pro Arg Ser Pro Leu Met Leu Glu Thr
2015                2020                2025

Ile Leu Ala Ile Trp Lys Cys Gly Ala Ala Tyr Val Pro Val Asp
2030                2035                2040

Pro Ala Tyr Pro Ala Gln Arg Val Glu Thr Ile Leu Thr Leu Ala

```
            2045                2050                2055

Arg Pro Ala Val Ile Val Thr Thr Asp Cys Val Pro Pro Pro Ala
    2060            2065                2070

Leu Ala Ser Ile Pro Leu Val Asp Pro Ala Arg Leu Pro Asp Arg
    2075            2080                2085

Arg Gly Ala Glu Ala Pro Ala Pro Val Thr Pro Arg Cys Arg Pro
    2090            2095                2100

Ala Asp Leu Ala Tyr Val Ile Phe Thr Ser Gly Ser Thr Gly Gln
    2105            2110                2115

Pro Lys Gly Ala Met Val Glu His Arg Gly Met Leu Asn His Val
    2120            2125                2130

Leu Ala Met Ala Arg Arg Val Gly Leu Gly Ala Gln Ser Ala Val
    2135            2140                2145

Ala Gln Thr Ala Ser His Cys Ser Asp Ile Ser Val Trp Gln Cys
    2150            2155                2160

Phe Ala Ala Leu Ala Ser Gly Gly Thr Thr Val Ile Tyr Pro Asp
    2165            2170                2175

Ala Val Ile Leu Glu Pro Ala Arg Leu Ile Asp Ser Leu His Arg
    2180            2185                2190

Asp Arg Ile Thr Ala Met Gln Phe Val Pro Ser Tyr Leu Ala Thr
    2195            2200                2205

Phe Leu Gly Glu Leu Glu Arg His Ala Ala Pro Ala Phe Pro His
    2210            2215                2220

Leu Asp Thr Leu Leu Thr Ile Gly Glu Thr Leu Gln Pro Ala Thr
    2225            2230                2235

Ala Gln Ala Trp Phe Arg Leu Asn Pro Ala Val Arg Leu Ile Asn
    2240            2245                2250

Ala Tyr Gly Pro Thr Glu Ala Ser Asp Ser Val Ala His Tyr Cys
    2255            2260                2265

Leu Thr Arg Ala Pro Asp Gly Pro Ala Ile Pro Ile Gly Arg Pro
    2270            2275                2280

Ile Glu Asn Leu Arg Leu Tyr Val Val Asp Ala Asp Met Asn Pro
    2285            2290                2295

Cys Pro Ala Gly Val Lys Gly Glu Ile Cys Ile Gly Gly Val Gly
    2300            2305                2310

Val Gly Arg Gly Tyr Leu Phe Asp Glu Ala Arg Thr Arg Ala Val
    2315            2320                2325

Phe Arg Asp Asp Pro Phe Ser Pro Glu Pro Gly Ala Arg Leu Tyr
    2330            2335                2340

Arg Thr Gly Asp Ile Gly Cys Phe Gly Ala Asp Gly Asn Leu His
    2345            2350                2355

Phe Phe Gly Arg Arg Asp Phe Gln Val Lys Ile Arg Gly Tyr Arg
    2360            2365                2370

Ile Glu Leu Gly Glu Ile Glu Ala Ala Leu Thr Ser Leu Ala Gly
    2375            2380                2385

Ile Ser His Ala Val Val Val Ala Arg Glu Thr Ser Asp Ala Glu
    2390            2395                2400

Met Thr Leu Cys Gly Tyr Ala Ser Gly Thr Gly Trp Thr Pro Gln
    2405            2410                2415

Arg Val Arg Asp Ala Leu Arg Asp Thr Leu Pro Ala His Met Val
    2420            2425                2430

Pro Asp Thr Val Met Leu Leu Pro Ala Leu Pro Val Met Pro Asn
    2435            2440                2445
```

-continued

```
Gly Lys Ile Asn Arg Ala Ala Leu Pro Leu Pro Asp Ala Ala Ser
    2450                2455            2460

Val Pro Asp Gly Val Arg Ala Glu Pro Arg Thr Pro Val Glu Ala
    2465                2470            2475

Ala Leu Leu Arg Leu Phe Ala Glu Val Leu Gly Arg Arg Pro Asn
    2480                2485            2490

Gly Val Asp Asp Asp Phe Phe Glu His Gly Gly Gln Ser Leu Lys
    2495                2500            2505

Ala Ile Gln Met Val Ser Arg Ile Pro Arg Ala Ala Leu Asn Val
    2510                2515            2520

Ala Val Ala Asp Ile Phe His Ala Pro Thr Pro Arg Ala Leu Ala
    2525                2530            2535

Gln Arg Leu Ala Ala Met Pro Val Asp Gly Ala Ala Asp Asp Asp
    2540                2545            2550

Ala Ile Ile Pro Ala Leu Ala Ala Gln Pro Ser Tyr Ala Val Ser
    2555                2560            2565

Arg Ala Gln Lys Arg Ile Trp Leu Ala Ser Arg Gly Ala Asp Pro
    2570                2575            2580

Ser Thr Tyr Asn Met Ala Gly Ala Leu Gln Leu Asp Gly Ala Val
    2585                2590            2595

Asp Thr Ala Arg Leu Val Arg Ala Phe Asp Thr Leu Val Asp Arg
    2600                2605            2610

His Glu Ser Leu Arg Thr Val Phe Ala Met Ile Glu Gly Glu Leu
    2615                2620            2625

Arg Gln Arg Val Leu Ser Arg Glu Ala Ser Gly Phe Arg Val Glu
    2630                2635            2640

Gln Arg Asp Leu Ala Asp Asp Ala Gly Pro Gln Ala Ile Asp Ala
    2645                2650            2655

Leu Ile Arg Ala Glu Cys Glu Gln Pro Phe Asp Leu Ala Ser Gly
    2660                2665            2670

Pro Leu Phe Arg Val Lys Leu Val Arg Leu Ser Gln Glu Lys His
    2675                2680            2685

Leu Leu Leu Leu Asn Met His His Val Ile Ser Asp Ala Trp Ser
    2690                2695            2700

Ile Arg Val Leu Thr Asp Asp Leu His Ala Leu Tyr Ala Gly Arg
    2705                2710            2715

Asp Leu Pro Pro Leu Ser Ile Gln Tyr Arg Asp Tyr Ala Ala Trp
    2720                2725            2730

His Asn Ala Ser Leu Ala Gly Pro Arg Ala Ala His Arg Ala
    2735                2740            2745

Tyr Trp Leu Glu Gln Leu Ala Pro Pro Leu Pro Arg Leu Gln Leu
    2750                2755            2760

Ala Ser Asp Phe Pro Arg Pro Glu Arg Leu Gly His Ala Gly Gln
    2765                2770            2775

Thr Leu Glu Val Glu Leu Pro Gln Pro His Ala Ala Glu Leu Ala
    2780                2785            2790

Thr Leu Ala Arg Ala His His Thr Ser Leu His Ala Val Leu Leu
    2795                2800            2805

Ala Ser Phe Cys Val Leu Met His Arg Tyr Thr Gly Arg Glu Asp
    2810                2815            2820

Ile Val Ile Gly Ser Val Ser Ala Gly Arg Asp Ser Glu Gln Leu
    2825                2830            2835
```

```
Glu Ser Gln Val Gly Val Tyr Leu Asn Thr Val Leu Arg Val
    2840                2845                2850

Pro Val Arg Lys Ser Ala Thr Val Ala Glu Val Ile Asp Gly Val
    2855                2860                2865

Ala Lys Ala Ser Ala Gln Ala Leu Glu His Ala Ser Tyr Pro Phe
    2870                2875                2880

Asp Val Leu Leu Glu Asp Leu Lys Ile Arg Thr Pro Ala Asn His
    2885                2890                2895

Phe Pro Ile Phe Asp Ile Gln Val Asn His Val Ser Met Pro Ala
    2900                2905                2910

Pro Gln Pro Gly Leu Arg Ile Thr Asp Ile Ser Pro Ala Asp Thr
    2915                2920                2925

Thr Ala Lys Phe Asp Leu Ser Phe Gln Val Val Glu Ser Glu Gly
    2930                2935                2940

Arg His Leu Ile Gln Phe Ile Tyr Asn Thr His Leu Phe Arg Pro
    2945                2950                2955

Ser Thr Ile Ala Ala Met Arg Asp Arg Leu Leu Ala Ile His Asp
    2960                2965                2970

Val Phe Arg Arg Asp Pro Ala Thr Pro Val Asp Arg Ile Pro Leu
    2975                2980                2985

Ser Asp Glu Ala Pro Ala Ala Gly Pro Arg Val Arg Val Gly Leu
    2990                2995                3000

Arg Leu Lys Arg Ala Pro Ala Val Thr Ala Asp Asp Ala Leu Glu
    3005                3010                3015

Glu Lys Thr
    3020

<210> SEQ ID NO 13
<211> LENGTH: 1306
<212> TYPE: PRT
<213> ORGANISM: Burkholderia contaminans
<220> FEATURE:
<221> NAME/KEY: MISC_FEATURE
<222> LOCATION: (1)..(1306)
<223> OTHER INFORMATION: putative nonribosomal peptide synthetase

<400> SEQUENCE: 13

Met Ser Glu Leu Asn Leu Asn Ala Leu Ser Thr Ser Gly Gln Tyr Gln
1               5                   10                  15

Glu His Val Ala Phe Trp Asn Asp Ala Leu Gly Arg Ile Asp Glu Asp
                20                  25                  30

Phe Arg Leu Gln Gln Ala Trp Gln Ala Tyr Ala Leu Pro Leu Gly Pro
            35                  40                  45

Glu Pro Ala Leu Thr Phe Ala Leu Asp Gly Asp Ala Ala Gln Val Leu
        50                  55                  60

Glu Arg Leu Ala Ala Gly Asn Glu Leu Gly Ala Phe Val Val Leu Leu
65                  70                  75                  80

Ala Ala Leu Phe Arg Val Leu Gly Arg Tyr Asn Gly Ala Ala Gly Leu
                85                  90                  95

Phe Val Ala Ser Pro Gln Leu Ile Val Glu Pro Ala Ser Gly Cys Ala
            100                 105                 110

Glu Pro Val Pro Leu Leu Asp Ala Gly Glu Pro Gly Pro Thr Val Arg
        115                 120                 125

Ala Tyr Leu Asn Gln Leu Arg Asp Ser Val Gln Arg Ser Tyr Ser Tyr
    130                 135                 140

Gln Asp Phe Pro Ile Ala Ala Leu Ala His Lys Leu His Gly Glu Arg
```

```
            145                 150                 155                 160
        Arg Ala Thr Asn Val Gly Val Arg Phe Asp Gly Leu His Glu Ala Trp
                        165                 170                 175

Ala Ala Ala Asp Tyr Asp Leu Ser Ile Glu Ile Arg His Arg Glu Arg
                        180                 185                 190

Tyr Glu Ile Val Leu Thr Gly Arg Pro Thr Val Phe Thr Leu His Tyr
                        195                 200                 205

Leu Gln His Val Ala Arg His Leu Arg Asn Val Val Ala Gly Phe Gly
                        210                 215                 220

Ala Leu Asp Ala Pro Leu Asp Thr Val Ser Leu Leu Asp Asp Glu Glu
        225                 230                 235                 240

Arg Ala Arg Leu Arg Ser His Ala Ala Pro Val Ala Val Gln Gly Thr
                        245                 250                 255

Phe Leu Glu Gln Phe Ala Gln Arg Val Ala Ala Pro Asp Ser Val
                        260                 265                 270

Ala Val Val Thr Ala Asp Ala Ser Leu Thr Tyr Ala Glu Leu Asp Asp
                        275                 280                 285

Gln Ala Ser Arg Leu Ala Ser Phe Leu Leu Ala Glu Tyr Ala Ile Glu
                        290                 295                 300

Arg Gly Asp Val Val Gly Val Val Ala Asp Arg Ser Glu Arg Trp Ile
        305                 310                 315                 320

Val Gly Met Leu Gly Ala Leu Lys Ala Gly Ala Val Tyr Leu Pro Leu
                        325                 330                 335

Asp Pro Glu Phe Pro Arg Glu Arg Leu Arg Phe Met Ile Glu Asp Ala
                        340                 345                 350

Lys Val Lys Ala Leu Leu Thr His Ser Glu His Leu Pro Leu Leu Ala
                        355                 360                 365

Asp Phe Trp Ala Ile Pro Met Phe Ala Leu Asp Phe Gln Leu Asp Thr
                        370                 375                 380

Leu Ala Pro Ala Ser Ala Ser Ala Gln Val Glu Val Arg Pro Asp Asp
        385                 390                 395                 400

Ala Ala Tyr Ile Ile Tyr Thr Ser Gly Ser Thr Gly Val Pro Lys Gly
                        405                 410                 415

Val Val Leu Glu His Ala Gly Leu Leu Asn Met Ala Gln Tyr His Val
                        420                 425                 430

Asp Ala Phe Gly Phe Asp Ser Ala Asp Arg Phe Val Gln Phe Tyr Ser
                        435                 440                 445

Pro Gly Phe Asp Gly Ser Ile Met Glu Ile Phe Val Thr Leu Leu Ala
                        450                 455                 460

Gly Ala Arg Leu Val Leu Ala Lys Thr Ala Val Ile Arg Asp Val Pro
        465                 470                 475                 480

Arg Phe Val Asp Tyr Ile Ala Gln Gln Gly Val Thr Thr Val Asn Ala
                        485                 490                 495

Thr Pro Ala Tyr Leu Ala Ala Leu Asp Trp His Ala Leu Gly Ala Val
                        500                 505                 510

Lys Arg Val Ile Ser Ala Gly Asp Ser Ala Arg Val Ala Asp Leu Arg
                        515                 520                 525

Glu Leu Ala Arg Thr Arg Thr Cys His Asn Ser Tyr Gly Pro Thr Glu
                        530                 535                 540

Ala Thr Val Cys Ile Ala Asp Tyr Val Val Asp Pro Ala Ile Thr Tyr
        545                 550                 555                 560

Gly Ala Arg Leu Pro Val Gly Arg Pro Ile His Asn Thr His Leu Tyr
                        565                 570                 575
```

Leu Leu Asp Glu His Gly Ala Leu Ala Pro Glu Gly Cys Ala Gly Glu
            580                 585                 590

Ile Cys Val Ser Gly Ile Ala Leu Ala Arg Gly Tyr Val Gly Arg Asp
            595                 600                 605

Asp Leu Thr Ala Ala Phe Val Ala His Pro Phe Glu Ala Gly Glu
610                 615                 620

Arg Leu Tyr Arg Thr Gly Asp Leu Gly Val Trp Leu Pro Asp Gly Asn
625                 630                 635                 640

Leu Glu Val Thr Gly Arg Arg Asp Thr Gln Val Lys Ile Arg Gly Tyr
                645                 650                 655

Arg Ile Glu Met Gly Glu Ile Glu Ala Ala Leu Arg Gln His Ala Gly
                660                 665                 670

Val Ala Asp Ala Ile Val Phe Val Arg Glu Asp Thr Pro Gln His Lys
                675                 680                 685

Gln Leu Val Ala Cys Val Ala Thr Ala Thr Ala Ser Val Ala Ser Leu
            690                 695                 700

Arg Glu His Leu Lys Glu Arg Leu Pro Glu Phe Met Val Pro Ala Ser
705                 710                 715                 720

Ile Val Thr Leu Glu Arg Leu Pro Leu Thr Pro Asn Gly Lys Pro Asp
                725                 730                 735

Arg Lys Ala Leu Ala Ala Leu Glu Leu Ala Pro Ala Pro Ser Glu Thr
            740                 745                 750

Ala Tyr Val Ala Pro Ala Asn Asp Val Glu Ala Arg Leu Gly Arg Ile
            755                 760                 765

Trp Cys Asp Val Leu Gly Arg Glu Pro Ile Gly Val His Asp Asn Phe
770                 775                 780

Phe Glu Leu Gly Gly Asp Ser Ile Leu Ile Ile Gln Val Met Ser Leu
785                 790                 795                 800

Ala Gln Gln Val Gly Leu Lys Phe Thr Ala Asp Gln Phe Phe Ala His
            805                 810                 815

Pro Thr Ile Ala Glu Leu Ala Gln Val Ala Thr Glu Ala Pro Ser Ile
            820                 825                 830

Arg Ile Ala Gln Glu Pro Val Val Gly Pro Ala Pro Leu Thr Pro Ile
            835                 840                 845

Gln His Trp Phe Phe Ala Gln Asp Val Ala Asp Pro His His Tyr Asn
850                 855                 860

Gln Ser Thr Met Ile Glu Val Pro Ala Ser Leu Arg Pro Asp Thr Ile
865                 870                 875                 880

Glu Arg Ala Leu Ala Ala Val Ala Thr His His Asp Ala Leu Arg Leu
                885                 890                 895

Ser Phe Ala Cys Val Ala Gly Val Trp Gln Gln Ser His Ala Ala Pro
            900                 905                 910

Pro Leu Ala Ile Pro Leu Gly Val Thr Ser Leu Ala Asp Ala Ala Pro
            915                 920                 925

Ala Ala Arg Gln Ala Ala Met Leu Ala Thr Ala Thr Gly Met Gln Glu
            930                 935                 940

Ser Phe Thr Leu Ser Ala Pro Pro Leu Leu Arg Ala His Leu Phe Gln
945                 950                 955                 960

Phe Gly Pro Asp Ala Pro Gln Arg Leu Leu Ala Val Ala His His Leu
                965                 970                 975

Val Ile Asp Gly Val Ser Trp Arg Ile Leu Phe Glu Asp Leu Tyr Thr
            980                 985                 990

-continued

Ala Cys Arg Gln Leu Glu Ala Gly Asp Ala Val Gln Leu Pro Ala Arg
        995                 1000                1005

Thr Thr Ala Trp Arg Asp Trp Ser Thr Arg Leu Ser Gly Leu Gly
    1010                1015                1020

Ala Thr Ala Leu Asp Gly Leu Gly Leu Asp Tyr Trp Leu Gln Gly
    1025                1030                1035

Asn Ala Gly Glu Pro Ala Cys Phe Asp Met Pro Ala Gly Thr
    1040                1045                1050

Val Ala Glu Ala Gly Ser Thr Ile Val Glu Phe Asp Ala Gln Gln
    1055                1060                1065

Thr Leu Ala Leu Leu Gln Asp Val Pro Arg Ala Phe Asn Thr Gln
    1070                1075                1080

Ile Asn Glu Val Leu Leu Thr Ala Leu Leu Ala Phe Gly Asp
    1085                1090                1095

Trp Thr Gly Asn Ala Ser Leu Val Val Asp Leu Glu Gly His Gly
    1100                1105                1110

Arg Glu Asp Ile Phe Asp Gly Val Asp Thr Ser Arg Thr Ile Gly
    1115                1120                1125

Trp Phe Thr Thr His Tyr Pro Val Cys Leu Asn Ala Gly Asp Ala
    1130                1135                1140

Thr Val Ala Val Asp Ala Leu Arg His Val Lys Glu Gln Leu Arg
    1145                1150                1155

Ala Val Pro Met Arg Gly Leu Gly Tyr Gly Ile Ala Arg Tyr Leu
    1160                1165                1170

Gly His Asp Ala Gly Ile Ala Ala Ala Leu Glu Arg Gln Pro Pro
    1175                1180                1185

Ala Pro Val Arg Phe Asn Tyr Leu Gly Gln Val Asp Arg Val Leu
    1190                1195                1200

Pro Asp Asp Thr Gly Trp Lys Pro Val Leu Asp Phe Gln Ser Pro
    1205                1210                1215

Glu His Ser Pro Arg Ala Arg Arg Gly His Leu Phe Glu Ile Asp
    1220                1225                1230

Gly Met Val Phe Asp Gly Arg Leu Arg Leu Thr Trp His Tyr Asn
    1235                1240                1245

Arg Glu Ala Cys Ala Pro Gly Val Ile Glu Gln Leu Thr Gln Cys
    1250                1255                1260

Tyr Arg Ser Arg Leu Leu Ser Ile Val Ala Ala Gly Gly Asp Gly
    1265                1270                1275

Pro Arg Ala Leu Ser Pro Ser Asp Phe Pro Ala Ala Arg Ile Ser
    1280                1285                1290

Gln Glu Ala Leu Asp Ala Leu Val Ser Arg Ile Lys Ser
    1295                1300                1305

<210> SEQ ID NO 14
<211> LENGTH: 538
<212> TYPE: PRT
<213> ORGANISM: Burkholderia contaminans
<220> FEATURE:
<221> NAME/KEY: MISC_FEATURE
<222> LOCATION: (1)..(538)
<223> OTHER INFORMATION: putative beta-lactamase domain protein

<400> SEQUENCE: 14

Met Thr Ile Ser Ser Ser Ala Gln Val Tyr Leu Arg Gln Asn Ile Gln
1               5                   10                  15

Phe Glu Pro Leu Ile Asn Ser Trp Tyr Ala Trp Tyr His Thr Leu Pro

```
            20              25              30
Pro Leu Thr Ala Ala Leu Asn Val Ala Glu Arg Phe Leu Pro Leu Leu
        35              40              45
Lys Ser Tyr Ala Ala Ser Pro Met Met His Ala Ala Cys Lys Asp
    50              55              60
Pro Ala Met Arg Gly Gly Pro Phe Leu Asp Leu Gly Gly Gln Arg Val
65              70              75              80
Asp Glu Ile Arg Thr Leu Ile Glu Gln Thr Thr Gln Arg Ala Thr Arg
            85              90              95
Gln Leu Glu Leu Ala Lys Ala Tyr Lys Ala Phe Ser Thr Leu Leu Leu
            100             105             110
Glu Arg Ala Thr Gly Met Ala Ser Asp Pro Leu Tyr Pro Glu Ile Pro
            115             120             125
Glu Val Leu Lys Gly Tyr Val Glu Ile Tyr Tyr Asp Leu Asn His Asn
            130             135             140
Pro Ser Phe Arg Val Phe Glu Ser Leu Leu Tyr Ala Ser Pro Phe Tyr
145             150             155             160
Ala Arg Asp Ala Gln Ser Ile Ala Leu Ser Ala Ile Glu Glu His Thr
            165             170             175
Pro Arg Pro Phe Ile Leu Ser Thr Pro Arg Leu Arg Asp Glu Arg Thr
            180             185             190
Val Phe Ser Asn Met Ala Phe Asp Asp Arg Ala Leu Asp Thr Leu Phe
            195             200             205
Arg Met Arg Asp Thr Pro Gly Ser Tyr Ala Lys Ile Val Asp Leu Met
            210             215             220
Arg Val Glu Glu Lys Asp Glu Pro Leu Phe Arg Ser Phe Phe Val Glu
225             230             235             240
Glu Ala Pro Ala Pro Lys Pro Asp Arg Ser Phe Asp Gly Asp Asp Ile
            245             250             255
Arg Ile Arg Tyr Tyr Gly His Ala Cys Val Leu Ile Gln Ser Arg Gly
            260             265             270
Val Ser Ile Leu Ile Asp Pro Val Ile Ser Tyr Gly Tyr Asp Thr Ala
            275             280             285
Leu Pro Arg Tyr Thr Phe Ala Asp Leu Pro Asp Gln Ile Asp Tyr Val
            290             295             300
Leu Ile Thr His Ser His His Asp His Ile Val Leu Glu Thr Leu Leu
305             310             315             320
Gln Leu Arg His Lys Val Lys Thr Val Val Gly Arg Asn Leu Asp
            325             330             335
Gly Phe Pro Gln Asp Pro Ser Met Glu Leu Ala Leu Arg Lys Leu Gly
            340             345             350
Phe Asp Asp Val Leu Glu Val Arg Asp Ala Gln Glu Ile Lys Val Pro
            355             360             365
Gly Gly Ala Ile Thr Ala Ile Pro Phe Met Gly Glu His Asn Asp Leu
            370             375             380
Ala Ile His Ser Lys Gln Ser Phe Met Ile Arg Phe Gly Ser Arg Ser
385             390             395             400
Val Leu Cys Ile Ala Asp Ser Cys Asn Leu Asp Pro Arg Leu Tyr Glu
            405             410             415
His Val Phe Arg Leu Ala Gly Lys Pro Asp Thr Leu Phe Val Gly Met
            420             425             430
Glu Thr Glu Gly Ala Pro Pro Ser Trp Val Tyr Gly Pro Leu Phe Pro
            435             440             445
```

```
Lys Ala Leu Pro Arg Asp Ile Asp Gln Ser Arg Arg Ala Arg Gly Cys
    450                 455                 460

Gln Phe Gly Glu Ala Ala Leu Val Asp Asp Phe Ala Phe Asn Ala
465                 470                 475                 480

Ala Tyr Val Tyr Ala Met Gly Gln Glu Pro Trp Leu Asn His Leu Leu
                485                 490                 495

Asp Asn Thr Phe Asp Glu Asn Ser Pro Ser His Ile Gln Ser Thr Gln
                500                 505                 510

Phe Val Ala His Cys Lys Ala Lys Gly Ile Ala Ser Glu Ile Leu Tyr
            515                 520                 525

Ala Thr Arg Glu Ile Val Leu Cys Gln Asn
    530                 535

<210> SEQ ID NO 15
<211> LENGTH: 4469
<212> TYPE: PRT
<213> ORGANISM: Burkholderia contaminans
<220> FEATURE:
<221> NAME/KEY: MISC_FEATURE
<222> LOCATION: (1)..(4469)
<223> OTHER INFORMATION: putative beta-ketoacyl synthase nonribosomal
      peptide synthetase

<400> SEQUENCE: 15

Met Asn Ala Lys Ala Thr His Ala Leu Lys Ala Leu Asp Glu Leu
1               5                  10                  15

Arg Leu Arg Arg Ala Glu Ile Ala Ala Leu Arg Ser Asp Arg Asn Glu
                20                  25                  30

Pro Ile Ala Val Ile Gly Met Ala Cys Arg Phe Pro Gly Arg Ser Asp
            35                  40                  45

Thr Pro Asp Ala Phe Trp Gln Leu Leu Asp Gly Ala His Asp Ala Val
        50                  55                  60

Thr Glu Val Pro Gly Glu Arg Trp Asp Ile Asp Arg Tyr Tyr Asp Pro
65                  70                  75                  80

Asp Pro Ser Thr Pro Gly Lys Met Ala Thr Arg His Gly Ala Phe Leu
                85                  90                  95

Glu Arg Val Asp Gln Phe Asp Ala Ala Phe Phe Gly Ile Ala Pro Arg
                100                 105                 110

Glu Ala Thr Tyr Leu Asp Pro Gln Gln Arg Leu Leu Leu Glu Val Ala
            115                 120                 125

Trp Glu Ala Leu Glu Asn Ala His Leu Ala Pro Glu Arg Phe Arg Gln
        130                 135                 140

Ser Ala Thr Gly Val Tyr Val Gly Ile Thr Cys Phe Asp His Ala Ile
145                 150                 155                 160

Gln Val Ser Asn Ala Ser Met Pro Ser Ser Tyr Ala Gly Thr Gly
                165                 170                 175

Ser Ala Leu Asn Met Ala Ala Gly Arg Leu Ser Phe Val Leu Gly Leu
                180                 185                 190

Thr Gly Pro Ser Met Ala Ile Asp Thr Ala Cys Ser Ser Ser Leu Val
            195                 200                 205

Cys Leu His Leu Ala Cys Glu Ser Leu Arg Ser Arg Glu Ser Asn Met
210                 215                 220

Ala Leu Ala Gly Gly Val Asn Leu Met Leu Ser Pro Glu Val Met Val
225                 230                 235                 240

Ser Phe Ser Gln Ala Arg Met Leu Ser Pro Asp Gly Arg Cys Lys Thr
                245                 250                 255
```

```
Phe Asp Ala Ala Ala Asp Gly Tyr Val Arg Gly Glu Gly Cys Gly Met
            260                 265                 270

Val Val Leu Lys Arg Leu Ala Asp Ala Leu Ala Asp Gly Asp Arg Val
            275                 280                 285

Leu Gly Ile Val Arg Gly Thr Ala Val Asp Gln Gly Gly Ala Gly Gly
            290                 295                 300

Gly Leu Thr Val Pro Ser Arg Asp Ser Gln Glu Arg Val Ile Arg Arg
305                 310                 315                 320

Ala Leu Asn Gln Ala Gly Leu Ala Pro Gly Asp Val Ser Tyr Val Glu
                325                 330                 335

Ala His Gly Thr Gly Thr Ser Leu Gly Asp Pro Ile Glu Val Glu Ala
                340                 345                 350

Leu Ala Gly Val Tyr Gly Pro Gly Arg Ala Ala Asn Glu Pro Leu Val
                355                 360                 365

Ile Gly Ser Val Lys Thr Asn Ile Gly His Leu Glu Ser Ala Ser Gly
            370                 375                 380

Ile Ala Gly Leu Ile Lys Val Leu Leu Ser Phe Glu His Asp Arg Ile
385                 390                 395                 400

Pro Ala His Leu His Phe Thr Gln Pro Asn Pro His Thr Pro Trp Gln
                405                 410                 415

Asp Ile Pro Ile Arg Val Ala Ala Asp Pro Val Ala Trp Arg Arg Gly
            420                 425                 430

Glu Arg Arg Arg Ile Ala Gly Val Ser Ala Phe Gly Phe Ser Gly Thr
            435                 440                 445

Asn Ala His Ala Ile Val Glu Glu Pro Pro Val Ala Pro Ala His Ala
            450                 455                 460

Ala Gln Arg Ala Leu Leu Leu Ser Ala Arg Ser Glu Ala Ala Leu
465                 470                 475                 480

Ala Ala Leu Val Pro Arg Tyr Glu Arg Ala Ile Ala Gly Ala Thr Pro
                485                 490                 495

Gln Glu Leu Ala Ala Ile Cys Arg Ala Ala Thr Gly Arg Ser His
                500                 505                 510

Tyr Pro Phe Arg Ala Ala Tyr Val Ser Gly Ala Arg Val Ala Ser Ala
            515                 520                 525

Ala Ala Pro Arg Thr Gly Lys Ala Leu Arg Met Gly Phe Gly Phe Gly
            530                 535                 540

Val Pro Asp Thr Gly Val Ala His Ala Leu His Ala Ser Glu Pro Leu
545                 550                 555                 560

Phe Arg Asp Ala Phe Ala Arg Cys Ser Val Pro Leu Asp Ala Leu Glu
                565                 570                 575

Thr Asp Ala Gly Arg Phe Ala Ile Gln Phe Ala Trp Ala Glu Leu Trp
                580                 585                 590

Lys Gly Trp Gly Leu Arg Pro Ala Val Val Ser Gly His Gly Ile Gly
            595                 600                 605

Glu Tyr Val Ala Ala Cys Val Ala Gly Val Val Ser Val Ala Asp Ala
            610                 615                 620

Leu Arg Leu Val Ala Ala Arg Ser Asp Ala Glu Ala Leu Arg Ala Val
625                 630                 635                 640

Leu Arg Asp Met Pro Leu Ala Arg Pro Ser Val Arg Leu Ile Ser Gly
                645                 650                 655

Tyr Leu Gly Thr Asp Val Thr Asp Glu Val Thr His Pro Gln Tyr Trp
            660                 665                 670
```

```
Leu Gln Leu Ala Gly Ala Ser Asp Gln Ala Asp Ala Ser His Pro Pro
            675                 680                 685

Glu Gly Leu Ala Asp Gly Trp Leu Pro Pro Cys Ala Gly Asp Ala
690                 695                 700

Leu Glu Arg Ala Leu Ala Ala Leu Tyr Val Gln Gly Ala Gln Phe Asp
705                 710                 715                 720

Trp Arg Ala Leu Phe Pro Ala Pro Ala Gln Pro Ala Thr Thr Leu Pro
                725                 730                 735

Asn Tyr Pro Phe Glu Arg Gln Arg Phe Ser Leu Glu Lys Ile Pro Ser
                740                 745                 750

Pro Ile Val Gly Met Asp Ala Gly Ser Ile Asp Ala Ala Leu Arg His
            755                 760                 765

Leu Lys Ser Ser Gly Lys Tyr Pro Glu Asp Met Leu Asn Ala Phe Pro
770                 775                 780

Asp Leu Leu Arg Thr Ala Phe Ala Ala Ala Glu Thr Val Ala Ser Asn
785                 790                 795                 800

Ala His Pro Leu Tyr His Val Val Trp Glu Gln Gln Ala Met Pro
                805                 810                 815

Ala Ala Pro Ala Ala Ala Asp Ala Ser Pro Trp Leu Ile Phe Ala Asp
            820                 825                 830

Ala Ser Gly Val Gly Glu Arg Leu Ala Ala Leu Leu Arg Ala Arg Gly
            835                 840                 845

Ala Ser Cys Ser Leu Val Arg Pro Gly Ile Asp Tyr Val Thr Gly Ala
            850                 855                 860

Glu Ala Gly Trp Gln Val Ala Pro Glu Arg Pro Asp Asp Phe Val Arg
865                 870                 875                 880

Leu Leu Asn Glu Thr Ala Ala Ser Gly Gln Arg Ile Val Phe Leu Trp
                885                 890                 895

Ala Leu Asp Glu Ala Val Gly Glu Thr Arg Met Ser Ala Ala Leu Leu
            900                 905                 910

His Leu Val His Ala Leu Val Gly Ser Glu Arg Glu Trp Thr Pro Ser
            915                 920                 925

Thr Arg Pro Arg Ile Ser Val Val Thr Arg Asp Ala Val Glu Ala Gly
930                 935                 940

Glu Ala Pro His Val Ser Gly Leu Ala Gln Ala Ala Leu Ser Gly Leu
945                 950                 955                 960

Ala Arg Gly Ala Met Ile Glu His Pro Glu Trp Phe Gly Thr Ala Ile
                965                 970                 975

Asp Leu Asp Pro Ala Ala Pro Gly Asn Glu Thr Gln Ala Leu Leu Gln
            980                 985                 990

Glu Met Leu Gly Glu Ser Arg Glu Glu Gln Val Ala Leu Arg His Gly
            995                 1000                1005

Ala Arg His Val Ala Arg Leu Ser Pro Leu Ala Pro Ala Glu Thr
    1010                1015                1020

Ala Ala Leu Pro Val Asp Pro Asp Ala Ala Tyr Leu Ile Thr Gly
    1025                1030                1035

Gly Phe Gly Ala Leu Gly Leu His Thr Ala Arg Trp Leu Ala Ala
    1040                1045                1050

Arg Gly Ala Gly Thr Leu Ile Leu Val Gly Arg Gln Gly Ala Ala
    1055                1060                1065

Ser Asp Glu Ser Gln Arg Ala Ile Ala Glu Leu Arg Glu Arg Asn
    1070                1075                1080

Val Thr Leu Arg Cys Glu Arg Leu Asp Ile Ala Asp Pro Ala Ala
```

```
                1085                1090                1095
Val Ala  Ala Phe Phe Ala Ala  Leu Arg Arg Asp Gly  Val Pro Leu
    1100                 1105                1110

Lys Gly  Ile Val His Ala Ala  Gly Ile Val Gly Tyr  Lys Pro Ile
    1115                 1120                1125

Met Gln  Val Glu Arg Asp Glu  Leu Asp Ala Val Leu  Gln Pro Lys
    1130                 1135                1140

Val Ala  Gly Ala Trp Leu Leu  His Gln Gln Ser Glu  His Phe Pro
    1145                 1150                1155

Leu Asp  Phe Phe Leu Leu Phe  Ser Ser Ile Ala Ser  Ala Trp Gly
    1160                 1165                1170

Ser Arg  Glu Gln Ala His Tyr  Ser Ala Ala Asn Arg  Phe Leu Asp
    1175                 1180                1185

Ala Leu  Ala His His Arg Arg  Gly Gln Gly Leu Pro  Ala Leu Ser
    1190                 1195                1200

Val Asn  Trp Gly Pro Trp Ala  Glu Gly Gly Met Thr  Phe Pro Glu
    1205                 1210                1215

Ala Glu  Ala Leu Leu Arg Arg  Val Gly Ile Arg Ser  Leu Ala Ala
    1220                 1225                1230

Asp Arg  Ala Leu Asp Val Leu  Asn Arg Leu Pro Ala  Val Pro Gln
    1235                 1240                1245

Val Ala  Val Val Asp Ile Asp  Leu Ala Leu Phe Gln  Gly Ser Tyr
    1250                 1255                1260

Glu Ala  Arg Gly Pro Lys Pro  Phe Leu Asp His Val  Arg Val Ala
    1265                 1270                1275

Lys Ser  Ala Pro Ser Ala Pro  Ala Met Pro Ala Leu  Ser Asp Ala
    1280                 1285                1290

Ser Pro  Arg Glu Arg Lys Arg  Leu Leu Ala Asp Ser  Ile Asp Arg
    1295                 1300                1305

Ala Val  Ala Gln Val Leu Gly  Tyr Asp Ala Gly Thr  Leu Asp Arg
    1310                 1315                1320

Asp Leu  Gly Phe Phe Glu Met  Gly Met Asp Ser Leu  Met Ala Leu
    1325                 1330                1335

Asp Val  Arg Thr His Leu Glu  Asn Ala Leu Gly Ile  Pro Leu Ser
    1340                 1345                1350

Val Ala  Leu Leu Phe Asp His  Pro Thr Val Asn Ala  Leu Ala Asp
    1355                 1360                1365

Phe Leu  Ala Glu Gln Ala Ser  Gly Thr Ala Gln Ala  Gln Thr Val
    1370                 1375                1380

Pro Pro  Gln Gln Gln Pro Arg  Pro Ile Ala Pro Ala  Ile Glu Ala
    1385                 1390                1395

Arg Asp  Ala Gly Thr Pro Glu  Pro Ile Ala Ile Val  Gly Met Ser
    1400                 1405                1410

Cys Arg  Phe Pro Gly Ala Ala  His Asp Leu Asp Ala  Tyr Trp Asn
    1415                 1420                1425

Leu Leu  Asn Asp Gly Val Asp  Ala Ile Ser Glu Val  Pro Arg Glu
    1430                 1435                1440

Arg Trp  Asp Val Asp Ala Tyr  Tyr Asp Pro Asp Pro  Glu Ala Pro
    1445                 1450                1455

Gly Arg  Met Tyr Ser Arg Phe  Gly Gly Phe Leu Asp  Asp Val Asp
    1460                 1465                1470

Gln Phe  Asp Pro Ala Phe Phe  Arg Ile Thr Pro Arg  Glu Ala Ala
    1475                 1480                1485
```

-continued

```
Ala Met Asp Pro Gln Gln Arg Leu Leu Leu Glu Val Ser His Glu
    1490            1495                1500

Ala Leu Glu His Ala Gly Ile Pro Val Asp Ser Leu Lys Gly Ser
    1505            1510                1515

Arg Thr Gly Val Phe Val Gly Ile Thr Thr Asn Asp Tyr Ala Asn
    1520            1525                1530

Leu Gln Leu Arg Asn Gly Gly Ser Gly Ile Asp Gly Tyr Phe
    1535            1540                1545

Phe Thr Gly Asn Pro Leu Asn Thr Ala Ala Gly Arg Ile Ser Tyr
    1550            1555                1560

Gly Leu Gly Val Gln Gly Pro Ser Met Ala Ile Asp Thr Ala Cys
    1565            1570                1575

Ser Ser Ser Leu Thr Ala Ile His Thr Ala Ser Gln Asn Leu Arg
    1580            1585                1590

Ser Gly Glu Cys Asp Leu Ala Ile Ala Gly Gly Val Asn Leu Ile
    1595            1600                1605

Leu Ser Pro Asp Asn Ser Ile Ala Val Ser Arg Thr Arg Ala Leu
    1610            1615                1620

Ala Pro Asp Gly Arg Cys Lys Thr Phe Asp Ala Ala Ala Asp Gly
    1625            1630                1635

Phe Val Arg Ser Glu Gly Cys Gly Ala Leu Val Leu Lys Arg Leu
    1640            1645                1650

Ser Asp Ala Leu Ala Ala Gly Asp Arg Val Leu Ala Val Leu Arg
    1655            1660                1665

Gly Ser Ala Val Asn His Asp Gly Ala Ser Ser Gly Phe Thr Ala
    1670            1675                1680

Pro Asn Gly Arg Ala Gln Glu Ala Val Ile Arg Gln Ala Leu Gly
    1685            1690                1695

Gly Leu Pro Ala Ala Ser Ile Asp Tyr Val Glu Ala His Gly Thr
    1700            1705                1710

Gly Thr Pro Leu Gly Asp Pro Val Glu Leu Gln Ala Leu Ala Thr
    1715            1720                1725

Val Phe Gly Ala Gly Arg Asp Ala Gly Arg Arg Leu Arg Val Gly
    1730            1735                1740

Ser Val Lys Thr Asn Ile Gly His Thr Glu Ser Ala Ala Gly Ile
    1745            1750                1755

Ala Gly Val Ile Lys Val Val Leu Ser Leu Asn His Asp Arg Leu
    1760            1765                1770

Pro Ala His Leu His Phe Arg Gln Pro Ser Pro Leu Val Gln Trp
    1775            1780                1785

Asp Ala Met Pro Val Glu Ile Cys Ala Glu Ala Ser Ala Trp Pro
    1790            1795                1800

Arg Gly Glu Arg Pro Arg Arg Ala Gly Val Ser Ala Phe Gly Ala
    1805            1810                1815

Ser Gly Thr Asn Ala His Leu Val Leu Glu Glu Ala Pro Ala Pro
    1820            1825                1830

Ala Arg Gln Ala Thr Pro Ser Arg His Lys Val His Pro Leu Val
    1835            1840                1845

Leu Ser Ala Lys Thr Pro Ala Ala Leu Arg Glu Leu Ala Gly Arg
    1850            1855                1860

Tyr Gln Arg Arg Leu Glu Ala Glu Pro Gly Leu Asp Ile Ala Ala
    1865            1870                1875
```

-continued

Val Ala Phe Ser Ala Ala Thr Gly Arg Ser His Phe Ala His Arg
1880                1885                1890

Leu Ala Trp Pro Val Thr Ser Leu Asp Asp Ala Ile Asp Lys Leu
1895                1900                1905

Arg Ala Phe His Ala Lys Glu Pro Ala Gly Ala Ala Gln Pro Ala
1910                1915                1920

Pro Arg Val Lys Met Ala Phe Leu Phe Thr Gly Gln Gly Ser Gln
1925                1930                1935

Tyr Ala Gly Met Gly Arg Arg Leu Tyr Asp Ala Tyr Pro Val Phe
1940                1945                1950

Arg Asp Ala Ile Asp Arg Cys Arg Ala Val Ala Asp Pro Leu Leu
1955                1960                1965

Asp Lys Pro Leu Leu Glu Val Leu Ser Ala Gln Gly Glu Asp Ile
1970                1975                1980

His Gln Thr Gly Tyr Ser Gln Pro Ala Leu Phe Ser Leu Gln Tyr
1985                1990                1995

Ala Leu Thr Thr Leu Leu Ala Ser Phe Gly Val Val Pro Asp Ala
2000                2005                2010

Val Met Gly His Ser Val Gly Glu Tyr Ala Ala Ala Cys Ala Ala
2015                2020                2025

Gly Val Phe Ser Pro Glu Asp Gly Leu Arg Leu Ile Ala Glu Arg
2030                2035                2040

Gly Arg Leu Met Gln Ala Leu Pro Arg Asp Gly Glu Met Ala Ala
2045                2050                2055

Ile Phe Thr Asp Leu Ala Thr Val Glu Arg Ala Ile Asp Ala Trp
2060                2065                2070

Pro His Glu Val Ala Val Ala Ala Val Asn Gly Pro Ala Ser Ile
2075                2080                2085

Val Ile Ser Gly Lys Arg Glu Arg Ile Ala Met Leu Val Asp Ala
2090                2095                2100

Phe Ala Ala Arg Asp Ile Arg Ser Val Pro Leu Asn Thr Ser His
2105                2110                2115

Ala Phe His Ser Pro Leu Leu Glu Pro Met Leu Asp Ser Phe Gln
2120                2125                2130

Leu Ala Ala Lys Thr Val Pro Val Ala Arg Pro Ala Ile Pro Phe
2135                2140                2145

Tyr Ser Asn Leu Thr Gly Ala Val Met Asp Glu Ala Pro Thr Asp
2150                2155                2160

Thr Tyr Trp Arg Arg His Cys Arg Glu Pro Val Gln Phe Ala Ser
2165                2170                2175

Ser Val Glu Arg Leu Ala Glu Ala Gly Phe Asn Val Leu Val Glu
2180                2185                2190

Ile Gly Pro Lys Pro Val Leu Val Asn Leu Ala Arg Ala Cys Cys
2195                2200                2205

Ala Pro Asp Ala Gly Ile Gln Phe Leu Ala Leu Gln Arg Pro Gln
2210                2215                2220

Val Glu Gln Gln Ala Leu Ile Glu Thr Leu Ser Ser Leu Tyr Ala
2225                2230                2235

Arg Gly Val Asp Val Asp Trp Ala Pro Thr Glu Thr Pro Ala Pro
2240                2245                2250

Ala Arg Ile Ala Leu Pro Ser Tyr Pro Phe Gln Arg Ser Arg Thr
2255                2260                2265

Trp Phe Gln Lys Ala Asp Thr Ser Met Thr Gln Thr Ser Ala Ser

```
                2270                2275                2280

Pro Ile Ala Ala Ala Pro Thr His Asn Arg Ser Gly Glu Ile Leu
        2285                2290                2295

Glu Trp Leu Arg Gly Lys Ile Gly Glu Leu Ile Gln Ala Asp Pro
        2300                2305                2310

Ala Thr Ile Asn Ile Glu Leu Pro Phe Leu Glu Met Gly Ala Asp
        2315                2320                2325

Ser Ile Val Leu Ile Glu Ala Ile Arg His Ile Glu Ala Glu Tyr
        2330                2335                2340

Gly Val Lys Leu Ala Met Arg Arg Phe Phe Glu Asp Leu Ala Thr
        2345                2350                2355

Val Gln Ala Leu Ala Glu Tyr Val Ala Asp Asn Leu Pro Ala Ala
        2360                2365                2370

Ala Ala Pro Ser Gly Ala Glu Ala Val Ala Val Ala Val Ala Ala
        2375                2380                2385

Ala Glu Pro Ser Thr Pro Ala Val Ala Val Thr Pro Ser Ala Ala
        2390                2395                2400

Gly Leu Ala Pro Leu Ala Ala Pro Ala Glu Trp Val Ala Ala
        2405                2410                2415

Glu Gly Gly Ser Thr Val Glu Arg Val Leu Arg Glu Gln Asn Gln
        2420                2425                2430

Leu Leu Ser His Val Met Ser Gln Gln Met Glu Leu Leu Arg Thr
        2435                2440                2445

Ser Leu Thr Gly Gln Pro Gly Val Arg Pro Ala Thr Ala Ala Val
        2450                2455                2460

Gln Ala Val Ala Ser Thr Ala Ser Val Ala Pro Lys Ala Ala Ser
        2465                2470                2475

Ala Ala Pro Ala Ala Pro Ala Ala Lys Pro Ala Pro Ala Ala
        2480                2485                2490

Ala Ala Ala Pro Ala Ala Asp Asn Pro Pro Lys Pro Met Met
        2495                2500                2505

Pro Trp Gly Ser Pro Val Gln Gln Arg Ala Arg Gly Leu Ser Ala
        2510                2515                2520

Ala Gln Gln Glu His Leu Glu Ala Leu Ile Val Arg Tyr Thr Thr
        2525                2530                2535

Arg Thr Arg Lys Ser Lys Asp Ser Val Gln Ala Ser Arg Pro Val
        2540                2545                2550

Leu Ala Asp Ser Arg Ala Thr Val Gly Phe Arg Phe Ser Thr Lys
        2555                2560                2565

Glu Met Leu Tyr Pro Ile Val Gly Asp Arg Ala Ala Gly Ser Arg
        2570                2575                2580

Leu Trp Asp Ile Asp Gly Asn Glu Tyr Ile Asp Phe Thr Met Gly
        2585                2590                2595

Phe Gly Val His Leu Phe Gly His Thr Pro Asp Phe Ile Gln Gln
        2600                2605                2610

Gln Val Thr Arg Glu Trp Gln Arg Pro Leu Glu Leu Gly Ala Arg
        2615                2620                2625

Ser Ser Leu Val Gly Glu Val Ala Ala Arg Phe Ala Arg Val Thr
        2630                2635                2640

Gly Leu Asp Arg Val Ala Phe Ser Asn Thr Gly Thr Glu Ala Val
        2645                2650                2655

Met Thr Ala Met Arg Leu Ala Arg Ala Val Thr Gly Arg Asp Lys
        2660                2665                2670
```

```
Ile Val Met Phe Thr His Ser Tyr His Gly His Ala Asp Gly Thr
2675                 2680                2685

Leu Ala Ala Ala Asn Ala Glu Gly Val Thr Glu Thr Ile Ala Pro
2690                 2695                2700

Gly Val Pro Phe Gly Ser Val Glu Asn Met Ile Leu Leu Asp Tyr
2705                 2710                2715

Gly Ser Asp Ala Ala Leu Glu Ala Ile Arg Gly Met Ala Ser Thr
2720                 2725                2730

Leu Ala Ala Val Met Val Glu Pro Val Gln Ser Arg Asn Pro Ser
2735                 2740                2745

Leu Gln Pro Val Ala Phe Leu Lys Glu Leu Arg Arg Ile Thr Glu
2750                 2755                2760

Glu Ala Gly Val Ala Leu Ile Phe Asp Glu Met Ile Thr Gly Phe
2765                 2770                2775

Arg Val His Pro Gly Gly Ser Gln Ala Met Phe Gly Ile Arg Ala
2780                 2785                2790

Asp Leu Ala Thr Tyr Gly Lys Ile Ile Gly Gly Gly Leu Pro Leu
2795                 2800                2805

Gly Val Ile Ala Gly Thr Ser Arg Phe Met Asp Ala Ile Asp Gly
2810                 2815                2820

Gly Met Trp Thr Tyr Gly Asp His Ser Phe Pro Ala Ala Asp Arg
2825                 2830                2835

Thr Ala Phe Gly Gly Thr Phe Cys Gln Tyr Pro Leu Ala Met Ala
2840                 2845                2850

Ala Ala Leu Ala Val Leu Glu Lys Ile Glu Gln Glu Gly Pro Ala
2855                 2860                2865

Leu Gln Ala Ala Leu Asn Glu Arg Thr Ala Gln Ile Ala Gly Thr
2870                 2875                2880

Leu Asn Ala Phe Phe Ala Glu Ala Glu Ala Pro Ile Lys Val Thr
2885                 2890                2895

Trp Phe Gly Ser Met Phe Arg Phe Glu Phe Thr Glu Asn Leu Asp
2900                 2905                2910

Leu Phe Phe Tyr His Met Leu Glu Lys Gly Ile Tyr Ile Trp Glu
2915                 2920                2925

Trp Arg Thr Cys Phe Leu Ser Thr Ala His Thr Asp Ala Asp Ile
2930                 2935                2940

Asp Arg Phe Ile Arg Ala Val Lys Asp Ser Val Ala Asp Leu Arg
2945                 2950                2955

Arg Gly Gly Phe Ile Arg Pro His Ser Lys His Gly Thr Val Ala
2960                 2965                2970

Ala Leu Ser Glu Ala Gln Arg Gln Leu Trp Val Leu Ser Glu Ile
2975                 2980                2985

Asp Pro Glu Gly Ser Leu Ala Tyr Asn Val Asn Thr Thr Leu Glu
2990                 2995                3000

Leu Asn Gly Arg Leu Asp Glu Ala Ala Met Arg Ala Ala Val Gln
3005                 3010                3015

Ser Leu Val Asp Arg His Glu Ala Leu Arg Thr Val Met Ala
3020                 3025                3030

Asp Gly Ser Gly Gln Ile Val His Pro Ser Leu Thr Leu Glu Ile
3035                 3040                3045

Pro Leu Ile Asp Thr Asp Pro Asn Ala Trp Arg Glu Gln Glu Ser
3050                 3055                3060
```

-continued

```
Arg Gln Pro Phe Asp Leu Val Asn Gly Pro Leu Phe Arg Ala Ala
    3065                3070                3075

Leu Val Arg Leu Gly Ser Glu Arg His Leu Leu Val Met Thr Ala
    3080                3085                3090

His His Ile Ile Cys Asp Gly Ser Thr Phe Gly Val Leu Leu Glu
    3095                3100                3105

Asp Leu Ala Arg Ala Tyr Ala Gly Ala Ala Pro Ala Asp Ala Pro
    3110                3115                3120

Leu Gln Phe Arg Ala Tyr Leu Lys Gln Leu Asp Gly Gln Arg His
    3125                3130                3135

Ser Pro Glu Thr Lys Ala Asn Arg Glu Tyr Trp Leu Ala Gln Cys
    3140                3145                3150

Ala Arg Gln Ala Ala Pro Leu Asn Leu Pro Val Asp Tyr Pro Arg
    3155                3160                3165

Pro Ala Val Lys Thr Phe His Gly Glu Arg Val Ser Leu His Leu
    3170                3175                3180

Asp Ala Ala Thr Ala Ala Thr Leu Arg Thr Ala Ala Arg Gln Asn
    3185                3190                3195

Gly Cys Thr Leu Tyr Met Val Leu Leu Ala Gly Phe Asn Leu Phe
    3200                3205                3210

Leu His Arg Val Ala Gly Gln Gln Glu Ile Val Thr Gly Ile Pro
    3215                3220                3225

Val Thr Gly Arg Ser Val Ala Gly Ser Asp Arg Leu Ala Gly Tyr
    3230                3235                3240

Cys Thr His Leu Leu Pro Leu His Ser Thr Leu Pro Glu Gln Ala
    3245                3250                3255

Thr Val Ala Ser Phe Leu Ala Gly Thr Arg Gln Asn Leu Leu Asp
    3260                3265                3270

Ala Leu Glu His Gln Asp Tyr Pro Phe Ala Glu Leu Val Arg Glu
    3275                3280                3285

Ile Gly Ala Gln Arg Asp Leu Asn Ala Ala Pro Leu Val Ser Ala
    3290                3295                3300

Val Phe Asn Leu Glu Pro Val Ser Ala Leu Pro Glu Leu Pro Gly
    3305                3310                3315

Leu Thr Val Gly Leu Val Ala Pro Leu Ile Arg His Thr Ala Phe
    3320                3325                3330

Asp Leu Asn Val Asn Val Leu Asp Ala Gly Gln Ala Leu Leu Ile
    3335                3340                3345

Asp Cys Asp Tyr Asn Thr Asp Leu Phe Asp Ala Ser Thr Val Gln
    3350                3355                3360

Arg Phe Leu Asp Ile Tyr Arg Thr Leu Leu Thr His Leu Ala Asp
    3365                3370                3375

Asp Ala Ser Ala Ala Val Ala Arg Leu Pro Leu Ser Ser Asp Ala
    3380                3385                3390

Glu Arg Asn Leu Leu Thr Val Glu Trp Asn Arg Thr Asp Thr Asp
    3395                3400                3405

Phe Gly Glu Asp Ala Ala Gln Pro Leu His Arg Leu Phe Glu Gln
    3410                3415                3420

Gln Val Glu Arg Thr Pro Asp Ala Val Ala Ile Val Phe Asp Asp
    3425                3430                3435

Thr Ala Leu Thr Tyr Ala Glu Leu Asn Leu Arg Ala Asn Arg Leu
    3440                3445                3450

Ala His His Leu Val Ala Leu Gly Val Gly Pro Asp Ser Leu Val
```

-continued

```
            3455                3460                3465
Gly Val Ala Met Glu Arg Ser Leu Asp Met Ser Val Ala Leu Leu
            3470                3475                3480
Ala Ile Leu Lys Ala Gly Gly Ala Tyr Val Pro Val Asp Pro Asp
            3485                3490                3495
Tyr Pro Ala Glu Arg Val Arg Phe Met Ile Asp His Ala Gln Leu
            3500                3505                3510
Arg Trp Leu Leu Thr Gln Gln His Leu His Asp Ala Leu Pro Asp
            3515                3520                3525
Thr Asp Ala His Val Ile Val Val Asp Arg Asp Ser Leu Asp Leu
            3530                3535                3540
Asp Ala Ala Ala Thr Ser Asn Pro Ala Pro Ala Leu Asn Gly Asp
            3545                3550                3555
Asn Leu Ala Tyr Met Ile Tyr Thr Ser Gly Ser Thr Gly Arg Pro
            3560                3565                3570
Lys Gly Ala Leu Asn Thr His Arg Ala Ile Thr Asn Arg Ile Leu
            3575                3580                3585
Trp Met Gln His Ala Tyr Ala Leu Gly Ala Asp Asp Ala Val Leu
            3590                3595                3600
Gln Lys Thr Pro Phe Ser Phe Asp Val Ser Val Trp Glu Leu Phe
            3605                3610                3615
Trp Pro Leu Val Thr Gly Ala Arg Leu Val Phe Ala Arg Pro Gly
            3620                3625                3630
Gly Gln Arg Glu Thr Asp Tyr Leu Val Glu Leu Ile Glu Arg Glu
            3635                3640                3645
Arg Ile Thr Thr Ile His Phe Val Pro Ser Met Leu Arg Ala Phe
            3650                3655                3660
Leu Asp His Pro Asp Leu Asp Ala His Cys Ala Ser Leu Arg Arg
            3665                3670                3675
Val Val Cys Ser Gly Glu Ala Leu Pro His Asp Leu Gln Gln Arg
            3680                3685                3690
Cys Leu Glu Arg Leu Asp Val Glu Leu Tyr Asn Leu Tyr Gly Pro
            3695                3700                3705
Thr Glu Ala Ala Val Asp Val Thr Ala Trp Glu Cys Arg Arg Asp
            3710                3715                3720
Asp Pro His Arg Ile Val Pro Ile Gly Arg Pro Ile Ala Asn Thr
            3725                3730                3735
Arg Leu Tyr Ile Val Asp Ala Gln Met Gln Pro Thr Pro Ile Gly
            3740                3745                3750
Val Ala Gly Glu Leu Leu Ile Gly Gly Thr Pro Val Gly Arg Gly
            3755                3760                3765
Tyr His Gly Glu Pro Glu Leu Ser Ala Glu Lys Phe Ile Ala Asp
            3770                3775                3780
Pro Phe Ser Ala Asp Pro Leu Ala Arg Leu Tyr Arg Thr Gly Asp
            3785                3790                3795
Leu Ala Arg Tyr Arg Pro Asp Gly Asn Ile Glu Phe Leu Gly Arg
            3800                3805                3810
Ile Asp His Gln Ile Lys Leu Arg Gly Leu Arg Ile Glu Pro Gly
            3815                3820                3825
Glu Ile Glu Ala Ala Leu Thr Ser His Pro Leu Val Asp Ala Ala
            3830                3835                3840
Val Val Ala Leu Arg Gly Val Asp Asp Gly Ala Arg Leu Val Gly
            3845                3850                3855
```

-continued

```
Trp Leu Cys Ser Ser His Pro Glu Ala Glu Leu Ile Glu Ala Val
    3860             3865             3870

Arg Gly His Leu Arg Gln Arg Leu Pro Asp Tyr Met Val Pro Ser
    3875             3880             3885

Ala Phe Val Val Val Ser Ala Phe Glu His Leu Pro Asn Gly Lys
    3890             3895             3900

Leu Asp Arg Thr Arg Leu Pro Glu Pro Gly Asp Gly Leu Asp His
    3905             3910             3915

Val Ala Pro Val Asn Ala Leu Glu Ala Gln Leu Ala Ala Ile Trp
    3920             3925             3930

Gln Glu Val Leu Gly Gln Ala Arg Ile Ser Thr Thr Gly Asn Phe
    3935             3940             3945

Phe Asp Leu Gly Gly Asn Ser Leu Leu Ala Thr Lys Val Val Ala
    3950             3955             3960

Arg Ile Arg Arg Asp Leu His Val Lys Leu Glu Ile Arg Ser Leu
    3965             3970             3975

Phe Ala Leu Pro Thr Ile Ser Ser Leu Ala Lys Arg Ile Ala Asp
    3980             3985             3990

Thr Gln Pro Ile Asp Tyr Ala Pro Val Thr Pro Leu Pro Ala Gln
    3995             4000             4005

Ala Ser Tyr Ala Leu Ser Pro Ala Gln Thr Arg Leu Trp Val Gln
    4010             4015             4020

Asp Arg Leu His Ala Ala Gln Ala Glu Gly Pro Leu Pro Thr Ser
    4025             4030             4035

Leu Leu Phe Glu Gly Val Leu Asp Val Asp Ala Leu Val Arg Ala
    4040             4045             4050

Phe Arg Ala Leu Ser Glu Arg His Glu Ile Leu Arg Thr Arg Phe
    4055             4060             4065

Val Leu Glu Gly Asn Gln Pro Val Gln His Val Leu Pro Pro Gly
    4070             4075             4080

Glu Ala Ala Phe Pro Val Glu Ile Val Asp Leu Gln Asp Ala Glu
    4085             4090             4095

Asp Arg Asp Ala Gln Ala Ala Ala Ile Gln Ala Ser Glu Arg Leu
    4100             4105             4110

Val Pro Met Asp Leu Ala Thr Gly Pro Leu Phe Arg Val Lys Leu
    4115             4120             4125

Leu Arg Leu Ser Glu Val Arg His Val Cys Leu Cys Thr Met His
    4130             4135             4140

His Ile Val Ser Asp Gly Trp Ser Thr Glu Val Leu Leu Asp Asp
    4145             4150             4155

Leu Ser Ala Leu Tyr Asp Ala Phe Val Gln Arg Arg Asp Asp Pro
    4160             4165             4170

Leu Pro Ala Leu Pro Ile Gln Tyr Lys Asp Tyr Ala Gly Trp Leu
    4175             4180             4185

Asn Arg Leu Leu Ala Gly Pro Asp Gly Ala Arg Met Lys Asp Tyr
    4190             4195             4200

Trp Leu Thr Lys Leu Gly Gly Gly Leu Arg Ala Leu Glu Leu Pro
    4205             4210             4215

Gly Asp Val Glu Gln Pro Ala Ala Pro Ser Trp Lys Ser Trp Arg
    4220             4225             4230

Phe Asp Leu Pro Ala Ala Glu Thr Ala Ala Leu Glu Ser Leu Gly
    4235             4240             4245
```

```
Lys Arg His Gly Ala Thr Leu Phe Ile Ala Leu Leu Ser Ala Ile
4250                4255                4260

Lys Ala Leu Phe Tyr Arg Arg Ser Gly Gln Glu Asp Ile Val Val
4265                4270                4275

Gly Thr Pro Val Ala Gly Arg Glu Leu Pro Glu Leu Glu Ser Gln
4280                4285                4290

Val Gly Pro Tyr Leu Asn Val Leu Ala Leu Arg Asp Arg Val Ala
4295                4300                4305

Gly Asp Asp Arg Phe Asp Thr Leu Leu Thr Arg Val Arg Asp Thr
4310                4315                4320

Thr Leu Glu Ala Phe Ser His Pro Leu Tyr Pro Leu Asp Arg Leu
4325                4330                4335

Leu Asp Glu Leu His Ile Lys Arg Val Ala Gly Arg Asn Pro Leu
4340                4345                4350

Phe Asp Ile Gly Leu Thr Leu Gln Asn Gln Arg His Gly Pro Val
4355                4360                4365

Asp Arg Tyr Ala Gly Gln Val His Ile Ala Glu Leu Pro Asp His
4370                4375                4380

Asp Pro Gln Arg Ala Asp Thr Glu Ala Ala Thr Asp Phe Trp Phe
4385                4390                4395

Leu Ala Glu Pro His Ala Glu Gly Leu Ala Ile Arg Val Val Tyr
4400                4405                4410

His Ala Gly Arg Phe Ser Glu Ala Leu Val Gln Gly Leu Ala Asn
4415                4420                4425

Glu Leu Thr Ser Val Ile Gly Glu Val Leu Ala Asn Pro Gly Val
4430                4435                4440

Arg Ile Arg Asn Leu Thr Leu Gly Gln Arg Ala Leu His Ala Glu
4445                4450                4455

Ala Arg Gln Pro Thr Val Glu Leu Ser Ala Phe
4460                4465

<210> SEQ ID NO 16
<211> LENGTH: 1107
<212> TYPE: PRT
<213> ORGANISM: Burkholderia contaminans
<220> FEATURE:
<221> NAME/KEY: MISC_FEATURE
<222> LOCATION: (1)..(1107)
<223> OTHER INFORMATION: putative short chain dehydrogenase/reductase
      SDR

<400> SEQUENCE: 16

Met Lys Phe Gly Leu Met Phe Phe Ala Ser Ser Glu Glu Ala Leu Ser
1               5                   10                  15

Gly Asn Lys Tyr Gln Leu Val Met Glu Ser Ala Arg Phe Ala Asp Ala
                20                  25                  30

Asn Gly Phe Ser Ser Val Trp Val Pro Glu Arg His Phe Thr Glu Phe
            35                  40                  45

Gly Ser Leu Tyr Pro Asn Pro Ala Val Leu His Ala Ala Leu Ala Ala
        50                  55                  60

Ala Thr Gln Arg Val Lys Leu Val Ala Gly Ser Val Ala Ala Leu
65                  70                  75                  80

His Asn Pro Ile Arg Ile Ala Glu Glu Trp Ser Met Val Asp Asn Leu
                85                  90                  95

Ser Asn Gly Arg Val Gly Val Ser Phe Ala Ser Gly Trp Asn Pro Asp
            100                 105                 110
```

```
Asp Phe Val Phe Ala Pro Asp Lys Tyr Ala Thr Arg Gln Asp Asp Met
            115                 120                 125

Leu Thr Thr Met Arg Ala Val Gln His Leu Trp Arg Gly Gly Thr Leu
130                 135                 140

Asp Ala Thr Asn Gly Val Gly Lys Pro Val Arg Leu Arg Val Tyr Pro
145                 150                 155                 160

Thr Pro Val Gln Pro Glu Leu Pro Val Trp Val Thr Ala Ala Ser Asn
                165                 170                 175

Pro Gln Thr Phe Val Arg Ala Gly Glu Ala Gly Ala Asn Leu Leu Thr
            180                 185                 190

His Val Leu Asp Gln Asp Arg Asp Gln Leu Ala His Lys Ile Ala Leu
        195                 200                 205

Tyr Arg Glu Ala Arg Ala Lys His Gly Phe Asp Pro Ala Ala Gly Thr
    210                 215                 220

Val Ser Val Met Leu His Thr Phe Val Gly Asp Asp Ala Ala Gln Ala
225                 230                 235                 240

Arg Glu Gln Ala Arg Val Pro Phe Cys Asn Tyr Ile Arg Ser Asn Ile
            245                 250                 255

Gly Leu Leu Asn Gly Leu Ala Gln Ser Arg Gly Gln Ser Val Asp Val
            260                 265                 270

Arg Ala Met Gly Ala Arg Glu Leu Asp Glu Phe Val Glu Phe Leu Tyr
        275                 280                 285

Glu Arg Phe Ala Gln Ser Arg Gly Leu Ile Gly Thr Pro Glu Thr Cys
    290                 295                 300

Val Glu Leu Val Arg Asp Leu Glu Ser Ile Gly Val Asp Glu Val Ala
305                 310                 315                 320

Cys Leu Leu Asp Phe Gly Pro Pro Val Glu Arg Ile Leu Gly Asn Leu
            325                 330                 335

Pro Gln Leu Arg Arg Leu Arg Glu Met Cys Ala Pro Arg Arg Ser Ala
            340                 345                 350

Ala Pro Thr Arg Phe Asp Ala Ala Glu Val Gln Ala Arg Cys Thr Glu
        355                 360                 365

Thr Thr Ser Gly Ala Asp Phe Asn Gly Glu Ile Arg Gln His Gly Val
    370                 375                 380

Gln Ile Asp Gly Val Phe Asp Ala Ile Arg Gln Ile Trp Arg Thr Thr
385                 390                 395                 400

Gly Glu Ala Leu Gly Lys Ile Ser Leu Pro Ala Asp Ala Leu Ala Ser
            405                 410                 415

Ser Pro Tyr Gln Val His Pro Ala Phe Leu Asp Ala Cys Ser Arg Val
            420                 425                 430

Leu Ala Ala Ile Asp Pro Asp Ala Leu Glu Ser Gly Asp Leu Tyr
        435                 440                 445

Leu Pro Ser Ser Ile Gly Ala Val Arg Val His Gln Pro Pro Ala Ser
    450                 455                 460

Thr Glu Ala Trp Ser His Ala Thr Leu Arg Thr Pro Ile Gly Gln Gly
465                 470                 475                 480

Ala Leu Glu Gly Asp Ile Arg Val His Asp Leu Ala Gly Arg Leu Leu
            485                 490                 495

Ile Glu Ile Asp Ala Leu Arg Leu Gln Gln Val Arg Ala Ala Arg Ala
            500                 505                 510

Val Glu Arg His Asp Phe Ala Ala Leu Leu Tyr Gln Arg Val Trp Arg
        515                 520                 525

Pro Ser Asn Val Asp Ala Ala Thr Gly Gly Ser Ala His Gly Glu Trp
```

```
            530               535               540
Leu Ile Leu Ala Asp Arg Gly Val Gly Ala Gln Leu Ser Ala Leu
545                 550                 555                 560

Leu Glu Ala His Gly Asp Thr Cys Thr Leu Arg Phe Ala Asp Ala Thr
                565                 570                 575

Pro Glu Leu Pro Ala Ala Asp Arg Pro Leu Lys Gly Val Ile His Leu
                580                 585                 590

Trp Ser Leu Asp Leu Ala Pro Ser Asp Ile Ala Ala Arg Arg Ala
            595                 600                 605

Ser Ala Ser Val Leu His Leu Val Arg Ala Leu Ala Ser Arg Ala Pro
        610                 615                 620

Ser Ala Arg Gln Ala Arg Leu Trp Leu Val Thr Ser Gly Ala Met Asn
625                 630                 635                 640

Val Leu Asp Gly Glu Ser Ile Ala Val Ala Gln Ala Pro Leu Trp Gly
                645                 650                 655

Leu Gly Arg Ala Ile Ala Val Glu His Ala Ala Leu Trp Gly Gly Leu
                660                 665                 670

Val Asp Leu Asp Pro Glu Gln Pro Ser Ala Ala Asp Ile Met Gln Ala
                675                 680                 685

Val Gln Ala Gly Gly Arg Glu Asp Met Ile Ala Phe Arg Arg Asp Gln
690                 695                 700

Arg Tyr Val Ala Arg Ile Ala Arg Asp Asn Arg Glu Tyr Val Ser His
705                 710                 715                 720

Arg Pro Ile Arg Phe His Gly Asp Ala Thr Tyr Leu Val Thr Gly Gly
                725                 730                 735

Leu Gly Gly Leu Gly Leu Arg Leu Ala Ser Trp Leu Ala Asp Asn Gly
                740                 745                 750

Ala Gly Lys Ile Val Leu Leu Gly Arg Gly Pro Ser Ala Ala Ala
            755                 760                 765

Gly Lys Ile Leu Arg Thr Leu Asp Ala Arg Phe Ile Arg Ala Asp Leu
770                 775                 780

Ser Arg Arg Glu Asp Val Gly Gln Ala Leu Gly Glu Ile Ala His Ser
785                 790                 795                 800

Met Pro Pro Leu Lys Gly Ile Phe His Leu Ala Gly Ala Leu Asp Asp
                805                 810                 815

Ala Leu Leu Thr Arg Gln Asp Asp Phe Phe His Arg Ala Gly Ser
            820                 825                 830

Gly Lys Ala Asp Gly Ala Trp Tyr Leu His Glu Leu Thr Ala Gly Leu
            835                 840                 845

Pro Leu Asp His Phe Val Leu Phe Ser Ser Met Ala Ala Leu Ile Thr
850                 855                 860

Met Pro Gly Gln Gly Asn Tyr Ala Ala Ala Asn Ser Phe Leu Asp Ala
865                 870                 875                 880

Leu Ala Gln His Arg Arg Ala Gln Gly Lys Pro Gly Leu Ser Val Asn
                885                 890                 895

Trp Gly Pro Trp Ala Glu Ile Gly His Ala Ala Thr Asp Tyr Gly Arg
            900                 905                 910

Arg Ala His Glu Gln Leu Gly Ala Leu Gly Val Gly Thr Leu Pro Pro
            915                 920                 925

Glu Leu Ala Ile Ala Thr Leu Glu Arg Leu Met Ala Ser Gly Val Ala
        930                 935                 940

Gln Ser Gly Val Ala Arg Ile Asp Trp Pro Thr Leu Phe Arg Val Asp
945                 950                 955                 960
```

-continued

```
Ala Pro Ala Ala Gly Ser Ala Leu Phe Ser Glu Leu Thr Gln Pro Ala
            965                 970                 975

Ala Gln Pro Ala Gln Gln Glu Thr Ala Leu Leu Arg Gln Leu His Ala
        980                 985                 990

Cys Ala Pro Arg Glu Arg Val Glu Arg Ile Thr Asp Thr Leu Ala Ala
        995                1000                1005

Met Leu Ala Glu Thr Leu Arg Leu Ser Gly Pro Asp Ala Ile Ala
   1010                1015                1020

Pro Glu Gln Ser Leu Leu Asp Leu Gly Leu Asp Ser Leu Val Ala
   1025                1030                1035

Leu Glu Leu Thr Asp Arg Leu Thr Lys Val Phe Gly Arg Pro Phe
   1040                1045                1050

Arg Ala Thr Leu Phe Phe Ser Tyr Pro Asn Leu Gln Thr Leu Ala
   1055                1060                1065

Gln Tyr Val Leu Asn Glu Leu Ser Pro Ser Leu Pro Ala Pro Val
   1070                1075                1080

Val Asp Glu Ala Ser Asp Asp Leu Asp Glu Asp Asp Leu Ser Glu
   1085                1090                1095

Leu Ile Ala Gln Glu Ile Gly Ala Gln
   1100                1105
```

<210> SEQ ID NO 17
<211> LENGTH: 1475
<212> TYPE: PRT
<213> ORGANISM: Burkholderia contaminans
<220> FEATURE:
<221> NAME/KEY: MISC_FEATURE
<222> LOCATION: (1)..(1475)
<223> OTHER INFORMATION: putative beta-ketoacyl synthetase

<400> SEQUENCE: 17

```
Met Leu Pro Asp Thr Lys Phe Arg Thr Val Thr Glu Ile Leu Leu Phe
1               5                  10                  15

Arg Gly Lys Val Glu Pro Glu Lys Thr Ala Phe Ile Phe Leu Glu Asn
            20                  25                  30

Gly Glu Ala Glu Leu Thr Arg Leu Thr Phe Gly Asp Leu Asp Lys Arg
        35                  40                  45

Ala Arg Gly Ile Ala Ala Arg Leu Gln Ala Ile Ala Gln Pro Gly Asp
    50                  55                  60

Arg Val Leu Leu Val Tyr Pro Pro Gly Leu Glu Phe Ile Cys Ala Trp
65                  70                  75                  80

Val Gly Cys Leu Tyr Ala Gly Leu Ile Gly Val Pro Ala Tyr Pro Pro
                85                  90                  95

Arg Arg His Arg Pro Ala Asp Arg Leu Lys Ala Ile Val Ala Asp Ala
            100                 105                 110

Thr Pro Val Val Ala Leu Thr Asp Ala Ala Thr Leu Asp Gly Ile Ala
        115                 120                 125

His His Ala Asp Gly Tyr Ser Asp Thr Leu Glu Leu Lys Ile Leu Ala
    130                 135                 140

Thr Asp Gln Arg Phe Asp Ala Pro Ala Glu Gln Trp Arg Ala Pro Asp
145                 150                 155                 160

Ile Thr Pro Gln Thr Leu Ala Leu Leu Gln Tyr Thr Ser Gly Ser Thr
                165                 170                 175

Gly Thr Pro Lys Gly Val Met Ile Ser His Ala Asn Ile Leu Ser Asn
            180                 185                 190
```

```
Met Ala Val Ile Ala Glu Ala Ser Asp Ala Asp Ala Ser Thr Val Phe
            195                 200                 205
Val Ser Trp Leu Pro Val Phe His Asp Met Gly Phe Phe Gly Lys Val
210                 215                 220
Leu Leu Pro Ile Tyr Leu Gly Val Leu Ser Val Leu Met Ala Pro Ala
225                 230                 235                 240
Ala Phe Val Gln Lys Pro Val Arg Trp Leu Gln Ala Ile Thr Lys Tyr
                245                 250                 255
Arg Gly Thr His Cys Ala Ala Pro Asp Phe Ala Tyr Asp Leu Cys Ala
            260                 265                 270
Arg Lys Ile Ala Asp Glu Ala Arg Ala Gln Leu Asp Leu Ser Ser Trp
        275                 280                 285
Arg Val Ala Phe Asn Gly Ala Glu Pro Val Arg Ala Glu Ser Val Ala
    290                 295                 300
Arg Phe Ser Arg Ala Phe Ala Ala Cys Gly Phe His Ala His Thr Met
305                 310                 315                 320
Arg Pro Val Tyr Gly Met Ala Glu Ala Thr Leu Phe Ile Ser Gly Gln
                325                 330                 335
Pro Ala Arg Ser Leu Pro Arg Val Ala Asp Tyr Asp Ala Asp Ala Leu
            340                 345                 350
Ala Gln Gly Val Ala Thr Arg Asn Asp Ser Gly Lys Arg His Ala Leu
        355                 360                 365
Val Ser Cys Gly Arg Thr Trp Ala Glu His Arg Val Arg Ile Val Asn
    370                 375                 380
Pro Asp Thr Gly Glu Arg Cys Ala Pro Gly Arg Ile Gly Glu Ile Trp
385                 390                 395                 400
Leu Thr Gly Pro Ser Val Gly Val Gly Tyr Trp Asn Arg Ile Asp Glu
                405                 410                 415
Thr Glu Arg Thr Phe Arg Ala Lys Leu Asp Gly Asp Asp Ala Arg Tyr
            420                 425                 430
Leu Arg Thr Gly Asp Leu Gly Phe Val Asp Gly Glu Asp Leu Phe Val
        435                 440                 445
Thr Gly Arg Leu Lys Asp Leu Ile Ile Val Ala Gly Arg Asn His Tyr
    450                 455                 460
Pro Gln Asp Leu Glu Gln Ser Ala Glu Gly Ser His Pro Ala Leu Ala
465                 470                 475                 480
Pro Asn Ala Ser Ala Ala Phe Ser Ile His Val Asp Asn Val Glu Arg
                485                 490                 495
Val Val Val Ala Cys Glu Val Arg Arg Glu Ala Leu Asn Thr Leu Asp
            500                 505                 510
Ala Glu Ala Val Ala Ala Glu Ile Arg His Thr Leu Ala Glu Val His
        515                 520                 525
Asp Val Asp Leu Tyr Ala Ala Val Leu Leu Lys Pro Ala Thr Ile Leu
    530                 535                 540
Arg Thr Ser Ser Gly Lys Ile Gln Arg Ser Arg Ile Arg Gln Ala Phe
545                 550                 555                 560
Leu Asp Glu Gln Gly Leu Ala Ile Ala Gly Glu Trp Arg Arg Ala Phe
                565                 570                 575
Ser Ala Pro Pro Ala Pro Pro Gln Thr Ala Glu Pro Arg Asp Thr Gln
            580                 585                 590
Ala Leu Val Gln Trp Cys Ile Glu Arg Val Ser Arg Leu Ser Gly Ile
        595                 600                 605
Ala Ser Gly Lys Ile Asp Pro Asp Ala Pro Phe Ser Val His Gly Leu
```

```
                  610                 615                 620
Asp Ser Lys Asp Ala Ile Met Leu Ser Gly Glu Leu Gln Asp Trp Leu
625                 630                 635                 640

Gly Arg Pro Val Ser Pro Thr Val Val Tyr Asp Phe Pro Ser Ile Ser
                    645                 650                 655

Leu Leu Ala Arg His Leu Ser Gly Thr Gly Ser Ala Met Pro Asp Gln
                660                 665                 670

Ala Pro Gly Ser Ala Glu Ala Arg Ala Asp Ile Ala Ile Val Gly Met
                675                 680                 685

Gly Cys Arg Phe Pro Gly Ala Gly Asn Pro Asp Ala Phe Trp Gln Leu
            690                 695                 700

Leu Leu Glu Gly Arg Asp Ala Val Gly Ala Ala Thr Gln Arg Ala Ala
705                 710                 715                 720

Asp Leu Pro Leu Ala Gly Leu Leu Asp Gln Val Asp Gln Phe Asp Ala
                    725                 730                 735

Ala Phe Phe Gly Ile Ser Ala Arg Glu Ala Glu Ser Met Asp Pro Gln
                740                 745                 750

Gln Arg Leu Leu Leu Glu Val Ala Trp Glu Thr Leu Glu His Ala Gly
            755                 760                 765

Ile Ala Pro Arg Ser Leu Ala Gly Gly Arg Thr Ala Val Ile Val Gly
770                 775                 780

Ile Ser Asn Ser Asp Tyr Ile Arg Leu Ala Gln Asp Glu Val Ala Asp
785                 790                 795                 800

Val Gly Pro Tyr Val Ala Thr Gly Asn Ala Leu Ser Val Ala Ala Asn
                    805                 810                 815

Arg Ile Ser Tyr Ala Leu Asp Leu Arg Gly Pro Ser Trp Ala Val Asp
                820                 825                 830

Thr Ala Cys Ser Ser Ser Leu Val Ala Val His Gln Ala Cys Arg Ala
            835                 840                 845

Leu Gln Arg Gly Glu Ser Asp Ala Ala Leu Ala Gly Gly Val Asn Leu
850                 855                 860

Ile Leu Ala Pro Gln Leu Ser Ala Ser Phe Thr Gln Ala Gly Met Leu
865                 870                 875                 880

Ser Pro Asp Gly Arg Cys Lys Ala Phe Asp Ala Ala Ala Asn Gly Tyr
                    885                 890                 895

Val Arg Gly Glu Gly Val Gly Met Val Leu Leu Lys Arg Leu Asp Asp
                900                 905                 910

Ala Leu Glu Asn Gly Asp Thr Val Phe Ala Val Ile Arg Gly Ser Ala
            915                 920                 925

Val Asn Gln Asp Gly Arg Ser Asn Gly Leu Thr Ala Pro Asn Gly Pro
930                 935                 940

Ala Gln Gln Ala Val Ile His Gly Ala Leu Arg Asp Ala Gly Val Arg
945                 950                 955                 960

Ala Gln Asp Ile Gly Phe Val Glu Thr His Gly Thr Gly Thr Pro Leu
                    965                 970                 975

Gly Asp Pro Ile Glu Leu Asn Ser Leu Ala Ala Val Leu Asn Glu Ser
                980                 985                 990

Arg Arg Pro Asp Asp Leu Cys Trp Ile Gly Ser Val Lys Thr Asn Ile
            995                 1000                1005

Gly His Leu Glu Ser Ala Ala Gly Ile Ala Ser Leu Ile Lys Thr
    1010                1015                1020

Ala Leu Ala Leu His His Arg Ala Ile Pro Pro Asn Leu His Phe
    1025                1030                1035
```

```
Arg Ser Ile Asn Pro Gln Ile Ala Leu Asp Gly Thr Pro Phe Arg
    1040            1045                1050

Ile Pro Arg Gln Val Thr Pro Trp His Ser Glu His Gly Pro Arg
    1055            1060                1065

Leu Ala Gly Val Ser Ser Phe Gly Phe Gly Gly Thr Asn Ala His
    1070            1075                1080

Leu Ile Leu Ser Glu Ala Pro Gly Leu Pro Glu Ile Glu Ala Glu
    1085            1090                1095

Pro Val Ala Pro Ala Ala Arg Val Val Thr Leu Ser Ala Arg Thr
    1100            1105                1110

Pro Asp Ala Leu Gln Ala Leu Ala Ala Ser Tyr Ala Ala Tyr Leu
    1115            1120                1125

Asp Ala His Pro Glu Ala Gly Val Arg Asp Val Ala Phe Thr Ala
    1130            1135                1140

Asn Thr Gly Arg Thr His Phe Thr Gln Arg Ala Ala Ile Val Ala
    1145            1150                1155

Pro Ser Arg Asp Ser Leu Arg Ala Gln Leu Asp Ser Val Ser Ser
    1160            1165                1170

Gly Glu Pro Ala Glu Thr Pro Pro Ala Val Thr Phe His Phe Cys
    1175            1180                1185

Ala Asp Asp Gly Ala Ser Ala Asp Ala Val Arg Gln Leu Arg Ala
    1190            1195                1200

Ala Ser Pro Ala Phe Asp Ala Leu Met Gln Arg Gln Ser Asp Ala
    1205            1210                1215

Ser Gly Ala Pro Ala Leu Ala Pro Asp Glu Ala Gly Phe Thr Arg
    1220            1225                1230

Phe Gln Arg Ala Leu Ala Gln Leu Trp Met Ser Phe Gly Ile Ala
    1235            1240                1245

Pro Asp Ala Val Ser Ser Thr Gly Asp Gly Gln Arg Ala Ala Ala
    1250            1255                1260

Ala Trp Ala Gly Val Pro Gln Ala Pro Asp Ser Gly Ala Ala Gly
    1265            1270                1275

His Pro Gly Ile Val Ile Asp Ile Gly Ala His Thr Ala Ala Trp
    1280            1285                1290

Asp Ala Ile Leu His Thr Leu Ala Ala Leu Tyr Val Arg Gly Ala
    1295            1300                1305

Ser Ile Asp Trp Asp Ala Val Glu Gln Gly Ala Pro His Arg Arg
    1310            1315                1320

Leu Ala Leu Pro Thr Tyr Pro Phe Glu Arg Arg Gly Phe Trp Ile
    1325            1330                1335

Arg Pro His Ala Arg Arg His Pro Leu Leu Gly Arg Leu Met Glu
    1340            1345                1350

Gln His Ala His Ala Pro Ala Thr Trp Ile Trp Gln Ser Arg Leu
    1355            1360                1365

Asp Ala Pro Ala Thr Asn Phe Leu Asp Gly His Arg Val Lys Gly
    1370            1375                1380

Ser Pro Val Leu Pro Tyr Ser Ala Phe Val Glu Met Ala Leu Ser
    1385            1390                1395

Ala Thr Ser Glu Ile Gly Ala Ala Gly His Thr Thr Leu Lys Asp
    1400            1405                1410

Leu Ala Leu His Ala Pro Leu Pro Leu His Pro His Glu Ser His
    1415            1420                1425
```

```
Thr Val Gln Thr Val Leu Ser Arg Arg Ser Trp Gly Pro Phe Ser
    1430                1435                1440

Phe Ala Val Tyr His Arg Ile Asp Asp Thr Arg Ala Ala Ala Thr
    1445                1450                1455

Trp Gln Met Cys Ala Ser Ala Glu Ile His Glu Ser Asp Arg Ser
    1460                1465                1470

His Ala
    1475

<210> SEQ ID NO 18
<211> LENGTH: 328
<212> TYPE: PRT
<213> ORGANISM: Burkholderia contaminans
<220> FEATURE:
<221> NAME/KEY: MISC_FEATURE
<222> LOCATION: (1)..(328)
<223> OTHER INFORMATION: putative taurine catabolism dioxygenase

<400> SEQUENCE: 18

Met Leu Gly Met Thr Glu Arg Lys Leu Leu Ala Glu Gly Ser Thr Pro
1               5                   10                  15

Trp Leu Leu Glu Pro Val Ser Asn Gly Arg Asp Leu Ala Gln Ala Val
            20                  25                  30

Asn Asp Asn Arg Ala Ala Leu Glu Ser Arg Leu Leu Glu His Gly Val
        35                  40                  45

Leu Leu Phe Arg Gly Phe Asp Val Ser Ser Val Gly Gly Phe Glu Ala
    50                  55                  60

Phe Ala Arg Ala Ile Ser Ala His Gln Ser Asp Tyr Val Tyr Arg Ser
65                  70                  75                  80

Thr Pro Arg Thr Ser Ile Gly Asn Gly Ile Phe Thr Ala Thr Glu Tyr
                85                  90                  95

Pro Pro Ser Glu Thr Ile Ala Leu His Cys Glu Asn Ala Tyr Gln Arg
            100                 105                 110

Ser Trp Pro Leu Arg Val Ala Phe Cys Cys Leu Thr Pro Ala Ala Thr
        115                 120                 125

Gly Gly Glu Thr Pro Ile Ala Asp Met Arg Glu Val Ser Arg Arg Ile
    130                 135                 140

Gly Pro Arg Ile Leu Asp His Phe Glu Ala Arg Gln Val Arg Tyr Val
145                 150                 155                 160

Arg His Tyr Arg Arg His Val Asp Ile Pro Trp Glu Thr Val Phe Gln
                165                 170                 175

Thr Ser Asp Arg Asn Gln Val Ala Ala Phe Cys Ala Asn Gly Ile
            180                 185                 190

Ala Leu Glu Trp Leu Asp Asp Thr Leu Arg Thr Ala Gln Ile Asn
        195                 200                 205

Gln Gly Val Ala Tyr His Pro Val Thr Gly Glu Arg Val Phe Phe Asn
    210                 215                 220

Gln Ala His Leu Phe His Ile Ser Asn Leu Glu Ala Ser Leu Ala Ser
225                 230                 235                 240

Ser Ile Val Ser Leu Phe Gly Glu Asp Arg Ile Pro Arg Asn Ala Cys
                245                 250                 255

His Gly Asp Gly Ser Pro Phe Asp Leu Ala Asp Leu Glu Gln Ile Arg
            260                 265                 270

His Ala Phe Arg Glu Cys Ala Ile Thr Phe Pro Trp Gln Arg Gly Asp
        275                 280                 285

Val Leu Leu Val Asp Asn Met Arg Phe Ala His Gly Arg Asn Pro Phe
```

```
                290                 295                 300
Glu Gly Glu Arg Lys Val Val Ser Leu Leu Asp Pro Tyr Thr Pro
305                 310                 315                 320

Asp Ile Glu Gly Ile Ala Asp Arg
                325

<210> SEQ ID NO 19
<211> LENGTH: 456
<212> TYPE: PRT
<213> ORGANISM: Burkholderia contaminans
<220> FEATURE:
<221> NAME/KEY: MISC_FEATURE
<222> LOCATION: (1)..(456)
<223> OTHER INFORMATION: putative transaminase

<400> SEQUENCE: 19

Met Lys Arg Phe Ser Cys Ala Ser Val His Gln Ser Ala Leu Gln Ala
1               5                   10                  15

Gly Ser Ala Arg Met Glu Lys Leu Glu Tyr Leu Lys Gln Val Glu Ser
            20                  25                  30

Asn Ala Arg Thr Tyr Ala Thr Ser Phe Pro Arg Leu Phe Thr His Ala
        35                  40                  45

Lys Gly Ile Arg Val Arg Asp Ala Asp Gly Gln Glu Tyr Ile Asp Cys
    50                  55                  60

Leu Ser Asn Ala Gly Thr Leu Ala Leu Gly His Asn His Pro Glu Val
65                  70                  75                  80

Asn Glu Ala Val Met Arg Phe Leu Ser Ser Asp Gln Met Gln Gln Ala
                85                  90                  95

Leu Asp Leu Ala Thr Pro Ala Lys His Ala Phe Val Glu Gln Leu Phe
            100                 105                 110

Ser Leu Leu Pro Gly Lys Ile Ala Glu Ser Gly Lys Ile Gln Phe Cys
        115                 120                 125

Ser Pro Ser Gly Ala Asp Gly Val Glu Ala Ala Ile Lys Leu Thr Arg
    130                 135                 140

His Tyr Thr Gly Arg Pro Thr Ile Met Ala Phe His Gly Ala Tyr His
145                 150                 155                 160

Gly Met Thr Ser Gly Ala Leu Ala Ala Ser Gly Asn Leu Thr Pro Lys
                165                 170                 175

Ser Ala Gly Gly Asn Gly Arg Asp Val His Phe Leu Pro Tyr Pro Tyr
            180                 185                 190

Ala Phe Arg Cys Pro Phe Gly Thr Asp Gly Ser Ala Thr Asp Gln Leu
        195                 200                 205

Ser Ile Asn Tyr Ile Arg Thr Val Leu Ser Asp Pro Glu Ser Gly Ile
    210                 215                 220

Thr Lys Pro Ala Ala Ile Ile Val Glu Val Gln Gly Glu Gly Gly
225                 230                 235                 240

Cys Ile Pro Ala Pro Asp Thr Trp Leu Ile Glu Leu Arg Glu Leu Thr
                245                 250                 255

Leu Arg His Glu Ile Pro Leu Ile Val Asp Glu Val Gln Thr Gly Leu
            260                 265                 270

Gly Arg Thr Gly Ala Leu Phe Ala Ile Glu His Ser Gly Ile Arg Pro
        275                 280                 285

Asp Val Leu Val Leu Ser Lys Ala Phe Gly Gly Tyr Pro Leu Ser
    290                 295                 300

Val Val Val Tyr Asp Glu Arg Leu Asp Thr Trp Pro Pro Gly Ala His
305                 310                 315                 320
```

-continued

Ala Gly Thr Phe Arg Gly Asn Gln Ile Ala Met Val Ala Gly Leu Ser
             325                 330                 335

Thr Met Arg Ile Val Glu Arg Glu Asp Leu Ser Ala His Ala Asp Arg
            340                 345                 350

Val Gly Lys Leu Leu Val Ala Gly Leu Glu Glu Leu Ala Glu Arg Phe
            355                 360                 365

Pro Cys Leu Gly Gln Ile Arg Gly Arg Gly Leu Met Ile Gly Ala Glu
        370                 375                 380

Val Val Val Pro Gly Thr His Gly Arg Ala Gly Pro Pro His Thr Glu
385                 390                 395                 400

Arg Ala Arg Ala Ile Lys Gln Asn Cys Leu Arg Asn Gly Leu Ile Val
                405                 410                 415

Glu Thr Gly Gly Arg Asn Gly Ala Val Leu Arg Phe Leu Pro Pro Leu
            420                 425                 430

Ile Val Ser Glu Ala Asp Ile His Asp Ile Leu Asn Arg Phe Glu His
        435                 440                 445

Ala Val Glu Thr Ala Cys Arg Ala
    450                 455

<210> SEQ ID NO 20
<211> LENGTH: 316
<212> TYPE: PRT
<213> ORGANISM: Burkholderia contaminans
<220> FEATURE:
<221> NAME/KEY: MISC_FEATURE
<222> LOCATION: (1)..(316)
<223> OTHER INFORMATION: putative epemerase/dehydratase

<400> SEQUENCE: 20

Met Gln Arg Asn Arg Lys Arg Ile Leu Val Thr Gly Gly Ala Gly Phe
1               5                   10                  15

Leu Gly Ser His Leu Cys Glu Arg Leu Val Glu Leu Gly His Asp Val
            20                  25                  30

Leu Cys Val Asp Asn Tyr Phe Thr Gly Thr Lys Gln Asn Val Ala Thr
        35                  40                  45

Leu Leu Gly Asn Pro Ser Phe Glu Ala Leu Arg His Asp Val Thr Phe
    50                  55                  60

Pro Leu Tyr Val Glu Val Asp Glu Ile Tyr Asn Leu Ala Cys Pro Ala
65                  70                  75                  80

Ser Pro Ile His Tyr Gln Phe Asp Pro Val Gln Thr Thr Lys Thr Ser
                85                  90                  95

Val Met Gly Ala Ile Asn Met Leu Gly Leu Ala Lys Arg Thr His Ala
            100                 105                 110

Arg Val Leu Gln Thr Ser Thr Ser Glu Val Tyr Gly Asp Pro Asp Val
        115                 120                 125

His Pro Gln Pro Glu Ser Tyr Arg Gly Asn Val Asn Pro Leu Gly Pro
    130                 135                 140

Arg Ala Cys Tyr Asp Glu Gly Lys Arg Cys Ala Glu Thr Leu Phe Phe
145                 150                 155                 160

Asp Tyr His Arg Gln Gln Asn Val Arg Ile Lys Val Val Arg Ile Phe
                165                 170                 175

Asn Thr Tyr Gly Pro Arg Met His Pro Asn Asp Gly Arg Val Val Ser
            180                 185                 190

Asn Phe Ile Val Gln Ala Leu Arg Gly Glu Asp Ile Thr Leu Tyr Gly
        195                 200                 205

```
Asp Gly Ser Gln Thr Arg Ala Phe Cys Tyr Val Asp Asp Met Val Asp
    210                 215                 220
Gly Leu Ile Arg Met Met Ala Thr Pro Ala Glu Leu Thr Gly Pro Ile
225                 230                 235                 240
Asn Leu Gly Asn Pro His Glu Ile Ala Val Ser Glu Leu Ala Gln Ile
                245                 250                 255
Ile Leu Arg Leu Thr Gly Ser Lys Ser Arg Leu Val Phe Arg Pro Leu
            260                 265                 270
Pro Lys Asp Asp Pro Thr Gln Arg Cys Pro Asp Ile Ser Leu Ala Arg
        275                 280                 285
Thr His Leu Asp Trp Glu Pro Thr Ile Gly Leu Glu Ala Gly Leu Gln
    290                 295                 300
Arg Thr Ile Asp Tyr Phe Cys Ser Thr Leu Ala Ala
305                 310                 315

<210> SEQ ID NO 21
<211> LENGTH: 239
<212> TYPE: PRT
<213> ORGANISM: Burkholderia contaminans
<220> FEATURE:
<221> NAME/KEY: MISC_FEATURE
<222> LOCATION: (1)..(239)
<223> OTHER INFORMATION: putative thioesterase

<400> SEQUENCE: 21

Met Arg Leu Ile Cys Phe Pro Tyr Ala Gly Gly Ser Ala Ala Val Tyr
1               5                   10                  15

Arg Thr Leu Gln Ala Ser Leu Pro Gly Ile Glu Val Cys Arg His Glu
            20                  25                  30

Leu Ala Gly Arg Gly Ser Arg Leu Ser Glu Pro Ala Val Arg Asp Met
        35                  40                  45

Ala Thr Leu Val Asp Thr Leu Leu Cys Asp Leu Asp Asp Cys Phe Asp
    50                  55                  60

Arg Pro Phe Ala Leu Leu Gly His Ser Met Gly Ala Ala Ile Ala Ala
65                  70                  75                  80

Glu Leu Ala Leu Arg Leu Pro Ala His Ala Arg Pro Asn Leu Arg His
                85                  90                  95

Leu Phe Val Ser Ala Arg Ala Ala Pro Gly Lys Glu Arg His Asp Arg
            100                 105                 110

Arg Met Gln Ala Leu Asp Asp Arg Ala Phe Ile Asp Ala Leu Arg Glu
        115                 120                 125

Met Gly Gly Thr Pro Lys Ala Val Leu Asp Asn Ser Glu Leu Met Ala
    130                 135                 140

Leu Leu Met Pro Ala Leu Arg Ala Asp Phe Thr Met Ile Glu Asn His
145                 150                 155                 160

Arg Pro Val Pro Gly Pro Arg Leu Ala Val Asp Ile Thr Ala Phe Ala
                165                 170                 175

Gly Arg Ala Asp Lys Glu Ile Pro Val Asp Ala Val Ala Gly Trp Gly
            180                 185                 190

Ala Ala Thr Thr Gly Arg Phe Asp Phe His Val Ile Glu Gly Asp His
        195                 200                 205

Phe Phe Leu Arg Asn Glu Met Arg Thr Met Ala Gly Ile Ile Ala Ala
    210                 215                 220

Arg Met Arg Arg Pro Glu His Ala Ala Ser Ser Ala Leu Gln Ala
225                 230                 235
```

<210> SEQ ID NO 22
<211> LENGTH: 95
<212> TYPE: PRT
<213> ORGANISM: Burkholderia contaminans
<220> FEATURE:
<221> NAME/KEY: MISC_FEATURE
<222> LOCATION: (1)..(95)
<223> OTHER INFORMATION: hypothetical protein

<400> SEQUENCE: 22

Met Gln His Arg Gln Lys Ala Val Pro Thr Gln Gln Val Ala Asn Glu
1               5                   10                  15

Arg Val Ile Val Thr Glu Trp Arg Phe Ala Pro Gly Ala Glu Thr Gly
            20                  25                  30

Trp His Val His Arg His Asp Tyr Val Val Pro Gln Thr Asp Gly
        35                  40                  45

Gln Leu Leu Leu Glu Thr Ala Gln Gly Asn Arg Glu Ser Gln Leu His
    50                  55                  60

Ala Gly Arg Ser Tyr Ala Gly Leu Lys Gly Val Glu His Asn Val Val
65                  70                  75                  80

Asn Ala Thr Asp His Glu Val Val Phe Val Glu Val Glu Ile Leu
                85                  90                  95

<210> SEQ ID NO 23
<211> LENGTH: 58101
<212> TYPE: DNA
<213> ORGANISM: Burkholderia contaminans

<400> SEQUENCE: 23

| | | | | | |
|---|---|---|---|---|---|
| aattcctgca | gcacggtgcg | cgaccagccc | cagatgtccc | cgctgagcgt | gagtgcgaga | 60 |
| ccggccgtcg | tgatggccag | ctgcgtctgg | ccgaacagcg | gcgtcaatgc | gccttcgccg | 120 |
| ccgatcacga | tccgcttgac | gagatccgag | atggactgcg | agatcgaatc | ggagaacgga | 180 |
| tagttgtacg | gctgcgtgac | ggcgcgcgac | aggaacggct | tgctgggcgt | cggcgtccag | 240 |
| accttgagcc | acggcttggt | cgtgaacggg | aaccagatgg | cttccacccg | gcccgagccg | 300 |
| tcgagaaacg | atgcgatcgt | gcggcccgtc | gtgccgggcg | cggcgaacag | ttcggaggcc | 360 |
| ggaatatcga | cgtagctctg | gcagcgtagc | cgctggttcg | gccctgccgt | cagcgtgact | 420 |
| tcgacgacga | gcgctcgccc | gatgtgcgcg | aggaacgcgc | cgatctcggg | atcgctgcgc | 480 |
| tcgaaccggc | gcagcacgta | ttgctgccgg | gccggatcga | acacgaccgc | cgtgagcgcg | 540 |
| accacgagat | tgctcagcga | gccgtaggta | tggcccggtt | gcaaggtttc | accggccgcg | 600 |
| ggcacggcgg | tgccgtgtgc | atcgatcgcg | agcgcgccgc | cgagcgtgat | gtcgcccggt | 660 |
| gccggcgcgg | caatcacgcc | gaggccaacc | tgctcgagcg | tcgcgagcag | cgactccagc | 720 |
| gagacgcccg | tttgggcggt | gacgcgcgcc | ggacgcgccg | acgtgtcgac | ggagacggcc | 780 |
| gtcagcgact | tcgtcgtatc | gagcagcacg | aggttcgcgg | cgccggcgcc | cgggtccagc | 840 |
| gtcagcggcg | accagttgtg | cgtgtagccg | cgcgggcgta | tccgatagcc | gtttgcgcgc | 900 |
| gcccagttga | cggttgcgac | gacgtcgtcg | gcggagcgcg | gcgcggcggt | ccatacgtcc | 960 |
| tgcacggcga | tctcgccgct | ccagttcagg | aacgcctgct | tgtaaagctg | gatgtcggcc | 1020 |
| gggaagccgg | gcggtgtctc | gccggccgtt | cgcgcgtgcg | ccgcaacctg | gtagagcggg | 1080 |
| gtccagccgg | tgacgatgcc | ggccgccgcg | agcttcgcca | tgtcggccag | gaaggcgcga | 1140 |
| cgcggcgcag | gttcgtctct | gaagtcgtga | ctcatggtgt | gctccaattt | ttcggaattg | 1200 |
| ttttgcagat | tggaaagacg | acaaatgacg | cgttgagact | cgtgtggcaa | ttcgagcagg | 1260 |

-continued

```
tgcgacgcgc gggaagtgtt gcgcgtgggt gggccaggat tgaaaaaaga cggtgcgttc    1320
ggcaatgcgc ggccgcacat catcacggac gtctaatagg aaatcggaaa accgcctggc    1380
gattgcttta attggccgtc ggccggttct gtcggcaagc agatagggag attcgacgga    1440
atcgcgcgcg gcgaagcgct agccgtggcg atcgataaaa gatgatttca cgtgaatatt    1500
aatcttcatg tttcgatttt taaataaacc cggccgcagt tcaaggttga ttgacgatgc    1560
gtcatgcatt tcggtcgaaa gcgtagcaat ttatctatcg ggtgacaagc ggcggagttg    1620
acgaattccg agtcatttaa tatggaaatt ttatgacggg aaatggcttc gtccgttgtg    1680
ggtattttgc aacgcggctg ccggtgtcgc gccacgtggg cttggagcgc aaattatgct    1740
ttgccgtcgc gtatattgaa tcgattgttg agcgaatcga ataacgtcc ggaagacaat    1800 agctgaagcc gggtcgatga gcgggaggta gggtgaaatc cgataattcc tctctcgaat    1860
aacgctcctg gatgaaaatt cgtggtatgc gtcgcccggg tgattattac aaaagttcgt    1920
ggtaaacgga tgtcgattta tcggtgtatt cataataatg ccaatgagcg gctcgcgaat    1980
tgattgattt ccggttcgtg aaagatgtgt tttaaaaaaa tagatgtcgg gctgactgca    2040
aatgtctgaa tcgtcgctat catacgcggc tgggatatac atggatcaaa ttcaatggaa    2100
agaatcgttt cgcttttga tcgcgatttt tctttgaatt cgccgggaac gcgcccgctt    2160
cgagccggcg ccgggttttc cgattcaggt ttcaggcacg tccggcggcg gcgcgttttc    2220
atccggcaac gcgaatcggc cgaaatggac gtttcagcct tttgcggctt cgcgagtcgc    2280
ccgcatcggg ctgaactggg aacggcacgc cgtcgtctcg catgagccgg acgcatcggc    2340
gcgcgctggc ggcggcgcgt tgcccgcctg aaaaaggcgc gcgacgcagc gcgacccgac    2400
gcgcgccgcg caaaccgtgc cggttcgccg gcgcttgcgt tgtgccaggt cctcaagcac    2460
gcacaacaag gagagtcaga tgttcgcgaa gctcgggaag gtgatttcga gcgcaggcag    2520
tgagcggttc gcatccgaca tgcatgcatt gctggtcgag tcgattccgc tcacgatcac    2580
ccggatgact gaatggacgc tcgacgagcc ggcgggcgaa gtcgtccgcg tgcaatcgct    2640
cggcgcggac ggcgcgccgg gcgatgacgg gcgcggcgcg ccggccgcgc acggcgagcg    2700
ggaaccggca gcgcatccgc cgttgaaccg gatcctggcg gcctgcgacc ggcagctcat    2760
tcacatcaat ccgctgatgc ggcgcggcaa tggcggcgaa gtcgcgccgt cgcgcgggcc    2820
gggcggcgga tttcagtgcc atctcgtgtc gggcaaggcg aatcgccgtt acgtgatctc    2880
gctgcatcgc acggcatcgc atcgcgactt ctcgttgcgt gagatgtcgt tcctgaagaa    2940
tttcgccgat acgctgctgc cgctcgtcga gtggcatgcg tcgacgtgcc ggcacggcga    3000
gcgggaaggt gcgacggcac ccggtgcgac ggcaggcatg cccggcgtcg aggcgctgcg    3060
ccacgagttc gaatcgcggc tcgcgcgcgc gagggtcgtg ttgtcggcgc gtgaaaacga    3120
agtgtgcctc ggcctgctcg cgggcaagat gctgcgcgaa atggccggcg agctcggtgt    3180
gaaggagagc acgatcgaga cgtacatcaa gcgagccgcg gtgaagctcg gcatcagcgg    3240
ccggcacggg ctcacgaaat ggatgatcga cgattccgta ccgtgcgcgt cggcggcgtg    3300
acaccgtcac gccatcacgc gcggacgcg cgacgcatgc cgcccggcat gcgcgttcgg    3360
gccgcgggcc ctcaggttcc gaggcgcggc gacgcgtagt cgcgccgcat gcttctcatg    3420
tcgcccccag cagcttccgt cgcggcccg gccgtctcgt cgagcatcca gcgcgtcagg    3480
ccatgacgcc cgctgaagcc cagcttgacg gccgcccgct tcaggtaggt ttcgacggtg    3540 cttcgcgca gcgcgaagcg catggcgatg gcaggcaccg tgtcaccggc caggagtgcc    3600
gtgcatgcct cgatctcgcg cgtcgacagc ttgacgcccg cttgctgcag gcgatcggcg    3660
```

```
aatcgccgcg ccacgcgctc ccggcccgat tgcgtcgccg gcggcgcggc ggtcgtcaca    3720
cgagcggccg gcggagccga atcgagcgcc gcgacatggc tctcgacgat cggaaacagc    3780
acgtgcgaga gttccttgag gaaggtccgc tcctgcggcg agaaatcgtc gaacgtacag    3840
gtgcgataca acgagatcac gtaacagtgg ccccgcttgc gggtcacgag gtggaattgc    3900
gcgtagcgcg gcgacacgat cgccgcctgc atgaggatga agcggtcgag ctgcgcgtgg    3960
atcgggccgt ggccggcgag cgtgtcgtcg acgtgcaggg ggctcgtgcc cgggcgcggc    4020
ggcatctgcg gcccgcaaca gacagcggcc gcgccggtct tcgcgagcgc cgcgccgacc    4080
gcgccgaggc tgcgcacctc gggagggccg tccggcacgt cgtcgatcgc aagctccgaa    4140
atgcggatct cgtcgacggg gaccgccgcg gcgatcaggt tgtacatcat ccggggaaaa    4200
cgtcggctcc cgctgctcga gatcgcttcg ccgacgtgtg cgaacaatct gctgaactcc    4260
atgaagggat tcctgatgag acgttgaagc tgcgcttgtg cgcatgaatg ccgacatgat    4320
ttaaacaccc ggttgcgaac gcgtctgtaa cggattgccg ggacagacgc aacattgccg    4380
gccgtcgaag ccggtacggc gcacggcgac cgttgcgccc gtctgcgacg gatggcgcgc    4440
accttgtccg agtccggatc gctgctcatc cggctgcctc ggcccggacg gcacacatgg    4500
ccgtatcgga gaagatgcgg ccgctatcca ggcgaatgac ccgatccgcc agcttgaagt    4560
actgatcgtc gtgggtgatg atgacaacgc atttcccgcg tgatttcaga tcggaaccca    4620
gcacttcata ggaaaatcgc ttgaacaccg gatcctgatc ggcggcccat tcgtccagga    4680
tataaatcgg acgatcctcg atgtacgcgc aaagcagcgc caagcgcttg cgttgccctg    4740
tcgataacgc gcgggtggtc gagtaggtcc ggccggaaat ctcgatcttg tccgccagtt    4800
tcagggtggc gaggtatttc cgggcaagct cgatgctttc attgcccga tccggtccga    4860 tgatgcgatt gaacaaatgg aaatcggtga agacggcgga aaacaggttt cggtagcgtt    4920
ccctcgcagc gtcgtcaacg acttttccgt cgagggaaat cgtgccgccg gtaggcgcat    4980
agaggccgct gaggaccttg ccaagcgtgc tcttgccgct gccgtttccg ccgatcacgt    5040
agacgagttc tccggcatga atcgtcatgt cgatggggcc gagcacgaag tcgaccgatg    5100
cttcattgtc acggtagttc atcgtcacgt ctttcaactc gatgaccttc catgacttgg    5160
ccgacagggt ttccacgttg cccgcagggc gcggttcctc gtgtgaggcc tgcgtgtcgt    5220
cgatcagaaa gccgaattcc gccagccggg cgagcgcggt cttgccttcg gccaccaccg    5280
gcagaacatt gatcagcatg gtcaagggcc ccatcatgta gagcacggcc agaatgctcg    5340
ccgtgagtac ggagggatcc acgacgccca gagaaggtac gccgaacagc aggcatccga    5400
gcaggaccgc tacggtgatc tggccgatgc tgtcgccgct catgaaccag aagcgttcta    5460
tgtaattgaa tcccgccacg cgcttcgacg acaattcgat cgcggcgcgg gtaaaccagc    5520
gtcgcctggc ccggttgagc ttgagctcct tgatgccgaa cacgaggcca tgtgtgtatt    5580
cgttgaactg gacgaattca tcgcgaaccc gctccgtaaa attgaccgcc ttccgataga    5640
aaaacagata aagcaccagg ccgacgaggg tcaggatgat cgtcgacgcg aacacgatcc    5700
acgagagata ggcgagatag gcgatgctgc agatcaggac gactgattga acgatgatcg    5760
tcgggatggt cagcagggtc tggctcagtt gcggaatgtc ctgtgtcagc atggtcagca    5820
cattgggggc gccgcgtctg tcgatttcat ccagcggggt tgccaggatc cgtttgcaca    5880
ggttgacgcg caacctcgtc atgactttca tgcaggcata ggaggcatc acggcggcgc    5940 agctcctgca gaccaccgcg acgacattca ccgcgatgaa cagcagcaac agcgtctggc    6000
```

-continued

```
gatcatcctg gtcgtgcagc acggtgctga tcaacccgac gcccgcgatc gacgcgatgc    6060
cgctgacgag gcccgtcacg accgtgccca gcgtcagcca gggatgactg cgccacatca    6120
gggtggcggc ggaatgccat ggcggcgatt tgctttgagc ggaatccatg agtggccaat    6180
aggtctcagt tgatcaggtg gctgagttcg acattgcttg ccgctgatct caacctcgac    6240
gaggtttcgt gcttgcccag gaacgtgatg cttccacga ttcccagcgg cgaatcggaa     6300
aacaggatgc agcacttcag caggcgctgc gcacgctccc agccgacgcc gtccggtgaa    6360
tcggccacgc ttcgcaacgc ggcctcgacc gaggcggccg tccagtcttc gctccgtgcc    6420
agccccgact cgatctgccg aagaaattgc aggagcgtgc ggggattgct ttcgatgctg    6480
tacatgagga tgtaatcgat ccgcagtttc ttcgtgatca gcggaaaaat caggtcgatc    6540
acgccggcgg tcgattcgca tttcccatat gccagtgaaa tcgcgtcgcc gagcttgcag    6600
tcccggtgaa gcgcatccag cgcggccttg acgaacgccg cttcgaggtc aacggtggtg    6660
agttgcatga tgttcagtgg cctgtcgagt gttggatcgc ggcgagcacg ggcggcaggc    6720
gttaccagcc gtccggaatg ggcatggaat aggtcagcgg cttctccggc atcacttcgt    6780
ccatgatgtc ggagtagccg gactcctgtc cgaccagatt cggctcgaag cagtagcaat    6840
tgaacgtctg ctgcaggacg aggttgttgc ggtcgttgat cgccggcggg ttttcgttga    6900
tcgcgatgaa tgcgtcgtaa agcgagttcc tgacgacgta cgcgtgcgcg gtgagcgtct    6960
ccacggcctt gacgatgttc ggcgcgacgg gaatcggcgg cgtgaagtga tacgcgccca    7020
ggaacagcat gtgccagtcg tccggcactt gcgcgatgaa ctcgggaaag cgcgcggcga    7080
aatcggcgtc gaagaacgcg tcgtcctcga agatcaggac ttctctcgca ccggcggcct    7140
tcgcctgttt caccgcggcg agatggctca tcgtgcagcc gtagtcctgc gcacgcatat    7200
ggctcaacga ttccggcacg ctcaccagcc ttgcatcgac ggcaggcagc cgttccaccg    7260
tgaggatgtt ctgctctgcg aattttcgtt gcatcgcttc ccagcggtcg ggcgccggt    7320
ccaggttgat gcagaccttg cgggcaaaag tattgtcgat cgtcggcgtt gatttcatga    7380
gggcgttttt tccagaaacg aattgacatg ggcggcgagg acaccggcat gcggatcgag    7440
cagcatggtc aggtggtcgc cggggacgtc cgtcaccgcg acggggtgcg ccgagaagcg    7500
agaccatccc caggtcgcgt ccaggcgaag ctgcgcgatc tcggacgacg gcgcgtagtc    7560
gccgggatcg cgctcggtgc tgcggaacaa cgcgatcggc acgggcagcg gggtggcgtg    7620
cggcgcgtag tgcgacttga agttggcctg atagacgcgc aggtaggcgc gcaggcggtc    7680
ggacccggcg tccgcgaacc agctgccgcg gtcgccgatc cgttcgagga tcaggccggc    7740
ctggccgtcg ggatcgagat ggacgaggtc cgctcgcgtc acctgaaggt cggtcccgag    7800
gaaggtgccg atttcgtggg cgatcgcgac cagccattcg gtgtcgtccc agtcctgcca    7860
gtaagtggcg gccgagctgt cgatgggcgc ggacgcgtcg aagatcgcca gcaatttcac    7920
gtcggcgccc ttggcgacca gttgcctgct catttcgagc gccacgtgcg cgccgaacga    7980
gtggcccgcc aggtagtacg gacccgcgcc caccagcggc cagatgcgtt cgatatgacg    8040
ggccgcgatg tcttccacgc gggtgagcgg ctcgcacgcg ccgtcgaggc cgagcgcttc    8100
cagcccgtga atcgcgtgag cgccgctcag gtggttcgcg agcgggcgga agtagaccac    8160
gttcccgccg gcgcccggca gcaggaagag cggcgcggcg gggccgccgt cgcgaatcgg    8220
cacgagcccg ccggcgggcg cggacggttc tttcgcggcc agcgccgccg ccagtttctc    8280
gatcgtcgga ttctcgaaga gacaggaaat cggcagcctg cgatcgaacg ccttctcgac    8340
atgggccatc agctggatcg cgatgatcga gtggccgccc aggtcgaaat agttgtcgct    8400
```

```
gaccgcgatg tcgtctcttt tgaagatccg ccgccagatc tccagcaacg tgctttcgtc   8460
cgccgcatgc gcgacggcgc gcgccgccgc ggccgcaccg gcagcggctt cgatggccgg   8520
cccggccccg ctgcgcggcg cgctcggccg gccgtcggcg gccggcggat cggcgagctg   8580
gccggtcaac tggcccgggt tctcggcgaa tcgctcgagc aacgtgcgga gggtatcgag   8640
catctgccgc acgacctccg gcgcgatgcg gtgggcatcg tgcgaaatat ggaagccgat   8700
gcgctcgttc gggtgcacgg tcagggtcag cgggtagttc gattccgcga acgcgcgggt   8760
gtcgaggatc tcgatgtcgt ccggcccgag atcggggggcg gcggcaaccg ggaagttctc   8820
gaagaccagc aggctgtcga acagactgtc gccggcgggg agttcgctcc acgactggat   8880
atcgaccagc gagctgtacg aatgcggctc catcgccgtc tgggctgcgt ggacctctgc   8940
cagccattcg atgaacgggc gctcgggcgc gatccgcagg cgcagcggca gcgtgttgat   9000
gaacagcccc acgatcgact cgacgccgtc gagcatcggc gggcgaccgg acacggtgac   9060
gccgaagacg acgtcgtccg ttccggcgtg gcgccgcagc accaacgccc agaccgcgcg   9120
gatcagcacg ttgagggtga cgcgatgcgt gcgcgtgagc gtttgcagcc gcgcggccag   9180
cgcctcgtcc agcaggaatt gctgggtccg gcgcttgtcc tgccgcgggg catcgccggt   9240
cgcctgccgg gccggactgg ccgcgaccgg cgtggcggcc ttgaagccgg ccagttcggc   9300
gcgccaccac gtttcgtcgg ccgagcgagg atgacgcgcg agccagtcga tgtacgcgcg   9360
gtatcccggc gccgacgccg cgaccgcggg catgccggtg cgggcgagcg acaggtagtc   9420
gtcgaacacc tccttcatca gggtcgcggt gctccagccg tcgaggatga tgtggtgcgc   9480
gctccagcag aagcgatggc gcgtgtccgt ttcctggatc agcgtgcagc ggaacaacgg   9540
cgcgcgctgc agatcgaagc cgcgccgccg gtcgtcggcg aggaacgcat cgaaatcctg   9600
cgcgcggcgg gacgcatcgc ggtgccgcca gtcaaggaac gtccatggca ggtcgaccgt   9660
gtgccgtacg gtctggacgg gatggtcgcg atcggcccac gcgaacgcgg tgcgcagcac   9720
ggcatggcgc gcgagcgcat ggcccacgc ctgccgagc gccggcacct ggagcgggcc   9780
gctgacgaca aagctgaact gctggaagta ggcggcagga tccaggtcgt acagcgaatg   9840
gaacaggatg ccctgttgca gcgacagagg cggatagctg tcctcgatat cgtccgctgc   9900
ggtgtcgggg accacgccg cgaagtcgag caaccggtcc ctgaagtgcg cggccaggtt   9960
ctcgaccgtc tgccgccggt ggagccgctc gccgtagcgc cagtccacct ggagcttgcc  10020
gtcggcaacg ccgcgacga tctcgaaggc atgcgtgcgc tgcgaccgcc cggcgcgcag  10080
cgaaccgagg tcttcggccg ccgggcgcca gccatcggat tgccgcaata cggtatcgag  10140
ctgcccgtga tagttgaaga ggatatcggc cttcggcaac gcggcgagac tgtcgcgcac  10200
ggcggcgtcg gggctctggt agcggagcag cgaataaccg agaccgtcgg ccggaatccg  10260
gcgcagctgc tgccgtgcgg cacgcagcgc ttgctccggc gcgtgcatcg cgtcggcgtc  10320
gagcacgacg gggtagatgg acgtgaacca gcccaccgtc cgggtgaggt cgagcggcgc  10380
atccgacacg tggcggccgt gactctcgag atcgatccgc gtgcgggtgt tacccgtgac  10440
catgctgcag gcttgcgcga gcgcgacgag caggacgtcg ttgatgcggg tgtcgtaggc  10500
ccgcggcagc cggcgcagca acgcggtggt atcggcttcg cccagctcga atgaaacgga  10560
cgacgcgtcg tcgactgcgt tgttggccgc gccgtgcct ggatagtcaa ccggcatcgg  10620
ctcgacgggc tgcgcgagga gggcttgcca cagccgtgct tcgtcgccga tggcgggcga  10680 ccggggccagt tgctgcagat gcaacgccca ttcgcggaac gaagtcgtct tcccgggcaa  10740
```

```
cggctggccg tggtaagcgg catgcaggtc ctcgagaagc acgcgccatg acacgccgtc   10800
caccgccagg tgatggatcg acacgaacag gcgggcgagc ggctcgtcgg ccaggcagaa   10860
gagccgggcc gccagcaacg ggccatgcgt gatgtcgatg ccgcgctccg cgtcagcggc   10920
ggcggcacgc atcgccgcca ggcgctcgcc tgcgtcgtcg gcgatcacct gtttcgcaaa   10980
gagcgccggc atctcgccgc cggcgacgac ctgctgggtc cagcggcccg catcgtgcga   11040
gaaacgcagt cgcaacgcat cgtgatgttc gtagacctgc cggaacgcgt cggcagcct   11100 cgatgcgtcg atatccgccg gcacctggat caggaccgtc tggttgtagt gcgacggcgc   11160
atcgatctcc tgttcgaaga accagtgctg caccggcgta agcggcgcat cgcccagcgg   11220
gctcaaggtc ggcgcgcagg ctgcccgctc ctcgggcgcg cggccagct gcgcgatcgt   11280 ctgatactgg aacagctgct tcgccgtcac gcgcagccct gcctgattgg cgcgcgcgat   11340
cacctggatg ctcaggatcg agtcgccgcc gagttcgaag aaattgtcgt ggatgccgac   11400
ggaaggcaac tgcagcacgt ctatgcagat cgacgccagc aggatttccc gcggcgtgac   11460
ggcaggtgca tgcggctggg ccgcgtcgcc ccgatccgcc ggaagcggca gcgccttgcg   11520
gttgatcttg ccgttgggca gcatcggcaa ggattcaagg gcgaagaact gcgacggcac   11580
catgtagtcg gcgagcttgc cgcccagata ccgcgcagaa tcggcgatgt ccggcgcggc   11640
ggtcgcgaca taggcgatca ggaacgttcg ggctccttcg gttttcgcga tcacgacgca   11700
gtcgtcgacc gacggatgcg cgcgcagcgc cgcctcgatt tcaccgggtt cgatgcgcag   11760
gccgcgcagc ttgatctggt gatcgatgcg gccgaggaac tcgatgttgc cgtcgggccg   11820
gtagcgcgcg aggtcgccgg tgcggtagag gcgcgcgagc gggtcggccg agaacggatc   11880
ggcgatgaac ttttcggcgc tcagttcggg ttcgccgtgg tagccgcgcc cgaccggtgt   11940
gccgccgatc agcaattcgc cggccacgcc gatcggcgtg gctgcatct gcgcgtcgac   12000 gatgtagagg cgggtgttgg cgatgggccg gccgatcggc acgatgcggt gcggatcgtc   12060
gcgccggcat tcccacgcgg tcacgtcgac ggcggcctcg gtggggccgt agaggttgta   12120
gagcttgacg tccaggcgct cgaggcaacg ctgctgcagg tcatggggca aggcctcgcc   12180
gctgcacacg acgcggcgca gcgacgcgca gtgcgcgtcg aggtccggat gatcgaggaa   12240
cgcgcgcagc atcgacggca cgaaatggat cgtggtgatg cgttcgcgct cgatgagctc   12300
gaccaggtag tcggtctcgc gctggccgcc ggggcgggcg aacacgaggc gcgcgccggt   12360
gacgagcggc cagaagagtt cccagaccga gacgtcgaag ctgaacgggg tcttctgcag   12420
cacggcatcg tcggcgtcga gcgcataggc gtgctgcatc cagaggatgc ggttggtgat   12480
cgcgcgatgg gtgttgagcg cgcccttggg gcggccggtc gagccggacg tgtagatcat   12540
gtaggcgagg ttgtcgccgt tcagcgcggg tgcggggttg gacgtcgccg cggcgtcgag   12600
gtcgagcgag tcgcgatcga cgacgatcac gtgcgcgtcg gtgtcgggca gcgcgtcgtg   12660
cagatgctgc tgggtgagga gccagcgcaa ctgcgcgtgg tcgatcatga agcgcacgcg   12720
ctcggcgggg tagtcggggt cgacggggac gtaggcgccg ccggccttga ggatcgcgag   12780
cagggcaacg ctcatgtcga gcgaacgctc catggcgacg ccgacgagcg agtcggggcc   12840
gacgccgagc gcgacgaggt ggtgggcgag gcggttggcg cgcaggttga gttcggcgta   12900
ggtgagcgcg gtgtcatcga agacgatcgc gacggcatcg ggcgtgcgct cgacctgctg   12960
ctcgaacagg cggtgcagcg gttgcgcggc gtcctcgccg aaatccgtgt cggtgcggtt   13020
ccactcgacg tcagcaggt tccgctccgc gtcattcgac aacgcacgcg cgccgagcgg   13080
ccggtccgga tcggcgatca cggcatcgac gagcgtgcgg aagtgttccg ccatgcgatc   13140
```

```
gatcgtggcg gcgtcgaaca gatccaggtt gtattccagc gagcccgcga ggccgtcgtc    13200
ggcatcctga acatgaagcg tgaggtcgaa cttcgcggtg tgggtctcca ccgccaccgg    13260
cgtggccacg agaccgggga agctcactgc ccggggttgc gctttctcgt atgcgaacac    13320
gacctggaac accggcgtgc ggcccaggtt gcgttcgagc tcgagcgagt ccaccacctg    13380
ctcgaacgga atctcctggc ggctgtagcc gtccagcgcg acgcgcttca cgcgcgccag    13440
caggtcgccg aaggtcggat tgcccgacag gtccacgcgc agcgcgagca tgttcgcgaa    13500
gaagccgatc agcggctcgg tcatgctgga acgccgattg gcgatcgggg agccgatgac    13560
gaggtcctgc tggttgctgt atcgcgacag gagcagcgca tacgcggcga gcacgaccat    13620
gaacgtgctg gtgccggacg cacgggcaat cgcgcgcagg ccgtcggcgc gttcggcgct    13680
cagctggaac ggcaggaccg cgccgcgaaa ctgctggacg gcgggccggg ggcggtcggt    13740
gggcagttcg atcaggtccg gcgcgtccgc cagcgcggcg ctcaggagcg ccagctcccg    13800
atgcgtgtcg gcggacgcca ggcgctcgtg ctgccacacg gcgtagtccg cgtactgcac    13860
ggccagttcc ggcagcgact cgccggcata gagcgcggcc agttcgccga tgaggatgcc    13920
tgacgaccat gcatcggaaa cgatgtgatg catcacgatg ccgaagacgt gcaggcgctc    13980
atggacgcga tacagcacga cgcgatagag cggcccggcg gcgagatcga acgggcggtc    14040
ggcttcctcc gcgagcagcg cgagcgtgtc ggattcgctg gcgacgtcga cgacgtcgag    14100
cgcgaccggc gccggcggcg caatgcgttg aaccccgcgg ccgtcgacgg cgggaaacgt    14160
cgtgcgcagg atctcgtgac gccggctgat ctcggacacg gcaaaccgca ggcgcgcgac    14220
gtcgagttcg ccttcgaagc gcagcgcgct cgagatgttg taggtggccg acgggccttc    14280
cagttgcgcg aggaaccaca gccgctgctg cggaaaggac agcggcaggt cgttcgcgcg    14340
cgagcggggc gggatggcgc cggccgtcga gccggggtgg ggcgacgacg cttcgatcag    14400
gtcggacacc gcgctgatgg tctggagttc gaagatcgcg tcgatgccga tctcgacgga    14460
gaagctgctc cagatccgcg agaccagttg catggcttgc agcgaatcgc cgccgtagtc    14520
gaagaagcgg ccggcgagat cgacggccgg attgtcgagc acgtcgcgcc agatgcgcac    14580
cagttcgcgc tgaatcggcg tggcgtcgag aggggcttcc tcgggcgcgg cggcaggctc    14640
cagggccagg agcgccgggc gatccagctt gccgttggcg ttgagcggga attcggcgat    14700
cgggatgatg tcgacgggga ccatgtagtc cggcagcttc ccggccaggt aggcccgcag    14760
gttcggcacg ctcaggctcg cggcgcccctt gacgtaggcc gccagcttgc gcaccccgtg    14820
ggcggattcg cgcagcatga ccgccgcgcc gacgacgtcc tcgtgcgcgg cgatcgcggc    14880
ctcgatctcg ccgagttcga cacggtgccc gcggatcttg acctggtggt cgacgcgtcc    14940
gtagcactgg atacgtccgt cgggcagcca ccggccgatg tcgccggtgc gatagatgcg    15000
cgcttcgccg ggaaacggat gctcgacgaa tttcgcggcg gtgacgtcgg gccgctggtg    15060
gtagccgcgt gcaaggccgg cgccggcgag gcagatttcc ccgggcacgc cgagcggaac    15120
cggccgcagc gcgtcgtcga gcatgtacac ccgggtgtcg gcgatgggac ggccgatcag    15180
caccgtgggc ggcgcgtcct cgacgcgctc gacgatgcag ccgaccgtcg cctcggtggg    15240
accgtactcg ttgtagattt cgatcgcggg atcgatcttg cgcagcgtgg cgatgtgctg    15300
gggcgtcagt tcctcgccgc ccacgatcac cttgcgcacg ccggagcgtg ccaggttcat    15360
gtattccagc aggtgaatgt gggtgggcgt gagcttgagg gtgtcgacgc cgctgccggg    15420
ctggaacatc cgggccagga tggtgtcgat gctttccgac tgcggataga tgcgcagcgt    15480
```

```
cttgccgcgc accagcgggc agaagatgtt ggtgagcgtg aagtcgaagc agagcgagct    15540
gtacaggccg aaactgccgg tcgtgctttc cggaaagtaa tacccggcgg cccacgcgat    15600
gtagtgggcc aggttccggt gttcgagcag gcagcctttg ggtttcccgg tcgagcccga    15660
cgtgtagagc acgtaggcca ggtgcgccgg ttcggcacgg tgcggcgggt tgtccggcag    15720
cggctgccag ccggggagtt cctggtccag cagcagcgtc acgccggaga attcatacca    15780
ctgcgcgagc tgactcgact gggtcaccag cagcgacagg cccgtgtcgc cgaggatgtg    15840
attgatccgc tcggccggat acgcggggtc cagcggaacg aacgccgccc ccgccttcag    15900
gatgccgaga atcgcgacga tcatccattc ggaacggtcg agcatgatgc cgaccagcga    15960
ttccggcccg acgccgtggt gttcgcgcaa gtgatgcgcg aggctgttgg cccgcgcgtt    16020
caggtcggcg taggtcatca gcgaactgtc ggtgaccagg gccggcgccg tcggcgtgcg    16080
tgcgacctgg gcttcgaaca tggcgacgac cgtcgggtgg ctggggccgg ccgtcgcggt    16140
ttcgttgaac gcggccagca gcgggccctg ttccggcggg ccgcttcga tgtcgccgac     16200 ggcgccgtcg aggtgttcga atgcctccag caccgcggcg aggctgccgg cgaaaccgtc    16260
gatgatgaaa ggctcgatgg ccccgctgta acgaagctcg atttcgccgc gcgcgagccg    16320
caggtgcaac tgcagatcgt cgtcccgacc ggtcggtgcg tggtgcacgc ggtcgtccgc    16380
cagcgcgact ttcgtgagct gcgcgagcgc catgtccttt tcgttgcgca cgagcgtttc    16440
cagcgggaat cgaggctcgg cgtagctgtc ttccacgatc ccggccacgc gcgacaggta    16500
gtcctcgatg cgctcgtcgg ggcggacctc gatgatcagc ggaacgatgg cggcccgggc    16560
cgacggatgc ccgccagcc ccggcgtgcc gagcaccgtg accggaatcc ggaagtattt     16620
ccagagcagg aacgcgatgc ccgccgccgc gacggcgaat tcggcaagct cgccgtcgcc    16680
gatgcgccgc aacaggtcga gcgacgcggg cgtgagccgc accgagcggg tcagcgggcg    16740
acccggctgc tggctcgggg cgtacgccgc gattccgtac acgccggcga cccgggaaag    16800
gctttcgcgc cagaaacgcg cggtggctgc atagcgatgg tcggtgacca gcacgttatt    16860
gtcttgcaca ggaaactcct tgagacgttt tgttcacctg aaacaacctg aagcagcacg    16920
cacgcgcgcg ccgctcgaa ccccggcggg cgcgcatcac gtcttctcct cgagcgcgtc     16980
gtcggccgtg accgcgggcg cgcgcttcag gcgcaggccg acccggactc gcgggccggc    17040 ggcgggcgc tcgtcggaga gcgggatgcg atcgaccggc gtggccggat cgcgacggaa     17100
gacgtcgtgg atcgcgagca gtcgatcgcg catcgcggcg atggtcgacg ggcggaacag    17160
gtgggtgttg tagatgaact ggatcaggtg ccggccttcg cttttccacga cctggaagga    17220 caggtcgaac ttggccgtcg tgtccgccgg cgagatgtcc gtgatgcgaa ggcctggctg    17280
cggcgccggc atcgacacgt ggttcacctg aatgtcgaag atcgggaaat ggttcgccgg    17340
cgtgcggatc ttcaggtctt ccagcaacac gtcgaacgga taggacgcat gctccagcgc    17400
ttgcgcggag gctttcgcca ccccgtcgat cacctccgcg accgtcgcgg atttccgcac    17460
cggcacgcgc agcacgacgg tgttgaggta cacgccgacc tgcgattcga gctgctcgct    17520
gtcgcgcccg gccgacacgc tgccgatgac gatgtcctca cgccccgtgt agcggtgcat    17580
cagcacgcag aacgacgcca gtagcaccgc gtggagcgac gtgtggtgag cgcgggccag    17640
cgtcgcgagt tccgccgcgt gcggctgcgg cagttcgact tcgagcgtct gcccggcatg    17700
accgagccgc tcgggacgcg ggaagtcgga tgccagttgc aggcggggca gggcggcgc    17760 cagttgctcg agccagtacg cgcgatgcgc ggcggcgcgc ggaccccgcga ggctcgcgtt   17820 gtgccacgcg gcgtagtcgc gatactggat cgacagcggc ggcaggtcgc gccccgcata    17880
```

```
cagcgcatgc aggtcgtcgg tcagcacgcg gatcgaccat gcatccgaga tcacgtggtg   17940
catgttcagc agcaacagat gcttctcctg cgacagccgg accagcttga cgcgaaagag   18000
cgggcccgac gcgagatcga acggctgctc gcattccgcg cgaatcagcg catcgatcgc   18060
ttgcggcccg gcatcgtccg cgagatcgcg ctgctcgacc cggaatccgg acgcttcgcg   18120
gctgaggacg cgttgccgca actcgccttc gatcatcgcg aacacggtgc gcaggctctc   18180
gtggcgatcg accagcgtgt cgaatgcacg gacgaggcgc gccgtatcga cggcgccgtc   18240
cagctgcagc gcgcccgcca tgttgtacgt ggacggatcc gcgccgcggc tggcgagcca   18300
gatccgcttc tgtgcacgag acaccgcgta ggacggttgc gcggccagcg ccgggatgat   18360
cgcgtcgtcg tcggcggcgc cgtcgacggg catggcagcc agcctttgtg cgagcgcgcg   18420
cggcgtcggc gcatggaaga gtcggcgac cgcgacgttc agtgcagccc ggggatccg   18480 gctgaccatc tggatcgcct tgaggctttg gcctccgtgc tcgaagaaat cgtcgtcgac   18540
gccgttcggc cggcggccga gcacctcggc gaagaggcgc agcagcgccg cttcgaccgg   18600
cgtgcgcggt tcggcccgca cgccgtcggg cacggacgcg gcatccggca gcggcagcgc   18660
ggcgcggttg atcttgccgt tcggcatgac gggcagcgcc ggcagcagca tcacggtgtc   18720
gggcaccatg tgcgccggca gcgtgtcgcg cagtgcgtcg cgcacgcgct ggggcgtcca   18780
gccggttccc gacgcgtagc cgcacagggt catttcggca tccgacgttt ccgggcgac   18840 caccacggcg tgggaaatgc cggcaagact ggtcagcgcg gcttcgattt ccccgagctc   18900
gatgcggtag ccacggatct tgacctggaa gtcgcggcgg ccgaagaagt gcagattgcc   18960
gtccgccccg aagcagccga tgtcgccggt gcgatacagg cgcgcgcctg gttccggact   19020
gaacggatcg tcgcggaaca ccgcccgggt gcgggcttcg tcgaacaggt agccgcgccc   19080
gacgccgacg ccccgatgc agatctcgcc cttgacgccg gccgggcacg gattcatgtc   19140
ggcatccacg acgtagaggc gcaggttctc gatcggccgg ccgatcggaa tcgccggccc   19200
atccggcgcg cgcgtcaggc agtaatgcgc gacggagtcc gacgcttcgg tcggcccata   19260
ggcgttgatg agccggacgg ccggattcag gcggaaccac gcttgcgcgg tggcgggctg   19320
cagcgtttcg ccgatcgtca gcaacgtgtc gaggtgaggg aaggccggtg ccgcgtgccg   19380
ttccagttcg ccgagaaagg tcgcgagata ggacggtacg aattgcattg ccgtgatgcg   19440
gtcgcggtgc aggctgtcga tcaggcgcgc gggctcgagg atcacggcat cgggatagat   19500
caccgtcgtg ccgcccgacg ccagcgccgc gaagcattgc cagaccgaaa tatcggagca   19560
gtgcgaagcg gtctgggcga ccgcgctctg cgcgccgagc ccgacccggc gcgccatcgc   19620
gagcacgtga ttgagcatgc cgcgatgttc gaccatcgcg cccttcggct ggccggtcga   19680
acccgacgtg aagatcacgt aggcgaggtc cgcgggccgg cagcgcggcg tcaccggcgc   19740
cggcgcttcg gcgccgcgac ggtcgggcag gcgggccgga tcgaccagcg ggatcgacgc   19800
cagcgccggc ggcggcacgc agtccgtcgt gacgatgacg gccggccgcg ccagcgtcag   19860
gatggtctcg acccgctggg ccgggtaggc cggatcgacc ggaacgtacg ccgcgccgca   19920
cttccagatg gccaggatcg tttccagcat cagcggcgag cgcggcatcc agacggcgat   19980
ccggtcgtcc ggctgcagcg gcgccgtctg cagaagatgc gcggcgatcc ggttggcgcc   20040
ttcgacgagg tcacggtagg tgcgaacctc cgtgccgcag cgaaccgcca cgcgctcggg   20100
gtgcgctgcg gcgacggcct cgatcagttc gggcagcgtc cggtcggacg gaaccggcgc   20160
gaacgtgtcg ttccagccga gcaggatggc gtcccgctcg gcggcagcga gaagcggcac   20220
```

-continued

```
gctgcggttc gggcgatctt ccgcgccggc caggccggtg agcagggtct cgacatggcg   20280
cagcaggcgg acgatcgtgt cgcgatcgaa ccggccgtcg tcgtacagca cctgcagcga   20340
caggcgcttg cccggcgtca cgaccagcgt cagcgggtaa ttgttcggat cggacacctc   20400
gaatgcgccg atccgcaggc cgggcagcgc atcggccagc gcttcttcca ccggataatt   20460
ctggaagatg agcaggcttt cgaagagcgg cacgccgggt ggcaggccgg cgaatttctg   20520
gatgtcggcc agcggatagt gcgcatagtc ctcctgctgc gcgagatcca tctgcaattg   20580
cgccagccac gctgacgtcg ggcgtgcgtc gatgcgcacc cgcaccggca gcgtgttgat   20640
gaacagcccg accatttcgt cggatgccgg cagcgacgcc gggcggccgg aaacgatcgt   20700
gccgaacacg acgtccgatt cgccgctgta gcggctcagc aactgcgccc atgcgccctg   20760
cgcgagcgtg ttcagggtga ggcggcggga ttgcgcgaat gcgacgagcc gttgcgtgtc   20820
gctttcggag agcagcagcg gctcttccac gtaggcgccc ggcgcggccg tgccgtcgag   20880 ttcgggcgg cccagcacga gcggcgtcgt cgccgggaaa tccgccagct tcgtcttcca   20940
gaaacgttgc gcggcggcgg cgtcctggcg tgccagccag cgcacgtaac cggcgaaggc   21000
aggcggcgcg tcccgctgcg gcgcgccttc ggccggcggc gcctgatagg cggcggccac   21060
gtcgctcagc aaccgggcgg agctccaccc gtcgagcagg atgtggtgat ggctccaatg   21120
gaagcgccat gcgtgctcgc ccacgcggaa cagcgcgagc cgcatcagcg gcgcgcgggt   21180
aaagtcgaag ccgcgcgccc ggtcttgcgc cacgtaggct tcccagcgct gttcggcctc   21240
cgcggcggac gccgcgcgca gatcctcgtc gtgccacggc aagtcgatcc ggcgatgcac   21300
gacctgcacg gggcttttcga tgtcttccca gtgaaacgac gtacgcagga tgtcgtgccg   21360
gtgcgccacg gtctcccacg cgcggcggaa ccgttcgacg tcgagcgccc cgtcgatacg   21420
gaaattcagg ctgctgaagt acgcatccga cgcgggttcg tacaggctgt ggaacagcat   21480
gccctgctgg gtcggcgtca gcgggtagac gtcggcgatc tcgtccggac tcaccgacgc   21540
cggcgccggc gcctgcggca acgcagtcgc gggccgggtc gatgcggacg ggacagcgtg   21600
gccggcgacc agggtttcga gcgccgcgat gtaggcttgc gcgacgcgca ggatggtggc   21660
cgtgtcgtgg caggcccggc tgaattccca cgcaacgtgc aggcgattac cggtcacgta   21720
cgcgttgatg tcgagcaggt gctcgcgcaa ctggttcgcg ttgcggccgt ccccgctcgg   21780
ctccgcggcc tgtttccagt cgcgtgcggc ggtgaacagc tggtcggtct gcccaggta   21840 gttgaactgc agtcgcggct gcggaagcgg gccgtcgagc cggtctagca gcaggccgta   21900
ggtgatgccc gcgttcggca ccgcgcgcag ccgcgtcctg accgatgcga cgaggctggc   21960
cggatcgtgc gaaccggcat cgaccgtcag caagaccggg aaaaccgacg taaaccagcc   22020
caccgtgcgc gagatgtcga gcgcgtcgat cagttcctcg cgcccgtgcg cttcgagatc   22080
cagcagcacg tcggcgcatc cgctccattc gctgacggca cgcgcgagcg cggcgagcag   22140
cacgtcgttg acctgcgcgt cgtaggcgcg gggcgcggcg cccagcaagg ccgtcgtcgc   22200
ggcttcgccc aactcgacga cgatcgtgtc ggcgacgac acggtattgg cgtcggcagg   22260
cgcatcgcga tcgagcggca ggccgggcag ggcggcacgc gcgagggcct gccaatgggc   22320
gaggtcggcc tcgcggcgc cggagccggc ccaggtcgag atcgcccggg tcatgcggt   22380 ccaggtcgcg ctgccgcctg cgaattcggg cgccttgccg ttgcgcagcc gggtataggc   22440
gtcgtacacg gtttcgagca gcgcgcccca cgacacgccg tcgacgacca gatgatgggc   22500
gaccagcagc aggcggagcg aacggccttc gtcgacgcg aacaggtccg cgcgcacgac   22560
ggggccgtcc gcgagattca ggctcgcatg cgactgcgcg acgtactgcg cgagctgatc   22620
```

```
gcgcgcaatg tcggacacga cgacggggat ctccgggtcg tcgacgactt cctgggtcca   22680
gccgctctcg ccctcgcgaa agcgcagccg cagcgcgtca tgccatttga ccgcatgccg   22740
cagcgcctgg cgcagcaaga ccggatcgag gtcggccggc acgtcgagca ggaccgcctg   22800
gttgtactgg tccgggtcgt gcttgccctg cgcgaagaaa cgcttctgga tgggcgtcag   22860
cggcagcggg ccggacgatg cgacgaacgc cgccgcgccg accgtgccgc gcgtcgccac   22920
ggcggcgagt tcgccaccg tcggatgctg aagatgagc cgggtggtga gcttcaggcc   22980
cgccttcgcg ccagcgaca cgatgcgcat gctcagaatc gaatcgccgc ccagcgcgaa   23040
gaggttgtcg tggatgccgg cgacggaat gcccagcgct tcgccccaga tgcggcacag   23100
cagcgtctcg gtaggcgtgc ggggcggcgt cggcgcgtgt gccgtggcgg cgagtcgcgc   23160
gcggtccagc ggcggcagcg cgttgcggtc gatcttgccg ttgccgctca ggggcagcgc   23220
gtcgagcacc acgtagatgc cgggcaccat gtagtccggc agcgtggcgg acagcgcggc   23280
ggcgatcccg gcgtcgctca gcgacgcgcc gtcgcggaac gcgacgtacg cgcacagcgc   23340
ggcgcggccg gcctcgtcgc gatagtcgag cgcggcggcc tggcggagtt ccgcgaatg   23400 gtcggccagt cgtcgttggt cgatctcccc gagctcgatg cggtagccgc ggatcttcag   23460
ctggtggtcc ttgcggccgt gcagcacgat cgttccgtcg ggcaggtagc agccgatgtc   23520
gcgggtgcgg tacaggcgga cgccgcgctg aggatggaac ggatcctcga cgaacgcgtc   23580
ctgcgtggcg gcttcattgt tcagatagcc gcgaccgacg gcgacgccgg acacgcacag   23640
ctcgccggga atcccgatcg ggcacaggtt catctgcggg tcgacgacgt agaggcgaac   23700
gttgcggatc ggcttgccga ccggtacgta aggcgtggac ggcgcgcccg tcatgcggtg   23760
ctgtgcgacg tcgtcggacg cttcggccgg gccgtacgcg ttcaccagcg ggatcgccgg   23820
gaacacgtcg aaccactgtt tcaccagcgc cgggctgacc atctcgccgg tgacgagcag   23880
gtgccgcaga tgccgcatca gcgccggccg ttccgacgcg cggtcgagca cggcggacag   23940
ataggacggc accagttcga ggatgctgat ccgggtggtt tccaggtacg cgacgaaacg   24000
cgcgggatcg cgaatgcagt cgtcgtcgac gatcacggtc ttgccgccga cgagcggcgc   24060
cgtgaaaaat tgccagaccg aaatatcgaa gcaatgcggc gcggtttgcg cgatcaccga   24120
cgacgccgag atcgagaact cgtcgatctc ggcgagcatg tggttcagca tgccggcgtg   24180
ctcgaccatc gcgcctttgg gcttgccggt ggagccggac gtgtagatca cgtaggcgag   24240
gctgtcgggc gacacggggc ggccgggatt ggagtcgtcg acggcgtcgg tggcggcgtc   24300
gagcgacacg accagcgcga tcccggccag ctccggggga aggagcccgt cgcaggtgat   24360
cacgagggcg gcgccggaat cctcgaggat ggtgcggatg cgggccaccg gataattcgg   24420
gtcgaccgga atataggcgg cgccgcactt ccagaccgcg aggatcgcct ccatcagctg   24480
ggcggaccgg tgcatgcaga ttgcgaccag cgcgtccggg cccaggtcgg cggcggcgag   24540
caggcggtgc gcgatgcggt tggcgcgcgc gttcagttcg cccgcgctca ggacgccatc   24600
ccggtactcg accgcgggcc gctcggggtg gtccgcggcg gcctgctcca ggcgatgcac   24660
cacggtgagc gcggcgtcga acggcacggc ggtgtcgttg aaggtctcca gcaactgccg   24720
gcgttccgcg tcgggcaaga tcggcacgcg gccgagcagc cggttcggat cggccgcgaa   24780
cgcgtcgagc gtcgcggcca cgtggcccag catccgctgc atcgtgtctt catcgaagcg   24840
ccgcgggtcg aacgacagtt ccatcttcca gtcgtcgcgc gccgtcacca cgaattcgag   24900
cggaatgtcg gcgcggttgt agagctgcac ctcgtcgacc gccagcccgt gcgcgccatg   24960
```

```
cgtgagcgac gcgtcgagcg ggtaattcat gaacgtgatg ttgctctcga acagcggcgc   25020
cgtcggcggc acgtcgctgc agcgctgaat gtcgggcaac ggggtgtgct cgaacgcgcg   25080
gcgggcggcc acgcgcgcct ggatcatctt cagccacggc accagcggct gcctcgggtc   25140
gacccgcacc cgcaccggca ccgtattgat gaacaggccg agcatggttt cgatccccgg   25200
caggttggcg ccccgcccgg acacgacggc gccgaacacc acgtcggttt ccccgctgta   25260
acgcgacagc acgagcgccc acgccgcttg cgcgagggta ttgagggtga cgtgatggcg   25320
ggccgcgaat tgccgcaggc gcgcgctcag gtcggccgac aggtcggcct gcacttgcgc   25380
gaggccctgg ccgaagcgtt cgtccgcgcc cgcgcgcgcg gccgtgggca gcggggtcgg   25440
tgtgcggaac ccttcgagat agcgcgtcca gtattgctgc gcggcttgcg gctcgtgctg   25500
ctgcagccac tggatatagt cgcgataggg gcgcaccggc gggagcgccg gcgacacgcc   25560
gcgcgcgagc gcgccataga cctcgaagat ctcctcgatg acgagcgaca ggcaccagcc   25620
atcggccagg atgtgatggt ggctccagct gaacaggtag gcgtcggcgg cgacgcgcac   25680
caggcgacag cgcacgagcg gcgcgcgatc gagcgcgaag ccctcggcca ggtcgttgtc   25740
gagatgcgcg cgccaccgtg agcgctgttc gtgttccggc aggtcgagcc agtcgtcctg   25800
cacccacggc agcgtggcgc gcgcgtgcac gacctgcatc ggcttgtcga actcctccca   25860
atggaacgac gtgcgcatca ccggatgccg atcgatgagc tgctgccacg cggcatgaaa   25920
cagcgcggga tcgaggctgc cggtgatccg gcaactgagc tggttgaagc tgcttctcga   25980
gccgggctcg tgcacggcat gaaagagcat cccctcctgc atcggggaga gctcgtagat   26040
atcggcgatg gtgggggatg tcacgatttg atccttgaga caagggcgtc cagcgcttcc   26100
tggctgatgc gcgcggccgg aaagtccgac gggctcagcg cgcgcgggcc gtcgccgccg   26160
gccgcgacga tcgacagcag gcggctgcgg tagcactgcg tcagctgttc gatgacgccg   26220
ggtgcgcagg cctcgcggtt gtagtgccag gtcaggcgca gacggccgtc gaacaccatc   26280
ccgtcgatct cgaacagatg gccgcgacgt gcgcgcgggc tgtgctcggg gctctggaag   26340
tcgagtaccg gcttccagcc cgtgtcgtcg ggcagcacgc gatcgacctg gccgagatag   26400
ttgaagcgca ccggcgccgg cggctgccgt tcgagcgccg ccgcgatgcc ggcgtcgtgg   26460
ccgaggtagc gggcgatgcc gtagccgagc ccgcgcatcg gaaccgcgcg cagctgctcc   26520
ttgacgtggc gcagcgcgtc gaccgccacg gtggcgtcgc cggcgttcag gcacaccgga   26580
tagtgggtgg tgaaccagcc gatcgtgcgc gacgtatcga cgccgtcgaa aatgtcctcg   26640
cggccgtggc cttcgagatc gacgaccagc gacgcgttgc cggtccagtc gccgaacgcg   26700
agcagcaggg ccgtcagcag gacttcgttg atctgcgtgt tgaacgcacg cggcacgtcc   26760
tgcaacagcg cgagtgtctg ctgcgcatcg aactcgacga tcgtcgagcc cgcttcggcg   26820
acggtgccgg ccggcatgtc gtcgaagcac gccggctcgc cggcgttgcc ctggagccag   26880
tagtccagcc ccaggccgtc gagcgcggtc gcgccgagtc cggacaggcg cgtcgaccag   26940
tcgcgccagg ccgtcgtcct ggccgggagc tgtaccgcgt cgcccgcttc gagctggcga   27000
catgcggtgt acaggtcttc gaacaggatg cgccacgaca cgccgtcgat caccaggtga   27060
tgcgcgaccg cgagcaggcg ctgcggcgcg tcggaccgga actggaacag gtgcgcgcgc   27120
agcagcggcg cgccgacag cgtgaagctt tcctgcatgc cggtggcggt cgcgagcatc   27180
gcggcctgcc gtgcggcagg cgccgcgtcc gccagcgacg tgacgccgag cggaatggcc   27240
agcggcggcg cggcatgcga ttgctgccac acgccggcga cgcacgcgaa actcagccgc   27300
agcgcgtcgt gatgcgtcgc gacggccgcc agcgcgcgct cgatcgtgtc cggccgcagc   27360
```

```
gatgcgggca cctcgatcat cgtcgactgg ttgtagtggt gcggatcggc gacgtcttgc    27420
gcgaagaacc agtgctggat cggcgtcagc ggggcggggc cgaccaccgg ctcctgcgcg    27480
atccggatcg acggcgcctc cgtcgcgacc tgggcgagct cggcgatggt cgggtgtgcg    27540
aagaactggt cggcggtgaa cttgagcccg acttgctggg ccagcgacat cacctggatg    27600
atcaggatcg agtcgccgcc cagttcgaag aaattgtcgt gcacgccgat cggctcgcgg    27660
cccagcacgt cgcaccagat cctgcccagg cgcgcctcga cgtcattggc cggtgcgacg    27720
taggcggttt cgctcggcgc gggcgccagt ccagcgcgg cgagcgcctt gcggtcgggc    27780
ttgccgttcg gcgtcagcgg caggcgttcg agcgtcacga tcgacgccgg caccatgaac    27840
tcgggcaggc gttccttcag gtgttcccgc aggctggcga cgctggccgt cgccgtcgcg    27900
acgcaggcca ccagctgctt gtgctgcggc gtgtcctcgc gcacgaacac gatcgcgtcg    27960
gcgacgccgg cgtgctgcct gagcgccgcc tcgatctcgc ccatttcgat ccggtagccg    28020
cgaatcttca cctgcgtgtc gcgccgcccg gtgacttcca ggttgccgtc cggcagccag    28080
acgccgaggt cgccggtgcg atagaggcgc tcgcccgcct cgaacgggtg gcgacgaac    28140 gcggcggccg tcaggtcgtc gcggccgaca tagccgcgcg ccagcgcgat gccggacacg    28200
cagatctcgc ccgcgcaacc ctcggggcc agcgccccgt gctcgtcgag caggtacagg    28260
tgcgtgttgt ggatcgggcg gcccaccggc agacgggcgc cgtaggtgat ggccgggtcg    28320
accacgtagt ccgcgatgca cacggttgcc tcggtcgggc cgtacgagtt gtggcacgtg    28380
cgggtccggg ccagctcgcg cagatccgcc acgcgggcgc tgtcgcccgc gctgatgacc    28440
cgtttcacgg cgccgagcgc atgccagtcg agcgcggcaa ggtaggccgg cgtcgcgttg    28500
acggtggtga cgccctgctg tgcgatgtag tcgacgaaac gcggcacgtc ccggatcacg    28560
gcggtctttg ccagcaccag gcgggcgccc gcgagcagcg tgacgaagat ttccatgatc    28620
gagccgtcga agcccgggga gtagaactgg acgaagcggt cggcggaatc gaaaccgaat    28680
gcgtccacgt ggtactgcgc catgttcagg agccctgcgt gttcgagcac gacgcccttg    28740
ggcacgcccg tggagccgga cgtgtagatg atgtatgccg cgtcgtccgg ccgcaccctcg    28800 acctgcgcca tgccgacgc gggtgccagc gtgtcgagct ggaagtcgag ggcgaacatc    28860
gggatcgccc agaaatcggc gagcaacggc aggtgttccg agtgcgtcag cagcgccttg    28920
accttcgcgt cctcgatcat gaagcgcagg cgctcccgcg gaaattccgg gtcgagcggc    28980
agatacaccg cgcccgcctt gagggcgccg agcatgccga cgatccagcg ctcggaacgg    29040
tcggccacca cgcccaccac gtcgccgcgt tcgatcgcgt attccgcgag caggaagctc    29100
gccagccggg acgcctggtc gtcgagttcg gcataggtca gcgatgcgtc ggcggtcacc    29160
accgcgacgc tgtccggcgc ggccgcgacc cgttgcgcga actgctccag gaaggtgccc    29220
tgtaccgcga cgggcgccgc atgcgaacgc aggcgcgcgc gctcttcgtc gtcgagcagc    29280
gagacggtgt cgagcggcgc atccagtgcg ccgaagccgg ccacgacgtt gcgcaggtgc    29340
cgtgcgacat gctggagata gtgcagcgtg aacaccgtcg gccggcccgt cagcacgatc    29400
tcgtagcgct cccgatgccg gatctcgatc gacaggtcgt agtcggccgc tgcccaggct    29460
tcgtgaaggc cgtcgaagcg cacgccgacg ttggtcgcgc gccgttcgcc atgcagcttg    29520
tgcgcgaggg cggcgatcgg gaaatcctgg tacgaatagc tgcgctgcac gctgtcgcgc    29580
agctggttca ggtacgcgcg aaccgttggg ccgggctcgc cggcgtcgag cagcgggaca    29640
ggctcggcgc agccgctcgc gggttcgacg atcagctgcg gcgacgccac gaacaggccg    29700
```

```
gccgcgccgt tgtagcgccc cagcacgcgg aacagcgcgg ccagcagcac gacgaacgcg    29760
cccagctcgt tgccggcggc gagccgctcc agcacctgcg ccgcgtcgcc gtcgagcgcg    29820
aacgtcagtg ccggctcggg gccgagcggc agcgcatacg cctgccacgc ctgctgaagg    29880
cggaaatctt catcgatgcg accgagcgcg tcgttccaga acgccacgtg ttcctggtat    29940
tgcccgctgg tcgagagcgc gttgagattc agttctgaca aagcacgatc tccctcgtcg    30000
cgtacaggat ttcggaagcg atgcccttgg ccttgcagtg cgcgacgaac tgggtggact    30060
ggatgtggct gggcgagttt tcgtcgaagg tgttgtcgag gaggtggttc agccagggct    30120
cctgacccat cgcatagaca tacgccgcgt tgaacgcgaa atcgtccacc agcgcggcgg    30180
cctcgccgaa ctggcagccg cgcgcccggc gtgattgatc gatgtcgcgc ggcagcgcct    30240
tgggaaacag cgggccgtag acccatgacg gcggcgcgcc ctcggtttcc atcccgacga    30300
acagggtgtc cggcttgccg gcgaggcgga agacatgctc gtagaggcgc gggtccaggt    30360
tgcacgaatc ggcgatgcac agcaccgagc gcgagccgaa gcggatcatg aagctctgct    30420
tgctgtggat cgccaggtcg ttgtgttcgc ccatgaacgg aatggcggtg atggcgccgc    30480
cgggcacctt gatttcctgc gcatcccgaa cttccagcac gtcgtcgaag ccgagcttgc    30540
gcaacgccag ctccatcgac ggatcttgcg gaaagccgtc gagattcctg ccgaccacca    30600
cggtcttgac cttgtggcga agctgcagca gcgtttcgag gacgatgtga tcgtgatggc    30660
tgtgcgtgat cagcacgtag tcgatctggt ccggcaggtc ggcgaacgta tagcgcggca    30720
gcgcggtgtc gtagccgtag ctgatcaccg gatcgatcag gatgctcacg ccccggctct    30780
ggatcagcac gcacgcgtgg ccgtagtagc ggatgcggat gtcgtcgccg tcgaacgaac    30840
gatccggttt cggcgccggc gcctcctcga cgaagaacga gcggaacagc ggctcgtcct    30900
tctcctccac gcgcatcagg tcgacgatct tcgcgtagct gccgggcgtg tcgcgcatgc    30960
ggaacagcgt gtcgagcgcg cggtcgtcga aggccatgtt gctgaacacc gtgcgctcgt    31020
cgcggagccg gggcgtgctg aggatgaacg gccgcggcgc gtgctcctcg atcgccgaca    31080
gcgcgatgct ctgcgcatcg cgcgcataga acgggctcgc gtacagcagg ctttcgaaca    31140
cccgaaggga cgggttgtgg ttcaggtcgt agtagatctc gacatagccc ttcagcacct    31200
ccggaatctc ggggtagagc gggtccgacg ccatccccgt ggcccgttcc agcagcagcg    31260
tggagaacgc cttgtatgcc ttcgccagtt ccagttgccg ggtcgcgcgt gggtggtct    31320 gctcgatcag cgtgcggatt tcgtcgacgc gctggccgcc caggtcgagg aacggcccgc    31380
cgcgcatcgc gggatccttg caggccgccg catgcatcat cggcgatgcg gcataggact    31440
tcagcagcgg caggaaccgc tccgccacgt tgagggcggc ggtcaacggc ggaagcgtgt    31500
gataccacgc gtaccagctg ttgatcagcg gttcgaactg gatgttttgg cgcaggtaga    31560
cctgcgcgct ggacgaaata gtcaacgaag gctccttaga atgcgctgag ttcgacggtg    31620
ggctggcggg cttcggcgtg cagcgcgcgt tgtcccaggg tcaggttccg gatgcgaacg    31680
cccggattgg cgagcacctc gccgatgacg gacgtcagct cgttggcgag gccttgcacc    31740
agggcttcgc tgaaccgccc cgcgtgatag acgacgcgga tcgcgagacc ctcggcgtgc    31800
ggctcggcca ggaaccagaa atcggttgcg gcttccgtgt ccgcgcgctg cgggtcgtgg    31860
tccggcagct cggcgatatg cacttgtccc gcgtagcgat cgacggggcc gtgtcgctgg    31920
ttctgcagcg tcaggccgat gtcgaagagc ggattgcgtc ccgccacgcg tttgatgtgc    31980
agctcgtcga gcaggcgatc cagcgggtac agcgggtgcg agaacgcttc gagcgtggtg    32040
tcccgcaccc gggtcagcag cgtgtcgaac cggtcgtcgc ccgcgacacg atcgcgcagc    32100
```

```
gccagcacgt tcaggtaggg gccgacctgc gactcgagtt cgggcagttc gcggcccgcg   32160
accggcgtgc cgacgacgat gtcctcctgg ccggagcggc ggtagaacag cgccttgatg   32220
gcggacagca gcgcgatgaa caaggtcgcg ccgtggcgct tgccgagcga ttccagcgcg   32280
gccgtctcgg cggcgggcag gtcgaatcgc caggatttcc agctcggcgc ggccggctgc   32340
tcgacgtcgc ccggcagttc cagtgcgcgc aggccgccgc ccagtttggt cagccagtag   32400
tccttcatgc gcgcgccgtc cggcccggcg agcaggcggt tcagccagcc ggcgtaatcc   32460
ttgtactgga tcgggagggc gggcagcgga tcgtcgcgac gctggacgaa tgcgtcatag   32520
agcgcggaca ggtcgtcgag cagtacctcc gtggaccagc cgtcgctcac gatgtgatgc   32580
atcgtgcaga ggcagacgtg acggacttcg gagagcctca gcagcttgac gcggaacagc   32640
gggccggtcg cgagatccat cggcacgagc cgttcgctcg cctggatcgc cgctgcctgg   32700
gcatcgcggt cctcggcatc ctgcagatcc acgatctcga ccgggaacgc ggcttcgccg   32760
ggcggcagca cgtgctggac cggctggttg ccttccagca cgaaacgcgt gcgcaggatc   32820
tcgtgacgct cgctcaacgc gcggaacgcc cgcacgagcg catccacgtc cagcacgccc   32880
tcgaacagca gcgacgtggg cagcggcccc tcggcttgcg ccgcatggag cgatcctgg    32940
acccacagcc gcgtctgtgc gggagagagc gcgtagcttg cctgcgccgg cagcggcgtc   33000
accggcgcgt aatcgatcgg ctgcgtatcg gcgatgcgct tcgcgaggct cgagatggtt   33060
gggagtgcga acaggctgcg gatttccagc ttcacatgca gatcgcgccg gatgcgcgcg   33120
acgaccttcg tcgccagcag cgaattgccg cccagatcga gaaattgcc ggtcgtgctg    33180
atccgcgcct ggccgagcac ttcctgccag atggcagcca actgcgcttc gagtgcgttg   33240
acgggcgcaa cgtggtccag gccgtcgccg ggttcgggca gcctggtgcg atcgagcttg   33300
ccgttgggca gatgctcgaa cgcgctcacg acgacgaacg cggagggcac catgtaatcc   33360
ggcagccgct gccgcaggtg gccgcgcacc gcttcgatca gttctgcttc ggggtgcgac   33420
gagcacagcc atccgaccag tctcgcgccg tcgtccacgc cgcgcagcgc gacgacggcg   33480
gcatcgacca gcgggtgcga cgtcagcgcc gcctcgattt caccgggttc gatgcgcagg   33540
ccgcgcagct tgatctggtg atcgatgcgg ccgaggaact cgatgttgcc gtcgggccgg   33600
tagcgcgcga ggtcgccggt gcggtagagg cgcgcgagcg ggtcggccga gaacggatcg   33660
gcgatgaact tttcggcgct cagttcgggt tcgccgtggt agccgcgccc gaccggtgtg   33720
ccgccgatca gcaattcgcc ggccacgccg atcggcgtgg gctgcatctg cgcgtcgacg   33780
atgtagaggc gggtgttggc gatgggccgg ccgatcggca cgatgcggtg cggatcgtcg   33840
cgccggcatt cccacgcggt cacgtcgacg gcggcctcgg tggggccgta gaggttgtag   33900
agctcgacgt ccaggcgctc gaggcaacgc tgctgcaggt catggggcaa ggcctcgccg   33960
ctgcacacga cgcggcgcag cgacgcgcag tgcgcgtcga ggtccggatg atcgaggaac   34020
gcgcgcagca tcgacggcac gaaatggatc gtggtgatgc gttcgcgctc gatgagctcg   34080
accaggtagt cggtctcgcg ctggccgccg gggcgggcga acacgaggcg cgcgccggtg   34140
acgagcggcc agaagagttc ccagaccgag acgtcgaagc tgaacggggt cttctgcagc   34200
acggcatcgt cggcgccgag ggcgtaggcg tgctgcatcc agaggatgcg gttggtgatc   34260
gcgcgatggg tgttgagcgc gcccttgggg cggccggtcg agccggacgt gtagatcatg   34320
taggcgaggt tgtcgccgtt cagcgcgggt cggggttgg acgtcgccgc ggcgtcgagg    34380
tcgagcgagt cgcgatcgac gacgatcacg tgcgcgtcgg tgtcgggcag cgcgtcgtgc   34440
```

```
agatgctgct gggtgaggag ccagcgcaac tgcgcgtggt cgatcatgaa gcgcacgcgc   34500
tcggcggggt agtcgggtc gacgggacg taggcgccgc cggccttgag gatcgcgagc    34560
agggcaacgc tcatgtcgag cgaacgctcc atggcgacgc cgacgagcga gtcggggccg   34620
acgccgagcg cgacgaggtg gtgggcgagg cggttggcgc gcaggttgag ttcggcgtag   34680
gtgagcgcgg tgtcatcgaa gacgatcgcg acggcatcgg gcgtgcgctc gacctgctgc   34740
tcgaacaggc ggtgcagcgg ttgcgcgcg tcctcgccga aatccgtgtc ggtgcggttc    34800
cactcgacgg tcagcaggtt ccgctccgca tcgctcgaca acggcagacg ggcaacggcg   34860
gccgacgcat cgtccgcgag atgcgtcagt agggtccggt agatgtcgag gaaacgctgc   34920
accgtgctcg cgtcgaacag atcggtgttg tagtcgcaat cgatcaggag tgcttgcccc   34980
gcgtcgagca cgttgacgtt caggtcgaac gcggtatggc ggatcagcgg cgccacgagg   35040
ccgaccgtca ggccgggcag ttcgggcagc gccgacacgg gttcgaggtt gaagaccgcc   35100
gataccagcg gcgcggcgtt gagatcgcgc tgtgcgccga tttcgcggac cagttcggcg   35160
aacggataat cctggtgctc gagcgcgtcg agcaggttct gccgggtgcc ggccaggaaa   35220
ctggccacgg tggcctgctc cggcagcgtg gagtgcagcg gcagcagatg cgtgcagtag   35280
ccggcgaggc gatcgctgcc ggccaccgag cggccggtca ccggaatgcc ggtgacgatc   35340
tcctgctggc cggcgacgcg gtgcaggaac agattgaagc cggcgagcag caccatgtag   35400
agcgtgcagc cgttctgacg ggccgcggtg cgcagcgtcg cggccgtcgc cgcgtccaga   35460
tgcagggaca cgcgctcgcc gtgaaacgtc ttcaccgcgg gccgcgggta gtccaccgga   35520
agattcagcg gtgcggcctg acgcgcgcat tgcgccagcc agtactcgcg attcgccttc   35580
gtttccgggc tgtggcgctg gccgtcgagc tgcttcaggt acgcgcgaaa ctgcagcggc   35640
gcgtcggccg gcgccgcacc ggcatacgcg cgggccagat cctcgagcag cacgccgaac   35700
gtcgagccgt cacagatgat gtgatgggcc gtcatcacca gcaggtgacg ctcgctgccg   35760
aggcgcacga gcgcggcccg aaagagcggc ccgttcacca ggtcgaacgg ctggcggctt   35820
tcctgctccc gccacgcgtt cgggtccgtg tcgatcagcg gaatctcgag tgtcagcgac   35880
gggtgcacga tctggcccga cccgtccgcc atcaccgtgg tgcgcagtgc ctcgtgccga   35940
tcgacgaggc tctggacggc cgcgcgcatc gcggcttcgt cgagccggcc gttcagttcg   36000
agcgtggtgt tgacgttgta ggcgagcgat ccttcgggat cgatttccga caacacccac   36060
agctggcgtt gcgcttcgct cagcgcggcc accgtgccgt gtttcgagtg cggccggatg   36120
aagccgcccc ggcgcaggtc ggcgacgctg tccttcaccg cccggatgaa gcggtcgata   36180
tcggcatcgg tatgcgcggt ggacaggaag caggtgcgcc attcccagat gtagatgccc   36240
ttttcgagca tgtgatagaa gaacaggtcg aggttctcgg tgaattcgaa gcggaacatc   36300
gagccgaacc acgtgaccttt gatcggcgcc tcggcctccg cgaagaatgc attcagcgtg   36360
ccggcgatct gcgcggtgcg ttcgttgagc gcggcctgca gcgccggccc ctcctgttcg   36420
atcttctcga gcacggccag cgccgccgcc atcgcgagcg gatactggca gaaggtgccg   36480
ccgaacgcgg tgcggtccgc cgcggggaac gagtggtcgc cgtaggtcca catgccgccg   36540
tcgatggcat ccatgaagcg gctggtgccg gcgatcacgc ccagcggcag gccgccgccg   36600
atgatcttgc cgtacgtcgc gagatcggcc ctgatgccga acatggcttg cgagccgccc   36660
ggatggacgc ggaaaccggt gatcatttcg tcgaagatca gtgcgacgcc ggcctcctcg   36720
gtgatgcgac gcagttcctt gaggaatgcg acgggctgca gggaagggtt gcggctctgc   36780
accggctcca ccatcacggc ggcgagggtc gacgccatcc cgcgaatggc ctcgagcgcg   36840
```

```
gcgtcgctgc cgtagtcgag caggatcatg ttctcgacgg agccgaacgg tacgcccggg   36900
gcgatggttt ccgtcacgcc ttccgcgttc gccgcggcga gcgtgccgtc ggcatggccg   36960
tgatacgaat gcgtgaacat cacgatcttg tcgcgcccgg tcacggcgcg cgcgagccgc   37020
atcgcggtca tgacgccctc ggtgccggtg ttcgagaacg ccacgcgatc gaggccggtc   37080
acgcgggcaa agcgcgcggc gacttcgccg acgaggctgg agcgcgcacc cagttcgagc   37140
gggcgctgcc attcccgcgt gacctgctgc tggatgaaat ccggcgtgtg gccgaacagg   37200
tgcacgccga agcccatcgt gaaatcgatg tactcgttgc cgtcgatgtc ccacagccgc   37260
gaaccggccg cgcgatcgcc gacgatcgga tacagcatct ccttggtcga aaagcggaag   37320
ccgaccgtgg cgcggctgtc ggccagcacc gggcgcgacg cctgcaccga gtccttcgat   37380
ttccgggtgc gcgtcgtgta gcgcacgatc agcgcctcga gatgctcctg ctgcgcgggc   37440
gacagcccgc gcgcccgctg ctggaccggg ctgccccacg gcatcatcgg cttgggcggc   37500
gggttgtcgg ccgcgggcgc ggcggcagct gcaggcgcgg gcttcgccgc gggtgcggcg   37560
gccggggccg cgctcgccgc tttgggtgcg acgctcgccg tgctcgcgac ggcttgcacg   37620
gcggccgtcg ccgccggac gccgggctgg ccggtcagcg acgtgcgcag cagttccatc   37680
tgctggctca tcacgtgcga cagcagctga ttctgctccc gcagcacgcg ctcgaccgtc   37740
gagccgcctt cggccgccac ccattccgcg ggggcggccg cgagcggcgc aagcccgcc   37800 gcggacggcg tgaccgcgac cgccggcgtg gacggttccg ccgcggccac ggctacggct   37860
acggcctcgg ccccggacgg tgcggcggct gccggcaggt tgtccgcgac atattcggcg   37920
agcgcctgca ccgtcgcgag gtcttcgaag aagcggcgca tggccagctt cacgccgtac   37980
tccgcctcga tgtgccggat ggcctcgatc agcacgatcg agtcggcgcc catctcgagg   38040
aagggcagtt cgatgttgat ggtggcggga tcggcctgga tcaattcgcc gatcttgccg   38100
cgaagccatt cgagaatctc gccgctgcga ttgtgcgtcg gtgctgcggc gatgggtgat   38160
gcgcttgtct gagtcatgga cgtgtccgct ttctggaacc aggtacggct gcgttggaag   38220
ggataggacg gcaatgcgat gcgcgcgggc gcggtgttt cggtcggggc ccagtcgaca   38280
tcgacgccgc gggcatacag gctcgacagc gtttcgatca gcgcttgctg ctcgacttgc   38340
ggccgctgca gggcaaggaa ctggatcccg gcgtccggcg cacagcacgc gcgggccagg   38400
ttgacgagca ccggcttcgg gccgatttcg accagcacgt tgaaaccggc ttcggcgagg   38460
cgctcgacgc tgctcgcgaa ctgcactggc tcccggcagt ggcggcgcca gtacgtgtcg   38520
gtgggtgcct cgtccatcac ggcgcccgtg agattcgaat agaacgggat cgccgggcgt   38580
gcgacgggca cggttttcgc cgcgagctgg aagctgtcca gcatcggctc gagcagcggc   38640
gagtgaaacg cgtgcgacgt attgagcggc acggaccgga tgtcccgcgc ggcgaacgca   38700
tcgaccagca tcgcgatgcg ctcgcgcttg ccggaaatca cgatgctcgc cgggccgttg   38760
acggccgcca ccgcgacctc gtgcggccac gcgtcgatcg cgcgctcgac cgtggcgagg   38820
tcggtgaaaa tcgccgccat ctcgccgtcg cggggcaacg cctgcatcag ccggccgcgt   38880
tcggcgatca ccgcgcaggcc gtcttccggc gagaagacgc cggccgcgca agccgccgcg   38940
tactcgccga cgctgtggcc catcacgcg tcgggcacca cgccgaacga cgccagcaac   39000
gtggtgagcg cgtactgcag cgagaacagg gccggctggc tgtagccggt ctggtggatg   39060
tcctcgccct gggccgacag cacttcgagc aacggcttgt cgagcaacgg atcgccacc   39120 gcgcggcaac ggtcgatggc gtctcggaac accggatacg cgtcgtacag gcggcggccc   39180
```

```
atgccggcgt attgcgagcc ctggccggtg aacaggaagg ccatcttcac gcggggggcg    39240
ggctgcgccg cgccggccgg ttccttcgcg tggaaggcgc gcagcttgtc gatggcgtcg    39300
tcgagcgacg tcaccggcca tgccagccga tgcgcgaaat gcgagcggcc ggtcgccgcc    39360
gaaaaggcca cggccgcgat gtcgagaccg ggttcggctt cgagccgccg ctgatagcgc    39420
ccggccagct cgcgcaacgc cgcgggggtc ttggccgaca gcaccagcgg atgcaccttg    39480
tgtctcgacg gcgtcgcctg ccgcgccggc gccggcgctt cttccagcac caggtgggca    39540
ttggtgccgc tcgcgccgaa cgcgctgacg ccggctcgcc gtggccgttc gccacgcggc    39600
cacgcgctcg cctcggcgca gatctcgacg ggcattgcgt cccactgcac cagcgggctc    39660
ggctggcgga aatgcaggtg ggcgggcagg cggtcgtggt tcagcgacag cacgaccttg    39720
atgacgcccg cgatgccggc ggcggactcc gtgtggccga tgttggtttt caccgagccg    39780
acgcgcagcc gccggcccgc gtcgcggcct gcgccgaaca ccgtcgccag cgcctgcaac    39840
tcgacgggat cgcccagcgg ggtgccggtg ccgtgcgctt ccacgtaatc gatggacgcg    39900
gcgggcaacc cgcccagcgc ctggcggatc acggcttcct gcgcacgacc gttcggcgcg    39960
gtaaagccgc tcgacgcgcc gtcgtggttg accgccgaac cccgcagcac ggccagcacg    40020
cgatcgcccg cggcgagcgc atcggacagg cgcttgagca ccagcgcgcc gcagccttcg    40080
ctgcgtacga agccgtccgc cgccgcgtcg aaggtcttgc agcggccgtc cggcgccagc    40140
gcccgcgtgc gcgagacggc gatggagttg tccggcgaca ggatcaggtt gacgccgccc    40200
gcgatggcga gatcgcactc gccgctgcgc aggttctggc tggcggtatg gatcgccgtg    40260
agcgacgacg agcaggcggt gtcgatcgcc atgcttggcc cctgcacgcc gagtccgtag    40320
gagatgcggc cggccgccgt gttcagcggg ttgccggtga agaaatagcc gtcgatgccg    40380
ctgccgccgc cgttgcgaag ctgcaggttc gcgtaatcgt tggtggtgat gccgacgaac    40440
acgccggtgc ggctgcccct gagactgtcg accggaatgc cggcatgctc cagcgcttcg    40500
tgactgacct cgagcaacag cgcgctgctg cggtccatcg cggccgcttc gcgcggcgtg    40560
atgcggaaga acgccggatc gaactggtcg acgtcgtcga aaaaccgcc gaagcggctg    40620 tacatacgcc ccggcgcttc cggatcggga tcgtagtacg cgtcgacatc ccagcgctcg    40680
cgcggcactt cggagatcgc atccacgccg tcgttcagca ggttccagta ggcgtcgaga    40740
tcgtgcgcgg cgcccggaaa ccggcagctc atgccgacga tcgcgatcgg ctccggcgtg    40800
ccggcgtcgc gggcctcgat ggccggcgcg atcggccgcg gctgctgctg cggcggcacg    40860
gtctgcgcct gcgccgtgcc ggacgcctgc tccgccagga aatccgcgag ggcgttgacc    40920
gtcggatgat cgaacaacag cgcgaccgac agcgggatgc ccagcgcatt ttcgaggtgc    40980
gtgcgcacgt ccagtgccat cagcgaatcc atgcccatct cgaagaagcc gagatcgcga    41040
tccagcgtcc ccgcgtcgta gcccagcacc tgggccaccg cgcgatcgat gctgtccgcc    41100
agcagccgct ttcgctcgcg cggcgatgcg tcgctcagcg ccggcattgc cggcgcgctc    41160
ggcgcgcttt tggccacccg cacgtggtcg aggaacggct tgggtccgcg cgcctcgtag    41220
gagccctgga acagcgccag gtcgatatcg acgaccgcga cctggggcac ggcggggaga    41280
cgattcagca cgtcgagcgc gcgatccgcc gccagcgacc ggatgccgac acgccgcagc    41340
agcgcttccg cctcggggaa cgtcatgccg ccttccgccc agggccccca gttcacgctc    41400
agcgccggca ggccctggcc gcggcgatga tgcgcgagcg cgtcgaggaa acggttcgct    41460
gcactgtagt gcgcctgctc acgcgagccc cacgcggacg cgatcgacga aaacaggagg    41520
aagaaatcga gcgggaagtg ctcgctctgc tgatggagca gccacgcgcc ggcgaccttc    41580
```

```
ggttgcagga ccgcgtccag ttcgtcgcgc tcgacctgca tgatcggctt gtagccgacg   41640
atgccggccg cgtgcacgat gcctttcagc ggcacgccgt cgcgccgcag cgcggcgaag   41700
aaagcggcga ccgctgcggg gtcggcgata tcgaggcgct cgcagcgcag cgtgacgttc   41760
cgctcacgca gctcggcgat cgcccgctgg ctctcgtcgc tcgcggcccc ttgccggccg   41820
accaggatca gcgtgcccgc accgcgcgcc gccagccatc gggcggtgtg cagcccgagc   41880
gcgccgaacc cgccggtgat caggtaggcc gcgtccgggt cgaccggcag cgcggccgtt   41940
tcggctggcg cgagcgggct caggcgcgcg acatggcgcg cgccgtgccg caacgccacc   42000
tgctcctcgc ggctctcgcc gagcatctcc tgaagcagtg cctgcgtctc gttctccggc   42060
gcggccggat cgagatcgat cgcggtgccg aaccattccg gatgctcgat cattgccccg   42120
cgtgcgaggc ccgacagcgc agcctgggcg agcccggata cgtgcggcgc ttcgccggct   42180
tccaccgcgt cgcgcgtgac caccgagatc ctgggccggg tcgaaggcgt ccactcgcgc   42240
tcgctgccga ccagcgcgtg cacgagatgc agcaggcgg cggacatgcg cgtttcgccg   42300
acggcttcgt ccagcgccca taaaaagacg atgcgctggc cggaagcggc ggtttcgttc   42360
agcaagcgga cgaaatcgtc cggccgctcg ggcgcgacct gccagcccgc ttccgcgccg   42420
gtgacatagt cgatgccggg gcggaccagc gagcaggatg cgccgcgcgc gcgcagcagc   42480
gctgcaagcc gctcgccgac accgctcgca tccgcgaaga tcagccacgg ggacgcgtcg   42540
gcggcggccg gtgccgccgg catcgcggcc tgctgctccc acaccacgtg atagagcggg   42600
tgtgcgttcg acgcgacggt ctcggcgcg gcgaatgcag tcctgagcag gtccggaaac   42660
gcgttcagca tgtcctccgg gtacttgccg gacgacttga ggtgccgcaa cgctgcgtcg   42720
atgctgccgg catccatgcc gacgatcggc gacggaatct tctccaggct gaagcgctgc   42780
cgctcgaacg ggtagttcgg cagggtcgtg gcgggctggg cgggcgccgg aaacagcgcg   42840
cgccagtcga actgcgcgcc ctgcacgtac agccgcgcga gtgcgcgctc cagtgcatcg   42900
cccgcgcagg gcggcggcag ccagccgtcg gcgagcccct ccggcgggtg cgatgcgtcg   42960
gcctgatccg acgcgccagc cagttgcaac cagtactgcg ggtgcgtcac ctcgtcggtc   43020
acgtcggtgc cgagatagcc cgaaatcagg cggaccgacg gccgtgcgag cggcatgtcc   43080
cgaagcacgg cgcgcaacgc ttcggcatcc gaacgggcgg ccacgaggcg cagcgcgtcg   43140
gccacgctca cgacgcccgc cacgcaggcc gcgacatatt cgccgatgcc atggcccgac   43200
acgacggccg ggcggaggcc ccatcccttc cacagttccg cccacgcgaa ctggatcgcg   43260
aaccggcccg cgtcggtctc gagtgcgtcc agcggcaccg agcaacgcgc gaacgcgtcg   43320
cggaacagcg gttccgacgc gtggagcgcg tgcgcgacgc cggtgtccgg cacaccgaac   43380
ccgaagccca tgcgcaacgc cttgcccgtg cgcggcgcgg ccgccgacgc taccctcgcg   43440
cccgatacat aggcggcgcg aaacggatag tgactccgcc cggtggcggc ggcacggcag   43500
atcgcggcta gctcctgcgg cgtcgcgccg cgatcgcgc gctcgtagcg tggcacgagc   43560
gccgccagcg ccgcttcgga ccttgccgac agcagcagca acgcgcgctg cgcggcgtgt   43620
gccggcgcga cgggcggttc ctcgacgatg gcgtgggcat tggtgccgct gaatccgaac   43680
gcgctcaccc cggcgatgcg cctgcgttcc ccgcgccgcc acgcgaccgg atcggccgcg   43740
acgcggatcg ggatgtcctg ccacggcgta tgcggattgg gttgcgtgaa atgcaggtgc   43800
gccggaatcc ggtcgtgctc gaacgacagc agcaccttga tcaggccggc gatgccgag   43860 gccgactcca gatgcccgat attggtcttg accgaaccga tcacgagcgg ctcgttcgcc   43920
```

```
gcgcgcccgg ggccatagac gccggccagc gcttcgacct cgatcgggtc gccgagggac    43980
gtgccggtgc cgtgggcctc gacgtaggac acgtcgccgg gcgcgaggcc ggcctggttc    44040
agtgcgcggc ggatcacccg ttcctgcgaa tcgcggctcg gcacggtcag cccgccgccc    44100
gcgccgccct ggtcgaccgc cgtgccgcgc acgatgccga gcaccggtc gccgtcggcg     44160 agcgcgtcgg cgaggcgctt gagcaccacc atgccgcacc cttcgccgcg cacatagccg    44220
tccgccgccg cgtcgaaggt cttgcagcgt ccgtccggcg acagcatgcg cgcctgcgag    44280
aagctgacca tgacctcggg cgacagcatc aggttgacgc cgcccgcgag cgccatgttg    44340 cttcgcgcg agcgcaggct ttcgcaggcg aggtgcaggc acaccagcga agacgagcag     44400
gcggtgtcga tcgccatgct cgggccggtg aggcccagca cgaacgacag ccggcccgcg    44460
gccatgttca gcgcgctgcc cgtgccggca tagctgctcg acggcatcga cgcattggac    44520
acctggatcg cgtggtcgaa gcaggtgatg ccgacgtaca cgcccgtggc ggactgccgg    44580
aagcgttcgg gcgcgagatg ggcgttctcg agcgcctccc acgccacttc gagcaggagc    44640
cgttgttgcg gatcgaggta ggtcgcttcg cgcggcgcga tcccgaagaa cgccgcgtcg    44700
aattgatcca cgccgttcgag aaaggcgccg tggcgggtcg ccatcttgcc gggcgtggac    44760
ggatcggggt cgtagtagcg atcgatgtcc cagcgttcgc cgggcacttc ggtgacggca    44820
tcgtgcgcgc cgtcgagcaa ttgccagaac gcgtccggcg tatcgctgcg tccggggaag    44880
cggcaagcca tgccgatgac ggcgatcggc tcgttgcggt cagaacgcag cgccgcgatt    44940
tccgcgcgcc gcaggcgcag ttcgtcgagc gcggctttca gtgcatgcgt ggccttggcg    45000
ttcattgggc gccgatctcc tgggcgatca gttcggaaag gtcgtcctcg tcgaggtcgt    45060
cggatgcttc gtcgacgacc ggcgcgggga cgacggcga cagttcgttg agcacgtact     45120
gggcgagcgt ctgcaggttc ggataggaaa agaacaacgt cgcgcgaaac ggtcttccga    45180
ataccttggt gaggcggtcc gtcagttcga cgcgaccag cgaatccagg ccgagatcga     45240
gcagcgattg ctcgggcgcg atggcatcgg ggccggaaag gcgcaaggtt tcagccagca    45300
tcgccgcgag cgtgtcggtg atgcgctcga cccgttcgcg cggcgcgcac gcatgcagct    45360
ggcgcagcaa cgccgtctcc tgctgcgccg gctgcgcggc cggttgcgtc agctcggaaa    45420
acagcgcgga cccggcggcc ggcgcatcga cccggaacag ggtcggccag tcgatccgcg    45480
cgactccgga ctgggcgacg ccggacgcca tcagccgttc cagcgtcgcg atggccagtt    45540
cgggcggcag cgtgccgacg ccgagcgcgc cgagttgttc gtgcgcgcgc cgtccgtagt    45600
cggtggcggc gtgccgatc tccgcccacg gcccccaatt gacgctgagc cccggtttcc     45660
cctgcgcgcg ccgatgctgg gcgagcgcgt cgaggaagct gttcgccgcc gcgtagttgc    45720
cctggcccgg catggtgatc agcgcggcca tcgacgagaa caggacgaaa tggtccagcg    45780
gcaagccggc cgtcagctcg tgcagatacc acgcgccgtc ggccttgccg ctgccggcgc    45840
gatggaagaa gtcgtcgtcc tggcgtgtca gcagcgcatc gtcgagcgcg ccggcgaggt    45900
gaaagatccc tttgagcggc ggcatcgaat gcgcgatttc accgagcgcc tgcccgacgt    45960
cctcgcgacg cgacaagtcg gcgcgaatga accgtgcgtc gagcgtgcgc aggattttcc    46020
cggctgcggc ggaaggttcg ccgcgcccca gcagcacgat tttcccggcg ccgttgtcgg    46080
caagccagga cgcgagccgc aggccgagcc cgccgagccc gccggtcaca agataggtcg    46140
cgtcaccgtg gaaccggatc ggccggtggc tgacgtattc gcgattgtcg cgggcgatgc    46200
gcgcgacgta cgcgctggtc g cggcgaaacg cgatcatgtc ttcacggccg ccagcctgta   46260
ccgcttgcat gatgtccgct gccgacggct gctcgggatc gaggtcgacg agcccgcccc    46320
```

```
acagcgccgc atgctccacc gcgatcgcgc ggcccaatcc ccacagcggc gcctgtgcca    46380
ccgcgatcga ttcgccatcc agaacattca tcgcacccga cgtcaccagc cacaggcgag    46440
cctgccgggc cgacggcgcg cgtgacgcaa gcgccctgac caggtgcagc acgctcgcgc    46500
tggcacgccg tctcgccgcg atgtcagagg gtgcagatc gagactccac aggtggatga    46560
cgcccttcag cgggcggtcg gccgcgggca gttccggcgt cgcgtcggcg aagcgcagcg    46620
tgcacgtatc gccgtgggct tccagcagag ctgacagctg ggcgcccacg ccgccgcggt    46680
ccgcgagaat cagccactcg ccgtgcgccg aaccgccggt tgccgcgtcg acgttcgacg    46740
gtctccagac gcgttgataa agcagcgcgg cgaagtcgtg ccgctcgacg gcgcgcgccg    46800
cgcgaacctg ttgcaaccgc agtgcatcga tctcgatcag cagtcggcca gcaaggtcat    46860
ggacgcggat gtcgccctcc agcgcgccct gtccgatcgg cgtgcgcagc gtggcgtgac    46920
tccatgcctc ggtcgacgcc ggcggctgat ggacccgtac cgcgccgatc gagctgggca    46980
ggtacaggtc gcccgactcc agcgcgtccg gatcgatggc ggcggcgagc acgcggctgc    47040
atgcgtcgag aaaggcgggg tgtacctggt acggcgacga cgccagcgca tctgccggca    47100
ggctgatttt ccccagcgcc tcgccggtcg tgcgccagat ctgccggatc gcgtcgaaca    47160
cgccgtcgat ctgcacgccg tgctgccgaa tttcgccgtt gaagtccgcg cccgacgtcg    47220
tttcggtgca gcgggcctgc acctcggcgg catcgaatcg cgtcggcgcg gcggatcgcc    47280 gggggggcaca catttcccgg agccggcgca gctgcggaag attgccgagg atccgctcga    47340
ccggcggacc gaaatcgagc aggcaggcca cttcatccac gccgatcgac tcgagatccc    47400
gcaccagttc gacgcaggtt tccggcgtgc cgatgagccc gcgcgattgc gcgaagcgtt    47460
catagagaaa ctcgacgaac tcgtccagct cgcgtgcgcc catcgcgcgc acgtcgaccg    47520
actggccgcg actctgcgcc agcccgttca atagcccgat attgctgcgg atgtagttgc    47580
agaacggcac acgcgcctgt tcgcgcgcct gcgccgcatc gtccgcgacg aacgtatgca    47640
gcatcacgga aacggtgccg gccgccggat cgaagccatg cttcgcacgc gcctcgcggt    47700
agagcgcgat cttgtgcgcg agctggtcac gatcctggtc gagcacgtgg gtcagcaggt    47760
tggcgccggc ttcgccggca cgcacgaatg tctgcggatt gctcgcggcg gtcacccaga    47820
cgggcagctc cggctgcacc ggcgtcggat agacacgcaa ccgcaccggc ttgccgacac    47880
cgttcgtcgc atccagcgtg ccgccgcgcc acagatgctg gacggcgcgc atcgtggtca    47940
gcatgtcgtc ctgccgggtc gcatatttgt ccggggcaaa cacgaagtcg tcaggattcc    48000
atccggaggc gaacgacacg cccacgcggc cgttcgacag gttgtccacc atcgaccatt    48060
cttccgcgat ccggatcggg ttgtgcagcg ccgcgaccac gctgcccgcg accagcttca    48120
cgcgctgggt ggccgcggcg agcgcggcgt gcaggacggc gggattcggg taaagcgagc    48180
cgaattcggt gaaatggcgc tccggcaccc agacgctgga gaacccgttc gcatcggcga    48240
aacgcgcgct ctccatcacg agctggtact tgttgccgga cagcgcctct tcactgctgg    48300
cgaagaacat cagtccgaat tcatgcgtg gctccgatcc gattcgtgaa tttcggcact    48360
cgcgcacatc tgccacgtcg cggcggcgcg ggtgtcgtcg atccggtgat agacggcaaa    48420
cgaaaacggt cccaggacc ggcggctcag cacggtctgc acggtgtgcg attcgtgcgg    48480
atgcagcggc aacggcgcat gcagtgcgag gtccttcaac gtcgtatggc cggctgcgcc    48540
gatttccgac gttgccgaca cgccatttc cacgaaggcg gaatagggca ggacgggcga    48600
ccccttgacg cgatgaccgt cgagaaagtt ggttgccggc gcatcgagac gcgattgcca    48660
```

-continued

```
gatccacgtg gccggcgcat gcgcgtgctg ctccatgagg cgcccgagca acggatgccg    48720
acgcgcatgt ggcctgatcc agaagccgcg ccgctcgaac gggtaggtcg gcagggcgag    48780
ccggcggtgc ggtgcacctt gctccacggc atcccagtcg atggatgcgc cgcgtacgta    48840
gagcgcggag agcgtgtgca ggatcgcgtc ccacgcggcc gtgtgcgcgc cgatgtcgat    48900
cacgatgccg gggtgtcctg ccgcaccgct gtccggcgcc tgcggcacgc cggcccacgc    48960
ggctgcggcg cgctgcccgt cgccggtgct gctgaccgca tccggtgcga tgccgaagga    49020
catccacagt tgcgcgagcg cgcgctggaa tctcgtgaac ccggcttcgt cggggcgag    49080 cgcgggcgcg ccggatgcgt cggactgccg ctgcatcagc gcgtcgaaag cggggctggc    49140
cgcgcgcaat tgccgaaccg cgtcggcgct ggcgccgtcg tcggcgcaaa agtggaacgt    49200
caccgcgggc ggtgtttcgg caggctcccc ggacgaaacg gaatcaagtt gcgcacgcaa    49260
cgaatcgcga ctcggtgcga cgatggccgc gcgctgcgtg aagtgggtgc gcccggtatt    49320
ggccgtgaac gcgacatccc gcacaccggc ctcgggatgg gcgtcgagat aggccgcata    49380
ggacgcagcg agcgcttgca acgcgtccgg cgtgcgcgcg gagagcgtca cgacgcgcgc    49440
cgcgggtgca accggttcgg cttcgatctc cgggagcccg ggtgcttctg acaggatcag    49500
gtgcgcgttg gtgccgccga agccgaacga gctcacccct gccaggcgcg gcccgtgttc    49560
cgaatgccag ggcgtgacct gccgaggaat ccggaagggc gtgccgtcga gcgcgatttg    49620
cggattgatc gaccggaaat ggaggttcgg cggaatcgcg cgatggtgta gtgcaagggc    49680
ggtcttgatc aggctggcga tgcccgcggc cgattccagg tggccgatgt tggtcttgac    49740
cgacccgatc cagcagagat cgtccgggcg gcgggattcg ttcaggacgg ccgccagcga    49800
gttcaactcg atcgggtcgc cgagcggcgt gcccgtcccg tgcgtctcga cgaagccgat    49860
gtcctgcgcg cgtacaccgg catcgcgcag cgcgccgtga atcacggcct gctgggccgg    49920
gccattcggc gcggtcaggc cgttgctgcg cccatcctga ttcaccgcgg agccgcggat    49980
cacggcgaac acgtgtcgc cgttctcgag cgcatcgtcg agccgcttga gcagcaccat    50040
gcccacgcct tcgccgcgaa cataaccgtt cgctgccgcg tcgaacgcct tgcatcggcc    50100
gtccggcgac agcatgcccg cttgcgtgaa ggacgcgctc aattgcggcg ccagaatcag    50160
gttgaccccg ccggccagcg ccgcatcgga ctcgccgcgc tgcagcgcgc ggcacgcctg    50220
gtgaaccgcg acgagcgagg acgaacacgc ggtgtcgacc gcccagctcg ggccgcgcaa    50280
atcgagcgcg taggaaatgc ggttggcggc gacgctgagc gcattgcccg tcgcgacata    50340
agggccgacg tccgcgactt cgtcctgcgc cagacggatg tagtccgaat tgctgatgcc    50400
gacgatgacc gcggtgcgtc cgccggcgag gctgcggggt gcgatcccg catgctcgag    50460 cgtctcccag gccacctcca gcagcaggcg ctgttgcgga tccatcgatt cggcttcgcg    50520
ggcgctgatg ccgaagaaag ccgcatcgaa ttgatcgacc tgatccagca gtccggcgag    50580
cggaaggtcg gccgcgcgct gcgtcgccgc accaccgcg tcccggccct ccagcagaag    50640
ctgccagaat gcgtcgggat tgccggcgcc ggggaagcgg catcccatcc cgacgatcgc    50700
gatatccgcg cgtgcttcgg ccgagcccgg cgcctggtcc ggcatggcac tcccggtgcc    50760
gctcaaatgg cgcgccagca gggaaatact cggaaaatca tagacgacgg tcggggaaac    50820
cggccgcccg agccagtcct gcagctcgcc cgagagcatg atggcgtcct tcgaatcgag    50880
cccgtggacg ctgaacggcg cgtcgggggtc gatcttgccg gaagcgattc ccgacagacg    50940
cgagacacgt tcgatgcacc attgcaccag cgcttgcgtg tcgcgtggct cggcagtctg    51000 cggggggggct ggcggcgcgg agaacgcacg ccgccattcg cccgcgatcg cgagcccctg    51060
```

```
ttcatcgagg aatgcctgcc tgatccggct ccgctggatt tttccgctgg acgtgcgcag   51120
gatcgtggca ggtttcaaca ggactgccgc atacagatcg acgtcgtgca cttcggcgag   51180
cgtgtgccgg atctcggcgg ccacggcttc cgcgtccagc gtgttgagcg cttcccggcg   51240
cacttcacag gcgacgacga cccgctccac gttatcgacg tggatcgaga aagccgccga   51300
tgcgttcggc gccagcgcgg ggtggctgcc ctccgcggat tgctcgagat cctgcgggta   51360
gtgattgcgg ccggcgacga tgatgaggtc tttcaagcgg ccggtaacga agagatcctc   51420
gccatcgacg aagccgagat cgcccgtgcg caggtaacgc gcgtcatcgc cgtccagctt   51480
cgcgcggaag gtgcgctccg tttcgtcgat acggttccag tagccgacgc cgacactcgg   51540
gccggtcagc cagatttcgc cgatccggcc gggcgcgcag cgctcaccgg tatccggatt   51600
cacgatgcgc acgcggtgct cagcccaggt ccggccgcat gagaccagcg cgtggcgctt   51660
gccggagtcg tttctcgtcg ccacgccttg tgccagcgcg tcggcatcgt agtccgccac   51720
gcgcggcagc gagcgtgccg gctggccgga gatgaacaag gtcgcctcgg ccatcccgta   51780
gacggggcgc atggtgtgcg cgtggaagcc gcacgcggcg aatgcgcgcg aaaaacgcgc   51840
caccgactcc gcgcgcaccg gttccgcgcc gttgaatgca cccgccagc tgctcaggtc   51900 cagctgcgcg cgcgcttcat cggcgatttt gcgagcacac aggtcatacg cgaaatccgg   51960
cgcggcacaa tgcgtgccgc gatacttcgt gatggcctgc agccagcgca cgggtttctg   52020
cacgaatgcc gcgggcgcca tcagcaccga cagcacgccg agatagatcg gcagcaacac   52080
cttcccgaag aaacccatgt cgtgaaacac cgggagccag ctgacgaaca ccgtcgacgc   52140
atcggcatcg ctcgcctcgg cgatgaccgc catattgctc aggatgttcg cgtggctgat   52200
catcacgcct ttgggcgtac cggtggagcc tgacgtgtat tgcagaagcg ccagcgtctg   52260
cggcgtgatg tccggtgcgc gccattgttc ggccggggcg tcgaagcgct ggtccgtcgc   52320
caggatcttc agttccagcg tgtcggaata accgtccgcg tgatgcgcga tgccgtcgag   52380
cgtcgcggcg tccgtcagcg cgacgaccgg cgtggcgtcg gcgacgatgg ccttgagacg   52440
atcggcggga cgatgcctgc gcggtggata cgcgggtacg ccgatcaggc cggcgtacag   52500
gcatcccacc catgcgcaga tgaattccag cccgggcgga taaaccagaa ggacgcgatc   52560
gcccggttga gcgatggctt gcagcctggc ggcgatgccg cgagcccgct tgtccaggtc   52620
gccgaacgtg aggcgggtca gctccgcttc gccgttctcg agaaaaatga atgcggtctt   52680
ctccggttcg accttgccgc gaaacaacaa aatttctgta acagtcctga attttgtatc   52740
gggaagcatg ctcaaccttc gttgtcttct aaacgttgaa tatctcagga ccggttgtgg   52800
cgatcccgcc aagcgtgctt catcggacgg tatcgaaatt agagcattgc tctaatccgg   52860
cgtctgcccc gtaatccaag gacacggcgt ttcgcgcact ggatcaatac ggcttgtcat   52920
tgatgtgcac gctcgctaac gatcggcgat tccttcgatg tcgggcgtgt acgggtccag   52980
cagcgacacg acgaccttgc gctcgccttc gaacgggttg cggccatgcg cgaagcgcat   53040
gttgtcgacc agcaggacgt cgcctcgttg ccacggaaac gtgatcgcgc attcgcggaa   53100
cgcgtggcgg atctgctcga ggtcggcgag atcgaacgga ctcccgtcgc catggcaggc   53160
attgcgcgga atgcgatcct cgccgaacag gctgacgatc gaactggcga gcgatgcttc   53220
caggttcgag atatggaaca gatgggcctg attgaagaac accgctcgc cggtgaccgg   53280 atggtaggcc acgccctggt tgatctgcgc ggtgcgcaac gtgtcgtcgt cgagccattc   53340
gagcgcgatg ccgttatccg cgcagaaggc tgcaacctgg ttgcggtcgc tggtctggaa   53400
```

```
cacggtctcc cacggaatgt cgacgtgccg ccggtagtgc ctgacatagc ggacctgtct   53460
cgcctcgaag tgatccagga tgcgcggtcc gatcctgcgg ctcacctccc gcatgtcggc   53520
aatcggcgtt tcgccgccgg tcgcggccgg cgtcaggcaa cagaaggcca ctcgcagcgg   53580
ccagcttcgt tgatacgcgt tttcgcaatg aagggcgatc gtctcgctcg gcggatactc   53640
ggttgcggtg aagatgccgt tgccgatcga ggtgcgcggc gtggaacggt aaacgtagtc   53700
ggactgatgg gccgaaatcg cgcgagcaaa cgcttcgaag ccgcccacgg atgaaacgtc   53760
gaagccacga acaggagta cgccgtgttc cagaagccgg gattcgagtg ccgcccggtt   53820
gtcgttcacc gcctgcgcca gatcgcgtcc attcgataca ggctccagca gccacggcgt   53880
gcttccctcg gcaagcaact tgcgttccgt catgcccagc atcgtcaata gtccttcct    53940 gtacgtggat cacggcgaag ccgaacgggc cggcccgcgt ggtcgcgccg cggtgcggct   54000
atgcgcggca ggccgtttcc acggcatgct cgaagcgatt gagaatgtcg tggatgtccg   54060
cttccgaaac gatcagcggc ggcaggaacc ggagcaccgc gccgttgcgg ccgccggttt   54120
cgacgatgag cccgtttcgc aggcagttct gcttgatggc tcttgcccgt tccgtgtggg   54180
gcgggccggc tcggccgtgg gtgccgggca cgacgacttc ggcgccgatc atcaggccgc   54240
ggccgcgtat ctggcccagg caggggaagc gttcggcaag ctcctcgagg ccggcaacca   54300
ggagtttgcc gaccctgtcc gcgtgcgccg acagatcttc tctctcgacg atgcgcatgg   54360
tcgacaagcc ggccaccatc gcaatctggt tgcctcgaaa ggtgccggca tgcgcgccgg   54420
gcggccaggt gtccaggcgc tcgtcataga ccaccaccga taacggatag ccgccgccga   54480
atgccttcga cagcaccagt acgtccggcc ggatgccgga atgttcgatc gcgaacaggg   54540
cgccggtgcg accgagtccg gtctgcactt catcgacgat caacgggatt tcatgccgca   54600
gcgtcagctc gcgcaactcg atcaaccagg tgtcgggagc ggggatgcag cctccttcgc   54660
cttgcacgac ttcgacgatg atggccgccg gcttcgtgat cccgctctcg ggatcggaca   54720
ggacggtccg gatgtagttg atgctgagtt gatcggtcgc cgagccgtcg gtgccgaacg   54780
ggcagcgaaa ggcgtaggga tagggcagga aatgaacgtc gcgtccgttg ccgccggccg   54840
acttgggcgt gaggtttccc gacgcggcga gtgcgccgga cgtcatgccg tggtaggcgc   54900
cgtggaacgc catgatcgtc ggccggccgg tatagtgccg ggtcagcttg atcgccgctt   54960
cgacgccatc cgccgccactg ggctgcaaa actggatctt gccggattcg gcgatcttcc   55020
cgggcagaag cgagaaaagc tgctcgacga atgcgtgctt ggccggcgtc gccagatcga   55080
gtgcctgttg catctgatcg gacgacgaaa accgcatcac ggcttcattg acttccgggt   55140
gattgtgtcc gagcgcgagc gtgcccgcat tcgacaggca gtcgatgtat tcctgcccgt   55200
cggcgtcgcg tacgcgtatg cctttcgcat gggtaaacag ccgcgggaag gaggttgcgt   55260
aggttcgcgc gttcgattcg acctgcttca gatactcgag ttttccatg cgcgcagatc    55320 cggcttgcaa ggcggattga tggacactgg cgcacgagaa tcgcttcatc ctggccaatg   55380
gtgtttaacg gtacgaccgg attggagcat ggtctccgta tcgcgtctgt cacgtaaaaa   55440
tgggacatcg gccatgcgac gtcaccacgt catgccgttg ccttccgatc atcgaagcgg   55500
tttccgggcg cgacgtcagg cagcgagggt cgagcagaaa taatcgatgg tccgttggag   55560 accgcttcg agcccgatcg tcggctccca gtcgaggtgg gtgcgtgcga ggctgatgtc    55620
ggggcaacgt tgcgtcggat cgtccttcgg cagcggacgg aatacgagcc gcgacttcga   55680
gccggtcagg cgcaagatga tctgcgccag ttcgctgacc gcgatctcgt gcggattgcc   55740
gaggttgatc gggccggtga gctccgcggg cgtggccatc atccggatca aaccgtcgac   55800
```

-continued

```
catgtcgtcg acatagcaga atgcccgggt ctggctgccg tcgccataca gcgtgatgtc   55860
ctcgccccgc agcgcctgca cgatgaagtt ggacacgacg cggccgtcgt tgggatgcat   55920
gcgcggcccg tacgtgttga agatgcgtac caccttgatt cgtacgttct gctggcggtg   55980
atagtcgaag aacagggtct ccgcgcaacg cttgccttcg tcgtagcagg cgcgcggccc   56040
gagcgggttg acgttgcccc ggtaactctc cggttgcgga tgcacatcgg ggtcgccgta   56100
caccctcgctc gtcgacgttt gcagaacgcg tgcatgcgtg cgcttggcga gcccgagcat   56160
gttgatcgcg cccatcacac tggtcttggt ggtctgcacg ggatcgaatt gatagtggat   56220
gggcgaagcc gggcaggcga ggttgtagat ctcgtccacc tccacgtaca acggaaaagt   56280
gacgtcgtgg cgcagcgcct cgaagctcgg gttgccgagc agcgtagcca cgttctgctt   56340
cgtgccggtg aaatagttgt cgacgcacaa tacgtcgtga ccgagttcga cgagacgctc   56400
gcaaagatgc gaaccgagga aacccgcgcc accgttacg aggattcgct ttcgattacg    56460
ttgcacaatt gcactccaag tatcgcgcgc tgggaagcga cgcggcctcc ccgcacgctt   56520
gaccggcccg cggcaccggc aggggagcgg atcaggcgcg cggcgtttg cattcgacga    56580
tcacggcgcc ggccggcacg ccgatcgcga ggatcggccc gtcatgcctg cagtgcgctc   56640
gacgcggcgt gctccgggcg ccgcatgcgc gccgcgatga tgccggccat cgttcgcatt   56700
tcgtttctca aaagaaatg atcccctttcg atgacgtgaa aatcgaagcg cccggtcgtc   56760
gcggcgcccc agcctgcaac ggcatcgacg gggatctctt tatccgcccg gcccgcgaac   56820
gcggtgatgt ccaccgccag cctgggcccg ggcacgggcc ggtggttttc gatcatcgtg   56880
aaatccgcac gcagcgccgg catcagcagc gccatcagtt cgctgttgtc cagcaccgcc   56940
ttcggtgtgc cgcccatttc gcgcagcgca tcgatgaagg cgcggtcgtc cagcgcctgc   57000
atgcgccgat cgtggcgctc cttgcccggt gcggcacgcg cgctcacgaa cagatgccgc   57060
aggttcggtc gtgcgtgggc gggaagccgc agggccagtt cggccgcaat ggccgcgccc   57120
atgctgtgtc cgagcagtgc gaagggacga tcgaagcagt cgtccaggtc gcacagcaac   57180
gtgtcgacca gcgtcgccat gtctcggacg gcaggcggg caggcggct gcctcggcct   57240
gcaagttcat gacggcacac ttcgatgccc ggtaacgacg cttgcagcgt gcgatagacg   57300
gcggccgagc cgcccgcata gggaaaaacag atcagacgca tgcggggggg tactcgagcg   57360
gctcatctgc tgccggcgcg caggcgatgg cgctgtggaa attcatgtgt tcggcgtttt   57420
tcaccattca ggttccagat ccggttgggc gtgagttaaa cacgaggctg cgtggatgta   57480
tgtcgtagga agaggggacg cgttgtcggc catgtcgaag cggttcgtct ctgaatggat   57540
cccggcgcgg acacggtatc ggcgaaaaca gatgcgcggg aaatcgcgac gcatctgagt   57600
gtgtcgaacg atgcgcttcg tctttagaat gggcagcgag catggcgagc catcagaatt   57660
gcggcatccg atggtgccgc cgcgctaccc gataagttgg agacatacta tgcaacaccg   57720
tcagaaagcc gtcccgaccc agcaagtcgc gaacgagcgc gtgatcgtca ccgaatggcg   57780
attcgcgccc ggcgccgaga ccggctggca tgttcaccgg catgactatg tcgtggtgcc   57840
gcaaacggac ggtcagcttc tcctcgaaac cgcacaaggc aaccgcgagt cgcaattgca   57900
cgccgggcgc agctatgcgg ggctgaaggg cgtcgagcat aacgtcgtca acgcgacgga   57960
ccacgaagtg gtgttcgtcg aagtcgagat tctctaaggg gcgtcaggcc ccgcgagcaa   58020
ggccacgaca gggagcagca ggatgaaaat gaccgacatc ccgtttggca cgaccgactg   58080
gcgcaccgtt gaaccgaccg a                                             58101
```